US006204023B1

(12) United States Patent
Robinson et al.

(10) Patent No.: US 6,204,023 B1
(45) Date of Patent: *Mar. 20, 2001

(54) MODULAR ASSEMBLY OF ANTIBODY GENES, ANTIBODIES PREPARED THEREBY AND USE

(75) Inventors: Randy R. Robinson, Mountain View, CA (US); Alvin Y. Liu, Bellevue, WA (US); Arnold H. Horwitz; Marc Better, both of Los Angeles, CA (US); Randolph Wall, Sherman Oaks; Shau-Ping Lei, Los Angeles, both of CA (US); Gary L. Wilcox, Mill Creek, WA (US)

(73) Assignee: XOMA Ltd. (BM)

(*) Notice: Subject to any disclaimer, the term of this patent is extended or adjusted under 35 U.S.C. 154(b) by 0 days.

This patent is subject to a terminal disclaimer.

(21) Appl. No.: 08/472,691

(22) Filed: Jun. 6, 1995

Related U.S. Application Data

(60) Continuation of application No. 08/450,731, filed on May 25, 1995, now Pat. No. 5,693,493, which is a division of application No. 08/299,085, filed on Aug. 18, 1994, now Pat. No. 5,595,898, which is a continuation of application No. 07/987,555, filed on Dec. 8, 1992, now abandoned, which is a continuation of application No. 07/501,092, filed on Mar. 29, 1990, now abandoned, which is a continuation-in-part of application No. 07/077,528, filed on Jul. 24, 1987, now abandoned, which is a continuation-in-part of application No. PCT/US86/02269, filed on Oct. 27, 1986, now abandoned, which is a continuation-in-part of application No. 06/793,980, filed on Nov. 1, 1985, now abandoned, said application No. 07/501,092, is a continuation-in-part of application No. 07/142,039, filed on Jan. 11, 1988, now abandoned.

(51) Int. Cl.[7] .................. A61K 39/395; C07K 16/00; C12P 19/34
(52) U.S. Cl. .................. 435/71.3; 435/69.6; 435/69.7; 435/328; 435/91.1; 530/387.3; 424/133.1; 536/23.53
(58) Field of Search ................. 435/172.3, 69.6, 435/69.7, 240.27, 252.33, 71.3, 328, 91.1; 424/133.1, 134.1; 530/387.3; 536/23.53

(56) References Cited

U.S. PATENT DOCUMENTS

| 4,338,397 | 7/1982 | Gilbert et al. ........................ 435/68 |
| 4,642,334 | 2/1987 | Moore et al. ........................ 530/388 |
| 4,656,134 | 4/1987 | Ringold .................................. 435/91 |
| 4,816,397 | 3/1989 | Boss et al. ............................. 435/68 |
| 4,816,567 | 3/1989 | Cabilly et al. ....................... 530/387 |
| 4,935,496 | 6/1990 | Kudo et al. .......................... 530/388 |
| 4,963,495 | 10/1990 | Chang et al. ......................... 435/320 |
| 5,576,195 | 11/1996 | Robinson et al. .................. 435/69.8 |
| 5,648,237 | * 7/1997 | Carter .................................. 435/69.1 |

FOREIGN PATENT DOCUMENTS

| 0 048 970 | 4/1982 | (EP) . |
| 0 055 942 | 7/1982 | (EP) . |
| 0 088 994 B1 | 9/1983 | (EP) . |
| 0 102 634 A1 | 3/1984 | (EP) . |
| 0 120 694 A2 | 10/1984 | (EP) . |
| 0 125 023 A1 | 11/1984 | (EP) . |
| 0 126 338 A1 | 11/1984 | (EP) . |
| 0 133 321 A1 | 2/1985 | (EP) . |

(List continued on next page.)

OTHER PUBLICATIONS

Abrahmsén, L. et al., "Secretion of heterologous gene products to the culture medium of *Escherichia coli*," *Nucl. Acids Res.* 14(18):7487–7500 (Aug. 1986).

Alexander, A. et al., "γ heavy chain disease in man: cDNA sequence supports partial gene deletion model," *Proc. Natl. Acad. Sci. USA* 79:3260–3264 (1982).

Anand, N.N. et al., "Synthesis and expression in *Escherichia coli* of cistronic DNA encoding an antibody fragment specific for a Salmonella serotype B O–antigen," *Gene* 100:39–44 (Jun. 1991).

Anand, N.N. et al., "Bacterial Expression and Secretion of Various Single–chain Fv Genes Encoding Proteins Specific for a Salmonella Serotype B O–Antigen," *J. Biol. Chem.* 266(32):21874–21879 (Nov. 1991).

Banerji, J. et al., "A Lymphocyte–Specific Cellular Enhancer Is Located Downstream of the Joining Region in Immunoglobulin Heavy Chain Genes," *Cell* 33:729–740 (1983).

Barbas III, C.F. et al., "Assembly of combinatorial antibody libraries on phage surfaces: The gene III site," *Proc. Natl. Acad. Sci. USA* 88(18):7978–7982 (Sep. 1991).

(List continued on next page.)

*Primary Examiner*—Julie Burke
(74) *Attorney, Agent, or Firm*—Sterne, Kessler, Goldstein & Fox P.L.L.C.

(57) ABSTRACT

The invention relates to cDNA genetic sequences, vehicles containing same as well as hosts tansformed therewith, for the production of chimeric immunoglobulin molecules, functional fragments thereof and immunoglobulin derivatives exhibiting novel functional properties comprising human constant region modules and non-human variable region modules, or for class switching antibody molecules and/or chains.

The invention also relates to DNA coding for pectate lyase signal peptide has been cloned on a plasmid to create a secretion vector which is capable of producing a chosen protein which is transported across the bacterial membrane. The secretion vector has been used to secrete extracellular thaumatin and extracellular chimeric antibody fragments. The proteins produced by this vector have biological activity. The thaumatin is properly folded and the antibody fragments are capable of binding antigens on target cancer cells. The invention also relates to the secretion of chimeric antibodies and fragments thereof from yeast in functional form.

60 Claims, 61 Drawing Sheets

FOREIGN PATENT DOCUMENTS

| | | |
|---|---|---|
| 0 154 539 A2 | 9/1985 | (EP) . |
| 0 171 496 A3 | 2/1986 | (EP) . |
| 0 173 494 A3 | 3/1986 | (EP) . |
| 0 184 187 A2 | 6/1986 | (EP) . |
| 0 194 276 B1 | 9/1986 | (EP) . |
| 0 234 592 A1 | 9/1987 | (EP) . |
| 0 266 663 A1 | 5/1988 | (EP) . |
| 0 278 355 A2 | 8/1988 | (EP) . |
| 0 324 162 * | 7/1989 | (EP) . |
| 2 137 631 | 10/1984 | (GB) . |
| 60-155132 * | 8/1985 | (JP) . |
| 61-47500 * | 3/1986 | (JP) . |
| 62-502586 * | 10/1987 | (JP) . |
| 63-68087 * | 3/1988 | (JP) . |
| WO 83/03971 | 11/1983 | (WO) . |
| WO 86/01533 | 3/1986 | (WO) . |
| WO 86/05513 | 9/1986 | (WO) . |
| WO 86/05812 | 10/1986 | (WO) . |
| WO 87/02671 | 5/1987 | (WO) . |
| WO 89/00999 | 2/1989 | (WO) . |
| WO 89/06283 | 7/1989 | (WO) . |
| WO 92/22324 | 12/1992 | (WO) . |
| WO 93/11794 | 6/1993 | (WO) . |
| WO 93/15210 | 8/1993 | (WO) . |

OTHER PUBLICATIONS

Bebbington, C.R. et al., "High–Level Expression Of A Recombinant Antibody From Myeloma Cells Usin A Glutamine Synthetase Gene As An Amplifiable Selectable Marker," *Bio/Tech.* 10:169–175 (Feb. 1992).

Beckwith, J. and S. Ferro–Novick, "Genetic Studies on Protein Export in Bacteria," *Curr. Top. Microbiol. Immunol.* 125:5–27 (Jul. 1986).

Beggs, J.D., "Multiple–copy Yeast Plasmid Vectors," *Mol. Genet. Yeast. Alfred Benzon Symp.* 16:383–389 (1981).

Bernstein, K.E. et al., "Nucleotide Sequence of a Rabbit IgG Heavy Chain from the Recombinant F–I Haplotype," *Immunogenetics* 18(4):387–397 (1983).

Better, M. et al., "*Escherichia coli* Secretion of an Active Chimeric Antibody Fragment," *Science* 240:1041–1043 (May 1988).

Better, M. and A.H. Horwitz, "Expression of Engineered Antibodies and Antibody Fragments in Microorganisms," *Meth. Enzymol.* 178:476–496 (Nov. 1989).

Better, M. et al., "Production And Scale Up Of Chimeric Fab Fragments From Bacteria," *Advances in Gene Technology: The Molecular Biology of Immune Diseases and the Immune Response. Proceedings of the 1990 Miami Bio/Technology Winter Symposia* 10:105 (Jul. 1990).

Better, M. et al., "Potent anti–CD5 ricin A chain immunoconjugates from bacterially produced Fab' and F(ab')$_2$," *Proc. Natl. Acad. Sci. USA* 90:457–461 (Jan. 1993).

Better, M. and A.H. Horwitz, "In Vivo Expression of Correctly Folded Antibody Fragments from Microorganisms," in: *Protein Folding—In Vivo and In Vitro*, Cleland, J.L., ed., Washington, D.C.: American Chemical Society pp. 203–217 (Apr. 1993).

Boss, M.A. et al., "Assembly of functional antibodies from immunoglobulin heavy and light chains synthesised in *E. coli*," *Nucl. Acids Res.* 12(9):3791–3806 (1984).

Boulianne, G.L. et al., "Production of functional chimaeric mouse/human antibody," *Nature* 312:643–646 (1984).

Brown, N.A. et al., "Immunoglobulin $J_H$, $C_\mu$, and $C_\gamma$ gene rearrangements in human B lymphocytes clonally transformed by Epstein–Barr virus," *Proc. Natl. Acad. Sci. USA* 82:556–560 (1985).

Cabilly S. et al., "Generation of antibody activity from immunoglobulin polypeptide chains produced in *Escherichia coli*," *Proc. Natl. Acad. Sci. USA* 81:3273–3277 (1984).

Calos, M.P. et al., "High mutation frequency in DNA transfected into mammalian cells," *Proc. Natl. Acad. Sci. USA* 80:3015–3019 (1983).

Carter, P. et al., "High Level *Escherichia coli* Expression And Production Of A Bivalent Humanized Antibody Fragment," *Bio/Technol.* 10:163–167 (Feb. 1992).

Chan, S.J. et al., "Biosynthesis and periplasmic segregation of human proinsulin in *Escherichia coli*," *Proc. Natl. Acad. Sci. USA* 78(8):5401–5405 (1981).

Clackson, T. et al., "Making antibody fragments using phage display libraries," *Nature* 352:624–628 (Aug. 1991).

Clontech Catalog, Bacterial Strains and Numberical Index, pp 224 and 277 (Jul. 1993).

Denèfle, P. et al., "Heterologous protein export in *Escherichia coli*: influence of bacterial signal peptides on the export of human interleukin 1β," *Gene* 85:499–510 (Dec. 1989).

Dickson, S., "Scientists Produce Chimeric Monoclonal Abs," *Genetic Engineering News* 5(3):1 and 33 (1985).

Dolby, T.W. et al., "Cloning and partial nucleotide sequence of human immunoglobulin μ chain cDNA from B cells and mouse–human hybridomas," *Proc. Natl. Acad. Sci. USA* 77(10):6027–6031 (1980).

Early, P. and L. Hood, "Mouse Immunoglobulin Genes," in: *Genetic Engineering—Principles and Methods*, vol. 3, Setlow, J.K. and A. Hollander, eds., New York: Plenum Press pp. 157–188 (1981).

Edelman, G.M. et al., "The Covalent Structure Of An Entire γG Immunoglobulin Molecule," *Proc. Natl. Acad. Sci. USA* 63(1):78–85 (1969).

Edens, L. et al., "Cloning of cDNA encoding the sweet–tasting plant protein thaumatin and its expression in *Escherichia coli*," *Gene* 18:1–12 (1982).

Ellison, J. and L. Hood, "Linkage and sequence homology of two human immunoglobulin in γ heavy chain constant region genes," *Proc. Natl. Acad. Sci. USA* 79:1984–1988 (1982).

Ellison, J.W. et al., "The nucleotide sequence of a human immunoglobulin $C_{\gamma 1}$ gene," *Nuc. Acids Res.* 10(13):4071–4079 (1982).

Ferenci, T. and T.J. Silhavy, "Sequence Information Required for Protein Translocation from the Cytoplasm," *J. Bacteriol.* 169(12):5339–5342 (Dec. 1987).

Fraser, T.H. and B.J. Bruce, "Chicken ovalbumin is synthesized and secreted by *Escherichia coli*," *Proc. Natl. Acad. Sci. USA* 75(12):5936–5940 (1978).

Gherna, R. et al., eds., *American Type Culture Collection—Catalogue of Bacteria and Phages*, Seventeenth edition, p. 97 (Feb. 1989).

Gillam, S. and M. Smith, "Site–Specific Mutagenesis Using Synthetic Oligodeoxyribonucleotide Primers: I. Optimum Conditions And Minimum Oligodeoxyribonucleotide Length," *Gene* 8:81–97 (1979).

Gillies, S.D. et al., "A Tissue–specific Transcription Enhancer Element Is Located in the Major Intron of a Rearranged Immunoglobulin Heavy Chain Gene," *Cell* 33:717–728 (1983).

Gray, G.L. et al., "Periplasmic production of correctly processed human growth in *Escherichia coli*: natural and bacterial signal sequences are interchangeable," *Gene* 39:247–254 (1985).

Hieter, P.A. et al., "Cloned Human and Mouse Kappa Immunoglobulin Constant and J Region Genes Conserve Homology in Functional Segments," *Cell* 22:197–207 (1980).

Hieter, P.A. et al., "Evolution of Human Immunoglobulin κ J Region Genes," *J. Biol. Chem.* 257(3):1516–1522 (1982).

Holland, I.B. et al., "Secretion of Proteins From Bacteria," *Bio/Technol.* 4:427–431 (May 1986).

Holland, I.B., "Secretion of *Escherichia coli* haemolysin," *Biochem. Soc. Trans.* 17(2):323–325 (Apr. 1989).

Horwitz, A.H. et al., "Secretion of functional antibody and Fab fragment from yeast cells," *Proc. Natl. Acad. Sci. USA* 85:8678–8682 (Nov. 1988).

Hsuing, H.M. et al., "High–Level Expression, Efficient Secretion And Folding Of Human Growth Hormone In *Escherichia coli*," *Bio/Technol.* 4:991–995 (Nov. 1986).

Huse, W.D. et al., "Generation of a Large Combinatorial Library of the Immunoglobulin Repetoire in Phage Lambda," *Science* 246:1275–1281 (Dec. 1989).

Itakura, K. et al., "Synthesis And Use Of Synthetic Oligo-nucleotides," *Ann. Rev. Biochem.* 53:323–356 (1984).

Johnston, S. et al., "High–level expression of M13 gene II protein from an inducible polycistronic messenger RNA," *Gene* 34:137–145 (1985).

Jones, P.T. et al., "Replacing the complementarity–determining regions in a human antibody with those from a mouse," *Nature* 321:522–525 (May 1986).

Kabat, E.A. et al., *Sequences Of Proteins Of Immunological Interest*, U.S. Department of Health, Introduction, index, and pp. 275–276 (1983).

Kato, C. et al., "Construction of an excretion vector and extracellular production of human growth hormone from *Escherichia coli*," *Gene* 54:197–202 (Jul. 1987).

Keen, N.T. and S. Tamaki, "Structure of Two Pectate Lyase Genes from *Erwinia chrysanthemi* EC16 and Their High–Level Expression in *Escherichia coli*," *J. Bacteriol.* 168(2):595–606 (Nov. 1986).

Kenten, J. et al., "Properties of a human immunoglobulin ε–chain fragment synthesized in *Escherichia coli*," *Proc. Natl. Acad. Sci. USA* 81:2955–2959 (1984).

Klausner, A., "Genentech Makes Monoclonal Precursors From *E. coli*," *Bio/Technol.* 1(5):396–397 (1983).

Kniskern, P.J. et al., "Unusually high–level expression of a foreign gene (hepatitis B virus core antigen) in *Saccharomyces cerevisiae*," *Gene* 46:135–141 (Dec. 1986).

Koshland, D. and D. Botstein, "Secretion of Beta–Lactamase Requires the Carboxy End of the Protein," *Cell* 20:749–760 (1980).

Kramer, W. et al., "The gapped duplex DNA approach to oligonucleotide–directed mutation construction," *Nucl. Acids Res.* 12(24):9441–9456 (1984).

Kurokawa, T. et al., "Expression of human immunoglobulin E ε chain cDNA in *E. coli*," *Nuc. Acids Res.* 11(10):3077–3085 (1983).

LaVallie, E.R. et al., "A Thioredoxin Gene Fusion Expression System That Circumvents Inclusion Body Formation in the *E. coli* Cytoplasm," *Bio/Technol.* 11:187–193 (Feb. 1993).

Lei, S.–P. et al., "Cloning of the pectate lyase genes from *Erwinia carotovora* and their expression in *Escherichia coli*," *Gene* 35:63–70 (1985).

Lei, S.–P. et al., "Characterization of the *Erwinia carotovora pelB* Gene and Its Product Pectate Lyase," *J. Bacteriol.* 169(9):4379–4383 (Sep. 1987).

Lei, S.–P. et al., "Characterization of the *Erwinia carotovora peh* gene and its product polygalacturonase," *Gene* 117:119–124 (Aug. 1992).

Li, P. et al., "Alteration of the amino terminus of the mature sequence of a periplasmic protein can severely affect protein export in *Escherichia coli*," *Proc. Natl. Acad. Sci. USA* 85(20):7685–7689 (Oct. 1988).

Liu, A.Y. et al., "Chimeric mouse–human IgG1 antibody that can mediate lysis of cancer cells," *Proc. Natl. Acad. Sci. USA* 84:3439–3443 (May 1987).

Liu, A.Y. et al., "Expression of mouse::human immunoglobulin heavy–chain cDNA in lymphoid cells," *Gene* 54:33–40 (Jul. 1987).

Liu, A.Y. et al., "Production Of A Mouse–Human Chimeric Monoclonal Antibody To CD20 With Potent Fc–Dependent Biologic Activity," *J. Immunol.* 139(10):3521–3526 (Nov. 1987).

Liu, F.–T. et al., "Expression of biologically active fragment of human IgE ε chain in *Escherichia coli*," *Proc. Natl. Acad. Sci. USA* 81:5369–5373 (1984).

Mackman, N. et al., "Release of a chimeric protein into the medium from *Escherichia coli* using the C–terminal secretion signal of haemolysin," *EMBO J.* 6(9):2835–2841 (Sep. 1987).

MacKenzie, C.R. et al., "Effective of $C_\lambda$–$C_\kappa$ Domain Switching on Fab Activity and Yield in *Escherichia coli*: Synthesis and Expression of Genes Encoding Two Anti–Carbohydrate Fabs," *Bio/Tech.* 12:390–395 (Apr. 1994).

Maki, R. et al., "The Role of DNA Rearrangement and Alternative RNA Processing in the Expression of Immunoglobulin Delta Genes," *Cells* 24(2):353–365 (1981).

Maniatis, T. et al., "Vectors That Express Cloned DNA in *Escherichia coli*," in: *Molecular Cloning: A Laboratory Manual*, Maniatis, T. et al., eds., New York: Cold Spring Harbor Press pp. 403–433 (1982).

Marks, J.D. et al., "By–passing Immunization: Human Antibodies from V–gene Libraries Displayed on Phage," *J. Mol. Biol.* 222:581–597 (Dec. 1991).

Marx, J.L., "Antibodies Made to Order—Chimeric antibodies–which are part mouse and part human–may help solve the problems hindering the therapeutic use of monoclonal antibodies," *Science* 229:455–456 (1985).

Max, E.E. et al., "Sequences of five potential recombination sites encoded close to an immunoglobul in κ constant region gene," *Proc. Natl. Sci. USA* 76(7):3450–3454 (1979).

McCafferty, J. et al., "Phage antibodies: fillamentous phage displaying antibody variable domains," *Nature* 348:552–554 (Dec. 1990).

McCarthy, J.E.G. et al., "Translational initiation frequency of atp genes from *Escherichia coli*: identification of an intercistronic sequence that enhances translation," *EMBO J.* 4(2):519–526 (1985).

Messing, J. et al., "A system for shotgun DNA sequencing," *Nuc. Acids Res.* 9(2):309–321 (1981).

Miller, J. et al., "Structural alterations in J regions of mouse immunoglobulin λ genes are associated with differential gene expression," *Nature* 295:428–430 (1982).

Morrison, S.L. et al., "Chimeric human antibody molecules: Mouse antigen–binding domains with human constant region domains," *Proc. Natl. Acad. Sci. USA 81*:6851–6855 (1984).

Morrison, S.L., "Transfectomas Provide Novel Chimeric Antibodies," *Science 229*:1202–1207 (1985).

Morrison, S.L. and V.T. Oi, "Genetically Engineered Antibody Molecules," *Adv. Immunol. 44*:65–92 (Jan. 1989).

Morrison, S.L., "In Vitro Antibodies: Strategies for Production and Application," *Annu. Rev. Immunol. 10*:239–265 (Apr. 1992).

Mullinax, R.L. et al., "Identification of human antibody fragment clones specific for tetanus toxoid in a bacteriophage λ immunoexpression library," *Proc. Natl. Acad. Sci. USA 87*:8095–8099 (Oct. 1990).

Munro, A., "Uses of chimaeric antibodies," *Nature 312*:597 (1984).

Neuberger, M.S. et al., "Recombinant antibodies possessing novel effector functions," *Nature 312*:604–608 (1984).

Neuberger, M.S. et al., "A hapten–specific chimaeric IgE antibody with human physiological effector function," *Nature 314*:268–270 (1985).

Nilsson, B. et al., "Immobilization and purification of enzymes with staphylococcal protein A gene fusion vectors," *EMBO J. 4(4)*:1075–1080 (1985).

Novagen Catalog, pET System, pp. 5–7 and 11 (Nov. 1993).

Ochi, A. et al., "Functional immunoglobulin M production after transfection of cloned immunoglobulin heavy and light chain genes into lymphoid cells," *Proc. Natl. Acad. Sci. USA 80*:6351–6355 (1983).

Ohmura, K. et al., "Length and structural effect of signal peptides derived from *Bacillus subtilis* α–amylase on secretion of *Escherichia coli* β–lactamase in *B. subtilis* cells," *Nuc. Acids Res. 12(13)*:5307–5319 (1984).

Oi, V.T. and S.L. Morrison, "Chimeric Antibodies," *BioTechniques 4(3)*:214–221 (May/Jun. 1986).

Oka, T. et al., "Synthesis and secretion of human epidermal growth factor by *Escherichia coli*," *Proc. Natl. Acad. Sci. USA 82*:7212–7216 (1985).

Orlandi, R. et al., "Cloning immunoglobulin variable domains for expression by the polymerase chain reaction," *Proc. Natl. Acad. Sci. USA 86(10)*:3833–3837 (May 1987).

Pack, P. and A. Plückthun, "Miniantibodies: Use of Amphipathic Helices To Produce Functional, Flexibly Linked Dimeric $F_V$ Fragments with High Avidity in *Escherichia coli*," *Biochem. 31(6)*:1579–1584 (Feb. 1992).

Pages, J.–M. et al., "Conditions Leading to Secretion of a Normally Periplasmic Protein in *Escherichia coli*," *J. Bacteriol. 169(4)*:1386–1390 (Apr. 1987).

Plückthun, A. and J.R. Knowles, "The Consequences of Stepwise Deletions from the Signal–processing Site of β–Lactamase," *J. Biol. Chem. 262(9)*:3951–3957 (Mar. 1987).

Plückthun, A. and A. Skerra, "Expression of Functional Antibody Fv and Fab Fragments in *Escherichia coli*," *Meth. Enzymol. 178*:497–515 (Nov. 1989).

Plückthun, A., "Antibody Engineering: Advances From The Use Of *Escherichia coli* Expression Systems," *Bio/Tech. 9*:545–551 (Jun. 1991).

Pugsley, A., "Early stages in the secretory pathway," in: *Protein Targeting*, Pugsley, A. ed., New York: Academic Press, Inc. pp. 45–111 and 241–267 (Jun. 1989).

Pugsley, A., "Applications of protein targeting," in: *Protein Targeting*, Puglsey, A. ed., New York: Academic Press, Inc. pp. 229–267 (Jun. 1989).

Queen, C. and D. Baltimore, "Immunoglobulin Gene Transcription Is Activated by Downstream Sequence Elements," *Cell 33(3)*:741–748 (1983).

Ravetch, J.V. et al., "Structure of the Human Immunoglobulin μ Locus: Characterization of Embryonic and Rearranged J and D Genes," *Cell 27*:583–591 (1981).

Roberts, T.M., "A lac Promoter System For The Overexpression of Prokaryotic And Eukaryotic Genes In *E. coli*," in: *Promoters: Structure and Function*, Rodriquez, R.L., ed., New York: Praeger Publishers pp. 452–461 (1982).

Rodrigues, M.L. et al., "Engineering Fab' Fragments for Efficient $F(ab)_2$ Formation in *Escherichia coli* and for Improved In Vivo Stability," *J. Immunol. 151(12)*:6954–6961 (Dec. 1993).

Rosenwasser, T.A. et al., "Compartmentalization of Mammalian Proteins Produced in *Escherichia coli*," *J. Biol. Chem. 265(22)*:13066–13073 (Aug. 1990).

Sahagan, B.G. et al., "A Genetically Engineered Murine/Human Chimeric Antibody Retains Specificity For Human Tumor–Associated Antigen," *J. Immunol. 137(3)*:1066–1074 (Aug. 1986).

Sakano, H. et al., "Sequences at the somatic recombination sites of immunoglobulin light–chain genes," *Nature 280*:288–294 (1979).

Sastry, L. et al., "Cloning of the immunological repertoire in *Escherichia coli* for generation of monoclonal catalytic antibodies: Construction of a heavy chain variable region–specific cDNA library," *Proc. Natl. Acad. Sci. USA 86(15)*:5728–5732 (Aug. 1989).

Schein, C.H., "Production Of Soluble Recombinant Proteins In Bacteria," *Bio/Tech. 7*:1141–1148 (Nov. 1989).

Schoner, B.E. et al., "Translation of a synthetic two–cistron mRNA in *Escherichia coli*," *Proc. Natl. Acad. Sci. USA 83(22)*:8506–8510 (Nov. 1986).

Seno, M. et al., "Monoclonal cloning and nucleotide sequencing of human immunoglobulin ε chain cDNA," *Nucl. Acids Res. 11(3)*:719–726 (1983).

Sharon, J. et al., "Expression of a $V_H C_\kappa$ chimeric protein in mouse myeloma cells," *Nature 309*:364–367 (1984).

Sharon, J. et al., "Expression of a $V_H C_\kappa$ chimeric protein in mouse myeloma cells," *Chem. Abstr. 101(7)*:147 Abstr. 49464x (1984).

Shiroza, T. et al., "Synthesis and secretion of biologically active mouse interferon–β using a *Bacillus subtilis* α–amylase secretion vector," *Gene 34*:1–8 (1985).

Sjöström, M. et al., "Signal peptide amino acid sequences in *Escherichia coli* contain information related to final protein localization. A multivariate date analysis," *EMBO J. 6(3)*:823–831 (Mar. 1987).

Skerra, A. and A. Plückthun, "Assembly of a Functional Immunoglobulin $F_V$ Fragment in *Escherichia coli*," *Science 240*:1038–1041 (May 1988).

Skerra, A. and A. Plückthun, "Secretion and in vivo folding of the $F_{ab}$ fragment of the antibody McPC603 in *Escherichia coli*: influence of disulphides and cis–prolines," *Prot. Engin. 4(8)*:971–979 (Dec. 1991).

Stader, J.A. and T.J. Silhavy, "Engineering *Escherichia coli* to Secrete Heterologous Gene Products," *Meth. Enzymol. 185*:166–187 (May 1990).

Studnicka, G.M. et al., "Human–engineered monoclonal antibodies retain full specific binding activity by preserving non–CDR complementarity–modulating residues," *Prot. Engin.* 7(6):805–814 (Jun. 1994).

Sun, L.K. et al., "Chimeric Antibodies with 17–1A–Derived Variable and Human Constant Regions," *Hybridoma* 5(*Suppl. 1*):S17–S20 (Feb. 1986).

Sun, L.K. et al., "Chimeric antibody with human constant regions and mouse variable regions directed against carcinoma–associated antigen 17–1A," *Proc. Natl. Acad. Sci. USA* 84:214–218 (Jan. 1987).

Takahara, M. et al., "Sectretion Of Human Superoxide Dismutase In *Escherichia coli,*" *Bio/Technol.* 6:195–198 (Feb. 1988).

Takahashi, H. et al., "A DNA sequence for gene expression and protein secretion, and its cloning from pectic acid lyase operon of Erwinia," *Chem. Abstr.* 110:187 Abstr. No. 52329y (Aug. 1989).

Takahashi, N. et al., "Structure of Human Immunoglobulin Gamma Genes: Implications for Evolution of a Gene Family," *Cell* 29:671–679 (1982).

Takeda, S. et al., "Construction of chimaeric processed immunoglobulin genes containing mouse variable and human constant region sequences," *Nature* 314:452–454 (1985).

Tan, L.K. et al., "A Human–Mouse Chimeric Immunoglobulin Gene With A Human Variable Region Is Expressed In Mouse Myeloma Cells," *J. Immunol.* 135(5):3564–3567 (1985).

Tsujimoto, Y. and C.M. Croce, "Molecular cloning of a human immunoglobulin λ chain variable sequence," *Nucl. Acids Res.* 12(22):8407–8414 (1984).

Van Brunt, J., "There's Nothing (Quite) Like The Real Thing," *Bio/Technol.* 4:835 and 839 (Oct. 1986).

Ward, E.S. et al., "Binding activities of a repertoire of single immunoglobulin variable domains secreted from *Escherichia coli,*" *Nature* 341:544–546 (Oct. 1989).

Ward, E.S., "Expression and Purification of Antibody Fragments Using *Escherichia coli* as a Host," in: *Antibody engineering—A Practical Guide*, Borrebaeck, C.A.K., ed., New York: W.H. Freeman and Co. pp. 121–137 (Jul. 1991).

Ward, V.K. et al., "Cloning, sequencing and expression of the Fab fragment of a monoclonal antibody to the herbicide atrazine," *Prot. Engin.* 6(8):981–988 (Nov. 1993).

Watson, M.E.E., "Compilation of published signal sequences," *Nucl. Acids Res.* 12(13):5145–5163 (1984).

Weidle, U.H. et al., "Reconstitution of functionally active antibody directed against creatine kinase from separately expressed heavy and light chains in non–lymphoid cells," *Gene* 51:21–29 (Mar. 1987).

Wetzel, R., "Active immunoglobulin fragments synthesized in *E. coli*—from Fab to Scantibodies," *Prot. Engin.* 2(3):169 and 176 (Sep. 1988).

Williams, G.T. and M.S. Neuberger, "Production of antibody–tagged enzymes by myeloma cells: application to DNA polymerase I Klenow fragment," *Gene* 43:319–324 (Aug. 1986).

Wood, C.R. et al., "The synthesis and in vivo assembly of functional antibodies in yeast," *Nature* 314:446–449 (1985).

Wood, D.L. and C. Coleclough, "Different joining region J elements of the murine κ immunoglobulin light chain locus are used at markedly different frequencies," *Proc. Natl. Acad. Sci. USA* 81(15):4756–4760 (1984).

Zemel–Dreasen, O. and A. Zamir, "Secretion and processing of an immunoglobulin light chain in *Escherichia coli,*" *Gene* 27:315–322 (1984).

Dialog World Patent Index 351 English Language Abstact for JP 60–155132, (Aug. 1985).

Dialog World Patent Index File 351 English Language Abstract for JP 61–47500, Mar. 1986.

Dialog World Patent Index File 351 English Language Abstract for JP 62–502586, Oct. '87.

Dialog JAPIO File 347 English Language Abstract for JP 63–068087, Mar. 1988.

Dialog World Patent Index File 351 English Language Abstract For EP 0 324 162, Jul. 1989.

Gillies et al HUman Antibodies Hybridomas vol. 1(1) 47–54, 1990.*

Lyons et al Prot Engineering vol. 3(8) 703–708, 1990.*

Walter et al Proc Natl Acad sci USA vol. 77 No. 9 5197–5200, Sep. 1980.*

Axelsson Acta Chemica Scandanavica Series B vol. 39(1) 69–77, 1985.*

Paulus et al Behring Inst Mitt No. 78 118–132, 1985.*

Zapata, G. et al., "Engineering linear F(ab)$_2$ fragments for efficient production in *Escherichia coli* and enhanced antiprolifertive activity," *Protein Engineering* 8(*10*):1057–1062 (1995).

Humphreys, D.P. et al., Formation of dimeric Fabs in *Escherichia coli*: effect of hinge size and isotype, presence of interchain disulphide bond, Fab' expression levels, tail piece sequences and growth conditions, *J. Immunol. Methods* 209:192–202 (1997).

Lo, K.–M. et al., "Expression and secretion of an assembled tetrameric CH2–deleted antibody in *E. coli,*" *Hum. Antibod. Hybridomas* 3:123–128 (1992).

Flamez, D. et al., "Production in *Escherichia coli* of a functional murine and murein::human chimeric F(ab')2 fragment and mature antibody directed against human placental alkaline phosphatase," *J. Biotechnol.* 42:133–143 (1995).

Appendix A to Patentee's [Celltech Therapeutics Limited] Letter of 8$^{th}$ of May 1996, filed in reply to oppositions against European Patent No. 0 120 694.

DeSutter, K. et al., "Production of functionally active murine and murine::human chimeric F(ab')2 fragments in COS–1 cells," *Gene* 113:223–230 (1992).

King, D.J. et al., "Expression, purification and characterization of a mouse–human chimeric antibody and chimeric Fab' fragment," *Biochem. J.* 281:317–323 (1992).

Proudfoot, K.A. et al., "Purification of Recombinant Chimeric B72.3 Fab' and F(ab)2 Using Streptococcal Protein G," *Protein Expr. Purif.* 3:368–373 (1992).

"The Evolution of Catalytic Function," Abstracts and papers presented at the LII Cold Spring Harbor Symposium on Quantitative Biology, May 27–Jun. 3, 1987, Cold Spring Harbor Laboratory, Cold Spring Harbor, New York, Mar. 1988, Plunckthen et al.

"DNA Sequence of the Promotor and NH$_2$–Terminal Regions of the Pectate Lyase I Gene from *Erwinia carotovora,*" Nikaido et al., *J. Gen. Appl. Microbiology,* 31:573–576 (1985).

"Cloning of a Pectate Lysase Gene from *Erwinia carotovor* and its Expression in *Escherichia coli,*" Nikaido et al., *Gen. Appl. Microbiology,* 31:293–296 (1985).

Amster, O. et al., "Synthesis of Part of a Mouse Immunoglobulin Light Chain in a Bacterial Clone," *Nucleic Acids Research* 8(9):2055–2065, 1980.

Briggs, Martha S. et al., "Molecular Mechanisms of Protein Secretion: The Role of the Signal Sequence," *Advances in Protein Chemistry* 38:109–180, 1986.

Ghrayeb, J. et al., "Secretion Cloning Vectors in *Escherichia coli*," *The EMBO Journal* 3(10):2437–2442, 1984.

Hendershot, L. et al., "The Role of Immunoglobulin Heavy Chain Binding Protein," *Immunol. Today* 8:111–114, 1987.

Nagahari, K. et al., "Secretion Into the Culture Medium of a Foreign Gene Product From *Escherichia coli*: use of the ompF Gene for Secretion of Human β–endorphin," *The EMBO Journal* 4(13A):3589–3592, 1985.

* cited by examiner

Ig heavy chain J-C region human heavy chain J regions

J|CH1

```
JH1       GCTGAATACTTCCAGCACTGGGGCCAGGGCACCCTGGTCACCGTCTCCTCAG
JH2       CTACTGGTACTTCGATCTCTGGGGCCGTGGCACCCTGGTCACTGTCTCCTCAG
JH3          ATGCTTTTGATGTCTGGGGCCAAGGGACAATGGTCACCGTCTCTTCAG
JH4          ACTACTTTGACTACTGGGGCCAAGGAACCCTGGTCACCGTCTCCTCAG
JH5          ACACTGGTTCGACTCCTGGGGCCAAGGAACCCTGGTCACCGTCTCCTCAG
JH6       AT(TAC)₅GGTATGGACGTCTGGGGGCAAGGGACCACGGTCACCGTCTCCTCAG
Consensus          TCGACCTCTGGGGCCAAGGAACCCTGGTCACCGTCTCCTCAG
``` mouse heavy chain J regions

J|CH1

```
JH1       TACTGGTACTTCGATGTCTGGGGCGCAGGGACCACGGTCACCGTCTCCTCAG
JH2              TACTTTGACTACTGGGGCCAAGGCACCACTCTCACAGTCTCCTCAG
JH3           CCTGGTTTGCTTACTGGGGCCAAGGGACTCTGGTCACTGTCTCTGCAG
JH4       TACTATGCTATGGACTACTGGGGTCAAGGAACCTCAGTCACCGTCTCCTCAG
Consensus        TTTGACTACTGGGGCCAAGGGACCACGGTCACCGTCTCCTCAG
```

Ig light chain J-C region human Kappa J region

J|C

```
JK1  GGACGTTCGGCCAAGGGACCAAGGTGGAAATCAAAC
JK2  ACACTTTTGGCCAGGGGACCAAGCTGGAGATCAAAC
JK3  TCACTTTCGGCCCTGGGACCAAAGTGGATATCAAAC
JK4  TCACTTTCGGCGGAGGGACCAAGGTGGAGATCAAAC
JK5  TCACCTTCGGCCAAGGGACACGACTGGAGATTAAAC
Consensus TTCGGCCAAGGGACCAAGGTGGAGATCAAAC
``` mouse Kappa J region

J|C

```
JK1  TGGACGTTCGGTGGAGGCACCAAGCTGGAAATCAAAC
JK2  TACACGTTCGGAGGGGGGACCAAGCTGGAAATAAAAC
JK3  TTCACATTCAGTGATGGGACCAGACTGGAAATAAAAC
JK4  TTCACGTTCGGCTCGGGGACAAAGTTGGAAATAAAAC
JK5  CTCACGTTCGGTGCTGGGACCAAGCTGGAGCTGAAAC
Consensus TTCGGTGGGGGGACCAAGCTGGAAATAAAAC
UIG[MJK]         ₃'TGGTTCGACCTTTATTTG₅'
``` human Lambda pseudo J region

J|C

```
JPSL1 CACATGTTTGGCAGCAAGACCCAGCCCACTGTCTTAG
``` mouse Lambda J region

J|C

```
JL1 TGGGTGTTCGGTGGAGGAACCAAACTGACTGTCCTAG
JL2 TATGTTTTCGGCGGTGGAACCAAGGTCACTGTCCTAG
JL3 TTTATTTTCGGCAGTGGAACCAAGGTCACTGTCCTAG
Consensus TTCGGCGGTGGAACCAAGGTCACTGTCCTAG
```

FIG. 2

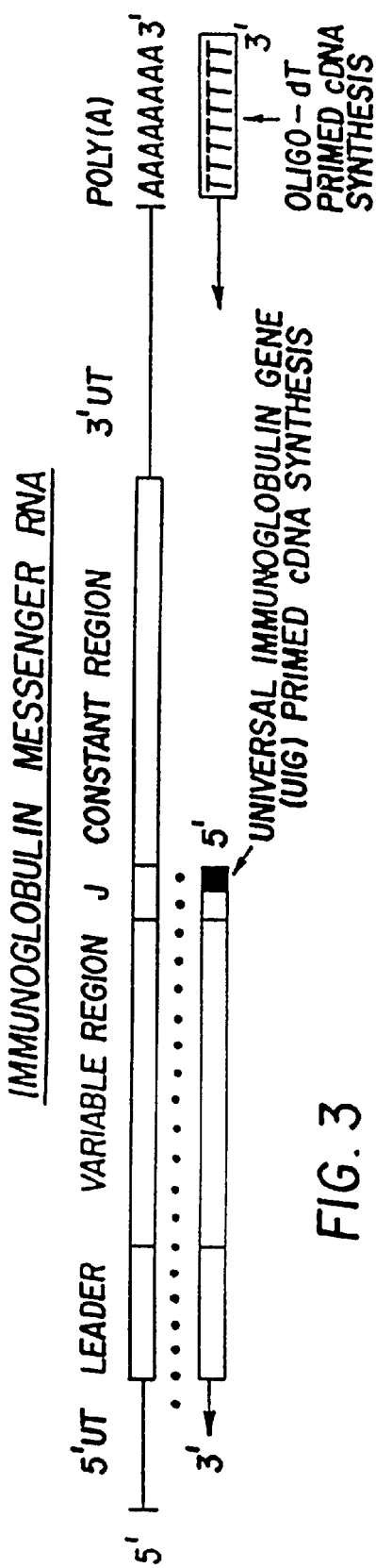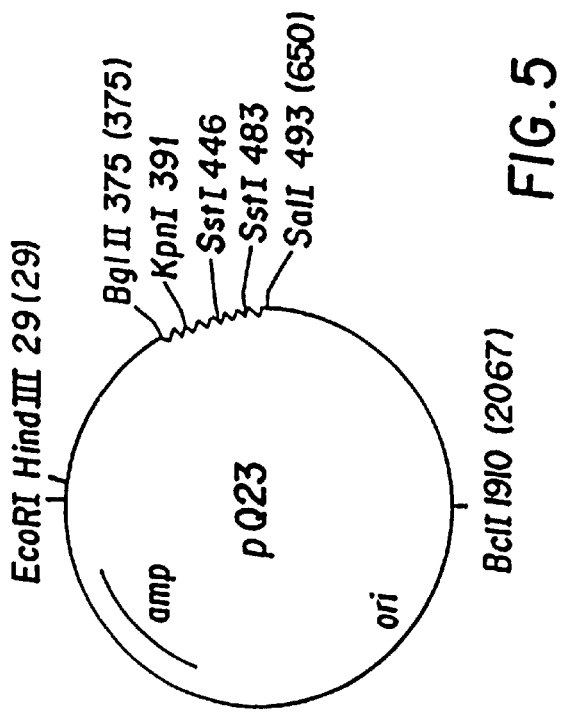
FIG. 3
FIG. 5

Ig HEAVY CHAIN J-C REGION

HUMAN IgG1 pGMH-6

```
                           ─── J REGION ───|── IgG1 CH1 REGION ───
                           GGTCACCGTCTCCTCAG CCTCCACCAAGGGCCCATC
                           ─────
                           BstEII
```

MOUSE HEAVY CHAIN J REGIONS AND PRIMERS

```
JH1  TACTGGTACTTCGATGTCTGGGGCGCAGGGACCACGGTCACCGTCTCCTCAG
[MJH1]                             GCCAGTGGCAGAGGAGTCGGT

JH2       TACTTTGACTACTGGGGCCAAGGCACCACTCTCACAGTCTCCTCAG
[MJ21]                             GAGAGTGTCAGACGAGTCGGT

JH3  CCTGGTTTGCTTACTGGGGCCAAGGGACTCTGGTCACTGTCTCTGCAG
[MJH3]                             ACCAGTGACAGAGACGTCGGT
[MJH3-BSTEII]        TCCCTGAGACCAGTGGCAGAG
[MJH3-BSTEII(13)]              ACCAGTGGCAGAG
                               ─────
                               BstEII

JH4  TACTATGCTATGGACTACTGGGGTCAAGGAACCTCAGTCACCGTCTCCTCAG
[MJH4]                             GTCAGTGGCAGAGGAGTCGGT
```

| | | MISMATCHES | | | |
|---|---|---|---|---|---|
| | N | JH1 | JH2 | JH3 | JH4 |
| | 21 | 0 | 4 | 4 | 1 |
| | 21 | 4 | 1 | 7 | 4 |
| | 21 | 4 | 7 | 0 | 5 |
| | 21 | 3 | 7 | 1 | 5 |
| | 13 | 1 | 4 | 1 | 2 |
| | 21 | 1 | 4 | 5 | 0 |

FIG.7A

Ig KAPPA CHAIN J-C REGION

```
                              — J REGION ———|——— IgK CONSTANT REGION ———
HUMAN KAPPA pK2-3             CTGGAGATGAAAC  GAACTGTGGCTGCACCATCTGTCTTCATCTTCCC
pING2016E                     TGATCAAAC      GAACTGTGGCTGCACCATCTGTCTTCATCTTCCC
                                 BclI
```

MOUSE HEAVY KAPPA J REGIONS AND PRIMERS

```
JK1         TGGACGTTCGGTGGAGGCACCAAGCTGGAAATCAAAC
[5JK1]           GCAAGCCACCTCCGTGG

JK2         TACACGTTCGGAGGGGGACCAAGCTGGAAATAAAAC
[JK2BGLII]           CCTGGTTCGACCTCTAGATT
                                       BglII
[5JK2]           GTGCAAGCCTCCCCCCTGG

JK4         TTCACGTTCGGCTCGGGGACAAAGTTGGAAATAAAAC
[5JK4]           GCAAGCCGAGCCCTGT
[JK4BGLII]          GCCCCTGTTTCAACCTCTAGATT
                                        BglII

JK5         CTCACGTTCGGTGCTGGGACCAAGTGGAGCTGAAAC
[5JK5]           GCAAGCCACGACCCTGG

[MJK]                       TGGTTCGACCTTTATTTTG
```

| | | MISMATCHES | | | |
|---|---|---|---|---|---|
| N | JK1 | JK2 | JK4 | JK5 | |
| 17 | 0 | 3 | 6 | 3 | |
| 21 | 3 | 3 | 5 | 3 | |
| 17 | 6 | 4 | 0 | 4 | |
| 23 | 7 | 6 | 3 | 6 | |
| 17 | 3 | 3 | 4 | 0 | |
| 19 | 1 | 0 | 2 | 3 | |

FIG.7B

MOUSE VARIABLE REGION CONSENSUS PRIMERS

MOUSE HEAVY CHAIN J SEGMENTS

```
JH1   TACTGGTACTTCGATGTCTGGGGCGCAGGGACCAC GGTCACC GTCTCCTCA
JH2           TACTTTGACTACTGGGGCCAAGGCACCAC TCTCACA GTCTCCTCA
JH3         CCTGGTTTGCTTACTGGGCCAAGGGACTCT GGTCACT GTCTCTGCA
JH4    TACTATGCTATGGACTACTGGGGTCAAGGAACCTC AGTCACC GTCTCCTCA
```

CONSENSUS PRIMER:  UIG-H       AGGGACCAC GGTCACC GTCTC
                                     BstEII
                               TCCCTGGTG CCAGTGG CAGAG
                               3'                    5'

MOUSE LIGHT CHAIN J SEGMENTS

```
JK1          TGGACGTTCGGTGGAGGCACC AAGCTG GAAATCAAA
JK2          TACACGTTCGGAGGGGGGACC AAGCTG GAAATAAAA
JK4          TTCACGTTCGGCTCGGGGACA AAGTTG GAAATAAAA
JK5          CTCACGTTCGGTGCTGGGACC AAGCTG GAGCTGAAA
```

CONSENSUS PRIMER:  UIG-K        GGGACC AAGCTT GAG
                                        HindIII
                                CCCTGG TTCGAA CTC
                                3'                5' pGML60                  GGAGGGACC AAGGTG GAGATGAAA
                        ---------C-T--------
                                HindIII

FIG.7C

MOUSE γ2a J/C JUNCTION PRIMER
MJ_H2-ApaI    TGTCAGAGGAGTCGGTCGTGTTTCCCGGGTA
              3'                          ApaI  5'

FIG.7D

```
pING2006E  GGA TCC CCC ACC     MET Gly Trp Ser Tyr Ile Leu Phe Leu Val Ala Thr Ala Arg Asp
pING2012E  GGA TCT GTC GAC     ATG GGA TGG AGC TAT ATC CTC TTT TTG GTA GCA ACA GCT AGA GAT
                                 2                    7                  12                17
                                                     30                  45                 60

Val His Ser Gln Val Gln Leu Gln Gln Pro Gly Ala Glu Leu Val Lys Pro Gly Ala Ser
           GTC CAC TCC CAG GTC CAA TTG CAG CAG CCT GGG GCT GAA CTG GTG AAA CCT GGG GCT TCA
                          22                   27                  32                  37
                          75                  90                  105                 120

Val Lys Cys Lys Ala Ser Gly Tyr Thr Phe Thr Ser Tyr Trp MET His Trp Val
           GTG AAG TGC AAG GCC TCT GGC TAC ACC TTC ACC AGC TAC ATG CAC TGG GTG
                          42                  47                  52                  57
                          135                 150                 165                 180

Lys Gln Arg Pro Gly Gln Gly Leu Asp Trp Ile Gly Glu Ile Asn Pro Ser Asn Gly Arg
           AAG CAG AGG CCT GGA CAA GGC CTT GAC TGG ATT GGA GAG ATT AAT CCT AGC AAC GGT CGT
                          62                  67                  72                  77
                          195                 210                 225                 240

Thr Asn Tyr Asn Glu Lys Phe Lys Ser Lys Ala Thr Leu Thr Val Asp Lys Ser Ser Ser
           ACT AAT TAC AAT GAG AAG TTC AAG AGC AAG GCC ACA CTG ACT GTA GAC AAA TCC TCC AGC
                          82                  87                  92                  97
                          255                 270                 285                 300

Thr Ala Tyr MET Gln Leu Ser Ser Leu Thr Ser Glu Asp Ser Ala Val Tyr Tyr Cys Ala
           ACA GCC TAC ATG CAA CTC AGC AGC CTG ACA TCT GAG GAC TCT GCG GTC TAT TAC TGT GCC
                          102                 107                           BstEII
                          315                 330                 345   112              117*

Ser Tyr Asp Tyr Trp Phe Ala Tyr Trp Gly Gln Gly Thr Leu Val Thr Val Ser Ser
           TCC TAT GAT TAC TGG TTT GCT TAC TGG GGC CAA GGG ACT CTG GTC ACC GTC TCC TCA
                          375                 390                 405                 420
```

FIG.12B

```
                                                                    MET Asp Trp Leu Trp Asn Leu
GG ATC CCC CCC CCC CCC CCC CAG TTT GTC TTA AGG CAC CAC TGA GCC CAA GTC TTA GAC ATC ATG GAT TGG CTG TGG AAC TTG
             15                     30                   45                     60                    75               90
                  LEADER PEPTIDE       FR1
Leu Phe Leu MET Ala Ala Ala Gln Ser Ala Gln Ile Gln Leu Val Gln Ser Gly Pro Glu Leu Lys Lys Pro Gly Glu Thr Val
CTA TTC CTG ATG GCA GCT GCC CAA AGT GCC CAA CAG ATC CAG CTG GTG CAG TCT GGA CCT GAG CTG AAG AAG CCT GGA GAG ACA GTC
          105                  120                   135                  150                   165                   180
                                  FR1        CDR1                   FR2
                              Asn Tyr Thr Phe Thr Gly MET Asn Trp Val Lys Gln Ala Pro Gly Lys Gly Leu Lys Trp MET
CTA TTC CTG TGC TCT GGG TAT ACC TTC ACA AAC TTC ATG AAC TGG GTG AAG CAG GCT CCA GGA AAG GGT TTA AAG TGG ATG
AAG ATC TCC TGC AAG GCT TCT GGG TAT ACC TTC ACA AAC TAT GCT ATG AAC TGG GTG AAG CAG GCT CCA GGA AAG GGT TTA AAG TGG ATG
          195                 210                   225                 240                  255                   270
   Bgl II    CDR2
      FR2                CDR2                                     FR3
Gly Trp Ile Asn Thr Tyr Thr Gly Gln Pro Thr Tyr Ala Asp Asp Phe Lys Gly Arg Phe Ala Phe Ser Leu Glu Thr Ser Ala Tyr Thr
GGC TGG ATA AAC ACC TAC ACT GGA CAG CCA ACA TAT GCT GAT GAC TTC AAG GGA CGG TTT GCC TTC TCT TTG GAA ACC TCT GCC TAC ACT
          285                300                   315                  330                  345                   360
                                                             CDR3
Ala Tyr Leu Gln Ile Asn Asn Leu Lys Asn Glu Asp MET Ala Asp Tyr Phe Cys Ala Arg Phe Ser Tyr Gly Asn Ser Arg Tyr Ser Asp
GCC TAT TTG CAG ATC AAC AAC CTC AAA AAT GAG GAC ATG GCT GAC TAT TTC TGT GCA AGA TTT ACC TAT GGT AAC TCA CCT TAC TCT GAC
          375                 390                   405                 420                   435                 450
                  J_H2   C_γ2a          DSP 2
CDR3    FR4
Tyr Trp Gly Gln Gly Thr Thr Leu Thr Val Ser Ala Lys Thr Thr Ala Pro Ser Val Tyr Pro Leu Ala Pro Val Cys Gly Asp Thr
TAC TGG GGC CAA GGC ACC ACT CTC ACA GTC TCC TCA GCC AAA ACA ACA GCC CCA TCG GTC TAT CCA CTG GCC CCT GTG TGT GGA GAT ACA
          465                  480                 495                    510                525                    540
Thr Gly Ser Ser Val Thr Leu Gly Cys Leu Val Lys Gly Tyr Phe Pro Glu Pro Val Thr Leu Thr Trp Asn Ser Gly
ACT GGC TCC TCG GTG ACT CTA GGA TGC CTG GTC AAG GGT TAT TTC CCT GAG CCA GTG ACC TTG ACC TGG AAC TCT GGA
          555                 570                   585                 600                   625
```

V_H   J_H2   C_γ2a
BamHI   BglII   BamHI
13-6a
An
200bp

FIG.15

```
                                                                                        MET Asp Trp Leu Trp Asn Leu
L6VH                                                                                        ATG GAT TGG CTG TGG AAC TTG
pH3-6a  GG ATC CCC CCC CCC CCC CAG TTT GTC TTA AGG CAC CAC TGA GCC CAA GTC TTA GAC ATC ATG GAT TGG CTG TGG AAC TTG
        BamHI                        ↑5              17                    32             47                        62

SalI
Cl-Δ4       GTC GAC TCT AGG CAC CAC TGA GCC CAA GTC TTA GAC ATC ATG GAT TGG CTG TGG AAC TTG

SalI
Cl-Δ21      GT CGA CTC TAG TTT GTC TTA AGG CAC CAC TGA GCC CAA GTC TTA GAC ATC ATG GAT TGG CTG TGG AAC TTG
```

FIG. 17a

```
          5'L6Vₖ
                         met asp phe
       —CCCCAAGACAAATGGATTTTC—
            | | |
            GTC
           ─────
            Sal I
```

FIG. 19A

2H7 heavy chain variable sequence

```
                                                              leader
                                          met gly phe ser arg ile phe
C33GTACCTCTCTACAGTCCCTGAAGACACTGACTCTAACCATG GGA TTC AGC AGG ATC TTT
       peptide                             ↑NcoI        FRI
leu phe leu leu ser val thr thr gly val his ser|gln ala tyr leu gln
CTC TTC CTC CTG TCA GTA ACT ACA GGT GTC CAC TCC CAG GCT TAT CTA CAG gln ser gly ala glu leu val arg pro gly ala ser val lys met ser cys
CAG TCT GGG GCT GAG CTG GTG AGG CCT GGG GCC TCA GTG AAG ATG TCC TGC
                            FRI | CDRI              CDRI | FR2
lys ala ser gly tyr thr phe thr|ser tyr asn met his|trp val lys gln
AAG GCT TCT GGC TAC ACA TTT ACC AGT TAC AAT ATG CAC TGG GTA AAG CAG
                                       FR2|CDR2
thr pro Qrg gln gly leu glu trp ile gly|ala ile tyr pro gly asn gly
ACA CCT AGA CAG GGC CTG GAA TGG ATT GGA GCT ATT TAT CCA GGA AAT GGT
                                  CDR2 | FR3
asp thr ser tyr asn gln lys phe lys gly|lys ala thr leu thr val asp
GAT ACT TCC TAC AAT CAG AAG TTC AAG GGC AAG GCC ACA CTG ACT GTA GAC lys ser ser ser thr ala tyr met gln leu ser ser leu thr ser glu asp
AAA TCC TCC AGC ACA GCC TAC ATG CAG CTC AGC AGC CTG ACA TCT GAA GAC
                       FR3 | CDR3
ser ala val tyr phe cys ala arg|val val tyr tyr ser asn ser tyr trp
TCT GCG GTC TAT TTC TGT GCA AGA GTG GTG TAC TAT AGT AAC TCT TAC TGG
         CDR3 | FR4         JH|                        FR4  DSP2
tyr phe asp val|trp gly thr gly thr thr val thr val ser
TAC TTC GAT GTC TGG GGC ACA GGG ACC ACG GTC ACC GTC TCG30
                 ↑
                BstEII              JHBstEII primer
```

FIG. 21

2H7 light chain variable sequence

```
                                                              leader peptide
                                    met asp phe gln val gln ile phe ser phe leu leu
      C23 CCCAAAATTCAAAGACAAAATG  GAT TTT CAA GTG CAG ATT TTC AGC TTC CTG CTA
                       GTC
                          SalI primer      FRI
      ile ser ala ser val ile ile ala arg gly | gln ile val leu ser gln ser
      ATC AGT GCT TCA GTC ATA ATT GCC AGA GGA  CAA ATT GTT CTC TCC CAG TCT
                                                                      FRI |
      pro ala ile leu ser ala ser pro gly glu lys val thr met thr cys arg |
      CCA GCA ATC CTG TCT GCA TCT CCA GGG GAG AAG GTC ACA ATG ACT TGC AGG
      CDR I                              CDRI | FR2
      ala ser ser ser val ser tyr met his | trp tyr gln gln lys pro gly ser
      GCC AGC TCA AGT GTA AGT TAC ATG CAC  TGG TAC CAG CAG AAG CCA GGA TCC
                          FR2 | CDR2             KpnI*        CDR2 | FR3   † BamHI
      ser pro lys pro trp ile tyr | ala pro ser asn leu ala ser | gly val pro
      TCC CCC AAA CCC TGG ATT TAT  GCC CCA TCC AAC CTG GCT TCT   GGA GTC CCT ala arg phe ser gly ser gly ser gly thr ser tyr ser leu thr ile ser
      GCT CGC TTC AGT GGC AGT GGG TCT GGG ACC TCT TAC TCT CTC ACA ATC AGC
                                              •  •  •  •  • FR3 | CDR3 •  •  •  •  •
      arg val glu ala glu asp ala ala thr tyr tyr cys | gln gln trp ser phe
      AGA GTG GAG GCT GAA GAT GCT GCC ACT TAT TAC TGC  CAG CAG TGG AGT TTT
       •  •  •  CDR3 | FR4 •  •  •            Jκ5              FR4
      asn pro pro thr | phe gly ala gly thr lys leu glu leu lys
      AAC CCA CCC ACG TTC GGT GCT GGG ACC AAG CTG GAG CTG AAA
                                                         T
                                                              Jκ HIND III primer
```

FIG. 22

2H7 Chimerae $V_H$  pH2-7 ($J_H1$) $J_H$BstEII clone, NcoI cut 5' ATG → pING 2101 neo SalI    met
5'   ↓
    GTC GAC ATG GGA joint
    mo↓hu             Cγ1
  ACG GTC ACC GTC TC(T) TCA | GCC TCC $V_K$  pL2-12 ($J_H5$) oligo(dT) clone, $J_K$HindIII mutagenesis, 5' SAL mutagenesis → pING2106neo
                                                                      pING2107gpt SalI    met
5'   ↓
    GTC GAC AAA ATG GAT joint
    neo↓hu             $C_K$
  ACC AAG CT(T) GAG (A)TG AAA | CGA ACT

FIG. 24

```
                                            DraI
                                    TTT AAA AGG AAA TTT TTT CTT ATA AAA

CCC AAA TTA TCC AAT CAT CAG TAT TAC AAA ATG TTT CAA CCG TAA TAC ATT TAA CAT TTC

ACC CTT GAA CTG ATC TTA TTT TTT GAC CAC ACT CCC CTT GGT TTT TCA CCA AAA CTG AGT

NdeI
TTC ATT TTT GTT GAA AAA TTT GTA CCT GCG ACA TCG GGC ATA TGG AAC GAT AAA TGC CCA

1
                                        MET Lys Tyr Leu Leu Pro Thr Ala Ala Ala
TGA AAA TTC TAT TTC AAG GAG ACA GTC ATA ATG AAA TAC CTA TTG CCT ACG GCA GCC GCT

HaeIII                              90
Gly Leu Leu Leu Leu Ala Ala Gln Pro Ala MET Ala Ala Asn Thr Gly Gly Tyr Ala Thr
GGA TTG TTA TTA CTC GCT GCC CAA CCA GCG ATG GCC GCA AAT ACG GGT GGC TAT GCC ACC
```

FIG. 36A

MODULAR ASSEMBLY OF ANTIBODY GENES, ANTIBODIES PREPARED THEREBY AND USE

This application is a continuation of U.S. application Ser. No. 08/450,731, filed May 25, 1995, now U.S. Pat. No. 5,693,493, which is a divisional of U.S. application Ser. No. 08/299,085, filed Aug. 18, 1994, now U.S. Pat. No. 5,595,898, which is a file-wrapper continuation of U.S. application Ser. No. 07/987,555, filed Dec. 8, 1992, abandoned, which is a file-wrapper continuation of U.S. application Ser. No. 07/501,092, filed Mar. 29, 1990, abandoned, which is a continuation-in-part of U.S. application Ser. No. 07/077,528, filed Jul. 24, 1987, abandoned, which is a continuation-in-part of PCT/US86/02269, filed Oct. 27, 1986, abandoned, which is a continuation-in-part of U.S. application Ser. No. 06/793,980, filed Nov. 1, 1985, abandoned, said U.S. application Ser. No. 07/501,092 also being a continuation-in-part of U.S. application Ser. No. 07/142,039, filed Jan. 11, 1988, abandoned; the contents of U.S. application Ser. Nos. 07/142,039, 07/077,528, 06/793,980 and of PCT/US86/02269 are incorporated herein by reference.

FIELD OF THE INVENTION

This invention relates to recombinant DNA methods of preparing immunoglobulins, genetic sequences coding therefor, as well as methods of obtaining such sequences.

BACKGROUND ART

The application of cell-to-cell fusion for the production of monoclonal antibodies by Kohler and Milstein (*Nature (London)*, 256: 495, 1975) has spawned a revolution in biology equal in impact to the invention of recombinant DNA cloning. Hybridoma-produced monoclonal antibodies are already widely used in clinical diagnoses and basic scientific studies. Applications of human B cell hybridoma-produced monoclonal antibodies hold great promise for the clinical treatment of cancer, viral and microbial infections, B cell immunodeficiencies with diminished antibody production, and other diseases and disorders of the immune system.

Unfortunately, yields of monoclonal antibodies from human hydridoma cell lines are relatively low 1 ug/ml in human x human compared to 100 ug/ml in mouse hydridomas), and production costs are high for antibodies made in large scale human tissue culture. Mouse x mouse hybridomas, on the other hand, are useful because they produce abundant amounts of protein, and these cell lines are more stable than the human lines. However, repeated injections of "foreign" antibodies, such as a mouse antibody, in humans, can lead to harmful hypersensitivity reactions.

There has therefore been recent exploration of the possibility of producing antibodies having the advantages of monoclonals from mouse-mouse hybridomas, yet the species specific properties of human monoclonal antibodies.

Another problem faced by immunologists is that most human monoclonal antibodies (i.e., antibodies having human recognition properties) obtained in cell culture are of the IgM type. When it is desirable to obtain human monoclonals of the IgG type, however, it has been necessary to use such techniques as cell sorting, to separate the few cells which have switched to producing antibodies of the IgG or other type from the majority producing antibodies of the IgM type. A need therefore exists for a more ready method of switching antibody classes, for any given antibody of a predetermined or desired antigenic specificity.

The present invention bridges both the hybridoma and monoclonal antibody technologies and provides a quick and efficient method, as well as products derived therefrom, for the improved production of chimeric human/non-human antibodies, or of "class switched" antibodies.

INFORMATION DISCLOSURE STATEMENT*

Approaches to the problem of producing chimeric antibodies have ben published by various authors.

Morrison, S. L. et al., *Proc. Natl. Acad. Sci., USA*, 81: 6851–6855 (November 1984), describe the production of a mouse-human antibody molecule of defined antigen binding specificity, produced by joining the variable region genes of a mouse antibody-producing myeloma cell line with known antigen binding specificity to human immunoglobulin constant region genes using recombinant DNA techniques. Chimeric genes were constructed, wherein the heavy chain variable region exon from the myeloma cell line S107 well joined to human IgG1 or IgG2 heavy chain constant region exons, and the light chain variable region exon from the same myeloma to the human kappa light chain exon. These genes wee transfected into mouse myeloma cell lines and transformed cells producing chimeric mouse-human antiphosphocholine antibodies were thus developed.

Morrison, S. L. et al., European Patent Publication No. 173494 (published Mar. 5, 1986), disclose chimeric "receptors" (e.g. antibodies) having variable regions derived from one species and constant regions derived from another. Mention is made of utilizing cDNA cloning to construct the genes, although no details of cDNA cloning or priming are shown. (see pp 5, 7 and 8).

Boulianne, G. L. et al., *Nature*, 312: 643 (Dec. 13, 1984), also produced antibodies consisting of mouse variable regions joined to human constant regions. They constructed immuoglobulin genes in which the DNA segments encoding mouse variable regions specific for the hapten trinitrophenyl (TNP) were joined to segments encoding human mu and kappa constant regions. These chimeric genes were expressed as functional TNP binding chimeric IgM.

For a commentary on the work of Boulianne et al. and Morrison et al., see Munro, *Nature*, 312: 597 (Dec. 13, 1984), Dickson, *Genetic Engineering News*, 5, No. 3 (March 1985), or Marx, *Science*, 229: 455 (August 1985).

Neuberger, M. S. et al., *Nature*, 314: 268 (Mar. 25, 1986), also constructed a chimeric heavy chain immunoglobulin gene in which a DNA segment encoding a mouse variable region specific for the hapten 4-hydroxy-3-nitrophenacetyl (NP) was joined to a segment encoding the human epsilon region. When this chimeric gene was transfected into the J558L cell line, an antibody was produced which bound to the NP hapten and had human IgE properties.

Neuberger, M. S. et al., have also published work showing the preparation of cell lines that secrete hapten-specific antibodies in which the Fc portion has been replaced either with an active enzyme moiety (Williams, G. and Neuberger, M. S. *Gene* 43:319, 1986) or with a polypeptide displaying c-myc antigenic determinants (*Nature*, 312:604, 1984).

Neuberger, M. et al., PCT Publication WO 86/01533, (published Mar. 13, 1986) also disclose production of chimeric antibodies (see p. 5) and suggests, among the technique's many uses the concept of "class switching" (see p. 6).

Taniguchi, M., in European Patent Publication No. 171 496 (published Feb. 19, 1985) discloses the production of chimeric antibodies having variable regions with tumor specificty derived from experimental animals, and constant regions derived from human. The corresponding heavy and light chain genes are produced in the genomic form, and expressed in mammalian cells.

Takeda, S. et al., *Nature*, 314: 452 (Apr. 4, 1985) have described a potential method for the construction of chimeric immunoglobulin genes which have intron sequences removed b the use of a retrovirus vector. However, an unexpected splice donor site caused the deletion of the V region leader sequence. Thus, this approach did not yield complete chimeric antibody molecules.

Cabilly, S. et al., *Proc. Natl. Acad. Sci., USA*, 81: 3273–3277 (June 1984), describe plasmids that direct the synthesis in *E. coli* of heavy chains and/or light chains of anti-carcinoembryonic antigen (CEA) antibody. Another plasmid was constructed for expression of a truncated form of heavy chain (Fd') fragment in *E. coli*. Functional CEA-binding activity was obtained by in vitro reconstitution, in *E. coli* extracts, of a portion of the heavy chain with light chain.

Cabilly, S., et al., European Patent Publication 125023 (published Nov. 14, 1984) describes chimeric immunoglobulin genes and their presumptive products as well as other modified forms. On pages 21, 28 and 33 it discusses cDNA cloning and priming.

Boss, M. A., European Patent Application 120694 (published Oct. 3, 1984) shows expression in *E. coli* of non-chimeric immunoglobulin chains with 4-nitrophenyl specificity. There is a broad description of chimeric antibodies but no details (see p. 9).

Wood, C. R. et al., *Nature*, 314: 446 (April, 1985) describe plasmids that direct the synthesis of mouse anti-NP antibody proteins in yeast. Heavy chain mu antibody proteins appeared to be glycosylated in the yeast cells. When both heavy and light chains were synthesized in the same cell, some of the protein was assembled into functional antibody molecules, as detected by anti-NP binding activity in soluble protein prepared from yeast cells.

Alexander, A. et al., *Proc. Nat. Acad. Sci. USA*, 79: 3260–3264 (1982), describe the preparation of a cDNA sequence coding for an abnormally short human Ig gamma heavy chain (OMM gamma$^3$ HCD serum protein) containing a 19-amino acid leader followed by the first 15 residues of the V region. An extensive internal deletion removes the remainder of the V and the entire $C_H1$ domain. This is cDNA coding for an internally deleted molecule.

Dolby, T. W. et al., *Proc. Natl. Acad. Sci., USA*, 77: 6027–6031 (1980), describe the preparation of a cDNA sequence and recombinant plasmids containing the same coding for mu and kappa human immunoglobulin polypeptides. One of the recombinant DNA molecules contained codons for part of the $C_H3$ constant region domain and the entire 3' noncoding sequence.

Seno, M. et al., *Nucleic Acids research*, 11: 719–726 (1983), describe the preparation of a cDNA sequence and recombinant plasmids containing the same coding for part of the variable region and all of the constant region of the human IgE heavy chain (epsilon chain).

Kurokawa, T. et al., ibid, 11: 3077–3085 (1983), show the construction, using cDNA, of three expression plasmids coding for the constant portion of the human IgE heavy chain.

Liu, F. T. et al., *Proc. Nat. Acad. Sci., USA*, 81: 5369–5373 (September 1984), describe the preparation of a cDNA sequence and recombinant plasmids containing the same encoding about two-thirds of the $C_H2$, and all of the $C_H3$ and $C_H4$ domains of human IgE heavy chain.

Tsujimoto, Y. et al., *Nucleic Acids Res.*, 12: 8407–8414 (November 1984), describe the preparation of a human V lambda cDNA sequence from an Ig lambda-producing human Burkitt lymphoma cell line, by taking advantage of a cloned constant region gene as a primer for cDNA synthesis.

Murphy, J., PCT Publication WO 83/03971 (published Nov. 24, 1983) discloses hybrid proteins made of fragments comprising a toxin and a cell-specific ligand (which is suggested as possibly being an antibody).

Tan, et al., *J. Immunol.* 135:8464 (November, 1985), obtained expression of a chimeric human-mouse immunoglobulin genomic gene after transfection into mouse myeloma cells.

Jones, P. T., et al., *Nature* 321:552 (May 1986) constructed and expressed a genomic construct where CDR domains of variable regions from a mouse monoclonal antibody were used to substitute for the corresponding domains in a human antibody.

Sun, L. K., et al., *Hybridoma* 5 suppl. 1 S17 (1986), describes a chimeric human/mouse antibody with potential tumor specificty. The chimeric heavy and light chain genes are genomic constructs and expressed in mammalian cells.

Sahagan et al., *J. Immun.* 137:1066–1074 (August 1986) describe a chimeric antibody with specificity to a human tumor associated antigen, the genes for which are assembled from genomic sequences.

For a recent review of the field see also Morrison, S. L., *Science* 229: 1202–1207 (Sep. 20, 1985) and Oi, V. T., et al., *BioTechniques* 4:214 (1986).

The Oi, et al., paper is relevant as it argues that the production of chimeric antibodies from cDNA constructs in yeast and/or bacteria is not necessarily advantageous.

See also Commentary on page 835 in *Biotechnology* 4 (1986).

*Note: The present Information Disclosure Statement is subject to the provisions of 37 C.F.R. 1.97(b). In addition, Applicants reserve the right to demonstrate that their invention was made prior to any one or more of the mentioned publications.

SUMMARY OF THE INVENTION

The invention provides a novel approach for producing genetically engineered antibodies of desired variable region specificity and constant region properties through gene cloning and expression of light and heavy chains. The cloned immunoglobulin gene products can be produced by expression in genetically engineered organisms.

The application of chemical gene synthesis, recombinant DNA cloning, and production of specific immunoglobulin chains in various organisms provides an effective solution for the efficient large scale production of human monoclonal antibodies. The invention also provides a solution to the problem of class switching antibody molecules, so as to readily prepare immunoglobulins of a certain binding specificity of any given class.

The invention provides cDNA sequences coding for immunoglobulin chains comprising a constant human region and a variable, either human or non-human, region. The immunoglobulin chains can either be heavy or light.

The invention also provides gene sequences coding for immunoglobulin chains comprising a cDNA variable region of either human or non-human origin and a genomic constant region of human origin.

The invention also provides genes sequences coding for immunoglobulin chains with secretion signal sequences of prokaryotic or eukaryotic origin.

The invention also provides sequences as above, present in recombinant DNA molecules, especially in vehicles such as plasmid vectors, capable of expression in desired prokaryotic or eukaryotic hosts.

The invention also provides a gene sequence having a single bacterial promoter coding a dicistronic message for the expression of multiple heavy and light chains.

The invention also provides consensus sequences and specific oligonucleotide sequences useful as probes for hybridization and priming cDNA synthesis of any hybridoma mRNA coding for variable regions of any desired specificity.

The invention provides hosts capable of producing, by culture, chimeric antibodies and methods of using these hosts.

The invention also provides chimeric immunoglobulin individual chains, whole assembled molecules, and immunoglobulin fragments (such as Fab) having human constant regions and non-human variable regions, wherein both variable regions have the same binding specificity.

Among other immunoglobulin chains and/or molecules provided by the invention are:
(a) a complete functional, immunoglobulin molecule comprising:
  (i) two identical chimeric heavy chains comprising a non-human variable region and human constant region and
  (ii) two identical all (i.e. non-chimeric) human light chains.
(b) a complete, functional, immunoglobulin molecule comprising:
  (i) two identical chimeric heavy chains comprising a non-human variable region and a human constant region, and
  (ii) two identical all (i.e. non-chimeric) non-human light chains.
(c) a monovalent antibody, i.e., a complete, functional immunoglobulin molecule comprising:
  (i) two identical chimeric heavy chains comprising a non-human variable region and a human constant region, and
  (ii) two different light chains, only one of which has the same specificity as the variable region of the heavy chains. The resulting antibody molecule binds only to one end thereof and tis therefore incapable of divalent binding;
(d) an antibody with two different specificities, i.e., a complete, functional immunoglobulin molecule comprising:
  (i) two different chimeric heavy chains, the first one of which comprises a non-human variable region and a human constant region and the second comprises a different non-human variable region, and a human constant region, and
  (ii) two different chimeric light chains, the first one of which comprises a non-human variable region having the same specificity as the first heavy chain variable region, and a human constant region, and the second comprises a non-human variable region having the same specificity as the second heavy chain variable region, and a human constant region.

The resulting antibody molecule binds to two different antigens.

The invention also provides for the production of functionally active chimeric immunoglobulin fragments secreted by prokaryotic or eukaryotic hots or fully folded and reassembled chimeric immunoglobulin chains.

Genetic sequencesm especially cDNA sequences, coding for the aforementioned combinations of chimeric chains or of non-chimeric chains are also provided herein.

The invention also provides for a genetic sequence, especially a cDNA sequence, coding for the variable region of an antibody molecule heavy and/or light chain, operably linked to a sequence coding for a polypeptide different than an immunoglobulin chain (e.g., an enzyme). These sequences can be assembled by the methods of the invention, and expressed to yield mixed-function molecules.

The use of cDNA sequences is particularly advantageous over genomic sequences (which contain introns), in that cDNA sequences can be expressed in bacteria or other hosts which lack RNA splicing systems.

Among preferred specific antibodies are those having specificities to cancer-related antigens.

BRIEF DESCRIPTION OF THE FIGURES

FIG. 2 shows the known nucleotide sequences of human and mouse J regions. Consensus sequences for the J regions are shown below the actual sequences. The oligonucleotide sequence below the mouse kappa J region consensus sequence is a Universal Immunoglobulin Gene (UIG) oligonucleotide which is used in the present invention.

FIG. 3 shows a scheme noting the use of the UIG oligonucleotide primer for the synthesis of cDNA complementary to the variable region of immunoglobulin messenger RNA, or the use of oligo-dT as a primer for cDNA synthesis, followed by in vitro mutagenesis.

FIGS. 4(A and B) shows the synthesis and analysis of human IgG1 genes, including three isolated clones (A.b), one of which (pGMH-6) is utilized as a cloning vector (B).

FIG. 5 shows the cloning vector pQ23, a modified pBR322, useful for cDNA cloning at the KpnI site. This vector also contains the useful restriction enzyme sites BqlII plus SalI. Not to scale.

FIGS. 7(A–D) show primers designed for immunoglobulin V region synthesis. 7(A) shows the heavy chain J-C regions and primers. A DNA version of each mouse J heavy region is shown directly above primers designed from that sequence. Mouse J regions are 5' t 3', left to right, while primers are 3' to 5', left to right. Primer names are included in brackets, and numbers of nucleotides (N) and number of mismatches with each $J_H$ region are listed to the right. Primers which introduce a BstEII site are underlined. 7(B) shows the light chain J regions and primers. The same as for 7(A) except for light chains. Primers designed to introduce a BqlII site are underlined, as is the BclI site present in pING2016E. 7(C) shows mouse variable region consensus UIG primers. The actual primer sequence is shown below the consensus sequence. The human $C_K$ HindIII vector pGML60 is shown below. 7(D) shows a mouse gamma 2a J/C junction primer.

FIG. 9 shows the construction of hybrid mouse-human immunoglobulin genes.

FIG. 15 shows the nucleotide sequence of the V region of the L6 $V_H$ cDNA clone pH3–6a. The sequence was determined by the dideoxytermination method using M13 subclones of gene fragments (shown below). Open circles denote amino acid residues confirmed by peptide sequence. A sequence homologous to $D_{SP.2}$ in the CDR3 region is underlined.

FIGS. 17(A–C) show the construction of chimeric L6-$V_H$ plus human C gamma 1 expression plasmids. FIG. 17A shows the sequences of the BAL-31 deletion clones M13mp19C1-delta 4 (C1-delta 4) and M13mp19-C1-delta 21(c1- delta 21). The 5' end of the cDNA clone, pH3-6a, is denoted with an arrow. M13 sequences are underlined. The oligonucleotide primer used for this experiment is H3-6a (5'-GACTGCACCAACTGG-3'), which primes in FR1 near the mature N terminus.

(a) Deletion of the oligo d[GC] segment 5' of $V_K$ of L6. The oligonucleotide is a 22-mer and contains a SalI site. The 3 mismatches are shown. The $V_K$ gene, after mutagenesis, is joined as a SalI—HindIII fragment to the human $C_K$ module. The expression plasmid thus formed is pING2119.

(b) pING2114, a heavy plus light chain expression plasmid. The expression plasmid pING2114 contains the L6 heavy chain chimeric gene from pING2111 and the chimeric light chain from pING2119 (bold line).

Figure 20:
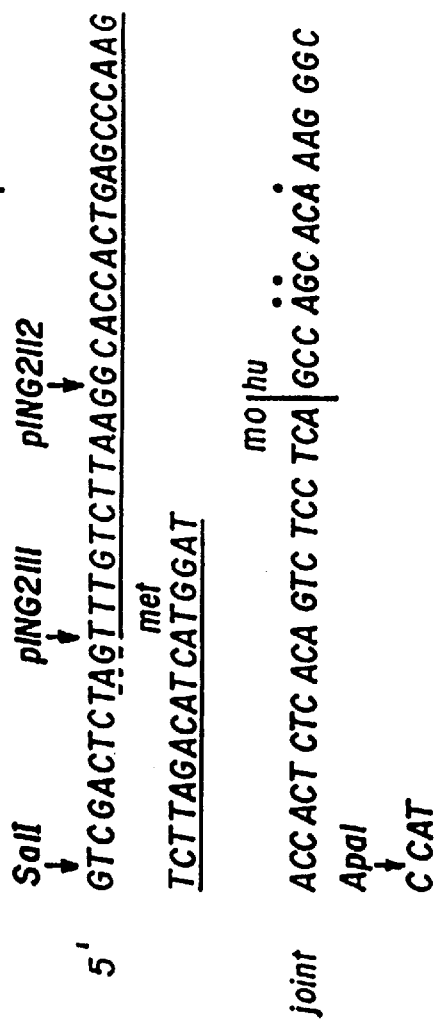

FIG. 20 shows a summary of the sequence alterations made in the construction of the L6 chimeric antibody expression plasmids. Residues underlined in the 5' untranslated region are derived from the cloned mouse kappa and heavy-chain genes. Residues circled in the V/C boundary result from mutagenesis operations to engineer restriction enzyme sites in this region. Residues denoted by small circles above them in the L6 heavy-chain chimera also result from mutagenesis. They are silent changes.

FIG. 21 shows the 2H7 $V_H$ sequence. The $V_H$ gene contains $J_H 1$ sequences and DSP.2 sequence elements. Small circles above the amino acid residues are those that matched to peptide sequences.

FIG. 22 shows the 2H7 $V_L$ sequence. The $V_K$ gene contains $J_K 5$ sequences. A 22-mer oligonucleotide was used to place a SalI site 5' of the ATG initiator codon. Small circles above the amino acid residues are those that matched to peptide sequences.

Figure 23:
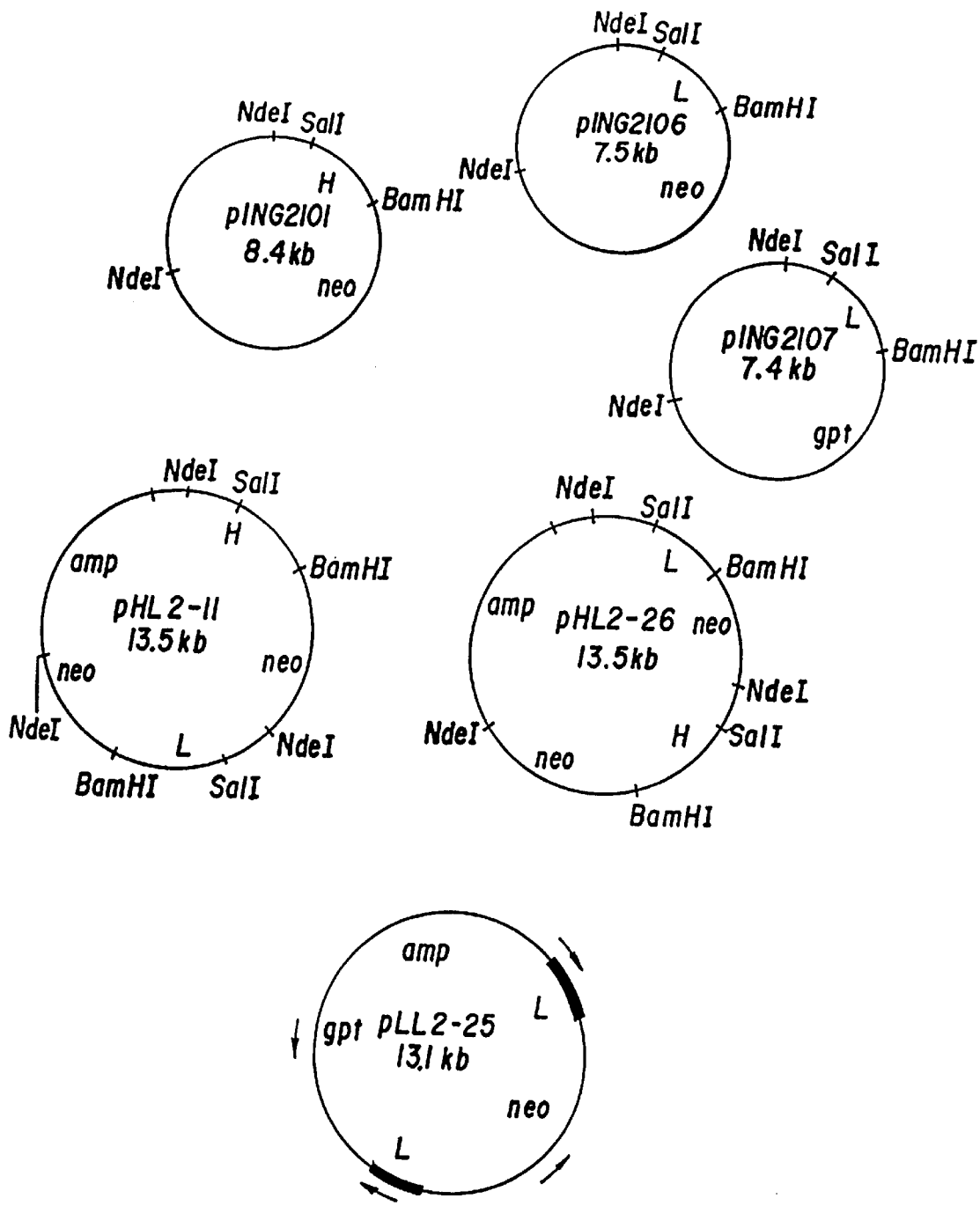

FIG. 23 shows the chimeric immunoglobulin gene expression plasmids of the 2H7 specificity. One gene plasmids are pING2101 ($V_H$, neo), pING2106 ($V_K$, neo) and pING2107 ($V_K$, gpt). The others are two-gene plasmids. Their construction involved the ligation of the larger NdeI fragments of pING2101 and pING2107 to linearized pING2106 partially digested with NdeI. pHL2-11 and pHL2-26 were obtained from pING2101 and pING2106; pLL2-25 was obtained from pING2107 and pING2106.

FIG. 24 shows a summary of the nucleotide changes introduced in the $V_H$ and $V_K$ in the construction of the chimeric plasmids. The cognate $V_H$ and $V_K$ nucleotide residues in the 5' end are underlined. Circles residues in the J—C junctions are derived from the human C modules.

Figure 25A:
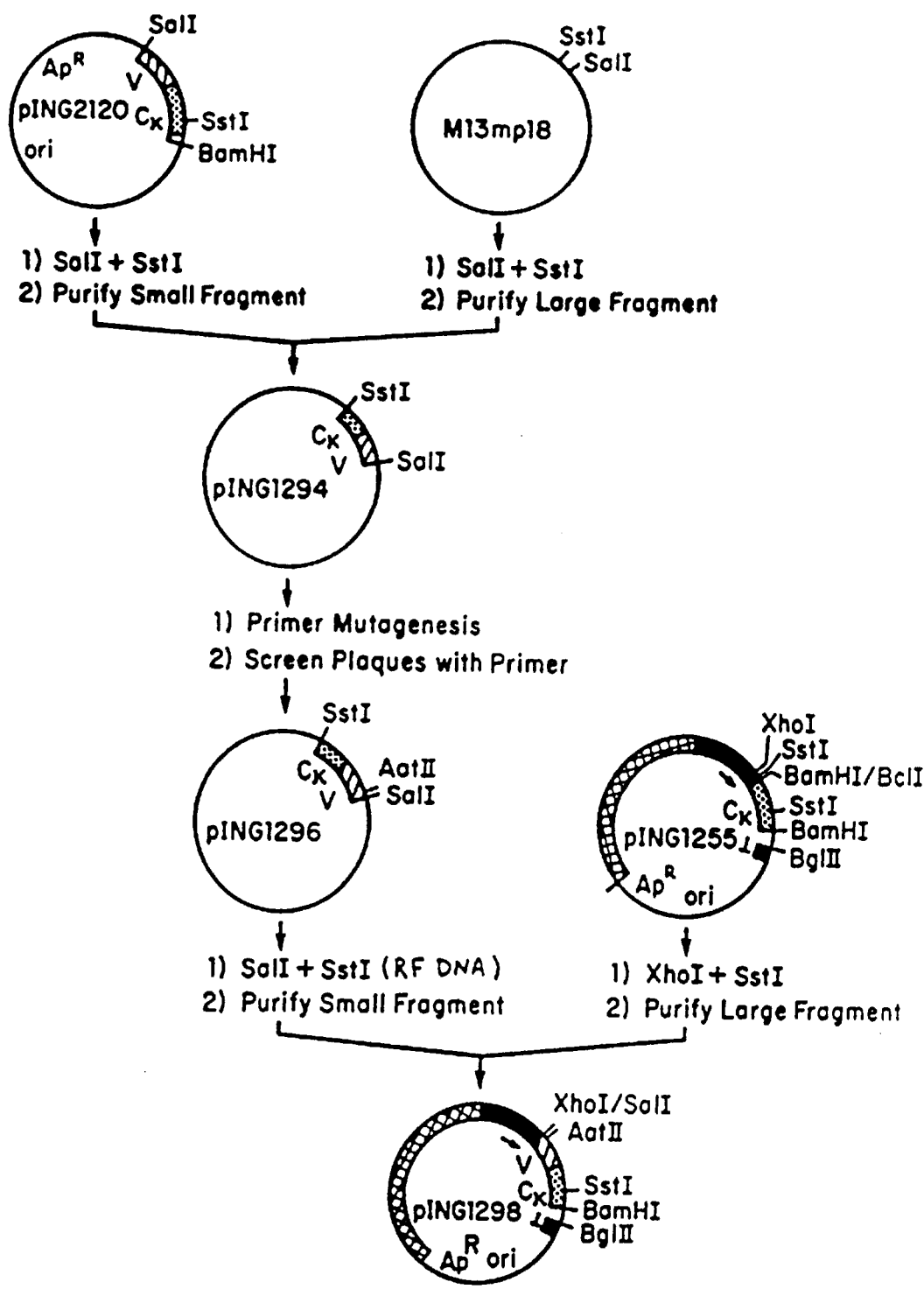

FIGS. 25(A–C) show the strategy used to fuse the mature L6 chimeric light chain sequence to the yeast invertase signal sequence and shortened PGK promoter. The open double line represents yeast invertase signal sequence DNA. The solid double line represents yeast PGK DNA; –> represents the PGK promoter; –| represents the PGK terminator; RF=Replicative Form. pING1225 was derived by fusing human $C_K$ DNA to the PGK promoter. pING1149 was derived by fusing the yeast invertase signal sequence to the yeast PGK promoter. (A) shows the strategy for introduction by in vitro mutagenesis of an AatII site in the signal sequence processing site. (B) shows the DNA sequence of the single-stranded mutagenesis primer and the corresponding unmutagenized DNA sequence. (C) shows the strategy used to construct a plasmid containing the mature light chain sequence fused to the invertase signal sequence and shortened PGK promoter.

Figure 25B:
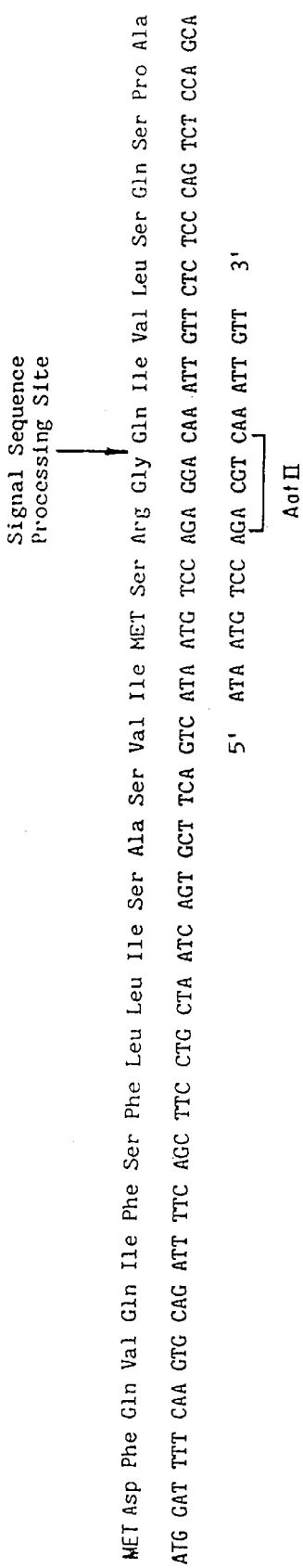
Figure 25C:
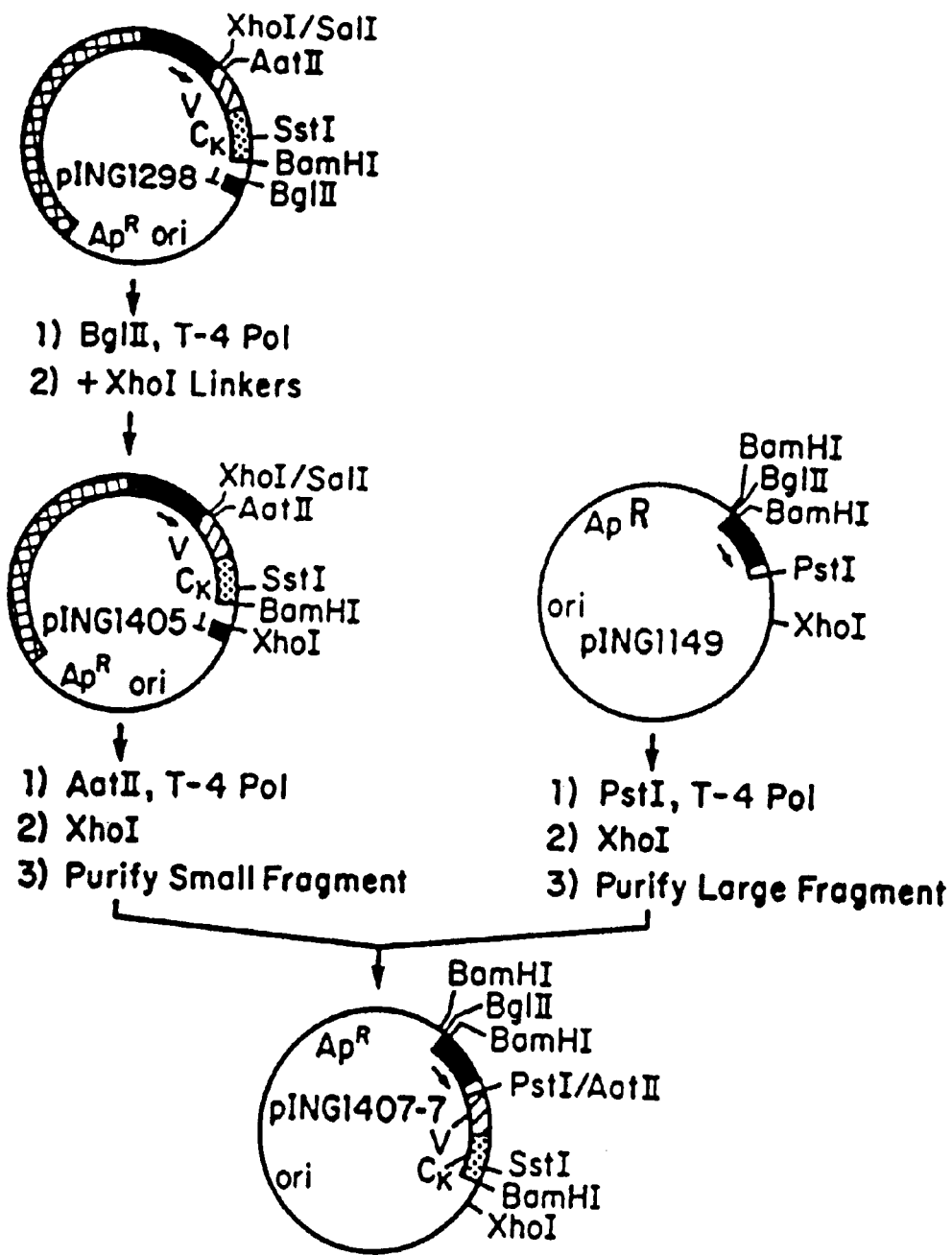
Figure 26A:
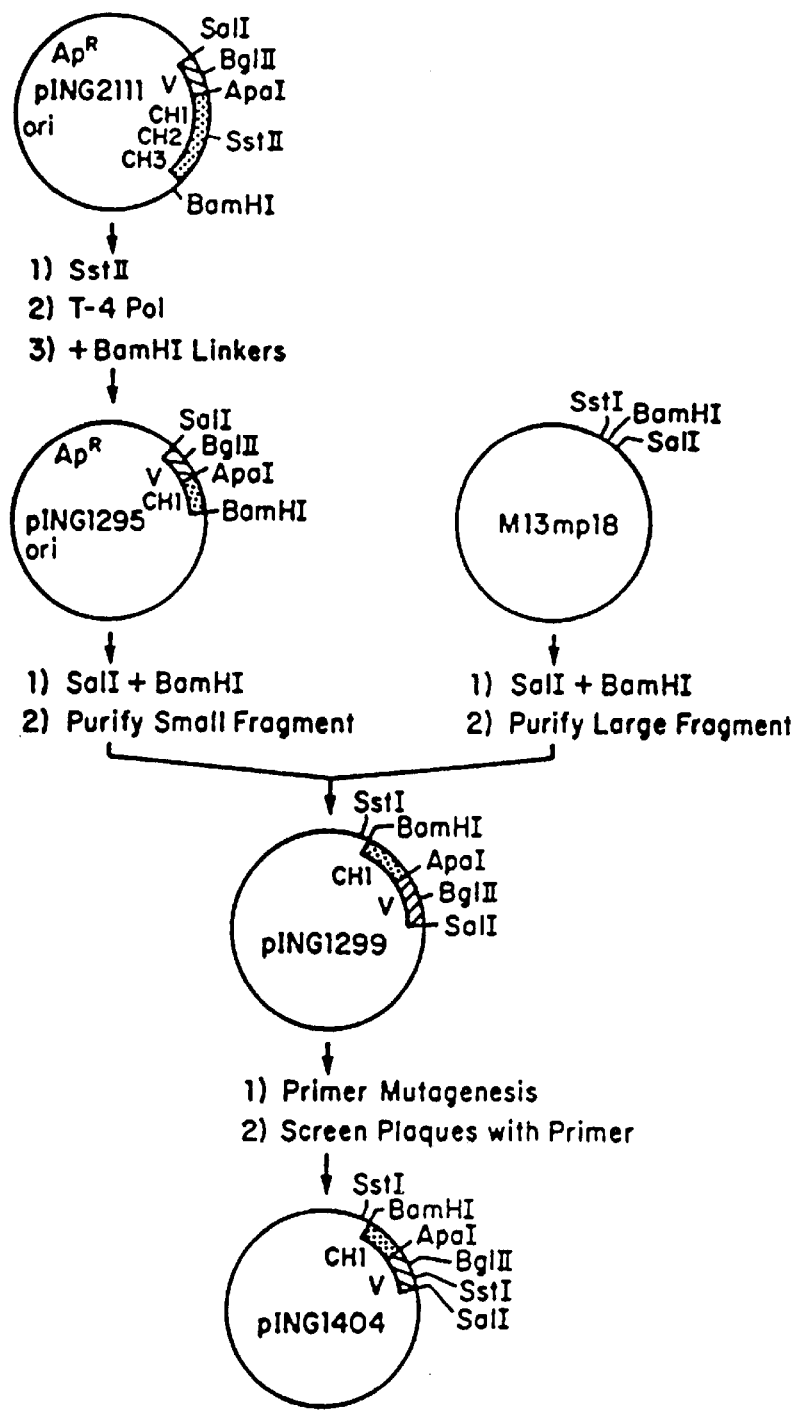

FIGS. 26(A–C) show the strategy used to fuse the mature L6 chimeric heavy chain sequence to the yeast invertase signal sequence and shortened PGK promoter. pING1288 contains the chimeric heavy chain gene with the variable region from the 2H7 mouse monoclonal antibody (see example IV). All symbols are as defined in legend for FIG. 25. (A) shows the strategy for introduction by in vitro mutagenesis of an SstI site in the signal sequence processing site. (B) shows the DNA sequence of the single-stranded mutagenesis primer and the corresponding unmutagenized DNA sequence. (C) shows the strategy used to construct a plasmid containing the mature heavy chain sequence fused to the invertase signal sequence and shortened PGK promoter.

Figure 27A:
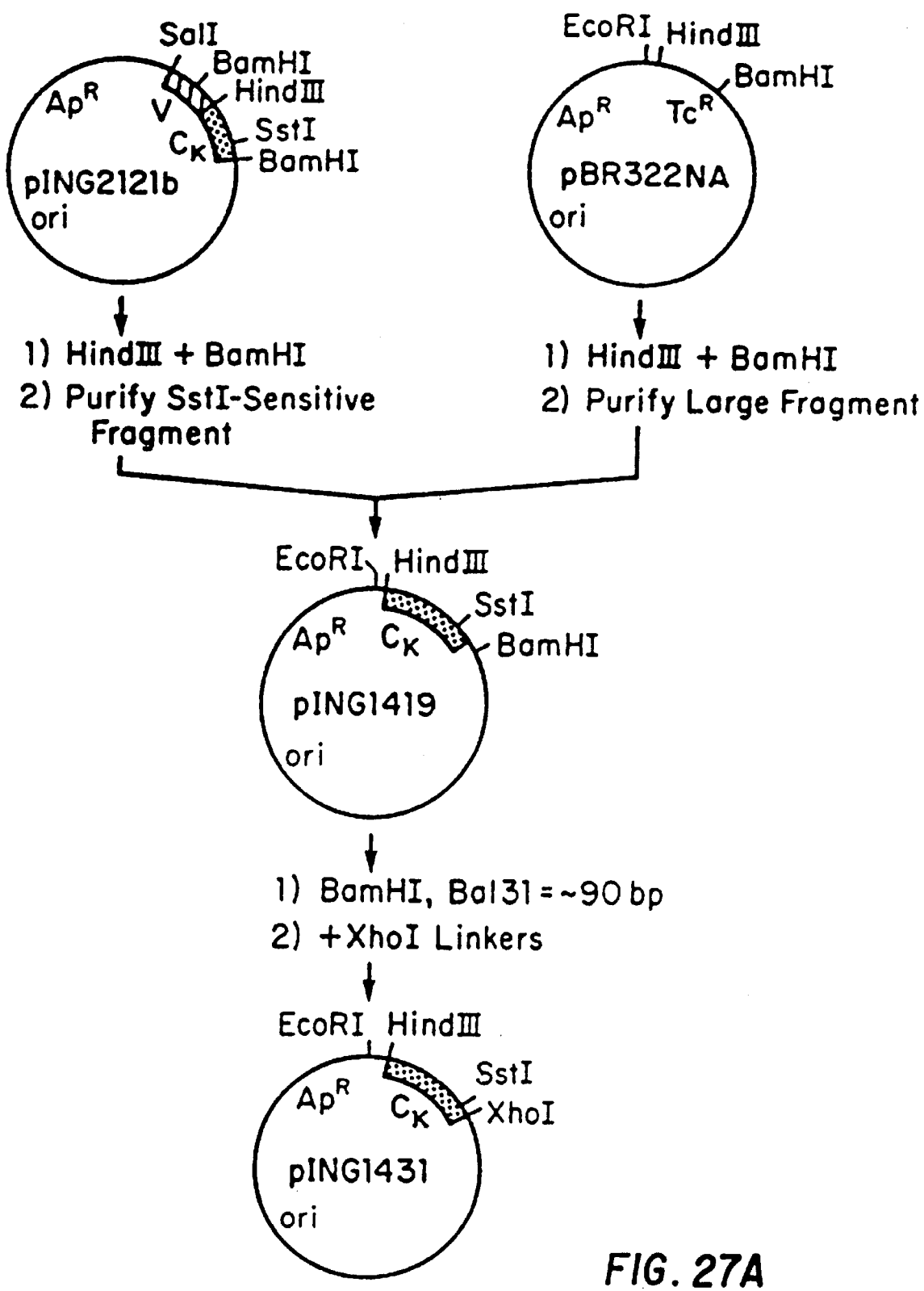
Figure 27B:
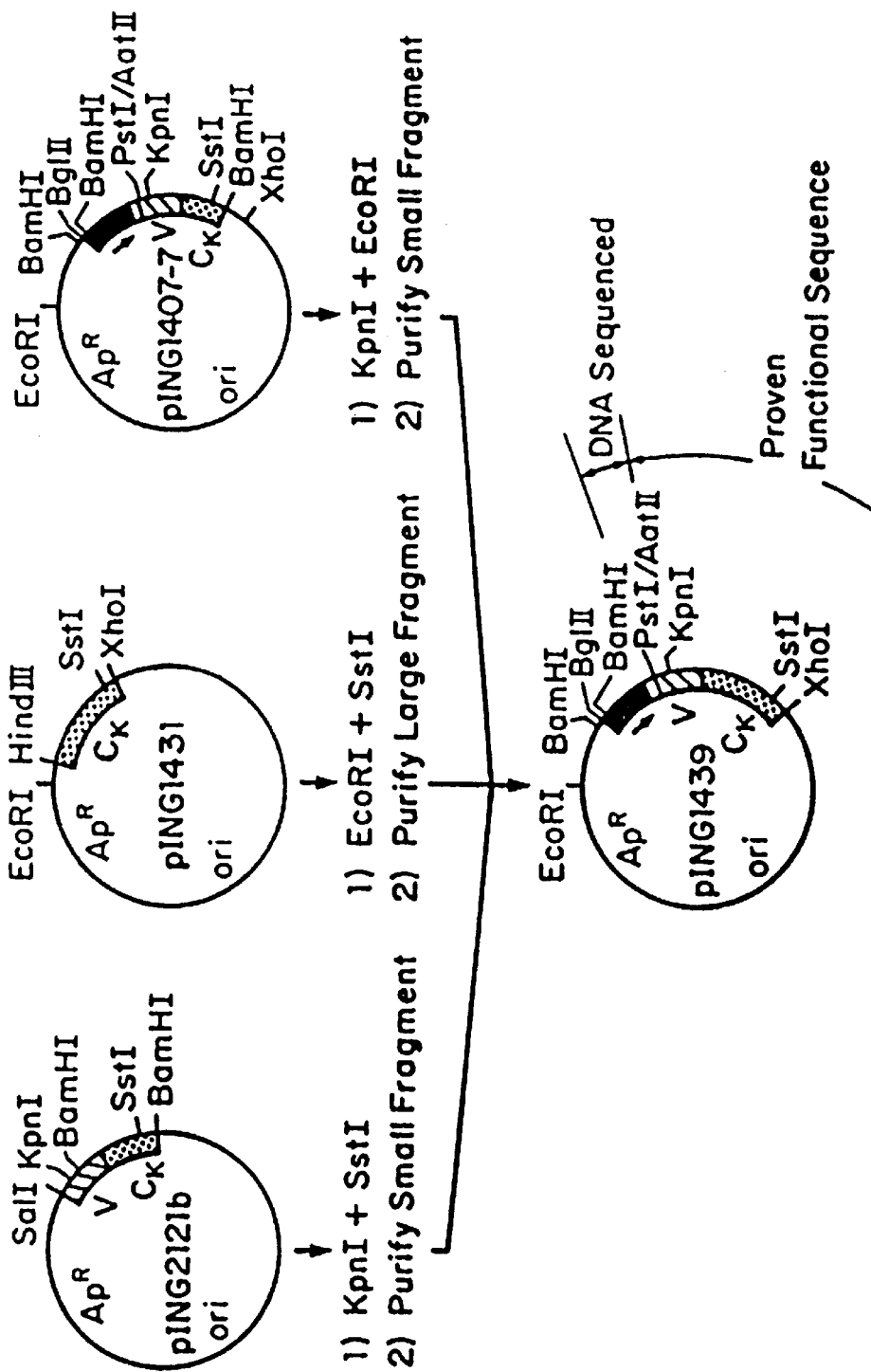

FIGS. 27(A and B) show the strategy used to remove non-yeast 3' untranslated DNA sequences from the L6 chimeric light chain gene and to construct a plasmid containing the light chain gene fused to the invertase signal sequence and shortened PGK promoter in which all sequences are either known by DNA sequence analysis or proven to be functional. pBR322NA is derived from pBR322 by deletion of DNA from NdeI to AuaI. FIG. 27A shows the construction of pING1431. FIG. 27B shows the construction of pING1439. Symbols are as defined in legend for FIG. 25.

Figure 28:
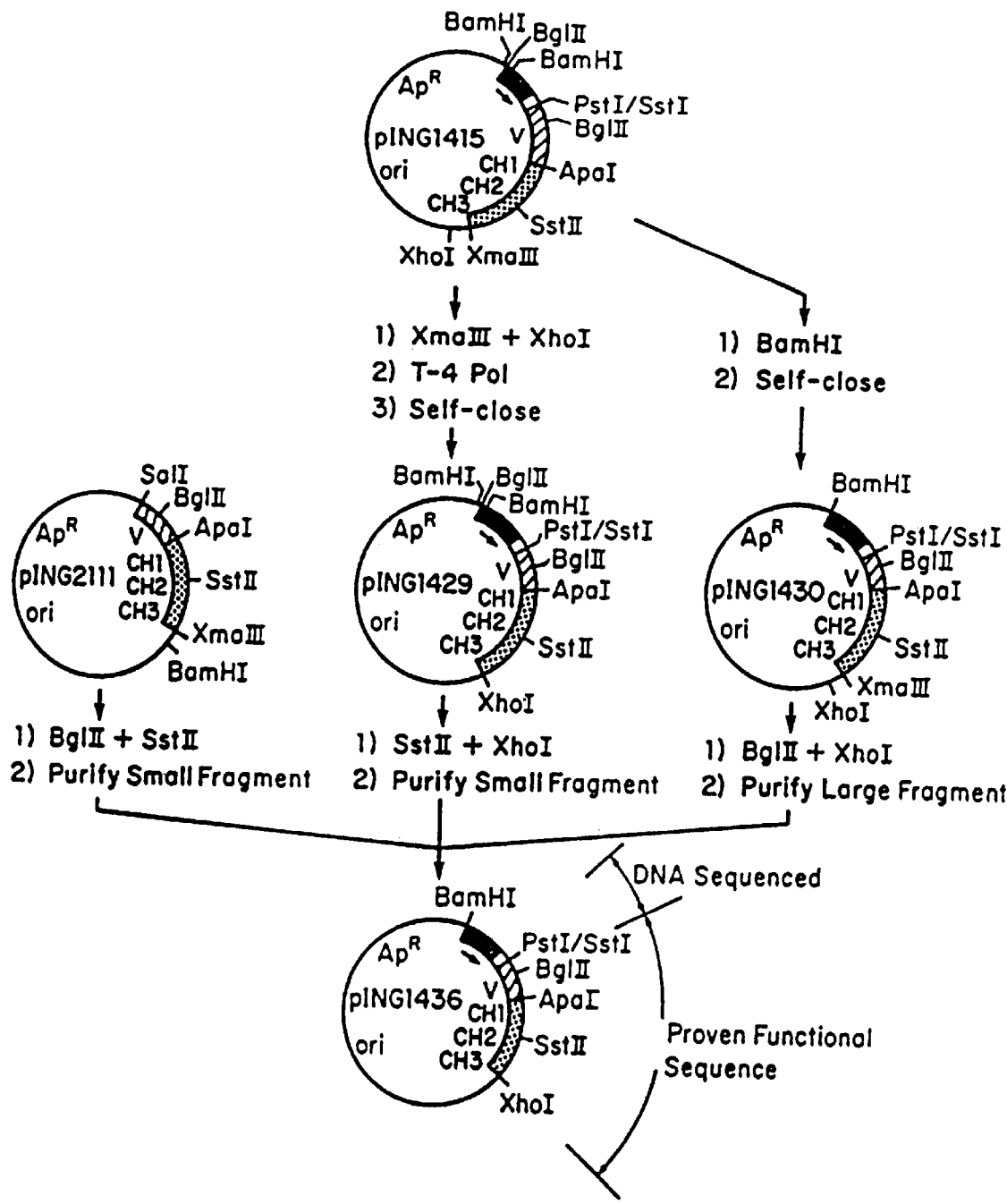

FIG. 28 shows the strategy used to remove non-yeast 3' untranslated DNA sequence from the L6 chimeric heavy chain gene and to construct a plasmid containing the heavy chain gene fused to the invertase signal sequence and shortened PGK promoter in which all sequences are either known by DNA sequence analysis or proven to be functional. Symbols are as defined in legend for FIG. 25.

Figure 29:
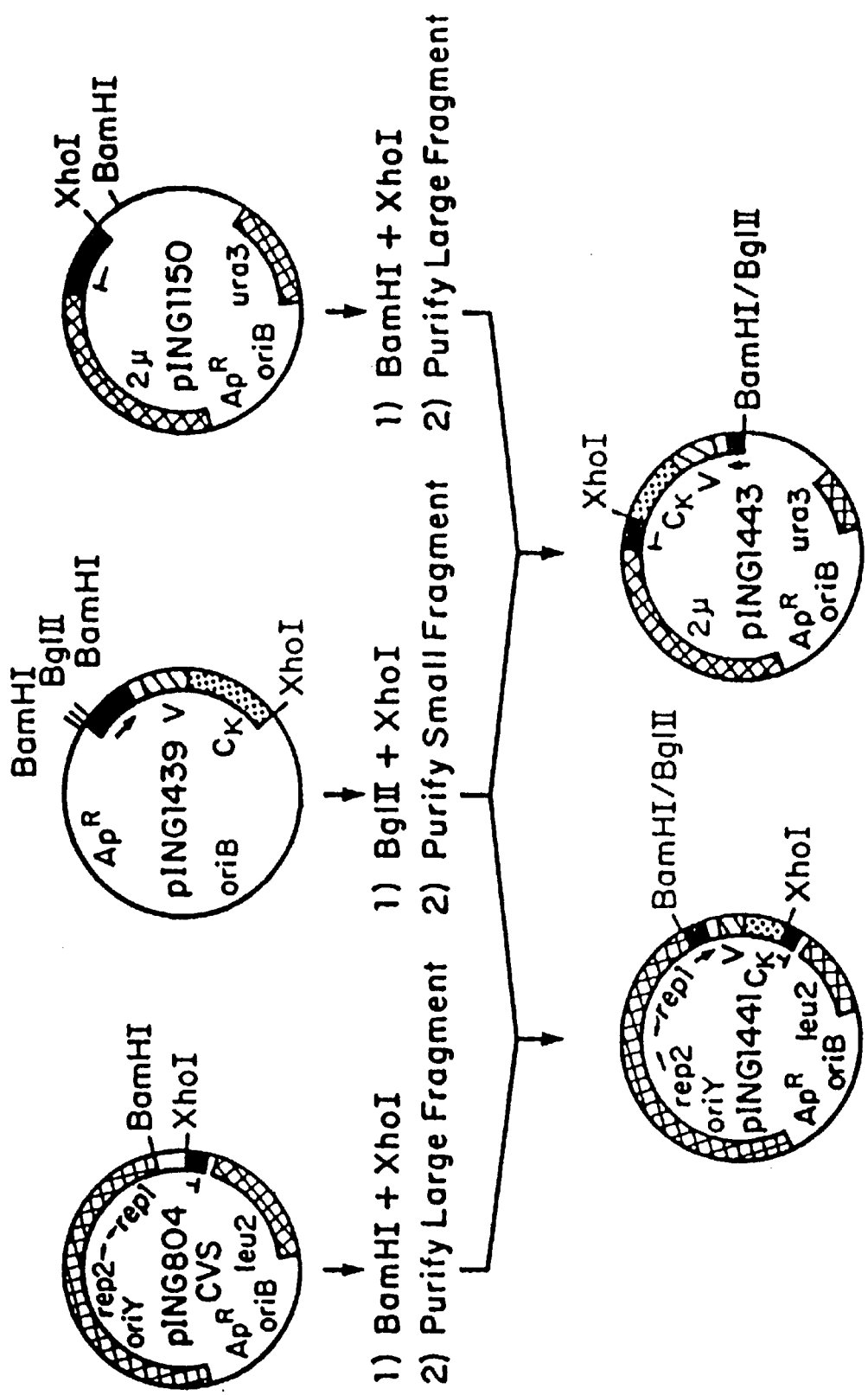

FIG. 29 shows the strategy used to clone the L6 chimeric light chain gene fused to the invertase signal sequence and shortened PGK promoter into yeast-E. coli shuttle vectors containing the PGK transcription termination-polyadenylation signal, yeast replication sequences, and genes for selection of transformants. Symbols are as defined in legend for FIG. 25.

Figure 30:
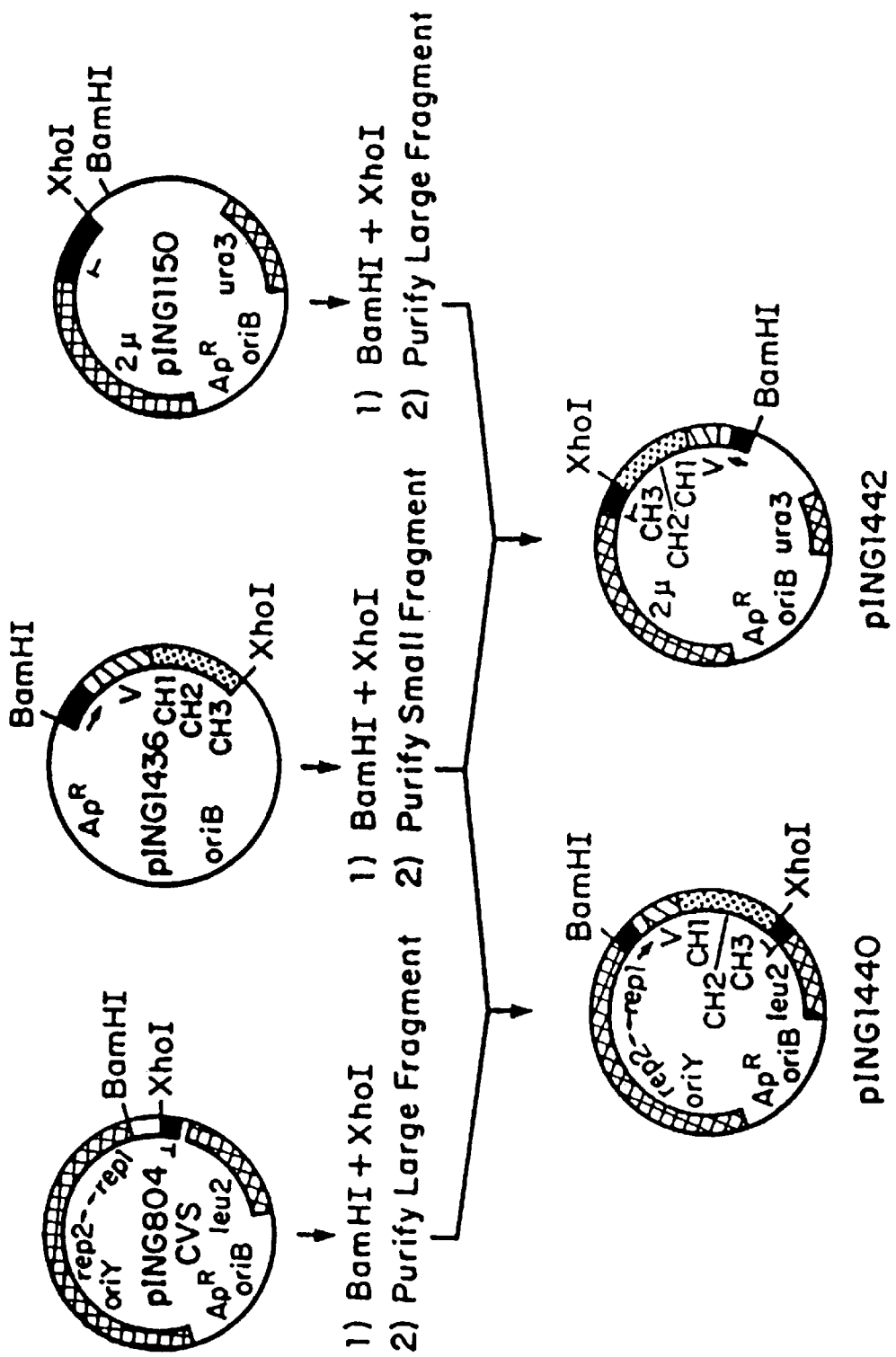

FIG. 30 shows the strategy used to clone the L6 chimeric heavy chain gene fused to the invertase signal sequence and shortened PGK promoter into yeast-E. coli shuttle vectors containing the PGK transcription termination-polyadenylation signal, yeast replication sequences, and genes for selection of transformants. Symbols are as defined in legend for FIG. 25.

Figure 31:
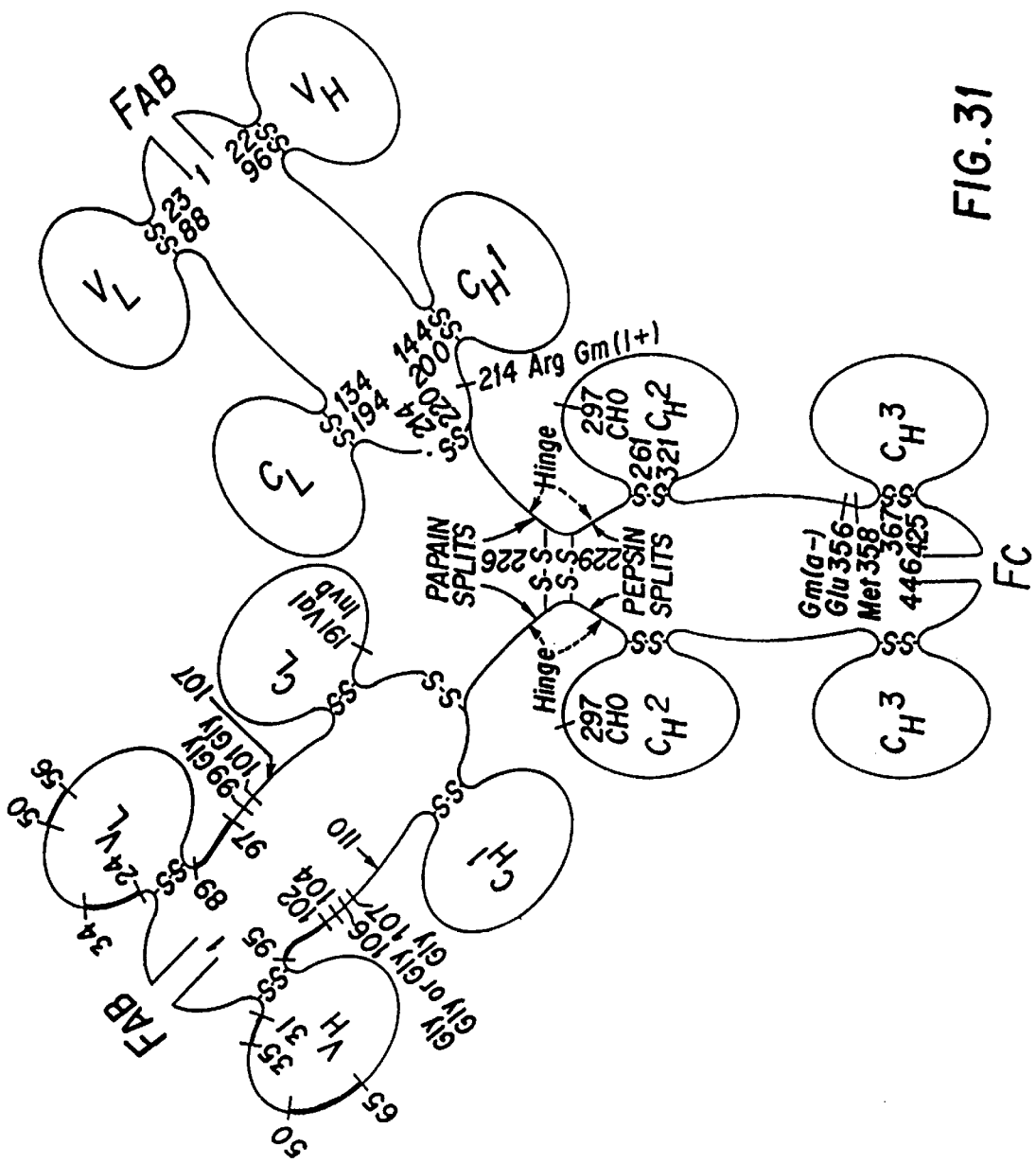

FIG. 31 shows a schematic diagram of the structure of human IgG1.

Figure 32A:
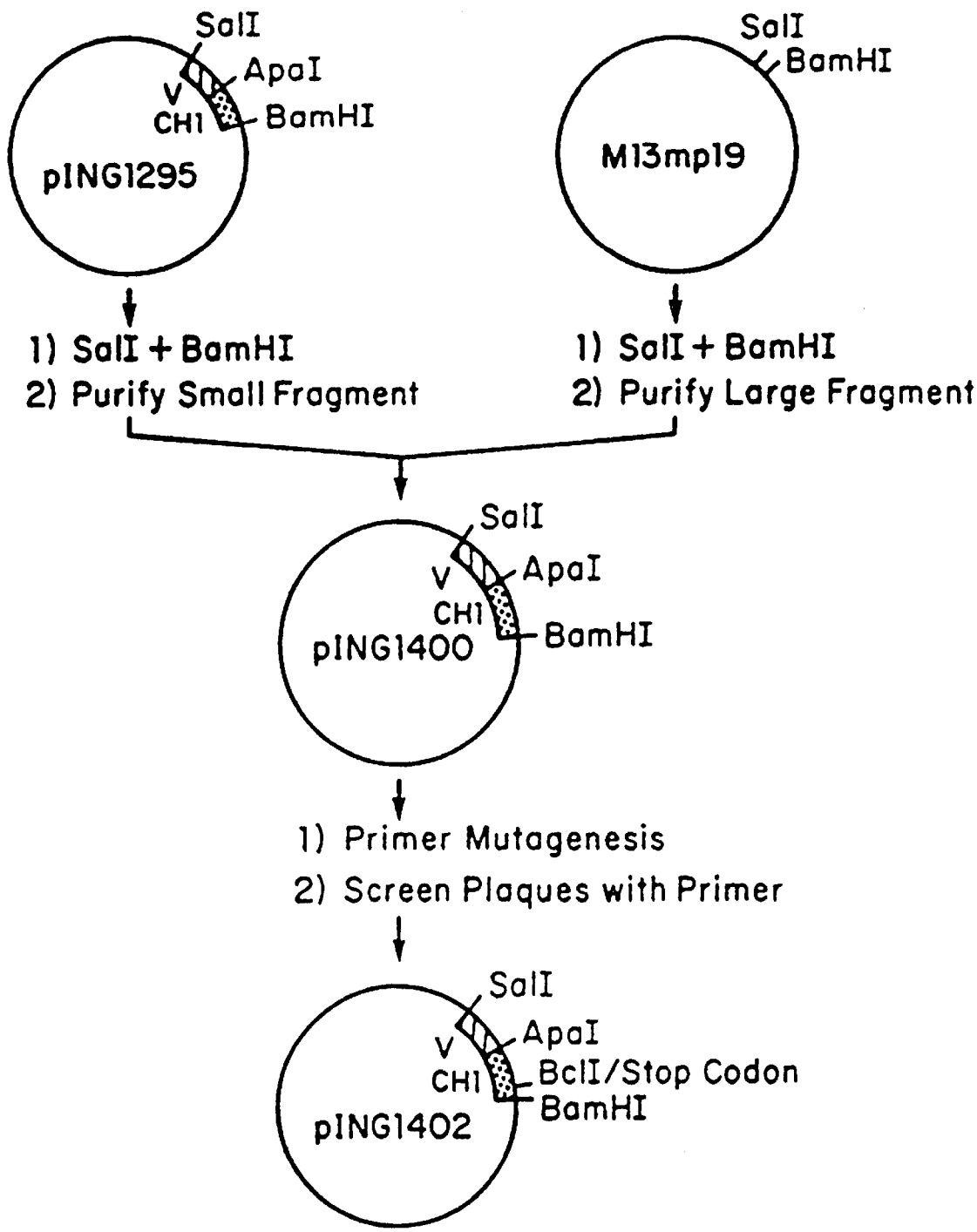

FIG. 32(A) shows the strategy used to introduce a stop codon and BclI site into the hinge region of human gamma 1. 32(B) shows the DNA sequence of the single-stranded primer used for in vitro mutagenesis of the gamma-1 hinge region and the corresponding unmutagenized sequence. Vertical arrows represent inter-chain disulfide bonds. Symbols are as defined in legend for FIG. 25.

Figure 33A:
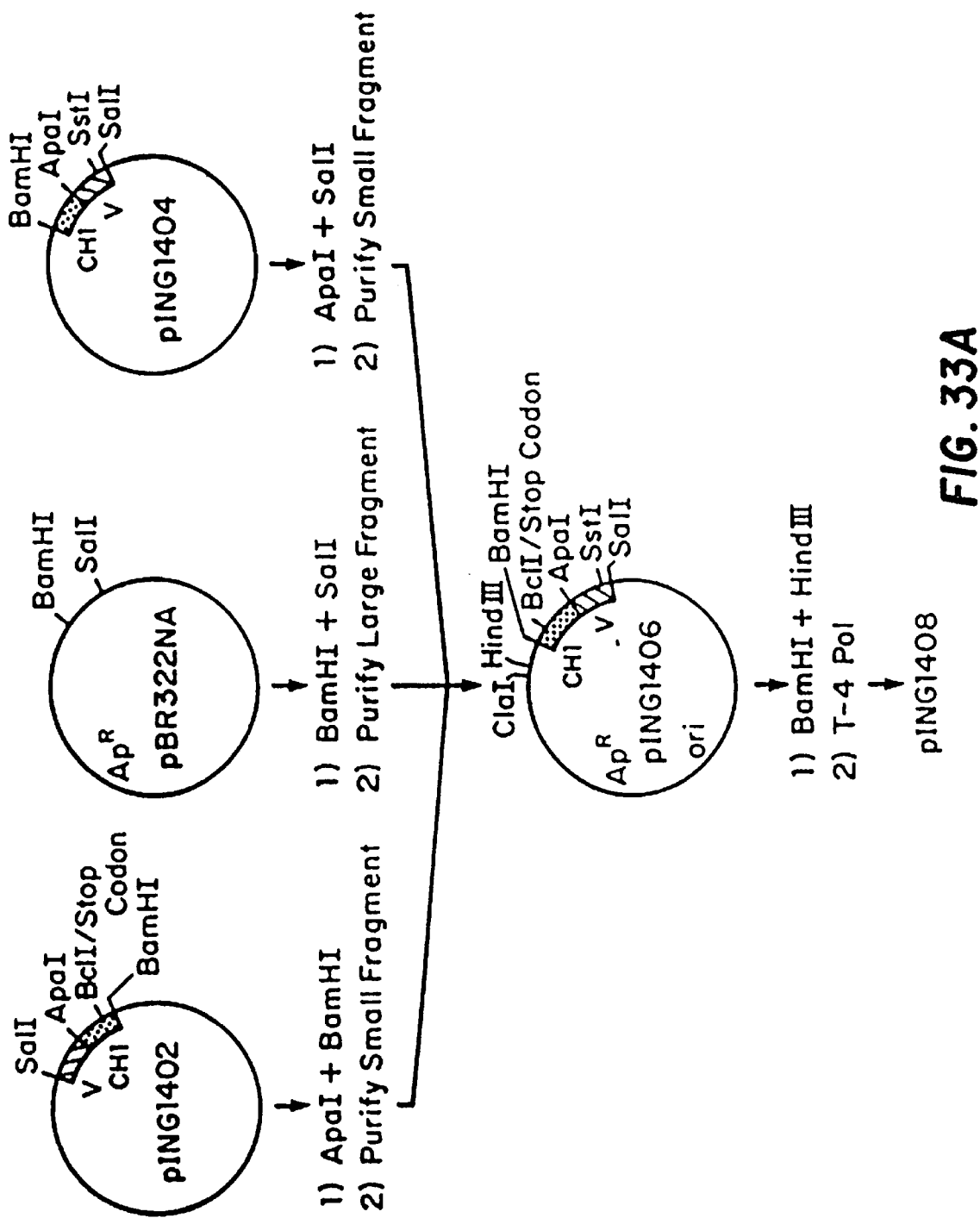
Figure 33B:
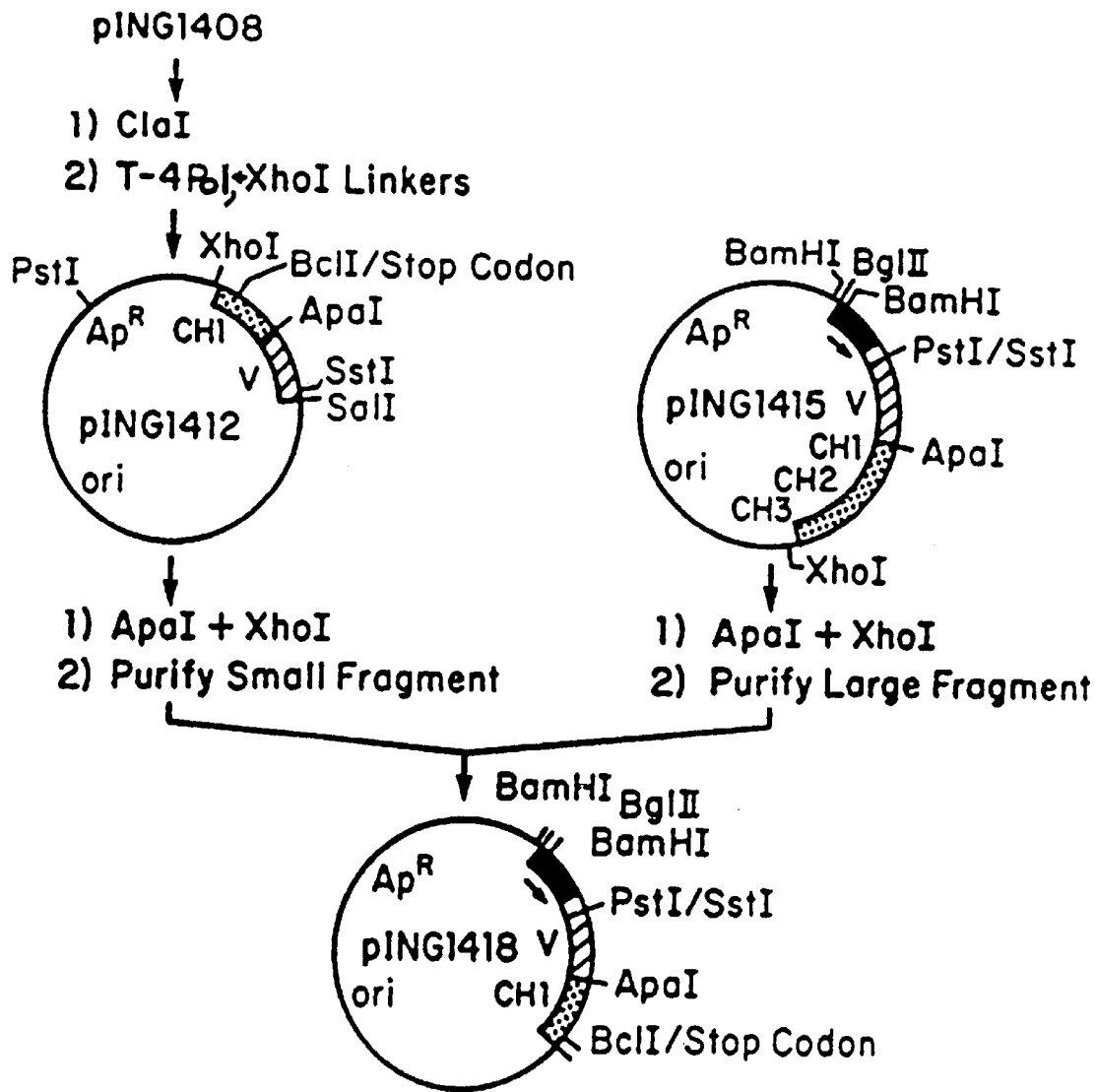

FIGS. 33(A and B) show the strategy used to fuse the L6 chimeric heavy chain gene containing a stop codon in the hinge region (Fd chain) to the yeast invertase signal sequence and shortened PGK promoter. FIG. 33(A) shows the construction of pING1408. FIG. 33(B) shows the construction of pING1418. Symbols are as defined in legend for FIG. 25.

Figure 34:
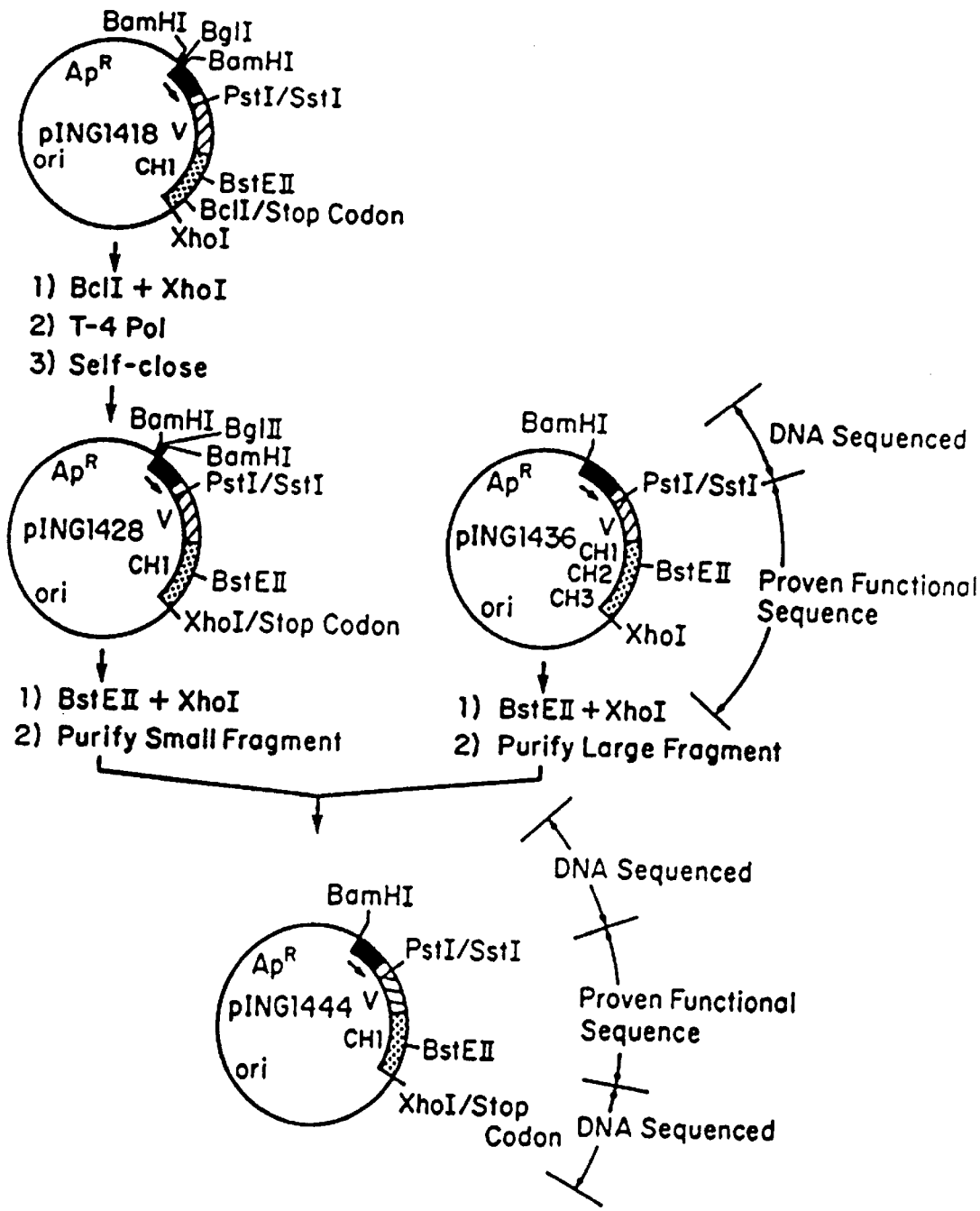

FIG. 34 shows the strategy used to remove non-yeast 3' untranslated sequences from the L6 chimeric Fd chain and to construct a plasmid containing the Fd chain fused to the invertase signal sequence and shortened PGK promoter in which all sequences are either known by DNA sequence analysis or proven to be functional. Symbols are as defined in legend for FIG. 25.

Figure 35:
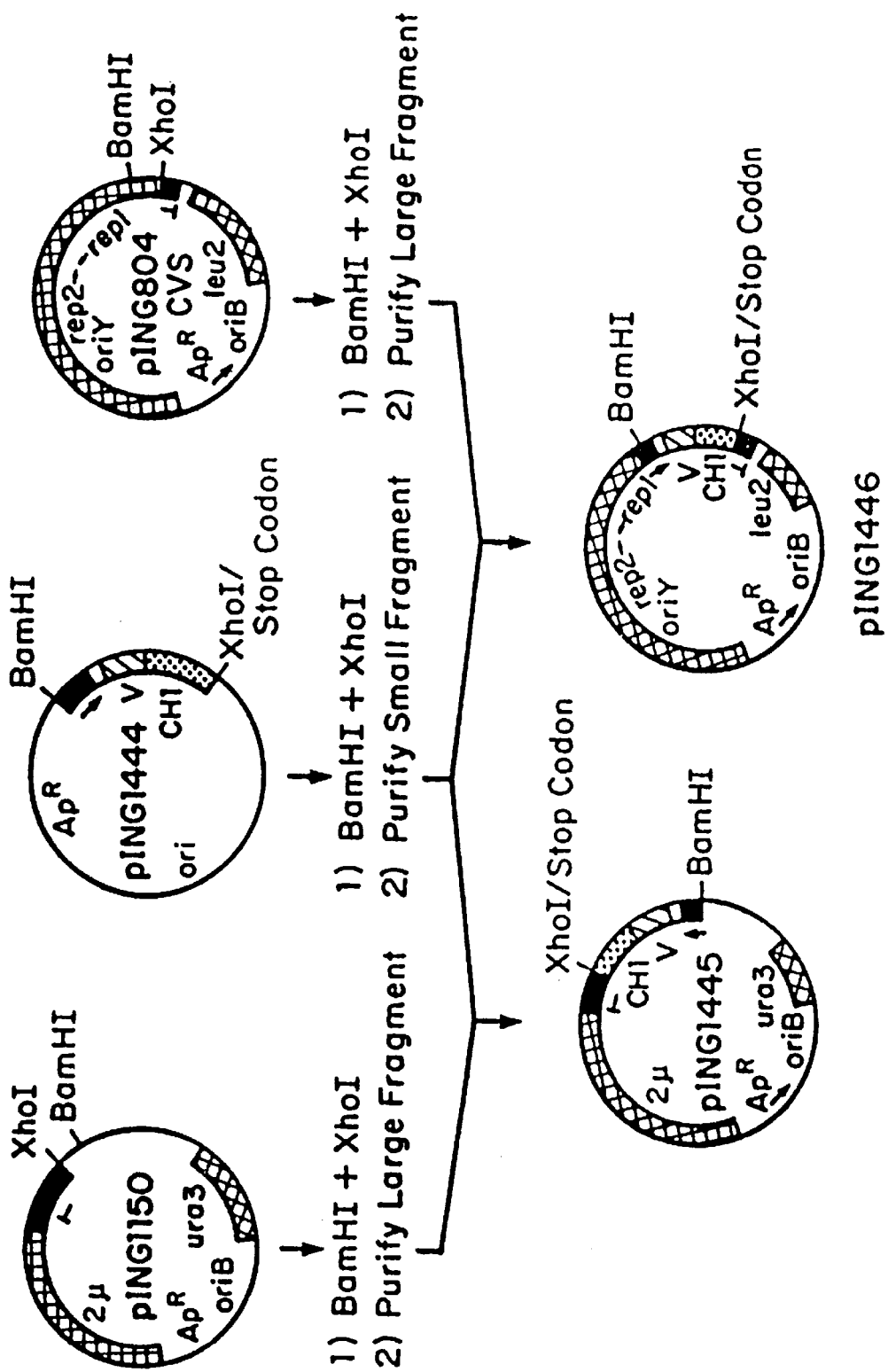

FIG. 35 shows the strategy used to clone the L6 chimeric Fd chain gene fused to the invertase signal sequence and shortened PGK promoter into yeast-E. coli shuttle vectors containing the PGK transcription termination-polyadenylation signal, yeast replication sequence, and genes for selection of transformants. Symbols are as defined in legend for FIG. 25.

Figure 36B:
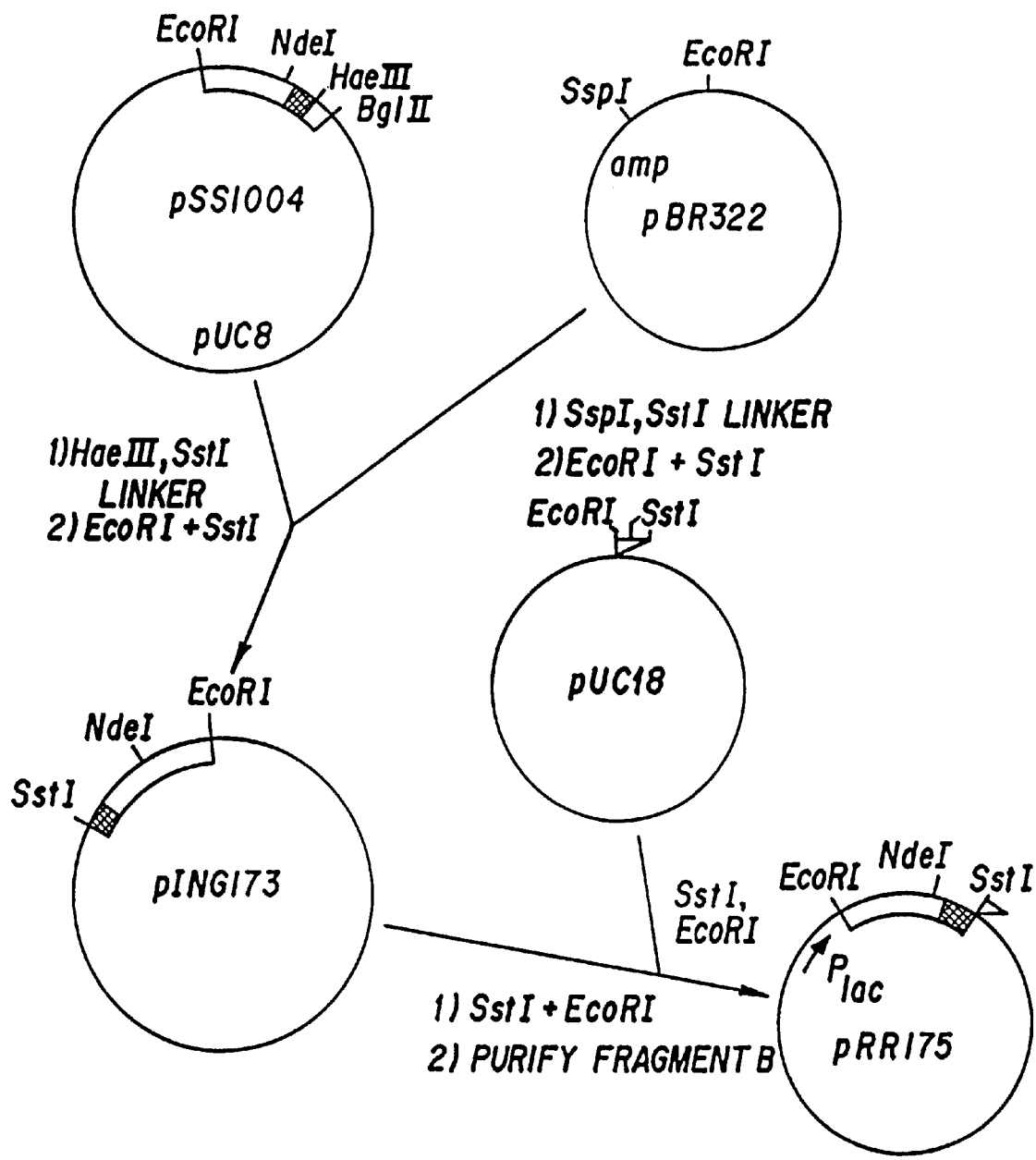

FIG. 36(A) shows the nucleotide sequence surrounding the N-terminus of the *Erwinia caratovora* pelB gene (Lei, S. P., et al., *J. Bacteriol.* 169:4379–4383 (1987). The NdeI and HaeIII sites used in cloning are shown. The arrow indicates the leader peptidase cleavage site for pectate lyase. 36(B) shows the cloning strategy for construction of the pelB leader cartridge. pSS1004 contains a 1.9 kb DraI fragment cloned into the SmaI site of pUC8. Symbols are defined in the legend for FIG. 39.

Figure 37A:
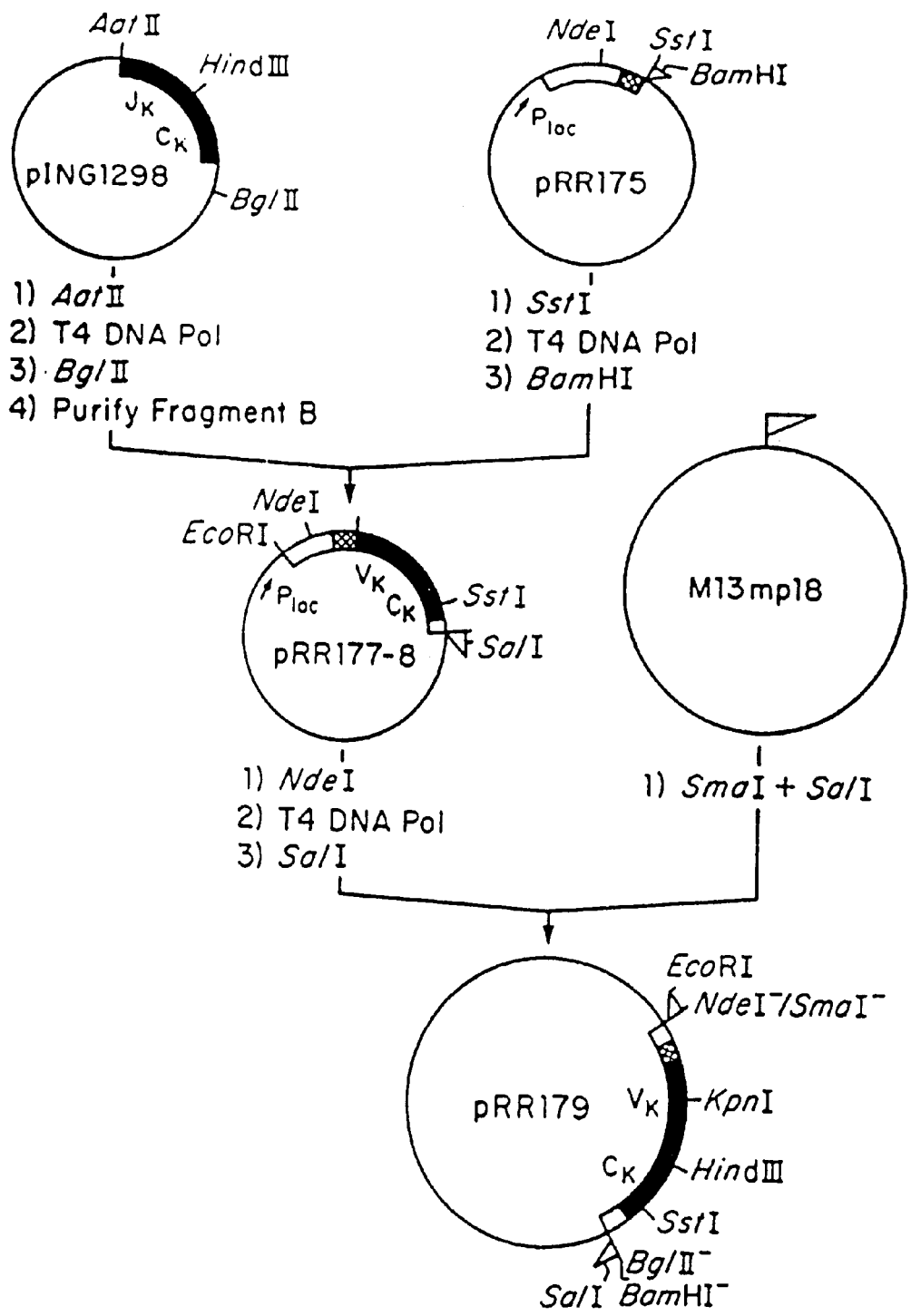
Figure 37B:
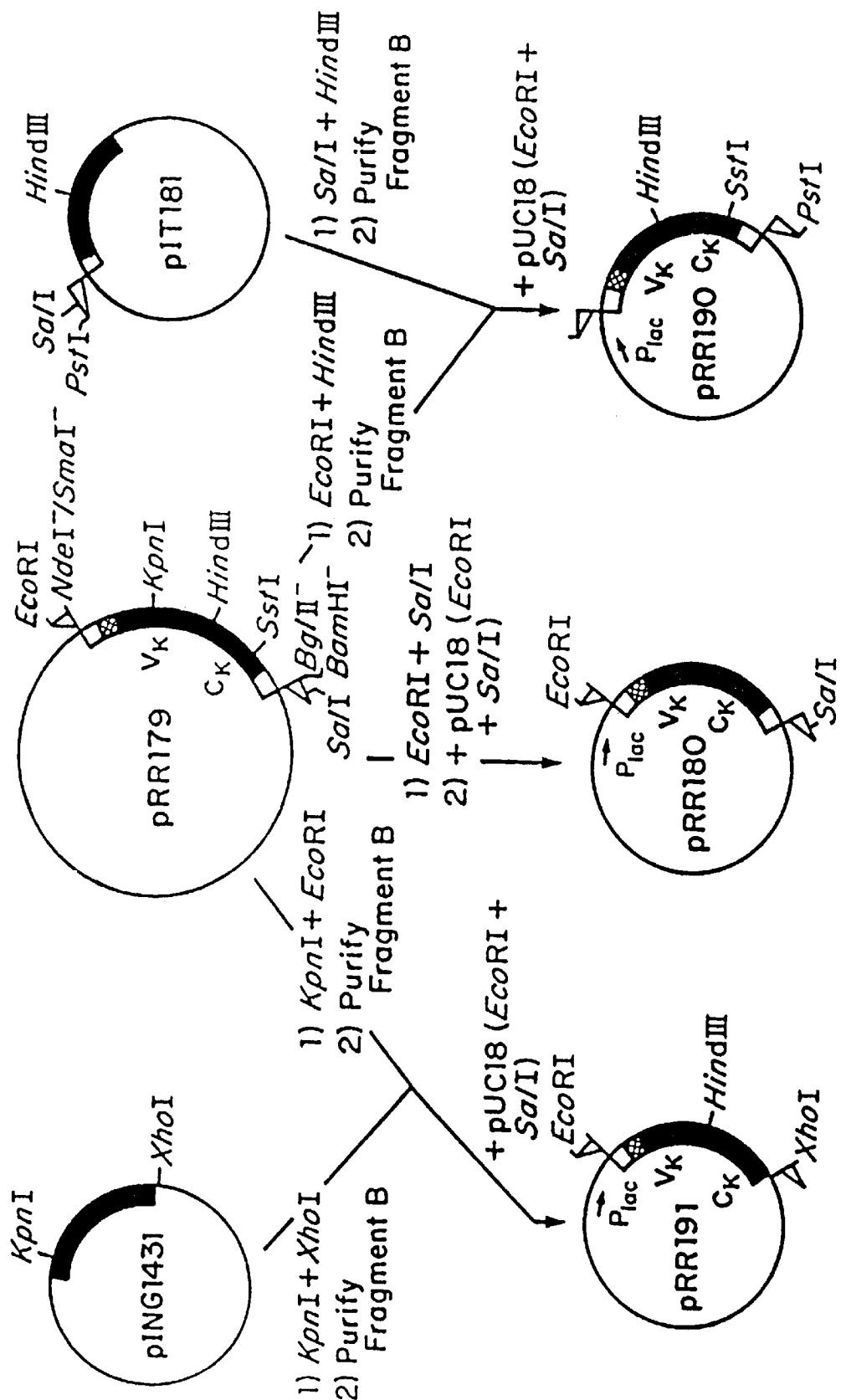

FIGS. 37(A and B) show the construction of light chain expression plasmids pRR177-8, pRR180, pRR190, and pRR191. In addition to the plasmids described in the test, M13mp18 and pIT181 were used. pIT181 contains the mature light chain gene fused directly following the ATG initiation codon of the araB gene in pIT2 (see FIG. 40). FIG. 37(A) shows the construction of plasmid pRR179. FIG. 37(B) shows the construction of plasmids pRR191, pRR180 and pRR190.

Figure 38A:
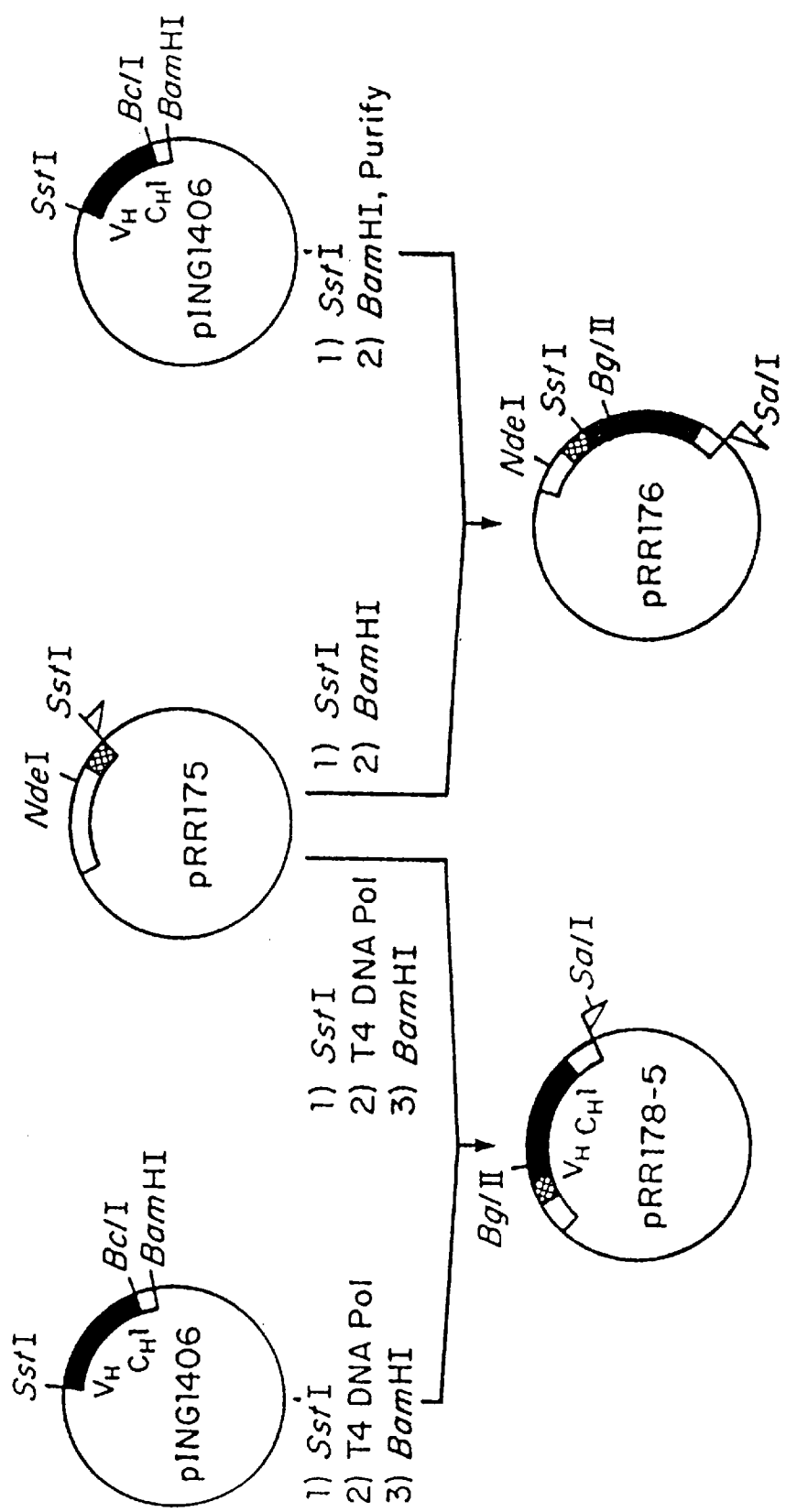
Figure 38B:
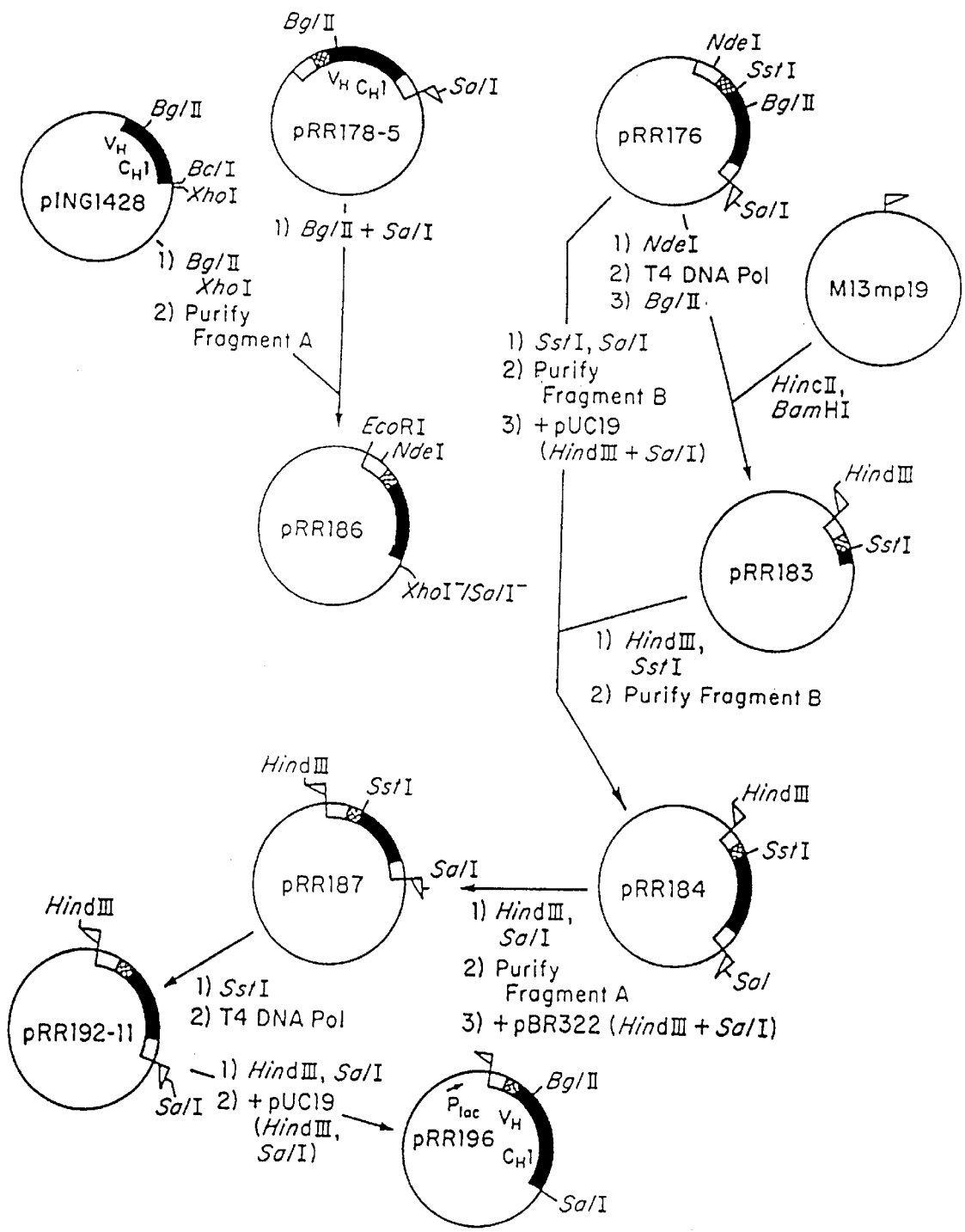

FIGS. 38(A and B) show the construction of Fd expression plasmids pRR178-5(FIG. 38(A)), pRR186 (FIG. 38(B)), and pRR196 (FIG. 38(B)).

Figure 39:
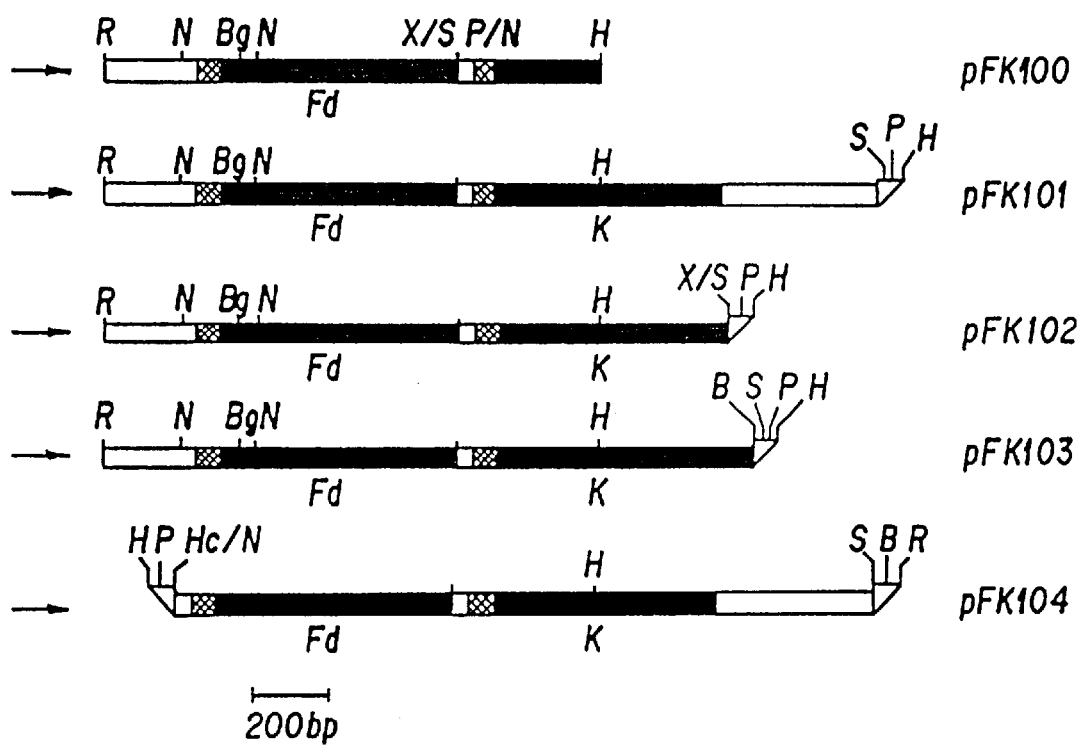

FIG. 39 shows the restriction maps of the light chain and Fd gene cassette in pFK100, pFK101, pFK102, pFK103, and pFK104. These plasmids were constructed as described in the text using plasmids outlined in FIG. 37 and 38. The arrow indicates the direction of transcription from the lac promoter. *E. caratovora* and eukaryotic non-coding sequences are shown as open bars. The pelB leader sequence is cross-hatched and the closed bar represents the antibody genes Fd and light chain (K).

Figure 40A:
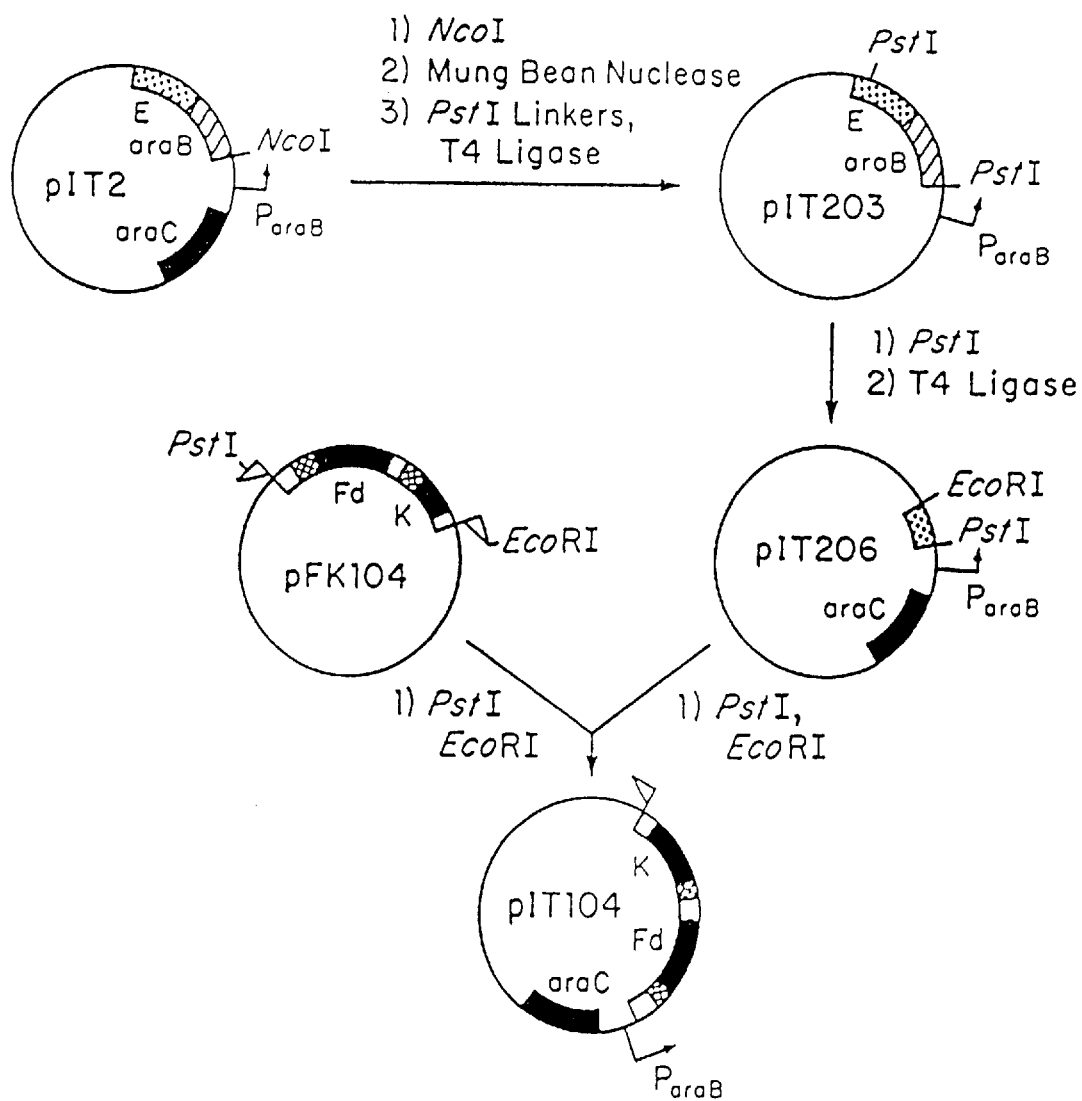

FIG. 40(A) shows the construction of a vector for arabinose inducible Fab expression. Plasmid pIT2 (Mason and Ray, *Nucl. Acids Res.* 14:5693 (1986)) is a 6431 bp plasmid encoding the araC gene, the araB promoter, and a portion of the araB gene from pING1 (Johnston, S., et al., *Gene* 34:134 (1985) in a derivative of pBR322. An NcoI site has been engineered at the ATG initiation codon of the araB gene. 40(B) shows the introduction of the laci gene into pFK102.

Figure 41:
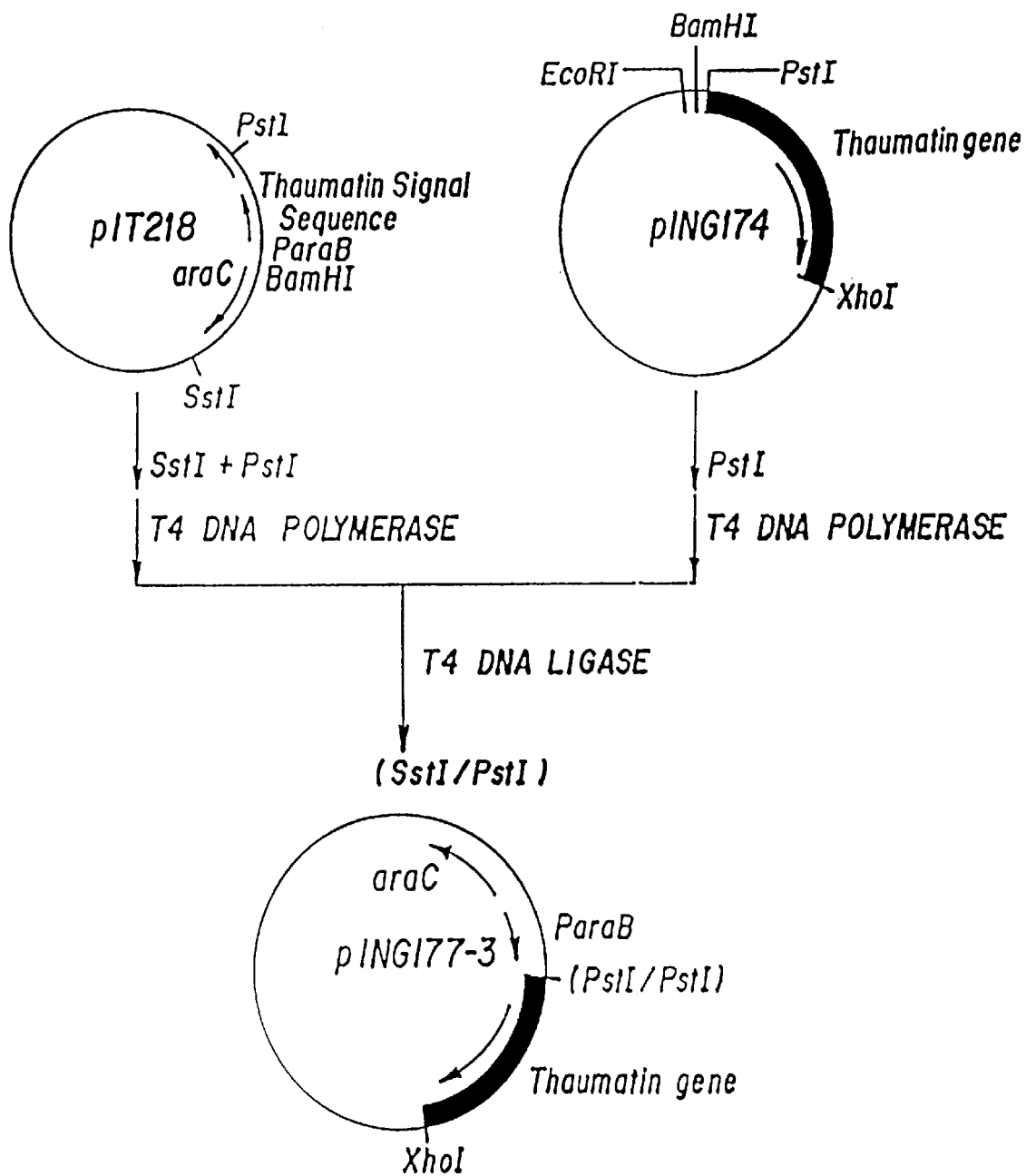

FIG. 41 outlines the procedures used to create plasmids pSS1004, containing the pelB gene, and pSS1038, containing the pelB gene under control of the araBAD promoter.

Figure 42:
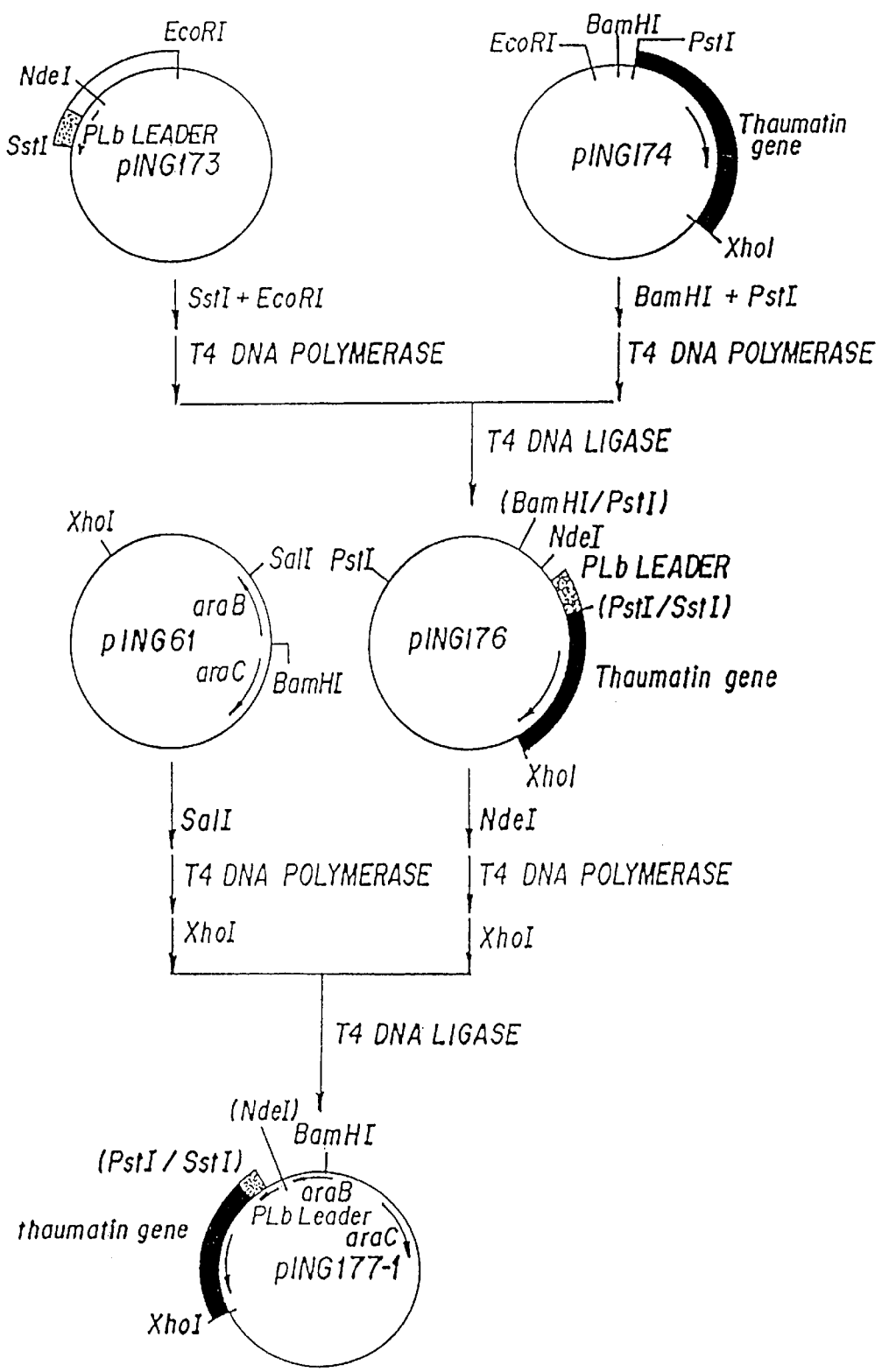

FIG. 42 outlines the procedure used in construction of the plasmid pING177-1, containing the pelB signal sequence and the plant thaumatin gene under control of the araBAD promoter.

Figure 43:
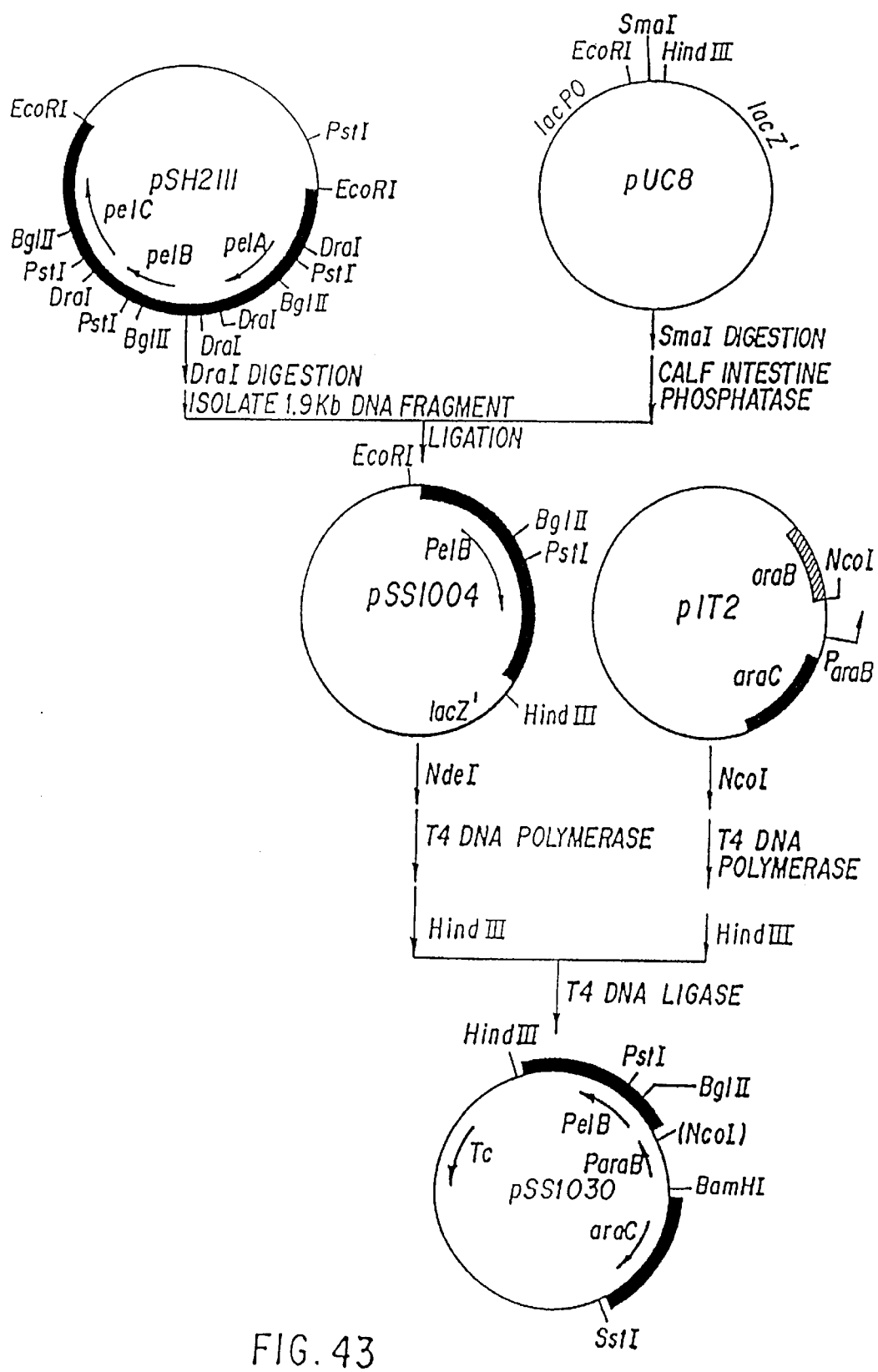

FIG. 43 outlines the procedures followed in construction of plasmid pING177-3, containing the plant thaumatin gene with the pre-thaumatin leader peptide sequence.

DESCRIPTION OF THE PREFERRED EMBODIMENTS

Introduction

Generally, antibodies are composed of two light and two heavy chain molecules. Light and heavy chains are divided into domains of structural and functional homology. The variable regions of both light ($V_L$) and heavy ($V_H$) chains determine recognition and specificity. The constant region domains of light ($C_L$) and heavy ($C_H$) chains confer important biological properties such as antibody chain association, secretion, transplacental mobility, complement binding, and the like.

Figure 1:
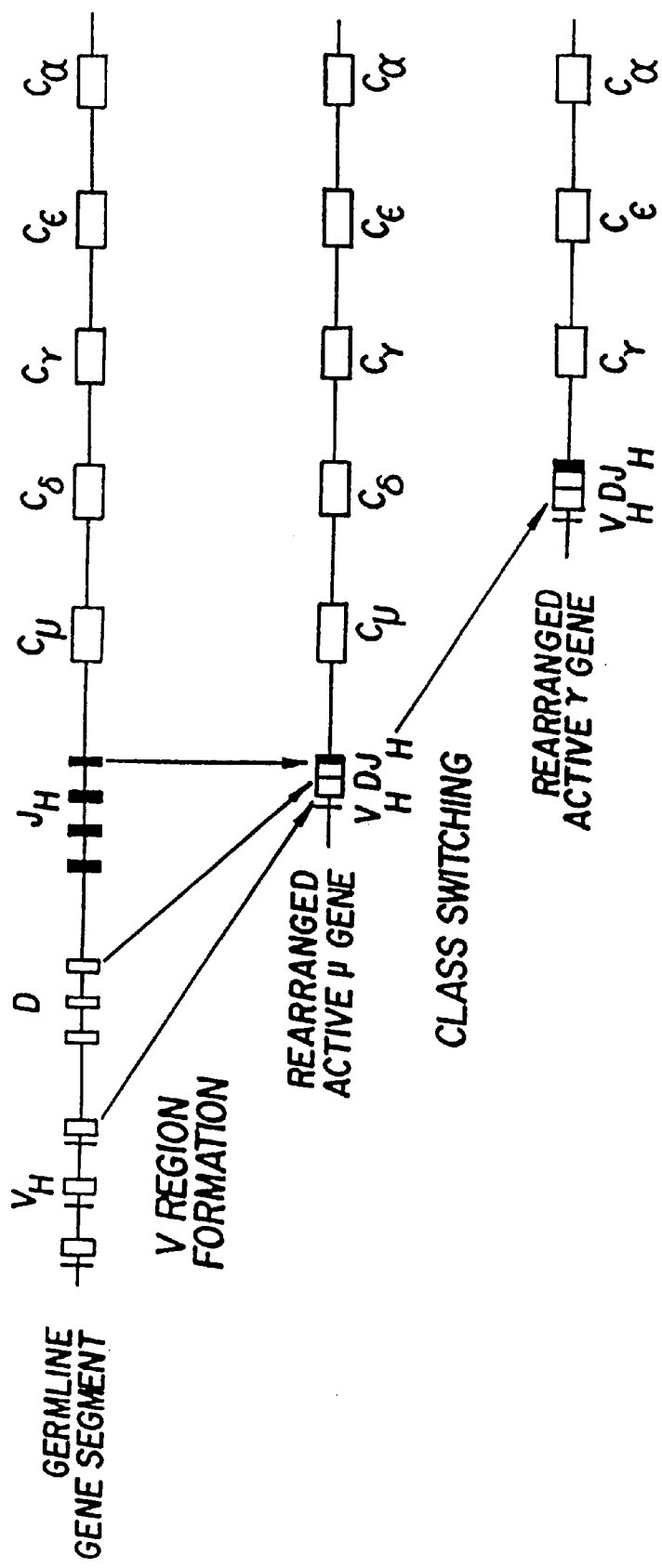
FIG. 1 shows the DNA rearrangements and the expression of immunoglobulin mu and gamma heavy chain genes. This is a schematic representation of the human heavy chain gene complex, not shown to scale. Heavy chain variable V region formation occurs through the joining of $V_H$, D and $J_H$ gene segments. This generates an active mu gene. A different kind of DNA rearrangement called "class switching" relocates the joined $V_H$, D and $J_H$ region from the mu constant C region to another heavy chain C region (switching to gamma is diagrammed here). The scheme emphasizes that the J region is a common feature of all expressed heavy chain genes. The J region is also a common feature of expressed light chain genes.

A complex series of events leads to immunoglobulin gene expression in B cells. The V region gene sequences conferring antigen specificity and binding are located in separate germ line gene segments called $V_H$, D and $J_H$; or $V_L$ and $J_L$. These gene segments are joined by DNA rearrangements to form the complete V regions expressed in heavy and light chains respectively (FIG. 1). The rearranged, joined ($V_L$—$J_L$ and $V_H$—D—$J_H$) V segments then encode the complete variable regions or antigen binding domains of light and heavy chains, respectively.

Definitions

Certain terms and phrases are used throughout the specification and claims. The following definitions are provided for purposes of clarity and consistency.

1. Expression vector—a plasmid DNA containing necessary regulatory signals for the synthesis of mRNA derived from gene sequences, which can be inserted into the vector.

2. Module vector—a plasmid DNA containing a constant or variable region gene module.

3. Expression plasmid—an expression vector that contains an inserted gene, such as a chimeric immunoglobulin gene.

4. Gene cloning—synthesis of a gene, insertion into DNA vectors, and identification by hybridization and the like.

5. Transfection—the transfer of DNA into mammalian cells.

6. Promoter region—a nucleotide sequence which provides a cell with the regulatory sequences needed to express an operably linked cistron or operon.

7. Secretion signal—a polypeptide present at the N-terminus of a chimeric immunoglobulin chain useful in aiding in the secretion of the chain to the outside of the host. Also called "leading peptide," or "leader."

Genetic Processes and Products

The invention provides a novel approach for the cloning and production of human antibodies with desired specificity. Generally, the method combines five elements:

(1) Isolation of messenger RNA (mRNA) from B cell hybridoma lines producing monoclonal antibodies against specific antigens, cloning and cDNA production therefrom;

(2) Preparation of Universal Immunoglobulin Gene (UIG) oligonucleotides, useful as primers and/or probes for cloning of the variable region gene segments in the light and heavy chain mRNA from specific human or non-human hybridoma cell lines, and cDNA production therefrom;

(3) Preparation of constant region gene segment modules by cDNA preparation and cloning, or genomic gene preparation and cloning;

(4) Construction of complete heavy or light chain coding sequences by linkage of the cloned specific immunoglobulin variable region gene segments of part (2) above to cloned human constant region gene segment modules;

(5) Expression and production of light and heavy chains in selected hosts, including prokaryotic and eukaryotic hosts, either in separate fermentations followed by assembly of antibody molecules in vitro, or through production of both chains in the same cell.

The invention employs cloned hybridoma B cell lines producing monoclonal antibodies of defined specificity for the isolation of mRNA for cDNA cloning. Because many lymphoid cell lines contain highly active nucleases which degrade mRNA during isolation, the invention uses mRNA preparation methods specifically developed for the isolation of intact mRNA from cells and tissues containing active nucleases. One such method yields total RNA preparations by cell or tissue disruption is an ethanol-perchlorate dry ice mixture which reduces nuclease action (Lizardi, P. M. et al., *Anal. Biochem.*, 98: 116 (1979)). This method gives intact translatable mRNA.

Other methods that have been used for this invention include extraction of cells with lithium chloride plus urea (Auffray, C., and Rougeon, F., *Eur. J. Biochem.*, 107: 303 (1980)) or guanidine thiocyanate (Chirgwin, J. M. et al., *Biochemistry*, 18: 5294 (1979)) to prepare total RNA.

One universal feature of all expressed immunoglobulin light and heavy chain genes and messenger RNAs is the so-called J region (i.e. joining region, see FIG. 1). Heavy and light chain J regions have different sequences, but a high degree of sequence homology exists (greater than 80%) within the heavy $J_H$ regions or the kappa light chain J regions. The invention provides consensus sequences of light and heavy chain J regions useful in the design of oligonucleotides (designated herein as UIGs) for use as primers or probes for cloning immunoglobulin light or heavy chain mRNAs or genes (FIGS. 2 or 7). Depending on the nature of design of a particular UIG, it may be capable of hybridizing to all immunoglobulin mRNAs or genes containing a single specific J sequence, such as UIG-MJH3 which detects only mouse $J_H3$ sequences (FIG. 7).

Another utility of a particular UIG probe may be hybridization to light chain or heavy chain mRNAs of a specific constant region, such as UIG-MJK which detects all mouse $J_K$ containing sequences (FIG. 7). UIG design can also include a sequence to introduce a restriction enzyme site into the cDNA copy of an immunoglobulin gene (see FIG. 7). The invention may, for example, utilize chemical gene synthesis to generate the UIG probes for the cloning of V regions in immunoglobulin mRNA from hybridoma cells making monoclonal antibodies of desired antigen specificities.

A multi-stage procedure is utilized for generating complete V+C region cDNA clones from hybridoma cell light and heavy chain mRNAs. In the first stage, the invention utilizes UIG probes as "primers" for reverse transcriptase copying of the complete V region and leader coding sequences of heavy and light chain mRNAs (FIG. 3). The complementary strand of the primer extended cDNA is then synthesized, and this double-stranded cDNA is cloned in appropriate cDNA cloning vectors such as pBR322 (Gubler and Hoffman, *Gene*, 25: 263 (1983)) or pQ23 (FIG. 5; Maniatis, T. et al., *Molecular Cloning: A Laboratory Manual*, Cold Spring Harbor Laboratory Publications, New York, page 224 (1982)). Clones are screened for specific hybridization with UIG oligonucleotide probes. Positive heavy and light chain clones identified by this screening procedure are mapped and sequenced to select those containing V region and leader coding sequences.

An alternative method is to make cDNA clones using oligo-dT as a primer, followed by selection of light and heavy chain clones by standard hybridization methods.

A second stage utilizes cloning of C region gene segments to form heavy and light chain module vectors. In one method cDNA clones of human heavy and light chain immunoglobulin mRNA are prepared. These cDNA clones are then converted into C region module vectors by site-directed mutagenesis to place a restriction site at a desired location near a boundary of the constant region. An alternative method utilizes genomic C region clones as the source for C region module vectors.

A third stage of cDNA cloning involves the generation of complete light and heavy chain coding sequences with linked V and C regions. The cloned V region segments generated as above are excised and ligated to light or heavy chain C region module vectors. For example, one can clone the complete human kappa light chain C region and the complete human gamma$_1$ C region. In addition, one can modify a human gamma 1 region and introduce a termination codon, and thereby obtain a gene sequence which encodes the heavy chain portion of an Fab molecule.

The coding sequences having operationally linked V and C regions are then transferred into appropriate expression systems for expression in appropriate hosts, prokaryotic or eukaryotic. Operationally linked means in-frame joining of coding sequences to derive a continuously translatable gene sequence without alterations or interruptions of the triplet reading frame.

One particular advantage of using cDNA genetic sequences in the present invention is the fact that they code continuously for immunoglobulin chains, either heavy or light. By "continuously" is meant that the sequences do not contain introns (i.e. are not genomic sequences, but rather, since derived from mRNA by reverse transcription, are sequences of contiguous exons). This characteristic of the cDNA sequences provided by the invention allows them to be expressible in prokaryotic hosts, such as bacteria, or in lower eukaryotic hosts, such as yeast.

Another advantage of cDNA cloning methods is the ease and simplicity of obtaining V region gene modules.

The term "non-human" as used in the invention is meant to include any animal other than a human, wherein an immune response can be generated which then leads to usable B cells resulting in corresponding hybridomas or B cell clones obtained by viral transformation and the like. Such animals commonly include rodents such as the mouse or the rat. Because of ease of preparation and great availability, the mouse is at present the preferred, non-human animal. Mouse—mouse hybridomas are thus utilized as the preferred sources for heavy and light chain variable regions.

Preferably, the invention provides entire V and/or C region cDNA sequences. This means that the sequences code for substantially operable V and/or C regions, without lacking any major structural portions thereof.

The terms "constant" and "variable" are used functionally to denote those regions of the immunoglobulin chain, either heavy or light chain, which code for properties and features possessed by the variable and constant regions in natural non-chimeric antibodies. As noted, it is not necessary for the complete coding region for variable or constant regions to be present, as long as a functionally operating region is present and available.

A wide range of source hybridomas are available for the preparation of mRNA. For example, see the catalogue *ATCC CELL LINES AND HYBRIDOMAS*, December, 1984, American Type Culture Collection, 12301 Parklawn Drive, Rockville, Md. 20852, U.S.A., pages 5–9 and the ECACC Catalogue, 2nd Edition; PHLS CAMR Porton Down, Salisbury, Wills; SP4OJG, U.K. pages 30–35 and 40–46. Hybridomas secreting monoclonal antibodies reactive to a wide variety of antigens are listed therein, are available from the collection, and usable in the invention. Of particular interest are hybridomas secreting antibodies which are reactive with viral antigens, including Dengue complex specific (ATCC HB 114), Dengue type 1 virus (ATCC HB 47), Dengue type 2 virus (ATCC HB 46), Dengue type 3 virus (ATCC HB 49), Dengue type 4 virus (ATCC HB 48), Epstein-Barr receptor (ATCC HB 135), Flavivirus group (ATCC HB 112), hepatitis B surface antigen (ATCC CRL 8017 and 8018), herpes simplex type I (ATCC HB 8068), herpes simplex type II (ATCC HB 8067), influenza virus (ATCC CL 189), influenza A virus, matrix protein (ATCC HB 64), influenza A virus, nucleoprotein (ATCC HB 65), influenza A Bangkok/1/79HA (ATCC HB 66), influenza AWSN NP (ATCC HB 67), SV40 large T antigen (ATCC TIB 115), SV40 large T antigen, C-terminal end (ATCC TIB 117), and SV40 nonviral T antigen (ATCC TIB 116). Examples of other hybridomas include those secreting antibodies to tumor associated antigens or to human lymphocyte antigens, such as those reactive to human tumor-associated CEA, high mw (ATCC CRL 8019); human tumor-associated alpha-fetoprotein, $IgG_1K$ (ATCC HB 134); human B lymphocyte HLA-DR, monomorphic, $IgG_{2b}$ (ATCC HB 104); human T lymphocyte T cell precursors, $IgG_1$ (ATCC CRL 8022); human T lymphocyte T cell subset, helper, $IgG_{2b}$ (ATCC CRL 8002); T subset, suppressor/cytotoxic, human, $IgG_1$ (ATCC CRL 8013); T cell subset, suppressor/cytotoxic, human, $IgG_{2a}$ (ATCC CRL 8014); T cells, peripheral, human $IgG_1$ (ATCC CRL 8000); T cells, peripheral, human $IgG_{2a}$ (ATCC CRL 8001); thymocytes, "common," human, $IgG_1$ (ATCC CRL 8020).

These lines and others of similar nature can be utilized to copy the mRNA coding for variable region, using the UIG probes. Of particular interest are antibodies with specificity to human tumor antigens.

Expression vehicles include plasmids or other vectors. Preferred among these are vehicles carrying a functionally complete human constant heavy or light chain sequence having appropriate restriction sites engineered so that any variable heavy or light chain sequence with the appropriate cohesive ends can be easily inserted thereinto. Human constant heavy or light chain sequence-containing vehicles are thus an important embodiment of the invention. These vehicles can be used as intermediates for the expression of any desired complete heavy or light chain in any appropriate host.

One preferred host is yeast. Yeast provides substantial advantages for the production of immunoglobulin light and heavy chains. Yeasts carry out post-translational peptide modifications including glycosylation. A number of recombinant DNA strategies now exist which utilize strong promoter sequences and high copy number plasmids which can be used for overt production of the desired proteins in yeast. Yeast recognizes leader sequences on cloned mammalian gene products and secretes peptides bearing leader sequences (i.e. prepeptides) (Hitzman, et al., 11th International Conference on Yeast, Genetics and Molecular Biology, Montpelier, France, Sep. 13–17, 1982).

Yeast gene expression systems can be routinely evaluated for the level of heavy and light chain production, protein stability, and secretion. Any of a series of yeast gene expression systems incorporating promoter and termination elements from the actively expressed genes coding for glycolytic enzymes produced in large quantities when yeasts are grown in mediums rich in glucose can be utilized. Known glycolytic genes can also provide very efficient transcription control signals. For example, the promoter and terminator signals of the iso-1-cytochrome C (CYC-1) gene can be utilized.

The following approach can be taken for evaluating optimal expression plasmids for the expression of cloned immunoglobulin cDNAs in yeast.

(1) The cloned immunoglobulin DNA linking V and C regions is attached to different transcription promoters and terminator DNA fragments;

(2) the chimeric genes are placed on yeast plasmids used for protein overproduction (see, for example. Beggs, J. D., *Molecular Genetics and Yeast,* Alfred Benzon Symposium, 16, Copenhagen (1981));

(3) Additional genetic units such as a yeast leader peptide may be included on immunoglobulin DNA constructs to obtain antibody secretion;

(4) A portion of the sequence, frequently the first 6 to 20 codons of the gene sequence may be modified to represent preferred yeast codon usage.

(5) The chimeric genes are placed on plasmids used for integration into yeast chromosomes.

The following approaches can be taken to simultaneously express both light and heavy chain genes in yeast.

(1) The light and heavy chain genes are each attached to a yeast promoter and a terminator sequence and placed on the same plasmid. This plasmid can be designed for either autonomous replication in yeast or integration at specific sites in the yeast chromosome.

(2) The light and heavy chain genes are each attached to a yeast promoter and terminator sequence on separate plasmids containing different selective markers. For example, the light chain gene can be placed on a plasmid containing the trp1 gene as a selective marker, while the heavy chain gene can be placed on a plasmid containing ura3 as a selective marker. The plasmids can be designed for either autonomous replication in yeast or integration at specific sites in yeast chromosomes. A yeast strain defective for both selective markers is either simultaneously or sequentially transformed with the plasmid containing light chain gene and with the plasmid containing heavy chain gene.

(3) The light and heavy chain genes are each attached to a yeast promoter and terminator sequence on separate plasmids each containing different selective markers as described in (2) above. A yeast mating type "a" strain defective in the selective markers found on the light and heavy chain expression plasmids (trp1 and ura3 in the above example) is transformed with the plasmid containing the light chain gene by selection for one of the two selective markers (trp1 in the above example). A yeast mating type "alpha" strain defective in the same selective markers as the "a" strain (i.e. tri1 and ura3 as examples) is transformed with a plasmid containing the heavy chain gene by selection for the alternate selective marker (i.e. ura3 in the above example). The "a" strain containing the light chain plasmid (phenotype: $Trp^+Ura^-$ in the above example) and the strain containing the heavy chain plasmid (phenotype: $Trp^- Ura^+$ in the above example) are mated and diploids are selected which are prototrophic for both of the above selective markers ($Trp^+ Ura^+$ in the above example).

Among bacterial hosts which may be utilized as transformation hosts, *E. coli* K12 strain 294 (ATCC 31446) is particularly useful. Other microbial strains which may be used include *E. coli* X1776 (ATCC 31537). The aforementioned strains, as well as *E. coli* W3110 (ATCC 27325) and other enterobacteria such as *Salmonella typhimurium* or *Serratia marcescens*, and various Pseudomonas species may be used.

In general, plasmid vectors containing replicon and control sequences which are derived from species compatible with a host cell are used in connection with these hosts. The vector ordinarily carries a replication site, as well as specific genes which are capable of providing phenotypic selection in transformed cells. For example, *E. coli* is readily transformed using pBR322, a plasmid derived from an *E. coli* species (Bolivar, et al., *Gene*, 2: 95 (1977)). pBR322 contains genes for ampicillin and tetracycline resistance, and thus provides easy means for identifying transformed cells. the pBR322 plasmid or other microbial plasmids must also contain, or be modified to contain, promoters which can be used by the microbial organism for expression of its own proteins. Those promoters most commonly used in recombinant DNA construction include the beta-lactamase (penicillinase) and lactose (beta-galactosidase) promoter systems (Chang et al., *Nature*, 275: 615 (1978); Itakura et al., *Science*, 198: 1056 (1977)); and tryptophan promoter systems (Goeddel et al., *Nucleic Acids Research*, 8: 4057 (1980); EPO Publication No. 0036776). While these are the most commonly used, other microbial promoters have been discovered and utilized.

For example, a genetic construct for any heavy or light chimeric immunoglobulin chain can be placed under the control of the leftward promoter of bacteriophage lambda ($P_L$). This promoter is one of the strongest known promoters which can be controlled. Control is exerted by the lambda repressor, and adjacent restriction sites are known.

The expression of the immunoglobulin chain sequence can also be placed under control of other regulatory sequences which may be "homologous" to the organism in its untransformed state. For example, lactose dependent *E. coli* chromosomal DNA comprises a lactose or lac operon which mediates lactose digestion by elaborating the enzyme beta-galactosidase. The lac control elements may be obtained from bacteriophage lambda pLAC5, which is infective for *E. coli*. The lac promoter-operator system can be induced by IPTG.

Other promoter/operator systems or portions thereof can be employed as well. For example, arabinose, colicine E1, alactose, alkaline phosphatase, tryptophan, xylose, tac, and the like can be used. Other bacterial gene expression control elements can be utilized to achieve the expression of immunoglobulin proteins. For example, a gene with a bacterial secretion signal peptide coding region can be expressed in bacteria, resulting in secretion of the immunoglobulin peptide which was originally linked to the signal peptide.

Other preferred hosts are mammalian cells, grown in vitro in tissue culture, or in vivo in animals. Mammalian cells provide post-translational modifications to immunoglobulin protein molecules including leader peptide removal, correct folding and assembly of heavy and light chains, glycosylation at correct sites, and secretion of functional antibody protein from the cell as $H_2L_2$ molecules.

Mammalian cells which may be useful as hosts for the production of antibody proteins include cells of fibroblast origin, such as Vero (ATCC CRL 81) or CHO-K1 (ATCC CRL 61), or cells of lymphoid origin, such as the hybridoma Sp2/0=Ag14 (ATCC CRL 1581) or the myeloma P3X63Ag8 (ATCC TIB 9), and its derivatives.

Several possible vector systems are available for the expression of cloned heavy chain and light chain genes in mammalian cells. One class of vectors utilizes DNA elements which provide an autonomously replicating extrachromosomal plasmid, derived from animal viruses, such as bovine papillomavirus (Sarver, N. et al., *Proc. Natl. Acad. Sci., USA*, 79: 7147 (1982)), polyoma virus (Deans, R. J. et al., *Proc. Natl. Acad. Sci., USA*, 81: 1292 (1984)), or SV40 virus (Lusky, M. and Botchan, M., *Nature*, 293: 79 (1981)). A second class of vectors relies upon the integration of the desired gene sequences into the host cell chromosome. Cells which have stably integrated the introduced DNA into their chromosomes can be selected by also introducing drug resistance genes such as *E. coli* gpt (Mulligan, R. C. and Berg, P., *Proc. Natl. Acad. Sci., USA*, 78: 2072 (1981)) or Tn5 neo (Southern, P. J. and Berg, P., *J. Mol. Appl. Genet.*, 1: 327 (1982)). The selectable marker gene can be either directly linked to the DNA gene sequences to be expressed, or introduced into the same cell by co-transfection (Wigler, M. et al., *Cell*, 16: 77 (1979)).

Since an immunoglobulin cDNA is comprised only of sequences representing the mature mRNA encoding an antibody protein or its precursor, additional gene expression elements regulating transcription of the gene and processing of the RNA are required for optimal synthesis of immunoglobulin mRNA. These elements may include splice signals, as well as transcription promoters including inducible promoters, enhancers, and termination signals. cDNA expression vectors incorporating such elements include those described by Okayama, H. and Berg, P., *Mol. Cell Biol.*, 3: 280 (1983); Cepko, C. L. et al., *Cell*, 37: 1053 (1984); and Kaufman, R. J., *Proc. Natl. Acad. Sci., USA*, 82:689 (1985).

An approach to evaluate optimal vectors for the expression of immunoglobulin cDNA in mammalian cells involves first placing the immunoglobulin DNA sequences into vectors capable of stably integrating into the cell genome, or replicating autonomously as an extrachromosomal plasmid. The vectors can be used to evaluate different gene expression elements for optimal immunoglobulin synthesis.

An additional advantage of mammalian cells as hosts is their ability to express chimeric immunoglobulin genes which are derived from genomic sequences. Thus, mammalian cells may express chimeric immunoglobulin genes which are comprised of a variable region cDNA module plus a constant region which is composed in whole or in part of genomic sequences. Several human constant region genomic clones have been described (Ellison, J. W. et al., *Nucl. Acids Res.*, 10: 4071 (1982), or Max, E. et al., *Cell*, 29: 691 (1982)). The use of such genomic sequences may be convenient for the simultaneous introduction of immunoglobulin enhancers, splice signals, and transcription termination signals along with the constant region gene segment.

Different approaches can be followed to obtain complete $H_2L_2$ antibodies.

First, one can separately express the light and heavy chains followed by in vitro assembly of purified light and heavy chains into complete $H_2L_2$ IgG antibodies. The assembly pathways used for generation of complete $H_2L_2$ IgG molecules in cells have been extensively studied (see, for example, Scharff, M., *Harvey Lectures*, 69: 125 (1974)). In vitro reaction parameters for the formation of IgG antibodies from reduced isolated light and heavy chains have been defined by Beychok, S., *Cells of Immunoglobulin Synthesis*, Academic Press, New York, page 69, 1979.

Second, it is possible to co-express light and heavy chains in the same cells to achieve intracellular association and linkage of heavy and light chains into complete $H_2L_2$ IgG antibodies. The co-expression can occur by using either the same or different plasmids in the same host.

In a preferred embodiment, the co-expression can occur with aid of secretion signals useful in yeast or bacteria. Under such conditions, fully folded and assembled $H_2L_2$ immunoglobulins can be obtained.

The present invention provides plasmid secretion vectors which, when used to transform bacterial host cells, enable the externalization of expressed foreign proteins. The plasmids comprise a DNA sequence coding for a pectate lyase signal sequence of a gram-negative bacterium. These plasmids are in turn used to prepare derivative plasmids containing a fragment consisting essentially of the signal sequence and a non-host protein gene sequence, and plasmids in which this fragment is positioned adjacent to a host-compatible promoter sequence. The latter plasmids, containing the promoter sequence, when used to transform a bacterial host cell, are capable of directing the translation and externalization of the foreign proteins by the host cell. The present invention thus provides a means by which foreign proteins can be produced in high volume by host cells without the necessity for cell lysis, and the attendant extensive purification procedures required to remove cytoplasmic contaminants. Isolation of expressed non-host proteins from the host would therefore be significantly facilitated if they can be externalized in this manner. The pectate lyase (pel) signal sequence functions well in the *E. coli* cell system, and the present secretion vectors have been shown to be capable of causing the secretion of virtually any protein used in the system. Secretion of the protein into the periplasmic space or extracellular environment is achieved by the insertion of a known gene sequence coding for a particular protein into the plasmid vector at some point after the pel signal sequence, and a suitable promoter sequence and then transforming a bacterial host cell with the secretion vector.

As disclosed herein, recombinant plasmids have been prepared which, when used to transform bacterial host cells, permit the secretion of foreign protein outside the cytoplasmic membrane of the host cell. The invention is based on the observation that when pectate lyase genes are cloned and expressed in *E. coli*, large quantities of pectate lyase are secreted either into the periplasmic space or culture fluid in which the bacterium is grown. This leads to the conclusion that the pectate lyase signal sequence is recognized and translated in a non-Erwinia bacterial system. When plasmids were prepared containing the signal sequence of the pel gene in combination with a foreign protein gene it was discovered that, in the presence of a host-compatible promoter, the signal sequence for the pel gene is capable of directing the distribution of the protein from the cytoplasm into a periplasmic space, or beyond the cell wall, into the extracellular environment. The secretion vectors of the present invention are particularly useful in that their utility is not limited to a single strain, but rather have been shown to function efficiently in a wide variety of readily available *E. coli* strains, all of which routinely secrete at least some of the recombinant protein directly into the culture medium. The plasmids have also been shown to be operable with a broad range of foreign gene sequences, both procaryotic and eucaryotic. Further, the proteins so produced have been confirmed to be secreted in their natural and proper configuration.

The manner of preparation of the plasmids, and their use in bacterial transformation is set out in greater detail below.

Identification and Isolation of the Pectate Lyase Gene

Pectate lyase is one of the enzymes which catalyzes the hydrolysis of polygalacturonic acid, and is found in a number of phytopathogenic bacterial and fungi. Three pectate lyases, referred to as PLa, PLb and PLc, have been identified from the bacterium *Erwinia carotovora*, and similar enzymes are also known in the bacterial *Erwinia chrysanthemi* (Keen et al., *J. Bacteriol.* 168: 595–606, 1986) and *Pseudomonas fluorescens*, as well as the fungus *Rhizoctonia solani*. The genes from both *E. carotovora* (Lei et al., *Gene* 35: 63–80, 1985) and *E. chrysanthemi* (Keen et al., supra) have been isolated. In the present case, the pelB gene from *E. carotovora* was used as a source of the pectate lyase signal sequence. Plasmid pSS1004 (Lei et al., *J. Bacteriol.* 169: 4379–4383, 1987) contains the *E. carotovora* pelB gene. The restriction sites around the signal sequence were identified based on the DNA sequence of the gene. The N-terminal amino acid sequence was also determined to confirm the location of the leader peptide. Treatment of the pSS1004 plasmid with HaeIII and EcoRI restriction enzymes produced a fragment containing the leader sequence. The gene sequence and the corresponding amino acid sequence of the pelB signal peptide is shown in FIG. 36A. Alternatively, the peptide sequence may be chemically synthesized by known methods of peptide synthesis.

Construction of Secretion Vectors

Once the fragment containing the appropriate signal sequence has been identified and isolated, it is then inserted into a cloning vehicle, preferably a plasmid. The present vectors are prepared in accordance with the general principles of vector construction known in the art. As used in the present specification and claims, "secretion" refers to transport of the protein into the periplasmic space, and "excretion" refers to the transport of the protein into the culture medium.

In order to eventually achieve transcription and translation of the inserted gene, the gene must be placed under the control of a promoter compatible with the chosen host cell. A promoter is a region of DNA at which RNA polymerase attaches and initiates transcription. The promoter selected may be any one which has been isolated from or is capable of functioning in the host cell organism. For example, *E. coli* has numerous promoters such as the lac or recA promoter associated with it, its bacteriophages or its plasmids. Also, phage promoters, such as the λ phage $P_L$ and $P_R$ promoters may be used to direct high level production of the products coded for having the segments of DNA adjacent to it. The products may be natural, synthetic or recombinant.

An initiation signal is also necessary in order to attain efficient translation of the gene. For example, in *E. coli* mRNA, a ribosome binding site includes the translational start condon (AUG or GUG) and another sequence complementary to the bases of the 3'-end of 16S ribosomal RNA. Several of these latter sequences (Shine-Dalgarno or S-D) have been identified in *E. coli* and other suitable host cell types. Any SD-ATG sequence which is compatible with the host cell system can be employed. These include, but are not limited to, the cro gene or N gene of coliphage lambda, or the *E. coli* tryptophan E, D, C, B or A genes.

A number of methods exist for the insertion of DNA fragments into cloning vectors in vitro. DNA ligase is an enzyme which seals single-stranded nicks between adjacent nucleotides in a duplex DNA chain; this enzyme may therefore be used to covalently join the annealed cohesive ends produced by certain restriction enzymes. Alternately, DNA ligase can be used to catalyze the formation of phosphodiester bonds between blunt-ended fragments. Finally, the enzyme terminal deoxynucleotidyl transferase may be employed to form homopolymeric 3'-single-stranded tails at the ends of fragments; by addition of oligo (dA) sequences to the 3'-end of one population, and oligo (dT) blocks to 3'-ends of a second population, the two types of molecules can anneal to form dimeric circles. Any of these methods may be used to ligate the gene segment, promoter and other control elements into specific sites in the vector. Thus, the coding sequence for a particular protein is ligated into the chosen vector in a specific relationship to the vector promoter and control elements and to the pel signal sequence, so that the protein gene sequence is in the correct reading frame with respect to the vector ATG sequence. The vector employed will typically have a marker function, such as ampicillin resistance or tetracycline resistance, so that transformed cells can be identified. The vector may be any of the known expression vectors or their derivatives; among the most frequently used are plasmid vectors such as pBR322, pAC105, pVA5, pACYC177, PKH47, pACYC184, pUB110, pMB9, pBR325, ColEl, pSC101, pBR313, pML21, RSF2124, pCR1 or RP4; bacteriophage vectors such as lambda gtll, lambda t-WES-lambdaB, Charon 28, Charon 4A, lambda gt-1-lambda BC, lambda-gt-1-lambda B, M13mp7, M13mp8, M13mp9; SV40 and adenovirus vectors, and yeast vectors.

The present invention preferably employs a plasmid as the cloning vector. For example, the approach taken in the present examples, in the cloning of a number of different proteins in *E. coli*, was to first separately clone the PLb signal sequence. This was achieved by isolation of the HaeIII+EcoRI digest fragment from plasmid pSS1004 which contains the entire pectate lyase B sequence. This fragment is then ligated into a pBR322 plasmid, which has been digested with SspI, ligated with an SstI linker, and then digested with EcoRI. Thus formed is the plasmid pING173 containing the pelB signal sequence. The pING173 plasmid is then used as a cloning vehicle for the pelB signal sequence, which may be subsequently ligated into a plasmid containing the sequence of the protein of interest. The plasmid so prepared contains a hybrid gene consisting of the pelB signal sequence adjacent to the relevant protein gene sequence; an appropriate promoter sequence may then be inserted at the 5'-terminus of the hybrid gene thus creating the final expression vector. Alternately, a plasmid containing the promoter sequence and the pelB signal sequence can first be prepared, and then the protein gene sequence may be inserted downstream of the promoter-signal sequences. Promoters which have proven particularly useful in the present invention are the *Salmonella typhimurium* araBAD and *E. coli* lac promoters in combination with an *E. coli* host system. However, any other suitable promoter which is compatible with the host system of choice may also be employed. Prepared by the foregoing method are plasmid expression vectors containing the genes for thaumatin, and L6 chimeric Fab, but it will be readily apparent to one skilled in the art that genes for any type of protein may be used in the present vectors and methods.

Isolation of the Gene Product

The present invention permits the gene product to be isolated from either the periplasmic space or the surrounding growth medium. The location of the expressed protein appears to be dependent on the particular strain utilized as the host. One of the most unexpected aspects of the present invention is that all strains tested were capable of excreting at least some of the recombinant product into the culture medium. The principal distinction between strains is the ratio of the amount of excreted product (i.e., that which is transported into the medium) to the amount secreted into the periplasmic space. Among those *E. coli* strains which show high levels of excretion are MC1061, JM103 and 706. While proteins which are excreted into the culture fluid are readily isolatable therefrom by known protein recovery techniques, the recovery of protein localized in the periplasmic space requires penetration of the cell wall in order to achieve release of the proteins without disruption of the cytoplasmic membrane. One technique of removal of periplasmic proteins is that originally described by Zinder and Arndt (*PNAS USA* 42: 586–590, 1956), which involves removal of the cell wall. Briefly, the cells are treated with egg albumin, which contains lysozyme, producing cellular spheres, on spheroplasts, which have large portions of the cell wall removed. Periplasmic proteins may also be isolated by a mechanism which does not require removal of the cell wall, but instead causes release of the proteins. Cells are placed in a hypertonic sucrose medium containing ethylene diamine tetraacetic acid (EDTA); this medium causes the cells to lose water and shrink, so that the cytoplasmic membrane draws away from the cell wall. The cells are then placed in a magnesium chloride solution which induces an osmotic shock: the osmotic pressure outside the cell decreases, causing water to rush into the cell, which swells the cell and causes the expulsion of periplasmic proteins beyond the outer membrane. Variations in the foregoing procedures will be readily apparent to one skilled in the art.

Also, preparation of chimeric Fab fragments can be carried out by the methods of the invention.

The methods described herein can also be used to switch the class of any antibody of a given specificity and class to an antibody of the same specificity but of a different class, whether human or non-human. For example, human IgM antibodies can be transmuted to human IgG antibodies by preparing constructs containing human constant IgG cDNA or genomic sequences, linked to variable human cDNA sequences obtained from a cell producing the original IgM antibody. These constructs are then introduced into appropriate hosts and expressed.

Polypeptide Products

The invention provides "chimeric" immunoglobulin chains, either heavy or light. A chimeric chain contains a constant region substantially similar to that present in the heavy chain or light chain respectively, of a natural human immunoglobulin, and a variable region having any desired antigenic specificity. The variable region is either from human or non-human origin.

The invention also provides immunoglobulin molecules having heavy and light chains associated so that the overall molecule exhibits desired binding and recognition properties. Various types of immunoglobulin molecules are provided: monovalent, divalent, dispecific (i.e., with different variable regions), molecules with chimeric heavy chains and non-chimeric light chains, or molecules with variable binding domains attached to peptide moieties carrying desired functions.

Antibodies having chimeric heavy chains of the same or different variable region binding specificity and non-chimeric (i.e., all human or all non-human) light chains, can be prepared by appropriate association of the needed polypeptide chains. These chains are individually prepared by the modular assembly methods of the invention.

Chimeric Fab fragments are also part of this invention.

Uses

The antibodies of the invention having human constant region can be utilized for passive immunization, especially in humans, without negative immune reactions such as serum sickness or anaphylactic shock. The antibodies can, of course, also be utilized in prior art immunodiagnostic assays and kits, in labelled form for in vitro imaging, wherein the label an be a radioactive emitter, or an NMR contrasting agent such as a carbon-13 nucleus, or an X-ray contrasting agent, such as a heavy metal nucleus. The antibodies can also be used in vitro localization of antigens by appropriate labelling.

The antibodies can be used for therapeutic purposes by themselves in complement mediated lysis or can be coupled to toxins or other therapeutic moieties.

Class switching of antibodies is useful when it is desired to change the association, aggregation or other properties of antibodies obtained from cell fusion or hybridoma technology. For example, most human-human monoclonals are of the IgM class, which are known for their ease of reduction and aggregation. Changing such antibodies to other antibody types, such as IgG, IgA, or IgE, is thus of great benefit.

Mixed antibody-enzyme molecules can be used for immunodiagnostic methods, such as ELISA. Mixed antibody-peptide effector conjugates can be used for targeted delivery of the effector moiety with a high degree of efficacy and specificity.

Having now generally described the invention, the same will be further understood by reference to certain specific examples which are included herein for purposes of illustration only and are not intended to be limiting unless otherwise specified.

EXPERIMENTAL

Materials and Methods

Tissue Culture Cell Lines

The human cell lines GM2146 and GM1500 were obtained from the Human Mutant Cell Repository (Camden, N.J.) and cultured in RPMI1640 plus 10% fetal bovine serum (M. A. Bioproducts). The cell lines Sp2/0 and CRL 8017 were obtained from the American Type Culture Collection and grown in Dulbecco's Modified Eagle Medium (DMEM) plus 4.5 g/l glucose (M. A. Bioproducts) plus 10% fetal bovine serum (Hyclone, Sterile Systems, Logan, Utah). Media were supplemented with penicillin/streptomycin (Irvine Scientific, Irvine, Calif.).

Recombinant Plasmid and Bacteriophase DNAs

The plasmids pBR322, pL1 and pUC12 were purchased from Pharmacia P-L Biochemicals (Milwaukee, Wis.). The plasmids pSV2-neo and pSV2-gpt were obtained from BRL (Gaithersburg, Md.), and are available from the American Type Culture Collection (Rockville, Md.). pHu-gamma-1 is a subclone of the 8.3 Kb HindIII to BamHI fragment of the human IgG1 chromosomal gene. A separate isolation of the human IgG1 chromosomal gene is described by Ellison, J. W. et al., Nucl. Acids Res., 10: 4071 (1982). M8alphaRX12 contains the 0.7 Kb XbaI to EcoRI fragment containing the mouse heavy chain enhancer from the J-C intron region of the M603 chromosomal gene (Davis, M. et al., Nature, 283: 733) (1979) inserted into M13mp10. G-tailed pUC9 was purchased from Pharmacia P-L. DNA manipulations involving purification of plasmid DNA by buoyant density centrifugation, restriction endonuclease digestion, purification of DNA fragments by agarose gel electrophoresis, ligation and transformation of E. coli were as described by Maniatis, T. et al., Molecular Cloning: A Laboratory Manual, (1982). Restriction endonucleases and other DNA/RNA modifying enzymes were purchased from Boehringer-Mannheim (Indianapolis, Ind.), BRL, New England Biolabs (Beverly, Mass.) and Pharmacia P-L.

Oligonucleotide Preparation

Oligonucleotides were either synthesized by the triester method of Ito et al., (Nucl. Acids Res., 10: 1755 (1982)), or were purchased from ELESEN, Los Angeles, Calif. Tritylated, deblocked oligonucleotides were purified on Sephadex-G50, followed by reverse-phase HPLC with a 0–25% gradient of acetonitrile in 10 mM triethylamine-acetic acid, pH 7.2, on a C18 uBondapak column (Waters Associates). Detritylation was in 80% acetic acid for 30 min., followed by evaporation thrice. Oligonucleotides were labeled with [gamma-$^{32}$P]ATP plus T4 polynucleotide kinase.

RNA Preparation and Analysis

Total cellular RNA was prepared from tissue culture cells by the method of Auffray, C. and Rougeon, F. (Eur. J. Biochem., 107: 303 (1980)) or Chirgwin, J. M. et al. (Biochemistry, 18: 5294 (1979)). Preparation of poly(A)$^+$ RNA, methyl-mercury agarose gel electrophoresis, and "Northern" transfer to nitrocellulose were as described in Maniatis, T. et al., supra. Total cellular RNA or poly(A)$^+$ RNA was directly bound to nitrocellulose by first treating the RNA with formaldehyde (White, B. A. and Bancroft, F. C., J. Biol. Chem., 257: 8569 (1982)). Hybridization to filterbound RNA was with nick-translated DNA fragments using conditions described by Margulies, D. H. et al. (Nature, 295: 168 (1982)) or with $^{32}$P-labelled oligonucleotide using 4×SSC, 10× Denhardt's, 100 ug/ml salmon sperm DNA at 37° C. overnight, followed by washing in 4×SSC at 37° C.

cDNA Preparation and Cloning

Oligo-dT primed cDNA libraries were prepared from poly(A)$^+$ RNA from GM1500 and GM2146 cells by the methods of Land, H. et al. (Nucl. Acids Res., 9: 2251 (1981)) and Gubler, V. and Hoffman, B. J., Gene, 25: 263 (1983), respectively. The cDNA libraries were screened by in situ hybridization (Maniatis, T., supra) with $^{32}$P-labelled oligonucleotides using the conditions shown above, or with nick-translated DNA fragments using the conditions of de Lange et al. (Cell, 34: 891 (1983)).

Oligonucleotide Primer Extension and Cloning

Poly(A)$^+$ RNA (20 ug) was mixed with 1.2 ug primer in 40 ul of 64 mM KCl. After denaturation at 90° C. for 5 min. and then chilling in ice, 3 units Human Placental Ribonuclease Inhibitor (BRL) was added in 3 ul of 1M Tris-HCl, pH 8.3. The oligonucleotide was annealed to the RNA at 42° C. for 15 minutes, then 12 ul of 0.05M DTT, 0.05M MgCl$_2$, and 1 mM each of dATP, dTTP, dCTP, and dGTP was added. 2 ul of alpha-$^{32}$P-dATP (400 Ci/mmol, New England Nuclear) was added, followed by 3 ul of AMV reverse transcriptase (19 units/ul, Life Sciences).

After incubation at 42° C. for 105 min., 2 ul 0.5 M EDTA and 50 ul 10 mM Tris, 1 mM EDTA, pH 7.6 were added. Unincorporated nucleotides were removed by Sephadex G-50 spun column chromatography, and the RNA-DNA hybrid was extracted with phenol, then with chloroform, and precipitated with ethanol. Second strand synthesis, homopolymer tailing with dGTP or dCTP, and insertion into homopolymer tailed vectors was as described by Gubler and Hoffman, supra.

Site-Directed Mutagenesis

Single stranded M13 subclone DNA (1 ug) was combined with 20 ng oligonucleotide primer in 12.5 ul of Hin buffer (7 mM Tris-HCl, pH 7.6, 7 mM MgCl$_2$, 50 mM NaCl). After heating to 95° C. in a sealed tube, the primer was annealed to the template by slowly cooling from 70° C. to 37° C. for 90 minutes. 2 ul dNTPs (1 mM each), 1 ul $^{32}$P-dATP (10 uCi), 1 ul DTT (0.1 M) and 0.4 ul Klenow DNA PolI (2u, Boehringer Mannheim) were added and chains extended at 37° C. for 30 minutes. To this was added 1 ul (10 ng) M13 reverse primer (New England Biolabs), and the heating/ annealing and chain extension steps were repeated. The reaction was stopped with 2 ul of 0.5M EDTA, pH 8, plus 80 ul of 10 mM Tris-HCl, pH 7.6, 1 mM EDTA. The products were phenol extracted and purified by Sephadex G-50 spun column chromatography and ethanol precipitated prior to restriction enzyme digestion and ligation to the appropriate vector.

Transfection of Myeloma Tissue Culture Cells

A variation of the method of Ochi, A. et al. (*Nature,* 302: 340 (1983)) was used for protoplast fusion. 50 ml of bacteria at $A_{600}$ of 0.7 were converted to protoplasts by the method of Sandri-Goldin, R. M. et al. (*Mol. Cell. Biol.,* 1: 743 (1981)), then diluted with 20 ml DMEM plus 10% FBS (final volume is 25 ml). Sp2/0 cells were harvested, pelleted at 2,200×g, washed, repelleted and resuspended in DMEM at $2-5\times10^6$/ml. Bacterial protoplasts (10 ml) were mixed with $10\times10^6$ Sp2/0 cells and pelleted by centrifugation at 4,000×g at 22° C. for 20 min. After pipetting off the supernatant, the pellet was suspended in the remaining drop of medium by flicking the tube. 2 ml of 10% DMSO, 37% (w/v) PEG6000 (Kodak) in DMEM was added dropwise with mixing over 45 sec. After 15 sec., 2 ml of 42% PEG6000 in DMEM was added over 45 sec. Complete DMEM (45 ml) was slowly added with mixing. Cells were pelleted at 2500×g, then washed and pelleted thrice.

The electroporation method of Potter, H. et al. (*Proc. Natl. Acad. Sci., USA,* 81: 7161 (1984)) was used. After transfection, cells were allowed to recover in complete DMEM for 48–72 hours, then were seeded at 10,000 to 50,000 cells per well in 96-well culture plates in the presence of selective medium. G418 (GIBCO) selection was at 0.8 mg/ml, mycophenolic acid (Calbiochem) was at 6 ug/ml plus 0.25 mg/ml xanthine, and HAT (Sigma) was at the standard concentration.

Assays for Immunoglobulin Synthesis and Secretion

Secreted immunoglobulin was measured directly from tissue culture cell supernatants. Cytoplasmic protein extract was prepared by vortexing $1\times10^6$ cells in 160 ul of 1% NP40, 0.15 M NaCl, 10 mM Tris, 1 mM EDTA, pH 7.6 at 0° C., 15 minutes, followed by centrifugation at 10,000×g to remove insoluble debris.

Double antibody sandwich ELISA (Voller, A. et al., in *Manual of Clinical Immunology,* 2nd Ed., Eds. Rose, N. and Friedman, H., pp. 359–371, 1980) using affinity purified antisera was used to detect specific immunoglobulins. For detection of human IgG, the plate-bound antiserum is goat anti-human IgG (KPL, Gaithersburg, Md.) at 1/1000 dilution, while the peroxidase-bound antiserum is goat anti-human IgG (KPL or Tago, Burlingame) at 1/4000 dilution. For detection of human immunoglobulin kappa, the plate-bound antiserum is goat anti-human kappa (Tago) at 1/500 dilution, while the peroxidase-bound antiserum is goat anti-human kappa (Cappel) at 1/1000 dilution.

Antibodies binding hepatitis B surface antigen were detected using a commercial (Abbott, AUSAB) assay.

EXAMPLES

The following examples show the preparation of chimeric antibodies each having a human constant region and a non-human variable region. These examples outline the step-by-step process of preparing the chimeric antibodies.

Example I

Human Antibody Constant Region Gene Modules and cDNA Expression Vectors (1) Preparation of cDNA Clones, and Vehicles Containing Same, for Heavy Chain Human Constant Region The cell line GM2146 was used as the source in mRNA preparation and cDNA cloning. This cell line secretes IgG1 (Simmons, J. G. et al., *Scand. J. Immunol.,* 14: 1–13, 1981). Tests of this cell line indicated that it secretes IgA as well as IgG.

Figure 4A:
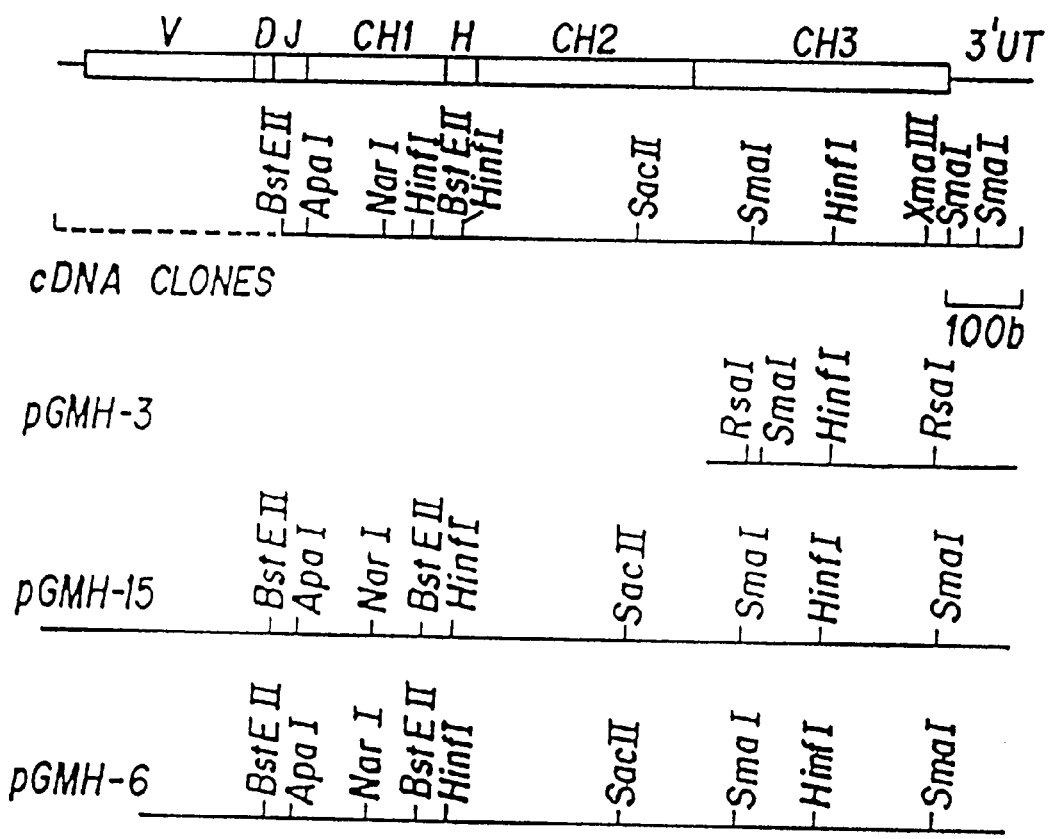
FIG. 4A: Synthesis of Human IgG1 human IgG1 heavy chain structure and cDNA clones.
Figure 4B:
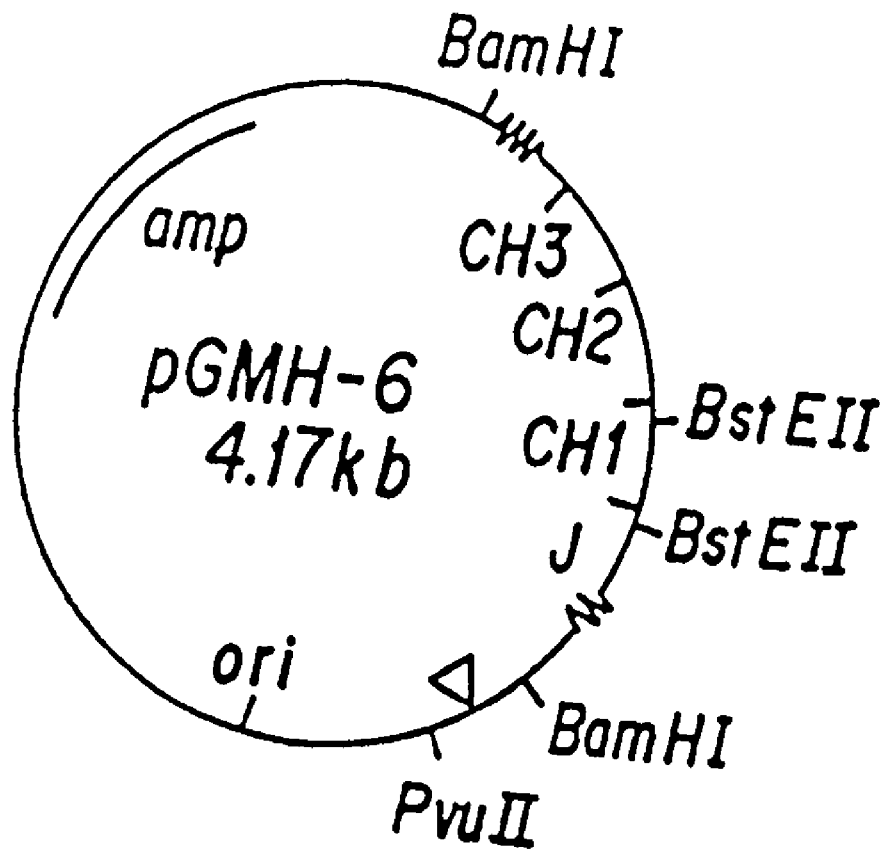
FIG. 4B: A human IgG1 constant region cloning vector, pGMH-6, for V region module insertion. A 1.5 kb deletion of pBR322 sequence between Bam HI and PvuII is marked. Not to scale.

The cell line was cloned, and results indicated that five of six subclones secreted IgG only, while one of six subclones secreted IgA only. Poly(A)$^+$ RNA was prepared from the cell line and a cDNA library was prepared from the poly(A)$^+$ RNA by the method of Gubler, U. and Hoffman, B. J., *Gene,* 25: 263–269 (1983). An initial plating of the cDNA transformed into *E. coli* strains HB101 and RR1 yielded a total of 1500 colonies, which were screened by hybridization to a HindIII to BamHI fragment of a genomic clone of human IgG1 (pHu-gamma-1). Four positive clones were found. A fragment containing the $C_H3$ coding region of one of these clones, pGMH-3 (FIG. 4), was used to rescreen the original library plus a new transformation of approximately 5000 colonies. Two of the largest clones, pGMH-6 and pGMH-15, were analyzed by restriction enzyme digestion (FIG. 4). Both clones contained the entire constant region of human IgG1, although it was discovered that pGMH-6 had deleted approximately 1500 base pairs of pBR322 DNA, apparently without affecting the IgG1 cDNA sequences.

Clone pGMH-6 provided the IgG1 constant region module in the construction of cloning vectors for heavy chain variable region cloning.

(2) Preparation of cDNA Clones, and Vehicles Containing Same, for Light Chain Human Constant Region A human cell line (GM1500) producing $IgG_2K$ was selected for the initial cloning phase. Poly(A)$^+$ RNA prepared from GM1500 is active in in vitro translation using rabbit reticulocyte extracts. A cDNA library was prepared from this RNA by the method of Land et al., *Nucl. Acids Res.,* 9: 2251–2266 (1981), utilizing KpnI digested and dG-tailed pQ23 as the cloning vector (FIG. 5). This vector contains BglII, KpnI and SstI sites inserted between the BamHI and SalI sites of pBR322.

In order to identify the cDNA clones generated from GM1500 RNA which correspond to light chain mRNA, a DNA probe, UIG-HuK, was synthesized and purified. The UIG-HuK oligonucleotide has the sequence 5'-AGCCACAGTTCGTTT-3', and is designed to hybridize to all functional human kappa mRNA species at the J-C junction. This probe was used to prime cDNA synthesis on GM1500 RNA in the presence of dideoxynucleotides and reverse transcriptase. From 1.2 ug of total GM1500 poly (A)$^+$ RNA was used in this experiment, the entire J sequence and some of the V region was read, demonstrating that (1) GM1500 RNA is intact, (2) the kappa probe is of the correct sequence, and (3) GM1500 light chain mRNA contains $J_K4$ sequences.

cDNA clones positive for hybridization to the light chain probe were selected. Since the probe hybridizes to the J-C junction, the most important point was to determine if the clones had complete constant region sequence in addition to the J region.

Figure 6A:
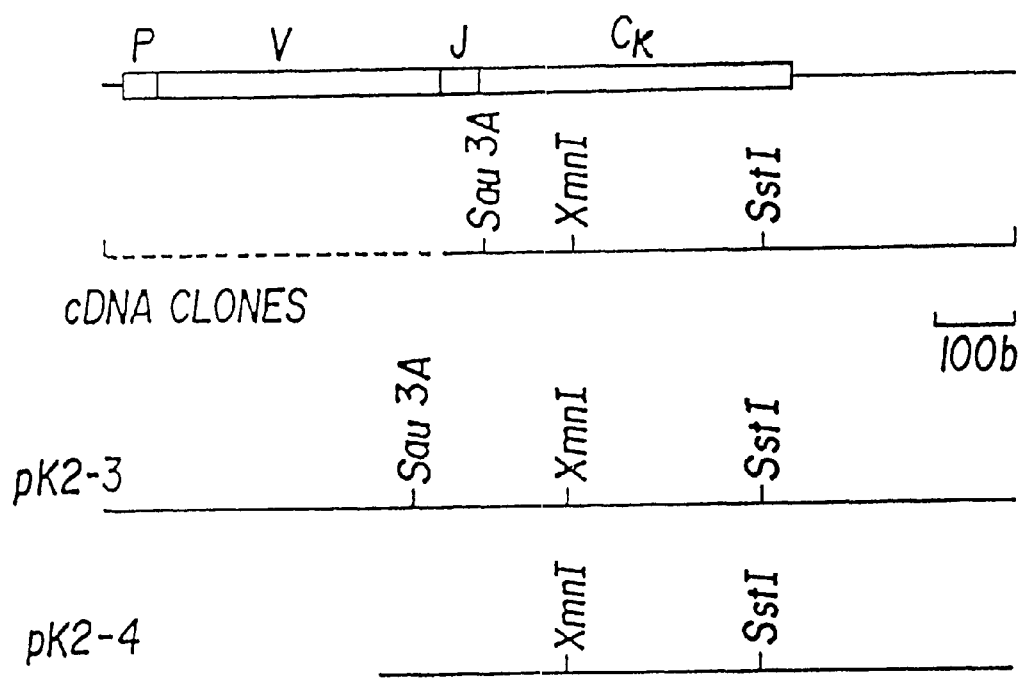
FIG. 6 shows in A. the synthesis and analysis of human light chain kappa genes. The Figure also shows in B. (not in scale) construction of a human $C_K$ region cloning vector pING2001.
Figure 6B:
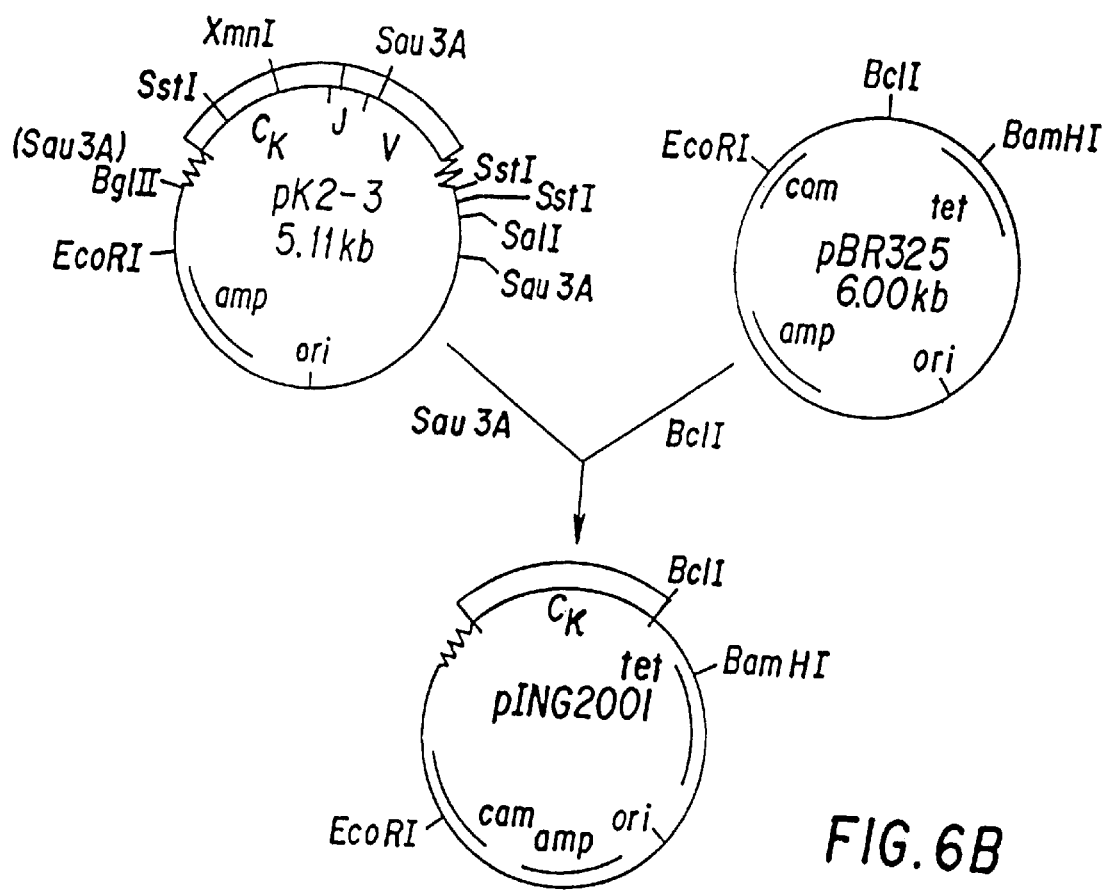

Insert sizes for the two largest kappa cDNA clones were 0.6 and 0.9 kb; restriction enzyme mapping indicated that the entire constant region coding sequence was present in both clones (FIG. 6). The human kappa cDNA clone pK2-3 was used to make the light chain constant region vector pING2001 by inserting the Sau3A fragment comprising the human kappa constant and J regions into the BclI site of pBR325 (FIG. 6B).

A variant of the human kappa cDNA clone was made by placing a HindIII site in the J region. This was carried out by in vitro mutagenesis using a $J_K$-HindIII oligonucleotide primer (FIG. 7c). The resultant plasmid is pGML60.

Figure 10:
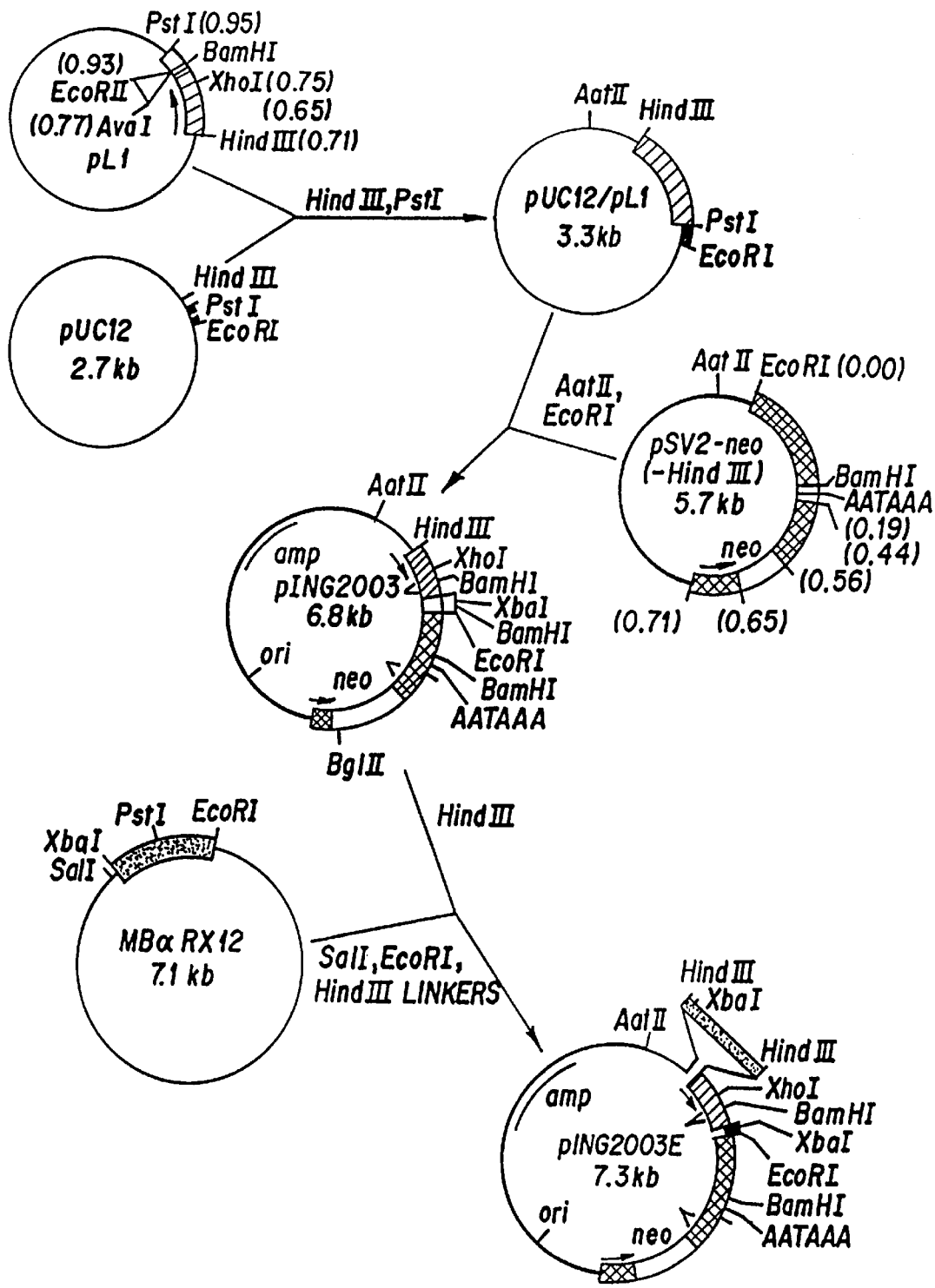
FIG. 10 shows the construction of cDNA cloning-expression shuttle vectors for mammalian cells. The vectors pING2003 and pING2003E are derived from pL1, pUC12, pSV2-neo and M8-alphaRX12. Stippled regions indicate mouse heavy chain enchancer DNA, hatched regions indicate SV-40 DNA from pL1, and cross-hatched regions indicate SV-40 DNA from pSV2-neo. In the vectors pING2003 and pIN2003E, thick lines represent pBR322 DNA from pSV2-neo, while thin lines present pUC12 DNA. Arrows indicate the locations and directions of SV-40 early region promoters, and indicates a complete SV-40 intron sequence. Not to scale.

A vector, pING2003, was constructed for the transfer and expression of cDNA sequences in mammalian cells (FIG. 10). This vector was constructed from pUC12 and two plasmids containing SV40 sequences. pL1 provides an SV40 early region promoter and an SV40 late region splice sequence. pSV2-neo sequences provide a selectable marker for mammalian cell transformation and SV40 polyadenylation signal sequences. pUC12 provides a multiple cloning site for cDNA insertion.

The pING2003 vector has several useful restriction sites for modifications. These include a HindIII site useful for the insertion of enhancer sequences, and a HindIII to XhoI fragment useful for the insertion of alternate promoter sequences. This vector is useful in the expression of cDNA genes in mammalian cells.

Addition of Enhancer Element to pING2003

Immunoglobulin enhancer elements have been shown to enhance transcription of genes in their vicinity in stably transformed mouse myeloma cells by several hundred fold (Gillies, S. D. et al., *Cell*, 33: 717, 1983; and Banerji, J. et al. *Cell*, 33: 729, 1983). To facilitate expression of the mouse-human immunoglobulin genes in mouse myeloma cells, the mouse immunoglobulin heavy chain enhancer element was added to the cDNA expression vector pING2003 (FIG. 10). The mouse heavy chain enhancer region DNA was isolated from an M13 subclone of mouse heavy chain genomic DNA (M8-alpha-RX12, Deans, R. J., unpublished). DNA isolated from a SalI plus EcoRI digestion of this subclone was modified with HindIII linkers and inserted into the HindIII site of pING2003, resulting in the new cDNA expression vector pING2003E. This vector is useful in the efficient expression of cDNA genes in mammalian cells, particularly mouse myeloma or hybridoma cell lines.

Example II

Human-Mouse Chimeric Anti-HBsAg Antibody Chain (1) Preparation of cDNA Clones and Vehicles Containing Same, for Heavy Chain Mouse Anti-HBsAg Variable Region The cell line CRL8017 was obtained from the ATCC and subcloned. Subclones were grown and tested for mouse IgG anti-hepatitis B binding activity using a commercially available anti HBsAg detection kit. Three positive subclones were found. Poly(A)+ RNA was prepared from one of these subclones, and was fractionated on a methylmercury agarose gel. The RNA contained intact light chain and heavy chain mRNA's as inferred from specific hybridization to kappa UIG-MJK primer, and to the mouse heavy chain UIG-MJH3 probe (see FIG. 7). In addition, the UIG-MJK primer was used for specific priming of anti-HBsAg poly(A)+ RNA in a dideoxy sequencing reaction. Sufficient sequence was read to show that a major kappa RNA of the anti-HBsAg cell line contains the $J_K2$ sequence.

The conditions for variable region cDNA synthesis were optimized by using heavy and light chain UIG primers on anti-HBsAg poly(A)+ RNA. Dideoxy chain extension experiments demonstrated that the mouse UIG-MJK primer and UIG-JH3 primer correctly primed kappa and heavy chain RNAs. When the reverse transcription was carried out in the absence of dideoxynucleotides, the main product using the kappa UIG-MJK primer was a 410+20 nucleotide fragment, while the main product using the heavy chain UIG-JH3 primer was a 430+30 nucleotide fragment. These correspond to the expected lengths of the variable and 5' untranslated regions of kappa and heavy chain immunoglobulin mRNAs. The conditions for the optimal priming of poly(A)+ RNA from CRL8017 cells should work well for poly(A)+ RNA isolated from any cell line producing a monoclonal antibody.

Figure 8:
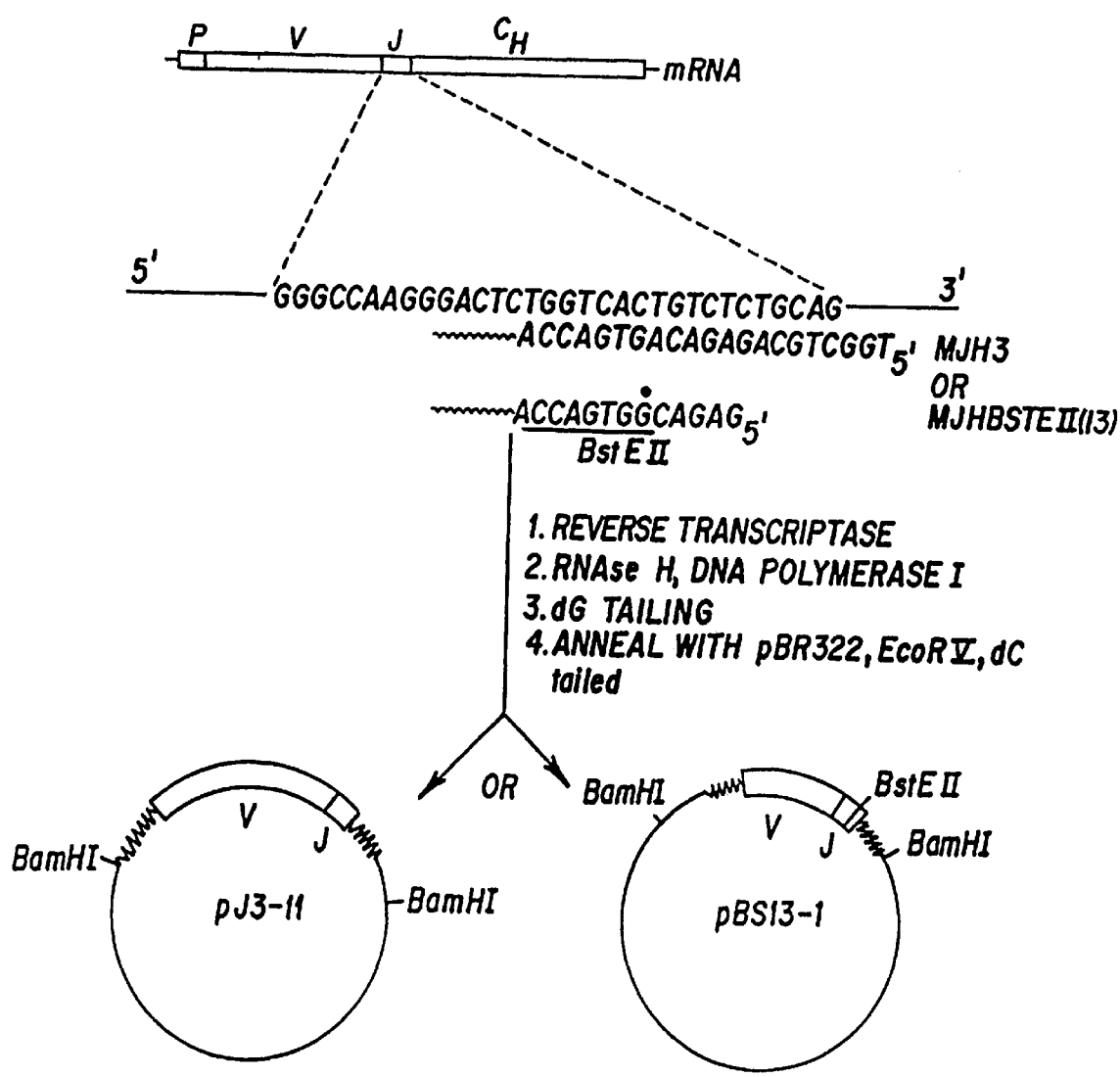
FIG. 8 shows the synthesis of heavy chain V region module genes using oligonucleotide primed cDNA synthesis. Not to scale.

After determining optimal conditions for priming hybridoma mRNA with oligonucleotide primers, two oligonucleotides were designed and used for heavy chain V region cDNA synthesis. These two oligonucleotides are UIG-MJHBSTEII(13) and UIG-MJH3 (FIGS. 7 and 8). It should be noted that the primer sequence was designed to introduce a BstEII recognition site (GGTGACC) in the clone so that it could be joined at this site to the human IgG1 constant module at the analogous position at the latter's J region. In this case, the primer had a single G to U mismatch with the mouse mRNA sequence that uses the $J_H3$ coding sequence. The UIG-MJHBSTEII(13) primer was 13 bases long and the mismatched residue was flanked by 7 matches 5' and 5 matches 3' of it. This was the 13-mer BstEII primer. To assess the priming efficiency of the 13-mer BstEII oligonucleotide, a 21-mer primer specific for mouse $J_H3$ (UIG-MJH3) was used. This primer had a perfect match for the 17 nucleotides on its 3' end.

These two primers and the $J_H3$ coding sequences are shown in FIG. 8. The first strand cDNA products made via the 13-mer BstEII and the 21-mer $J_H3$ primers included bands of approximately 430 nucleotides, which represented the entire $V_H$ region. Under the standard priming conditions used, the priming efficiency of the 13-mer BstEII was much less than that of the 21-mer $J_H3$. Accordingly, a cDNA library was generated from the first strand synthesis from each of these primers, using the method of Gubler and Hoffman, supra.

First, the 21-mer $J_H3$ library was screened with the 21-mer $J_H3$ oligonucleotide. Filter hybridization was done at 30°, overnight, according to de Lange, T. et al., *Cell*, 34: 891–900 (1983). The filters were then washed at 51° in 6×SSC, 0.1% SDS. Five colonies were selected. The largest had an insert of approximately 460 bp. More significantly, it contained three restriction sites predicted from the known $J_H3$ sequence, which are present upstream of the primer sequence. This clone, pJ3-11, was sequenced using the $J_H3$ primer by the chain-termination method (Wallace, R. B. et al., *Gene*, 16: 21–26 (1981)). The sequence obtained has the remaining $J_H3$ coding segment. Just upstream, a 13-nucleotide segment matched to a published D segment sequence (Dsp 2.2) (Kurosawa, Y. et al., *J. Exp. Med.*, 155: 201 (1982), and Tonegawa, S., *Nature*, 302: 575 (1983)). A nonapeptide predicted from this area showed characteristic homology to the published mouse heavy chain V subgroups at amino acid residues 86 to 94, comprising the FR3 of heavy chain molecules. Plasmid pJ3-11 represented a rearranged VDJ sequence, and apparently contained the anti-hepatitis $V_H$ sequence produced by the cell line.

In order to isolate a $V_H$ region cDNA clone that had a BstEII site in the J region, an AluI to Sau96I, 265 nucleotide long, probe from pJ3-11 was next used to screen the cDNA library generated from the 13-mer BstEII primer. Six positive clones were isolated. The largest, pBs13-1, was further analyzed. The insert was 280 nucleotides long and its restriction map agreed with that of pH3-11 except for the introduced BstEII site. FIG. 9 illustrates how these two inserts were recombined to generate pMVHCa-13, a $V_H$ clone with the module-joining BstEII site. Three additional $V_H$ cDNA clones were isolated from a cDNA library generated from the 21-mer oligonucleotide UIG-MJH3BSTEII primer containing a BstEII site. These clones may provide alternate $V_H$ cDNA sequences to join to human $C_H$ sequences.

(2) Preparation of cDNA Clones, and Vehicles Containing Same, for Light Chain Mouse Anti-HBsAg Variable Region Since the $J_K2$ sequence is present in mRNA prepared from the anti-hepatitis hybridoma cell line, the oligonucleotide UIG-JK2BGLII (FIG. 7B), was designed to introduce a BglII site into the $J_K2$ region. Digestion with BglII would then allow direct insertion of a $V_K$ cDNA coding region into the BclI site of the previously noted human $C_K$ vector, pING2001. This insertion would result in the precise joining of a mouse variable region segment (including the J region) to a human kappa constant region segment, each in the proper coding frame and with no alteration in amino acid sequence for either mouse variable or human constant region.

The JK2BGLII oligonucleotide was used to prime anti-HBsAg mRNA to form a cDNA library as for heavy chain, supra, in pUC9. The cDNA was size-selected by polyacrylamide gel electrophoresis prior to cloning, and 80% of the cDNA clones were shown to have insert sized between 300 and 750 nucleotides in length. Replica filters of this library were screened with two oligonucleotides, the original primer and a second probe complementary to $J_K2$ sequence 5' to the original primer.

It was discovered that the anti-hepatitis B monoclonal cell line CRL 8017 secretes immunoglobulins with at least two different light chains. One of them is derived from the myeloma NS-1, which was used as a fusion partner in generating the anti-hepatitis B cell line. Since NS-1 is derived from the myeloma MOPC21, the possibility was investigated that MOPC21 $V_K$ mRNA may be present in the $V_K$ cDNA library from the anti-hepatitis monoclonal cell line. Indeed, one cDNA clone (p6D4B) analyzed has an identical restriction enzyme map to that of MOPC21 $V_K$ cDNA, except for the inserted BglII site.

Two conclusions can be drawn from these results. The first is that it is possible to effectively use an oligonucleotide to introduce a restriction enzyme site while cloning a $V_K$ region from a hybridoma cell line. The second is that one must carefully monitor hybridoma cell lines for the presence of multiple V region sequences, only one of which is the desired sequence.

In order to further characterize the kappa light chain J regions present in the cell line mRNA, poly(A)⁺ RNA was bound to nitrocellulose by the formaldehyde "Dot blot" procedure of White and Bancroft, *J. Biol. Chem.*, 257: 8569 (1982). The RNA was hybridized to $^{32}$P-labeled oligonucleotide probes specific for each functional kappa J region. These probes are shown in FIG. 7B as the UIG probes 5JK1, MJK, 5JK4, and 5JK5. The results showed that the mRNA hybridized strongly to both MJK and 5JK4 oligonucleotide probes, indicating that both $J_K2$ and $J_K4$ sequences were present. Since $J_K2$ mRNA had been previously identified as the one derived from the parental hybridoma partner NS-1, it was concluded that the $J_K4$ mRNA encoded the anti-hepatitis binding specificity of the CRL 8017 cells.

Two different cDNA libraries were screened to isolate V region clones encoding $J_K4$ sequences. The first was primed by JK2BGLII, supra. The second was made by using the oligonucleotide primer, JK4BGLII, which is specific for $J_K4$ mRNA and introduces a BglII site into the J region of cloned V regions. The JK4BGLII primer was used to prime first strand cDNA synthesis to construct a cDNA library by the same method used to construct a JK2BGLII primed cDNA library, except that cDNA was not size selected prior to cloning.

FIG. 7B tabulates the mismatches that each primer has with other functional mouse kappa J region sequences. Note that $J_K4$ has five mismatches in 21 nucleotides when compared with the JK2BGLII primer, and 3 in 23 with the JK4BGLII primer.

Both libraries were screened for V region clones containing $J_K4$ sequences by hybridizing to an oligonucleotide probe specific for $J_K4$ sequences (5JK4). The results of this screen are shown in Table 1.

TABLE 1*

| Library | Probe Specificity | |
| --- | --- | --- |
| | $J_K2$ | $J_K4$ |
| JK2BGLII | 2% (30/1500) | 0.15% (2/1500) |
| JK4BGLII | N/D | 3.5% (31/875) |

*Percentage of clones containing $J_K2$ or $J_K4$ sequence plus a V region. The probes used were the oligonucleotide 5JK4 ($J_K4$ specificity, FIG. 7) and p6D4B, which contains the NS-1 (MOPC21) V region sequence. N/D, not done.

Several $J_K4$ region cDNA clones isolated from both libraries were characterized. These clones have identical restriction enzyme maps, including the engineered BglII site resulting from the oligonucleotide primed cDNA cloning procedure. The restriction map and sequence of one clone, pV17, show that pV17 contains V region gene sequences.

These results show that the JK2BGLII primer could correctly, although inefficiently, prime $J_K4$ mRNA sequences. Since the JK2BGLII primer had less mismatches with any other $J_K$ region mRNA than with $J_K4$ mRNA (FIG. 7B), it is expected that the other $J_K$ mRNAs can be primed at the correct location with better efficiency using the JK2BGLII primer. Thus, efficient cDNA cloning of any functional mouse kappa V region may be obtained by using a mixture of the JK2BGLII and JK4BGLII primers.

Figure 9A:
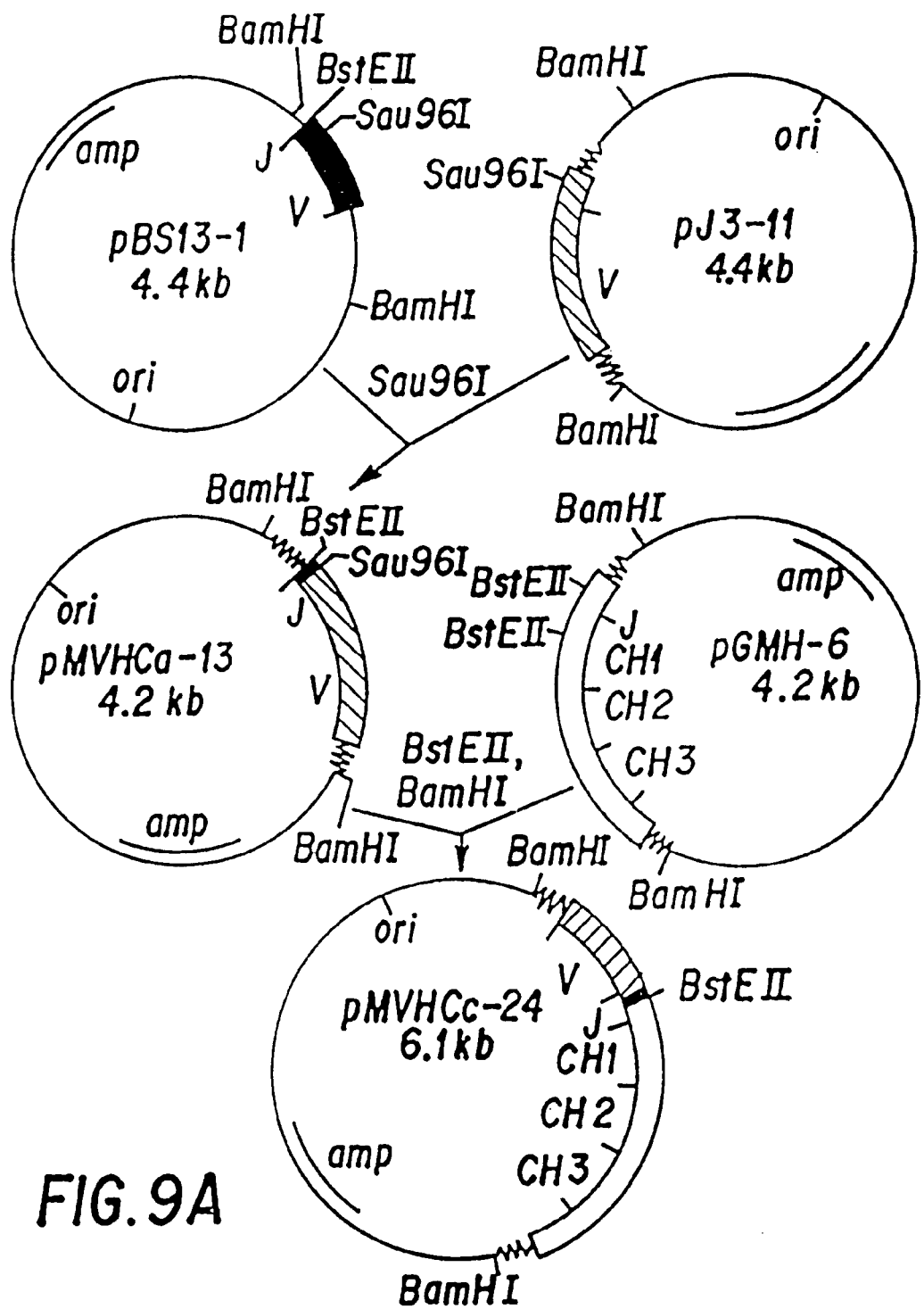
FIG. 9A shows construction of a heavy chain gene. Stippled regions show C region modules, while hatched or black regions show V region modules. Not to scale.
Figure 9B:
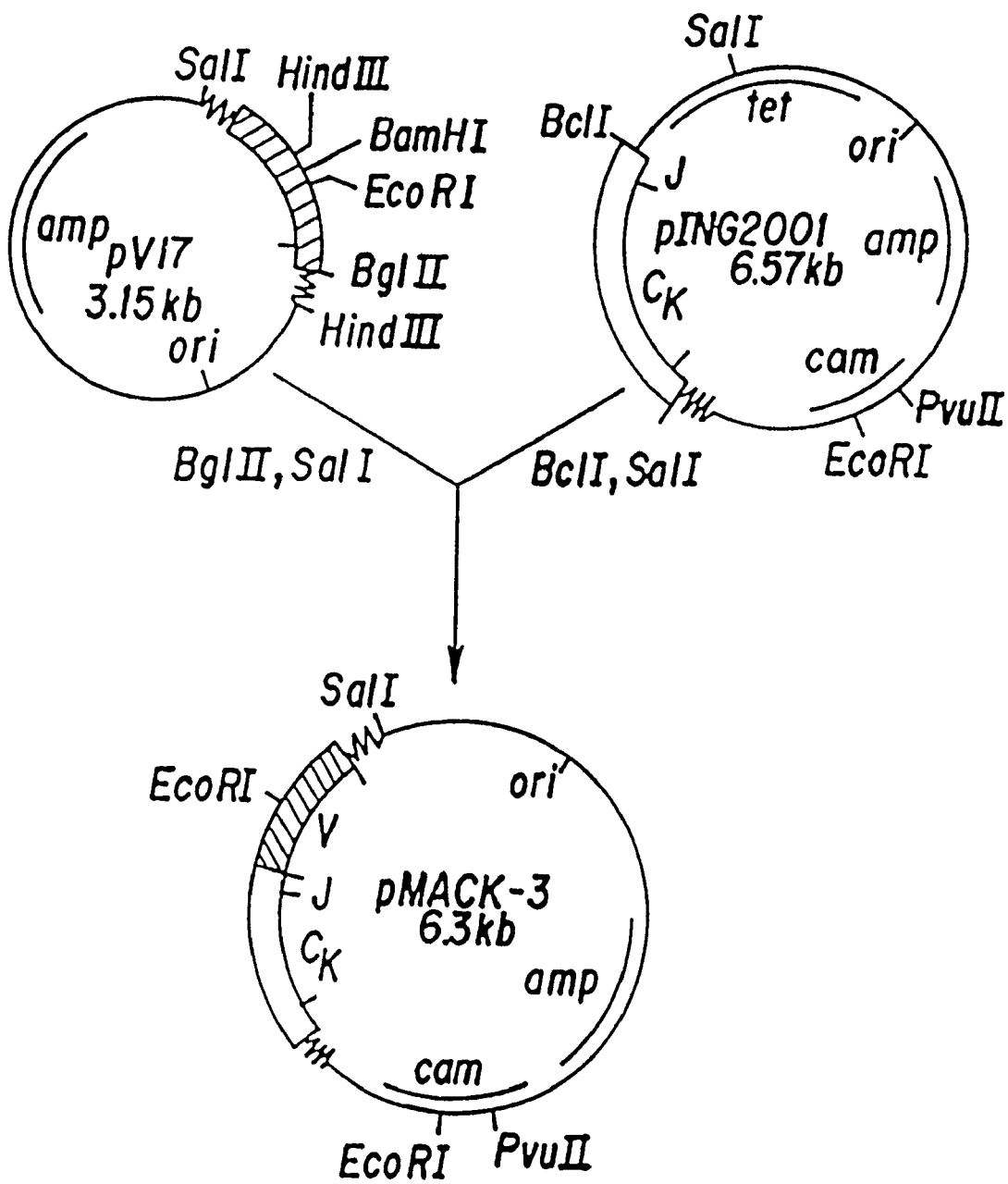
FIG. 9B shows the construction of pMACK-3.

The placement of a BglII site into the J region during cDNA cloning of the V regions allows joining of the cloned mouse V region gene module to the human kappa constant region gene module (FIG. 9B).

After the aforementioned experiments were carried out it was found that the cDNA clone pV17 lacked a complete 5' coding region. Nucleotide sequencing showed that the A of the initiator codon ATG was not copied in pV17. This was not a random cDNA cloning artifact because two other cDNA clones had the same defect. Two approaches were devised to obtain a light chain gene with a complete 5' coding region.

First, a new cDNA library was constructed by first priming with an oligonucleotide (5'-ATATTTGCTGATGCTCT-3') complementary to pV17 sequences 155 bases from the 5' end. From this library, clones hybridizing to a pV17 DNA fragment probe were selected, and some of these new cDNA clones have the initiator ATG plus about 20 nucleotides of 5' untranslated region. One of these clones, p2-12, supplies a 5' untranslated region of 23 nucleotides and a complete ATG initiator codon. When p2-12 was combined with pV17 derived sequences, a variable region with a complete 5' end was formed (pING2013E).

Second, site-directed mutagenesis on the existing light chain clone was used to simultaneously remove the poly-G tract and place a ribosome recognition sequence adjacent to the initiator ATG. The PstI fragment from pV17 was subcloned into M13mp18. An oligonucleotide (V17-IVM; 5'-GTGTCGACTCAGCATGAGGTTCCAGGTTC-3') was then used as a primer to mutate the pV17 sequence to include a SalI site and an initiator ATG into the pV17 sequence. The resultant plasmid pV17-IVM provided an alternate mouse variable region for joining to human constant region modules.

The complete nucleotide sequence of the variable region from pV17 was then determined. The sequence shows that pV17 contains a $V_K$-$J_K$ junction region, containing several conserved amino acids, and the hybrid $J_K2/J_K4$ region formed by priming the $J_K4$ RNA with the UIG-JK2BGLII oligonucleotide. However, the $V_K$ region in pV17 is non-functional, because the $V_K$ and $J_K$ regions are not in the same coding frame. Translation of the pV17 V region would thus result in an abnormal immunoglobulin light chain where the J region is translated in an incorrect frame. This defect may be caused by aberrant V-J joining, resulting in a non-functional kappa mRNA, as has been observed by Kelley, D. E. et al., *Mol. Cell. Biol.*, 5:1660–1675 (1985).

Since the pV17 V region encodes an abnormal immunoglobulin, it is highly unlikely that this light chain is part of a functional anti-hepatitis antibody molecule. These results show the importance of monitoring hybridoma cells for the presence of multiple RNA species encoding V regions, only one of which is the desired sequence.

Further screening of CRL 8017 cDNA libraries was done to search for $V_K$ cDNA clones which are not from either of the two $V_K$ cDNA classes found so far (MOPC21-p6D4B, pV17). First an oligo-dT primed cDNA library made from CRL8017 RNA was screened with a DNA fragment probe specific for the kappa constant region, and separately with probes specific for MOPC21 and pV17 $V_K$ regions. A cDNA clone (p1E9L-81) that contains the kappa constant region, but has a different $V_K$ region than that of MOPC21 or pV17 was discovered. This method of screening oligo-dT primed cDNA libraries is a useful alternative to oligonucleotide screening of cDNA libraries, because nick-translated probes of high specific activity are used. Also, this method allows the simultaneous isolation of several classes of V region clones, such as all $V_K$ clones, by appropriate probe choice. Second, the UIG-JK2BGLII-primed cDNA library made from CRL 8017 RNA was screened with the UIG-5JK2 oligonucleotide probe (see FIG. 7). A new class of $V_K$ cDNA clones was found whose members are homologous to p1E9L-81 and hybridize to the UIG-5JK2 probe, but not to a MOPC21 $V_K$ probe. The restriction endonuclease site maps and nucleotide sequences of these clones also differ from MOPC21-homologous $V_K$ cDNA clones from CRL8017 cells. These clones, however, have an aberrant V-J joint which results in a nonfunctional mRNA, and appear to be identical to one described by Cabilly and Riggs (*Gene*, 40:157 (1985)).

It was therefore concluded that the anti-hepatitis B cell line CRL8017 has at least three classes of $V_K$ mRNA corresponding to the above described cDNA clones p6D4B (MOPC21), p1E9L, and pV17. The pIE9L and pV17 clones are derived from mRNA from aberrantly rearranged Kappa genes, while the p6D4B clone is derived from the parent hybridoma fusion partner NS-1. None of these clones appear to encode the desired anti-hepatitis light chain.

(3) Preparation and Expression of Heavy Chain Containing Human Constant/Mouse Variable Regions The V region sequences in pMVHCa-13 were joined to the human IgGl CH1 region of pGMH-6, a multi-step ligation was required. First, the 220 nucleotide BstEII fragment from the J-CH1 region of pGMH-6 was ligated to the 1100 nucleotide IgG region BstEII to BamHI fragment of pGMH-6. In a separate ligation, the 420 nucleotide BstEII to BamHI fragment of pMVHCa-13, which comprises the mouse V region, was joined to a calf intestine phosphatase treated BamHI plasmid vector. The two ligations were then combined, ligase was added, and the products were transformed into HB101, resulting in the chimeric mouse V-human C clone pMVHCc-24 (FIG. 9A).

The V region of the hybrid heavy chain gene in pMVHCc-24 was further analyzed by partial sequence analysis. This analysis showed that the cloned V region contained a D sequence which matches a known D sequence, DSP2.2 (Kurosawa and Tonegawa, supra). The sequence also predicted a 19 amino acid leader peptide similar to known mouse V heavy chain leader peptide sequences, and a 5' untranslated region of at least 3 nucleotides.

Figure 11:
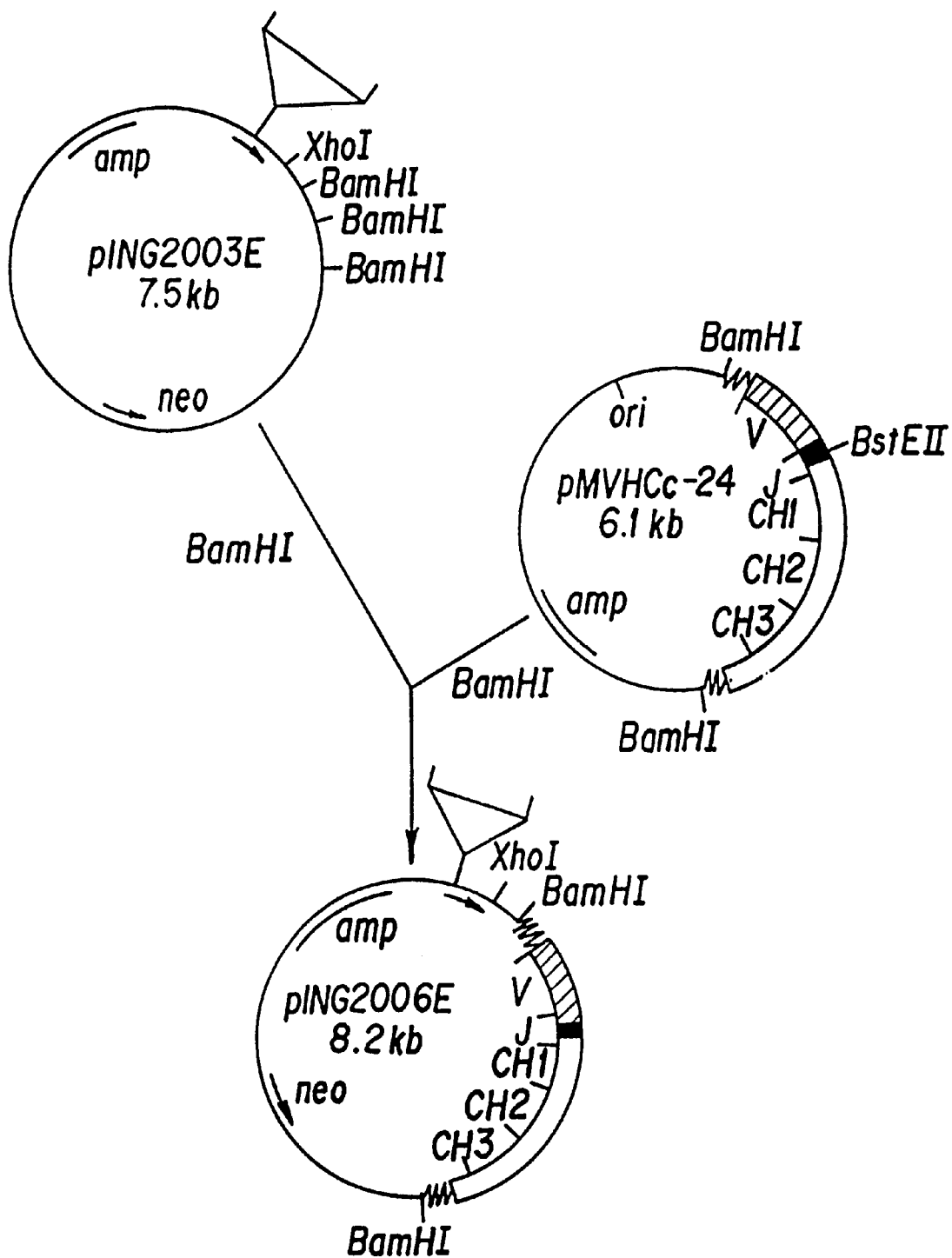
FIG. 11 shows the construction of the heavy chain expression plasmid pING2006E. Arrows show SV-40 promoter locations and directions of transcription. Hatched and black areas show mouse V region modules, while stippled areas show human C region modules. Not to scale.

The BamHI fragment containing the mouse-human hybrid heavy chain gene of pMVHCc-24 was cloned into BamHI digested pING2003E vector, resulting in the expression plasmid pING2006E (FIG. 11). The pING2006E plasmid should have an increased probability of efficient expression of the mouse-human chimeric immunoglobulin gene in B lymphoid cells because of the presence of the mouse heavy chain enhancer region.

Figure 12A:
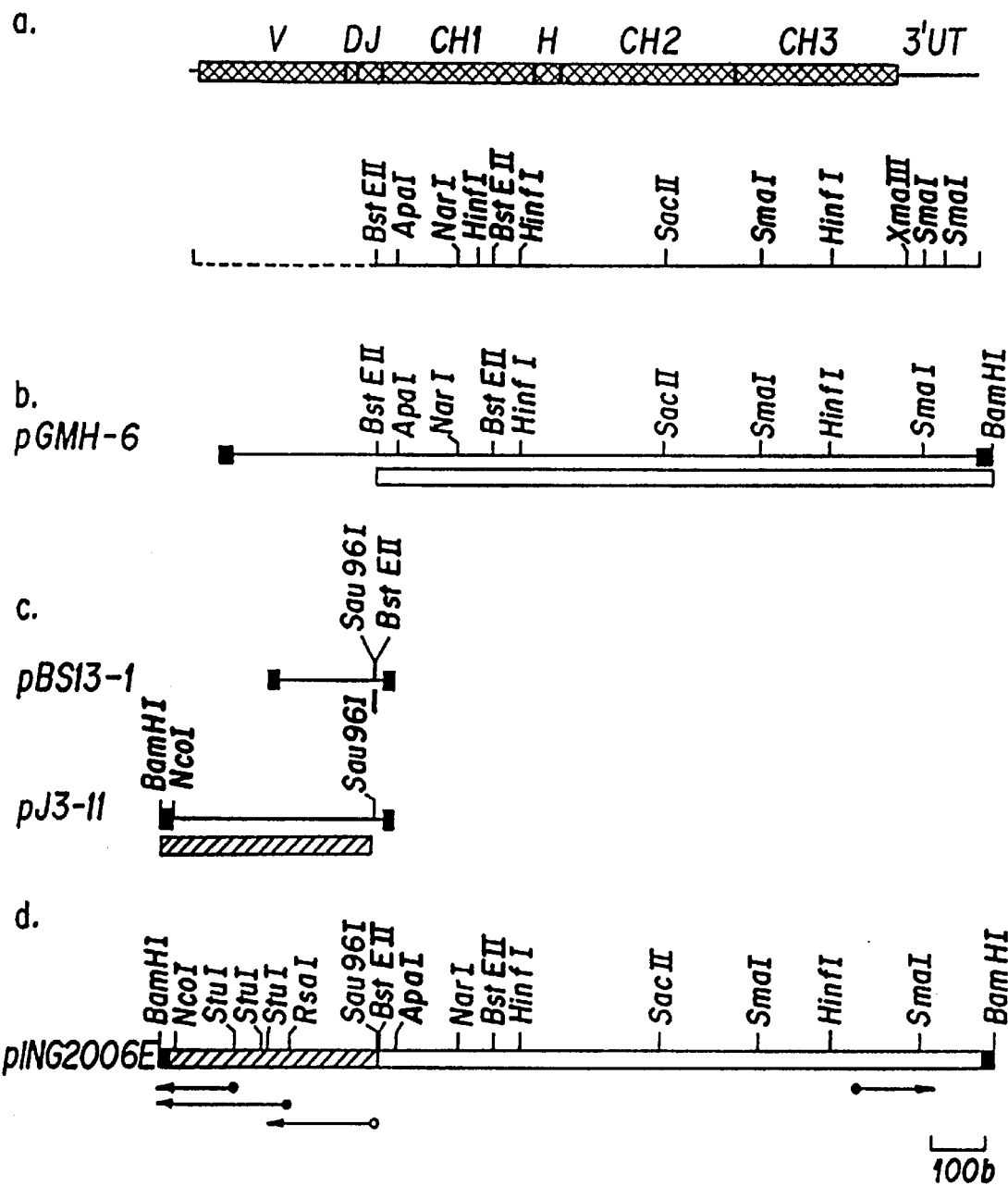
FIG. 12 shows the structure of the chimeric anti-hepatitis heavy chain genes in the expression plasmids pING2006E and pING2012E. Panel A shows the structure of mouse-human chimeric anti-hepatitis heavy chain genes. The structure of human IgG1 mRNA and cDNA is shown in A.a. The human heavy chain constant region cDNA clone pGMH-6 and the mouse heavy chain variable region cDNA clones pBS12-1and pJ3-11 were used to make the hydbrid gene used in pING2006E. Hatched gene blocks indicate mouse variable region sequences, while open gene blocks show human IgG1 constant region sequences. A.b: pGMH-6; A.c: pBS13-1 and pJ3-11; A.d: pING2006E.
FIG. 12B shows the nucleotide sequence of the anti-hepatitis B heavy chain variable region in pING2006E and pING2012E. pING2012E was constructed by first inserting a BglII site at the SalI site of pING1202 (See FIG. 16) to form pING1202BglII. The chimeric heavy chain gene from this plasmid was inserted into the expression vector pING2003E, resulting in pING2012E. pING2012E differs from pING 2006E in the region immediately upstream of the initiator ATG. Underlined nucleotides denote human J region sequences from the cDNA clone pGMH-6. Aste-risked amino acid 117 indicates a single change at this site from mouse to human sequence (Ala to Ser) introduced in the chimeric gene J region. Sequencing was by the Sanger method on plasmid (open circle) and M13 (closed circle) templates.
Figure 13:
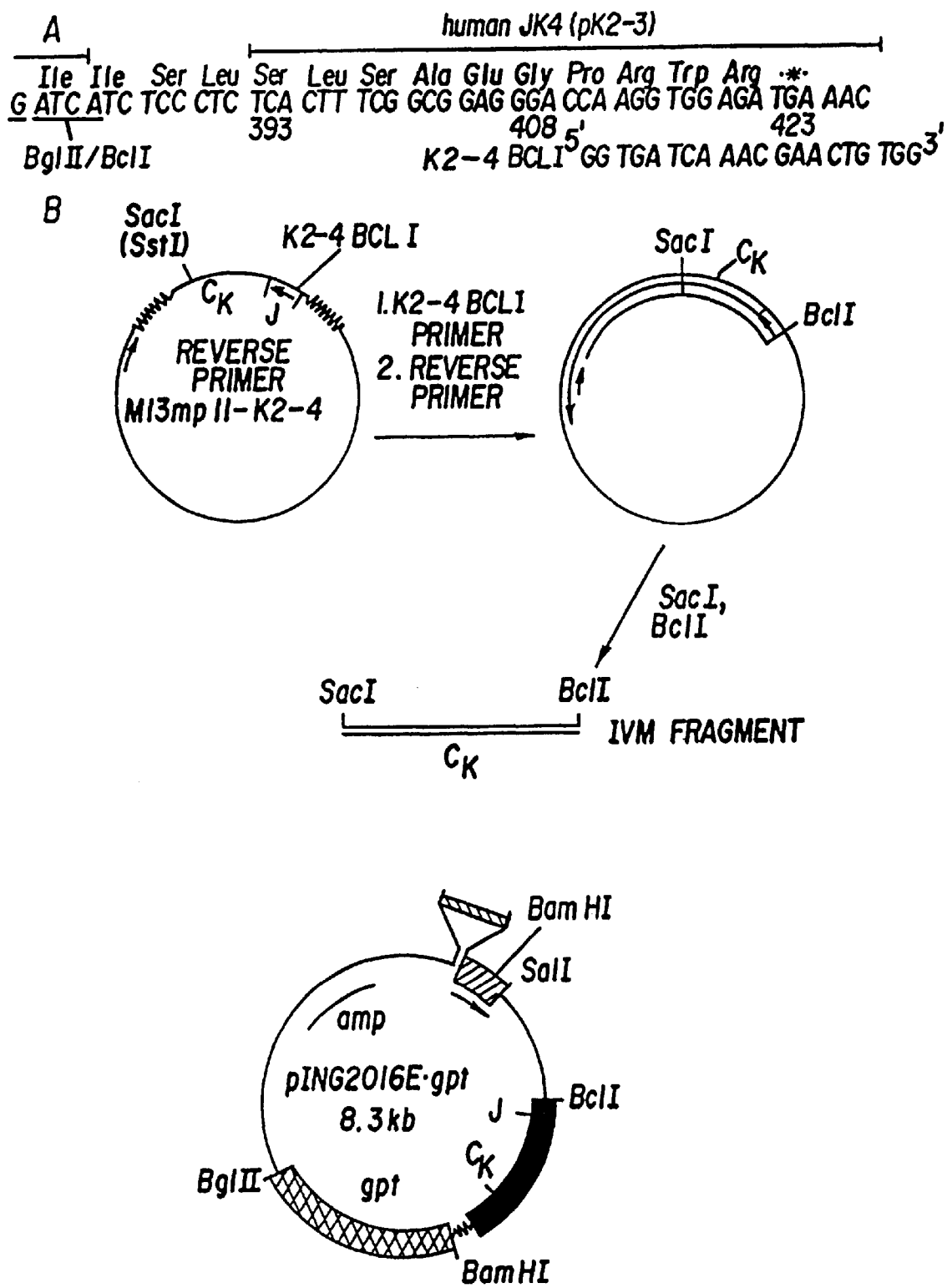
FIG. 13 shows in panel A the J-C junction region nucleotide sequence in light chain clones derived from pING2001 (pMACK-3), pING2013E, pIN2007E, pING2010E-gpt and pING2014E-gpt). The J region sequence originating from pK2–3 is marked human JK4. The G nucleotide not predicated by genomic sequencing is marked with an asterisk. The olignonucleotide primer (K2-4BCLI) used to modify this sequence is shown below the human JK4 sequence. Panel B diagrams the method of site-directed mutagenesis used to make pING2016E-gpt. Not to scale.

A modification of the chimeric heavy chain gene present in pMVHCc-24 was done to provide an alternate heavy chain gene which lacks the oligo-dC region preceding the initiator ATG. The pING2012E and pING2006E vectors are identical except for the nucleotides immediately preceding the ATG, as shown in FIG. 12.

Bacteria harboring the pING2006E and pSV2-neo plasmids were converted into protoplasts by the method of Sandri-Goldin, R. M. et al., *Mol. Cell. Biol.*, 1:743 (1981). The protoplasts were then separately fused to SP2/0-Ag14 hybridoma cells (ATCC CRL 1581) by treatment with polyethyleneglycol (Ochi, A. et al., *Nature*, 302: 340, 1983). The fused cells were allowed to recover for 72 hours in complete medium before plating at 10,000 or 50,000 cells per well in a 96-well tissue culture plate. The cells were selected with G418 at 0.8 mg/ml for two weeks, then growth in some wells was clearly evident. Under these selection conditions, Sp2/0 cells were completely killed within 4–7 days by G418. Only cells which have integrated and expressed the neo gene present in the vectors will grow under G418 selection. The number of wells positive for growth by these integrative transfectants are shown in Table 2.

TABLE 2*

| Strain/Plasmid | 10,000 cells/well | 50,000 cells/well |
| --- | --- | --- |
| MC1061/pING2006E | 3 (13%) | 12 (50%) |
| MC1061/pSV2-neo | 7 (29%) | 4 (17%) |
| MC1061/none | 0 | 0 |

*Percentage of wells showing positive growth out of 24 wells.

Cells transfected with pING2006E and pSV2-neo were tested for immunoglobulin gene expression at the RNA and protein level. Total cell RNA was prepared from transfected cells, bound to nitrocelluluose and hybridized to nick-translated probes specific for the mouse-human hybrid heavy chain gene. Two clones were found which have a strong signal, representing expression of the gene at the RNA level. The amount of total cellular RNA hybridizing to the mouse-human probe appeared to be approximately 1/10 the level of heavy chain RNA in the original hybridoma cells. This probably represented about 1% of the total mRNA of the transfected cell.

The transfected mouse cells were also tested for production of cytoplasmic human heavy chain protein by an ELISA assay. It was found that 3 out of 7 pING-2006E transfected cell lines produced detectable levels of human heavy chain protein. The mouse cell transformant producing the most mouse-human heavy chain protein gave a signal in the ELISA array comparable to that of a 1/100 dilution of a human B cell line producing intact human immunoglobulin IgG1. This modest level of detected mouse-human heavy chain protein may be due to several factors, including instability of heavy chains in the absence of light chains in hybridoma cells, or incorrect processing of the chimeric gene transcript.

(4) Gene Amplification of the Integrated Chimeric Gene

Southern blot analysis showed that multiple copies of the pING2006E DNA sequences were integrated in tandem in the mouse genome. Restriction enzymes ApaI and BglII both cleave pING2006E singly. In the transformant, 2AE9, a band, from an ApaI or BglII digestion, of the expected size (8.2 kb) was found to hybridize to the human C gamma 1 sequence (data not shown) and a BamHI band of the correct size (1.6 kb) was found to hybridize to the human as well as the 1E9 $V_H$ sequences. A Gene-copy titration experiment (FIG. 14) indicated that there are about 5 copies of pING2006E in the 2AE9 genome. That fact that only a single band was detected in the ApaI or BglII lane indicates that these individual copies are in a tandemly arranged array. A set of double digestions showed that pING2006E sequences suffered no rearrangement in their introduction into the mouse DNA (data not shown).

Figure 14:
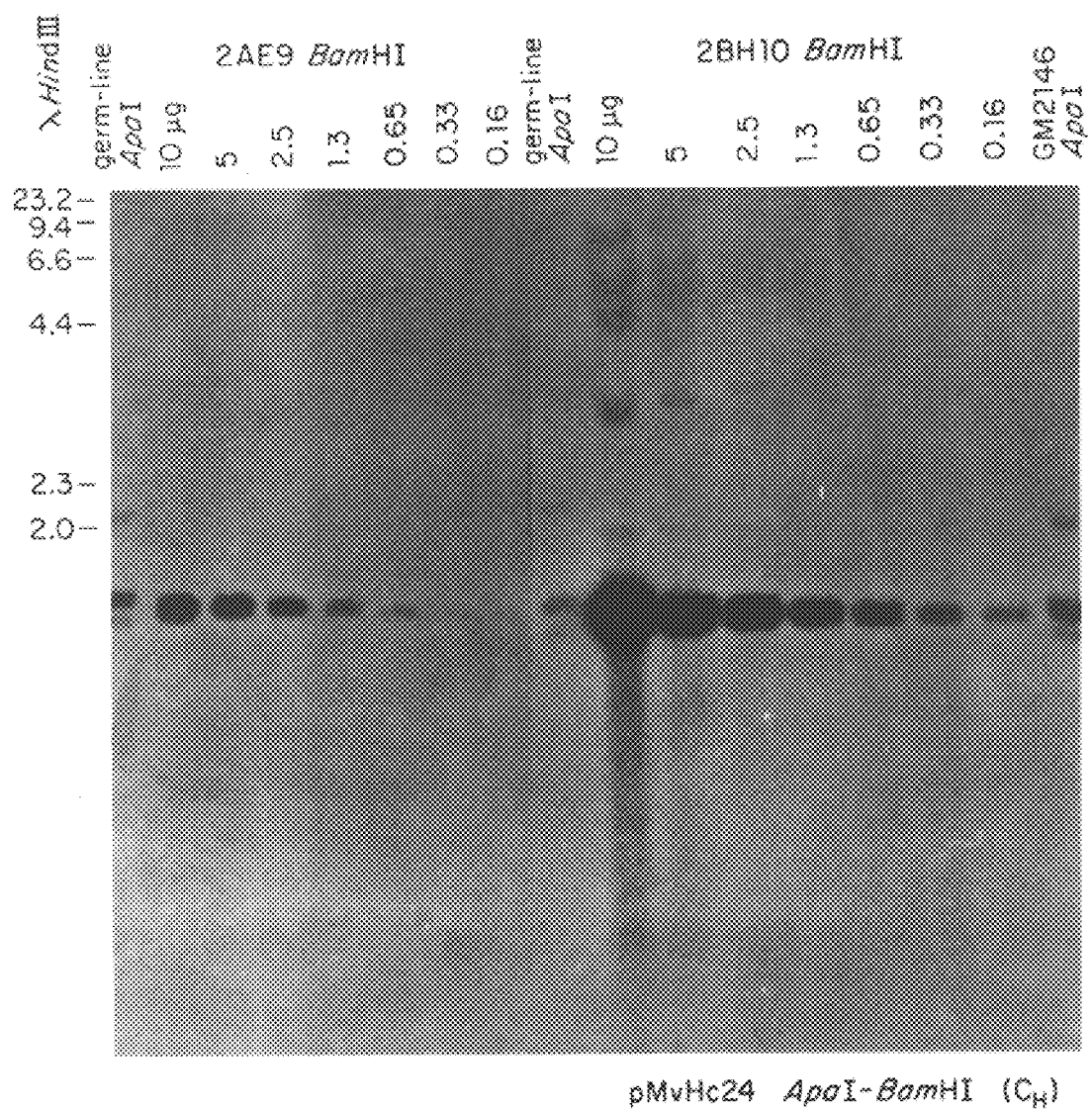
FIG. 14 Gene cop number of the transfected sequences in two transformants. nDNA from 2AE9, 2BH10 were digested with the enzymes indicated. The concentration of DNA is titrated down across the lanes with the amount indicated above them. The probe contains human C gamma 1 sequences (pmvHc24 ApaI-BamHI). The reference is germ-line of GM2146 nDNA digested with ApaI. The 3' ApaI site is 2 bp beyond the site of poly(A) addition.

We next transfected the 2AE9 cells with a plasmid that contains a different selectable marker, the gpt gene, and selected clones growing out in DMEM-HAT. One clone, 2BH10, has about 38 ng soluble human gamma 1 protein per $10^6$ cells. Southern analysis showed that 2BH10 has about 30 copies of pING2006E (FIG. 14). They were amplified from the 5 copies in 2AE9 without rearrangement of the DNA sequences. (Compare the 2AE9 panel to the 2BH10). S1 data (data not shown) revealed that this increase in template led to a higher amount of IgG gene transcripts. We believe that these sequences were co-amplified with contiguous cellular sequences as a result of the second selection.

Example III

A Human-Mouse Chimeric Antibody with Cancer Antigen Specificity (1) Antibody L6

L6 monoclonal antibody (Mab) was obtained from a mouse which had been immunized with cells from a human lung carcinoma, after which spleen cells were hybridized with NS-1 mouse myeloma cells. The antibody binds to a previously not identified carbohydrate antigen which is expressed in large amounts at the surface of cells from most human carcinomas, including lung carcinomas (adeno, squamous), brease carcinomas, colon carcinomas and ovarian carcinomas, while the antigen is only present at trace levels in normal cells from the adult host. MAb L6 is an IgG2a and can mediate antibody dependent cellular cytotoxicity, ADCC, in the presence of human peripheral blood leukocytes as a source of effector cells, so as to lyse L6 positive tumor cells, and it can lyse L6 positive tumor cells in the presence of human serum as a source of complement; the lysis is detected as the release of $^{51}$Cr from labelled cells over a 4 hour incubation period. MAb L6 can localize to L6 positive tumors xenotransplanted onto nude mice, and it can inhibit the outgrowth of such tumors. MAb L6 is described in *Cancer Res.* 46:3917–3923, 1986 (on MAb specificity) and in *Proc. Natl. Acad. Sci.* 85:7059–7063, 1986 (on MAb function).

(2) Identification of J Sequence in the Immunoglobulin mRNA of L6.

Frozen cells were thawed on ice for 10 minutes and then at room temperature. The suspension was diluted with 15 ml PBS and the cells were centrifuged down. They were resuspended, after washes in PBS, in 16 ml 3M LiCl, 6M urea and disrupted in a polytron shear. The preparation of mRNA and the selection of the poly(A+) fraction were carried out according to Auffray, C. and Rougeon, F., *Eur. J. Biochem.* 107:303, 1980.

The poly (A+) RNA from L6 was hybridized individually with labeled $J_H1$, $J_H2$, $J_H3$ and $J_H4$ oligonucleotides under conditions described by Nobrega et al. *Anal. Biochem* 131:141, 1983). The products were then subjected to electrophoresis in a 1.7% agarose-TBE gel. The gel was fixed in 10% TCA, blotted dry and exposed for autoradiography. The result showed that the L6 $v_H$ contains $J_H2$ sequences.

For the analysis of the $V_K$ mRNA, the dot-blot method of White and Bancroft *J. Biol. Chem.* 257:8569, (1982) was used. Poly (A+) RNA was immobilized on nitrocellulose filters and was hybridized to labeled probe-oligonucleotides at 40° in 4×SSC. These experiments show that L6 contains $J_K5$ sequences. A faint hybridization to $J_K2$ was observed.

(3) V Region cDNA Clones

A library primed by oligo (dT) on L6 poly (A+) RNA was screened for kappa clones with a mouse $C_K$ region probe. From the L6 library, several clones were isolated. A second screen with a 5' $J_K5$ specific probe identified the L6 ($J_K5$) light-chain clones. Heavy chain clones of L6 were isolated by screening with the $J_H2$ oligonucleotide.

Figure 16:
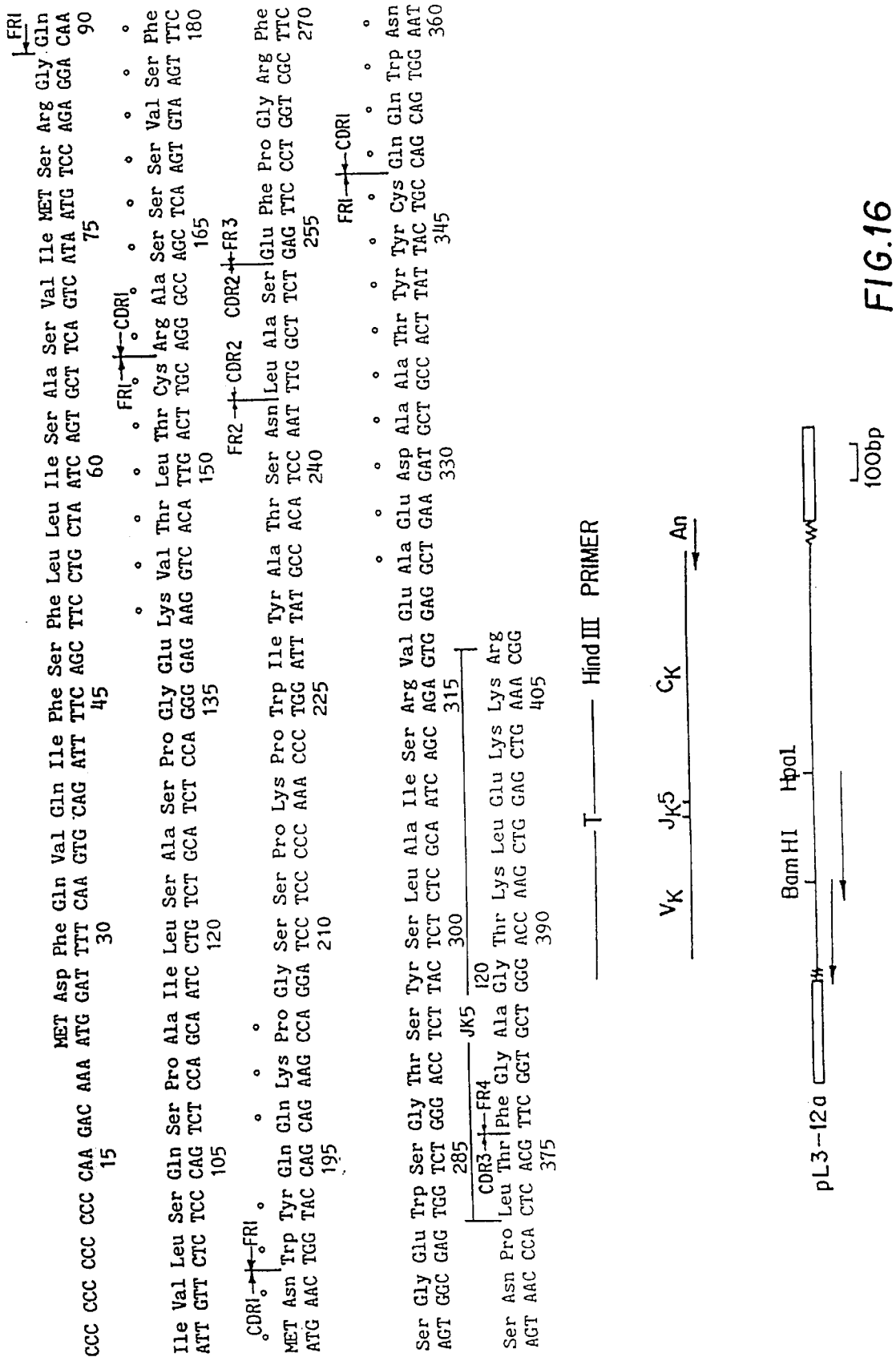
FIG. 16 shows the nucleotide sequence of the V region of the L6 $V_K$ cDNA clone PL3–12a. The oligonucleotide primer used for site-directed mutagenesis is shown below the $J_K5$ segment. Open circles denote amino acid residues confirmed by peptide sequence.

The heavy and light chain genes or gene fragments from the cDNA clones, PH3–6a and pL3–12a were inserted into M13 bacteriophage vectors for nucleotide sequence analysis. The complete nucleotide sequences of the variable region of these clones were determined (FIGS. 15 and 16) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., *Sequences of Proteins of Immunological Interest;* U.S. Dept of HHS, 1983).

The L6 $V_H$ belongs to subgroup II. The cDNA predicts an N-terminal sequence of 24 amino acid residues identical to that of a known $V_H$ (45–165 CRI; Margolies et al. *Mol. Immunol.* 18:1065, 1981). The L6 $V_H$ has the $J_H2$ sequence. The L6 $V_L$ is from the $V_K$-KpnI family (Nishi et al. *Proc. Nat. Acd. Sci.* USA 82:6399, 1985), and uses $J_K5$. The cloned $V_6$ $V_L$ predicts an amino acid sequence which was confirmed by amino acid sequencing of peptides from the L6 light chain corresponding to residues 18–40 and 80–96.

(4) In Vitro Mutagenesis to Engineer Restriction Enzyme Sites in the J Region for Joining to a Human C-Module, and to Remove Olido (dC) Sequences 5' to the V Modules.

Figures 17B, 17C:
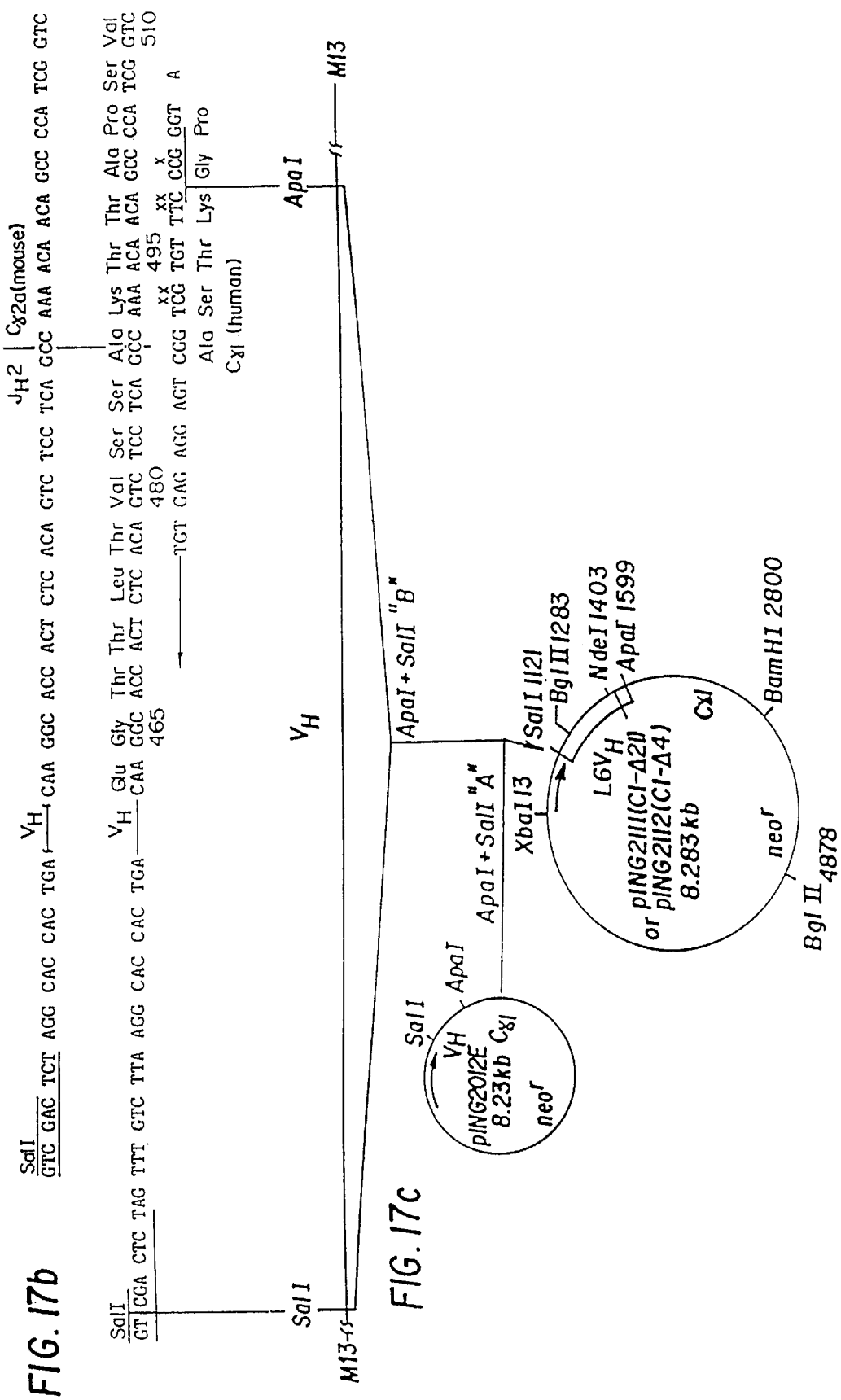
FIG. 17B shows the strategy for site-directed mutagenesis of 1 ug of clones Cl-delta 4 and Cl-delta 21, each annealed to 20 ng of the 31-mer oligonucleotide MJH2-ApaI. Complementary strand synthesis with the Klenow fragment of DNA polymerase was at room temperature for 30 min, then 15° C. for 72 hours. Transfected phage plaques were adsorbed to nitrocellulose, fixed with NaOH, and hybridized to $^{32}$P-labelled MJH2-ApaI oligo-nucleotide at 65° C., 18 hours, in 4xTBS (0.6 M NaCl, 0.04 M Tris-HCl (pH 7.4), 0.004 M EDTA) plus 10% dextran sulfate. Final wash of the filters was at 65° C., 4xSSPE, 0.1% SDS for 15 min. (Maniatis, T., et al., *Molecular Cloning: A Laboratory Manual*, 1982). Positive plaques were detected by overnight exposure to Kodak XAR film, and were directly picked for growth and restriction enzyme anaysis of RF DNA. Mismatches of the MJH2-ApaI oligo-nucleotide to the mouse $C_H$1 are denoted, resulting in the coding changes shown below the oligonucleotide.
FIG. 17C shows the strategy of the substitution of each of the mutagenized L6-$V_H$ modules for the resident $V_H$ of the chimeric expression plasmid pING2012 to generate pING2111 and pING2112.

Both clones generated from priming with oligo (dT) L6 $V_K$ and $V_H$ need to be modified. For the L6 $V_K$, the J-region mutagenesis primer $J_K$HindIII, as shown in FIG. 17B, was utilized. A human $C_K$ module derived form a cDNA clone was mutagenized to contain the HindIII sequence (see FIG. 17A). The mutagenesis reaction was performed on M13 subclones of these genes. The frequency of mutant clones ranged from 0.5 to 1% of the plaques obtained.

It had been previously observed that the oligo (dC) sequence upstream of the AUG codon in a $V_H$ chimeric gene interferes with proper splicing in one particular gene construct. It was estimated that perhaps as much as 70% of the RNA transcripts had undergone the mis-splicing, wherein a cryptic 3' splice acceptor in the leader sequence was used. Therefore the oligo (dC) sequence upstream of the initiator AUG was removed in all of the clones.

Figure 19B:
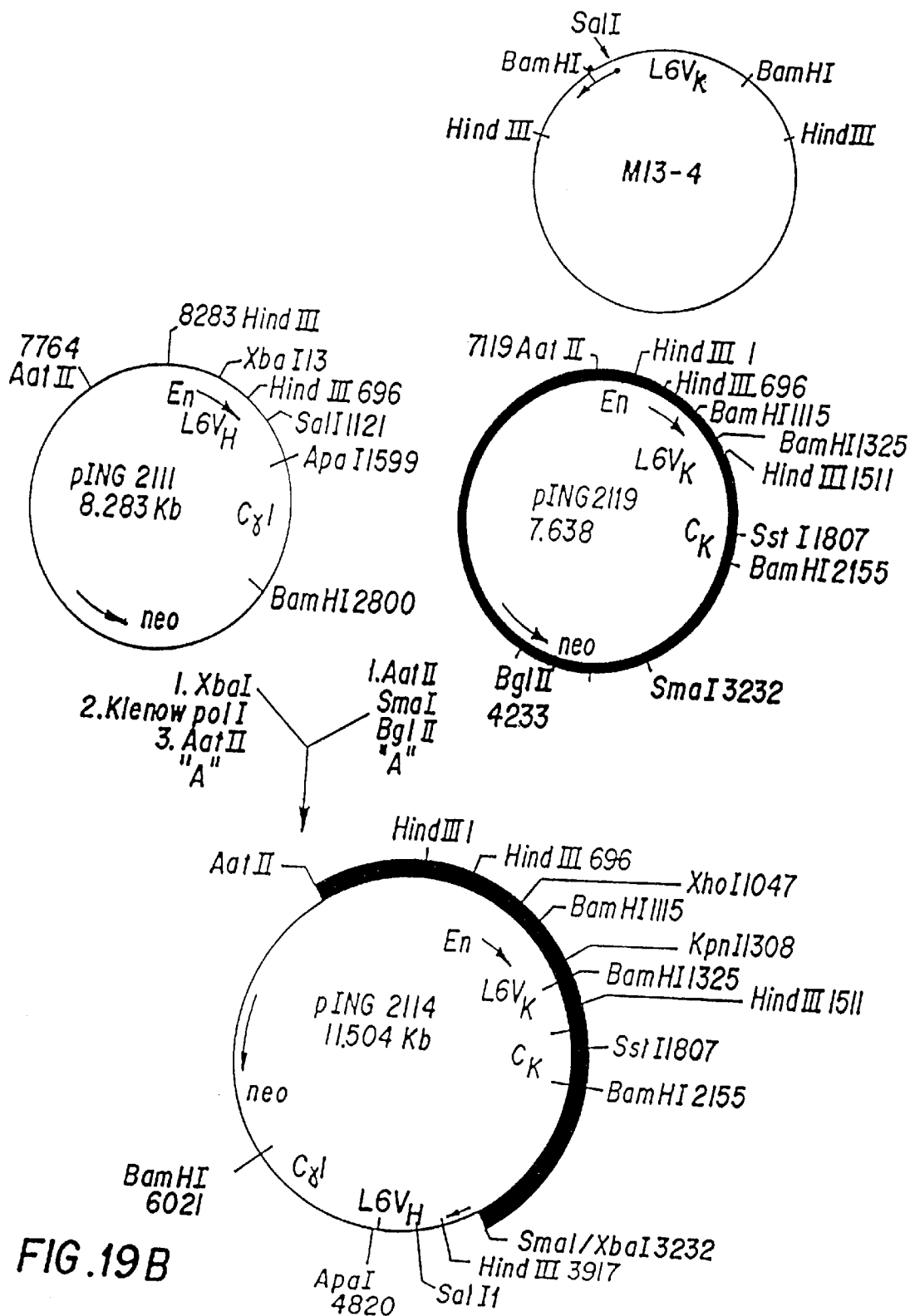
FIGS. 19(A and B) show the modification of the $V_K$ gene and its use in constructing light chain and heavy plus light chain expression plasmids.

In one approach, an oligonucleotide was used which contains a SalI restriction site to mutagenize the L6 $V_K$ clone. The primer used for this oligonucleotide-directed mutagenesis is a 22-mer which introduces a SalI site between the oligo (dC) and the initiator met codon (FIG. 19).

In a different approach, the nuclease BAL-31 was used to chew away the olig (dC) in the L6 $V_H$ clone pH3–6a. The size of the deletion in two of the mutants obtained was determined by nucleotide sequencing and is shown in FIG. 17(A). In both of these mutuants (delta 4 and delta 21), all of the olig (dC) 5' to the coding region were deleted.

These clones were then modified by oligonucleotide-directed mutagenesis with the MJH2-ApaI primer (FIG. 17). This 31-base primer introduces an ApaI site in the mouse $C_H$ gene at a position analogous to an existing ApaI site in human Cgamma1 cDNA gene module. The primer introduces the appropriate codons for the human C gamma 1 gene. The chimeric heavy chain gene made by joining the mutagenized mouse $V_H$ gene module to a human $C_H$ module thus encodes a chimeric protein which contains no human amino acids for the entire $V_H$ region.

The human C gamma 1 gene module is a cDNA derived from GM2146 cells (Human Genetic Mutant Cell Repository, Newark, N.J.). This C gamma 1 gene module was previously combined with a mouse $V_H$ gene module to form the chimeric expression plasmid pING2012E.

(5) L6 Chimeric Expression Plasmids

L6 chimeric heavy chain expression plasmids were derived from the replacement of the $V_H$ module pING2012E with the $V_H$ modules of mutants delta 21 and delta 4 to give the expression plasmids pING2111 and pING2112 (FIG. 17(C)). These plasmids direct the synthesis of chimeric L6 heavy chain when transfected into mammalian cells.

Figure 18:
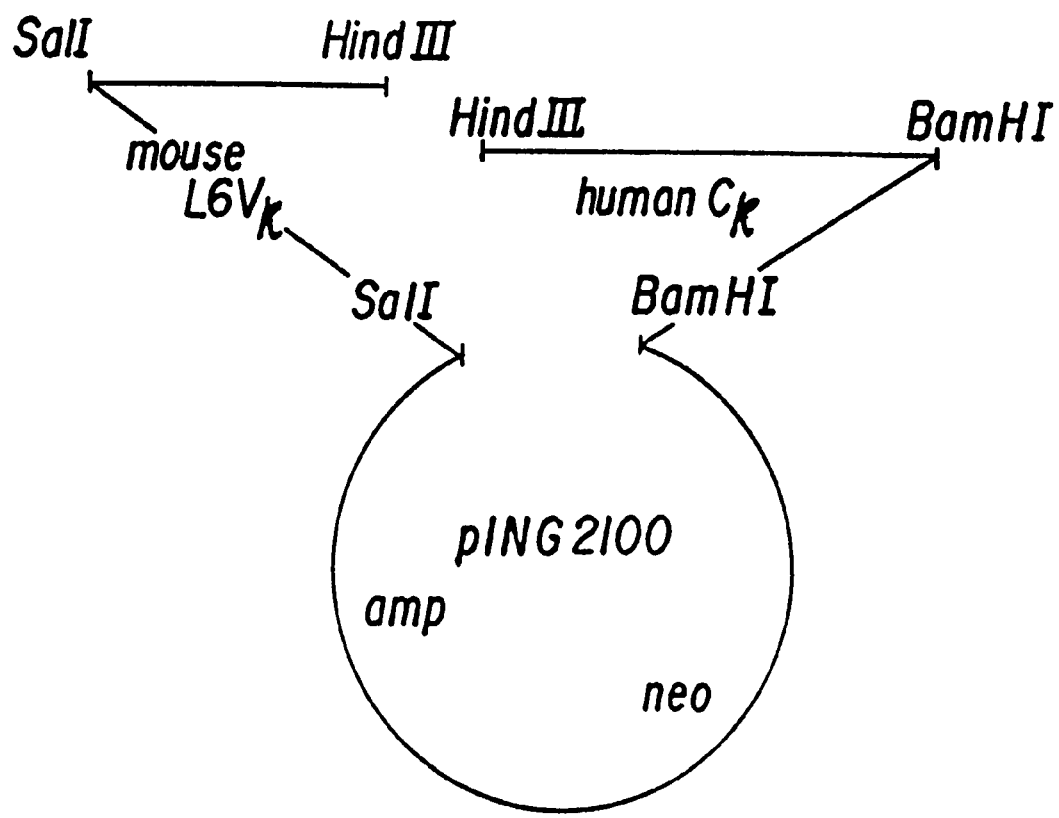
FIG. 18 shows the construction of the chimeric L6 expression plasmid pING2119. The SalI to BamHI fragment from pING2100 is identical to the SalI to BamHI A fragment from pING2012E.

For the L6 light chain chimeric gene, the SalI to HindIII fragment of the mouse $V_K$ module was joined to the human $C_K$ module by the procedure outlined in FIG. 18, forming pING2119. Replacement of the neo sequence with the *E. coli* gpt gene derived from pSV2-gpt resulted in pING2120, which expressed L6 chimeric light chain and confers mycophenolic acid resistance when transfected into mammalian cells.

The inclusion of both heavy and light chain chimeric genes in the same plasmid allows for the introduction into transfected cells of a 1:1 gene ratio of heavy and light chain genes leading to a balanced gene dosage. This may improve expression and decrease manipulations of transfected cells for optimal chimeric antibody expression. For this purpose, the DNA fragments derived from the chimeric heavy and light chain genes of pING2111 and pING2119 were combined into the expression plasmid pING2114 (FIG. 19). This expression plasmid contains a selectable $neo^R$ marker and separate transcription units for each chimeric gene, each including a mouse heavy chain enhancer.

The modifications and V-C joint regions of the L6 chimeric genes are summarized in FIG. 20.

(6) Stable Transfection of Mouse Lymphoid Cells for the Production of Chimeric Antibody Electroporation was used (Potter et al. supra; Toneguzzo et al. *Mol. Cell Biol.* 6:703 1986) for the introduction of L6 chimeric expression plasmid DNA into mouse Sp2/0 cells. The electroporation technique gave a transfection frequency of $1-10 \times 10^{-5}$ for the Sp2/0 cells.

The two gene expression plasmid pING2114 was linearized by digestion with AatII restriction endonuclease and transfected into Sp2/0 cells, giving approximating fifty G418 resistant clones which were screened for human heavy and light chain synthesis. The levels of chimeric antibody chain synthesis from the two procedures, D7 and 3E3, are shown in Table 3. Chimeric L6 antibody was prepared by culturing the D7 transfectant cells for 24 hours at $2 \times 10^6$ cells/ml in 5 1 DMEM supplemented with HEPES buffer and penicillin and streptomycin. The supernatant was concentrated over an Amicon YM30 membrane in 10 mM sodium phosphate buffer, pH 8.0. The preparation was loaded over a DEAE-Cellulose column, which separated the immunoglobulin into unbound and bound fractions. Samples from the DEAE-unbound, DEAE-bound and the pre-DEAE preparations (from 1.6 ul of medium) was separately purified by affinity chromatography on a Protein-A Sepharose column, eluting with ρ.1 M sodium citrate pH 3.5. The eluted antibody was neutralized and concentrated by Amicon centricon filtration, in phosphate-buffered saline. The yields for the three preparations were 12 ug (DEAE unbound), 6 ug (DEAE bound), and 9 ug (pre-DEAE column). Western analysis of the antibody chains indicated that they were combined in an $H_2L_2$ tetramer like native immunoglobulins.

(7) A second purification for Chimeric L6 Antibody Secreted in Tissue Culture a. Sp2/0.pING2114.D7 cells were grown in culture medium [DMEM (Gibco #320-1965), supplemented with 10% Fetal Bovine Serum (Hyclone #A-1111-D), 10 mM HEPES, 1×Glutamine-Pen-Strep (Irvine Scientific #9316) to $1 \times 10^6$ cell/ml.

b. The cells were then centrifuged at 400×g and resuspended in serum-free culture medium at $2 \times 10^6$ cell/ml for 18–24 hr.

c. The medium was centrifuged at 4000 RPM in a JS-4.2 rotor (3000×g) for 15 min.

d. 1.6 liter of supernatant was then filtered through a 0.45 micron filter and then concentrated over a YM30 (Amicon Corp.) filter to 25 ml.

e. The conductance of the concentrated supernatant was adjusted to 5.7–5.6 mS/cm and the pH was adjusted to 8.0.

f. The supernatant was centrifuged at 2000×g, 5 min., and then loaded onto a 40 ml DEAE column, which was pre-equilibrated with 10 mM sodium phosphate, pH 8.0.

g. The flow through fraction was collected and loaded onto a 1 ml protein A-Sepharose (Sigma) column preequilibrated with 10 mM sodium phosphate, pH 8.0.

h. The column was washed first with 6 ml 10 mM sodium phosphate buffer pH=8.0, followed by 8 ml 0.1M sodium citrate pH=3.5, then by 6 ml 0.1 M citric acid (pH=2.2). Fractions of 0.5 ml were collected in tubes containing 50 ul 2M Tris base (Sigma).

i. The bulk of the IgG was in the pH=3.5 elution and was pooled and concentrated over Centricon 30 (Amicon Corp.) to approximately 0.06 ml.

j. The buffer was changed to PBS (10 mM sodium phosphate pH=7.4, 0.15M NaCl) in Centricon 30 by repeated diluting with PBS and reconcentrating.

k. The IgG solution was then adjusted to 0.10 ml and bovine serum albumin (Fraction V, U.S. Biochemicals) was added to 1.0% as a stabilizing reagent.

(8) Production and Purification of Chimeric L6 Antibody Secreted in Ascites Fluid a. The ascites was first centrifuged at 2,000×g for 10 min.

b. The conductance of the supernatant was adjusted to 5.7–5.6 mS/cm and its pH adjusted to 8.0.

c. Supernatant was then loaded onto a 40 ml DEAE-cellulose column pre-equilibrated with 10 mM $Na_2HPO_4$ pH 8.0.

d. The flow through from the DEAE column was collected and its pH was adjusted to 7.4, and then loaded onto a 1.0 ml goat anti-human IgG (H+L)—sepharose column.

e. The column was washed first with 6 ml of 10 mM sodium phosphate, 0.5 M sodium chloride, followed by 8 ml of 0.5 M $NH_4OH$, and 3 M sodium thiocyanate.

f. The sodium thiocyanate eluate was pooled and dialyzed against 2L PBS overnight.

The antibody can be further concentrated by steps j. and k. of the previous procedure.

TABLE 3

Levels of Secreted Chimeric L6 Chains from Sp2/0 Transfectants[a]

| | Culture Condition | FBS | Sp2/0.D7 Kappa[b] | Sp2/0.D7 Gamma[c] | Sp2/0.3E3 Kappa[b] | Sp2/0.3E3 Gamma[c] |
|---|---|---|---|---|---|---|
| 1. | 20 ml, 2d, seed @ 2 × $10^5$/ml | + | 17 | 77 | 100 | 700 |
| 2. | 200 ml, 2d, seed @ 2.5 × $10^5$/ml | + | 0.9 | 6 | 80 | 215 |
| 3. | 200 ml, 1d, seed @ 2 × $10^6$/ml | – | 1.9 | 3.8 | 97 | 221 |
| 4. | Balb/c ascites | – | 5,160 | 19,170 | ND | ND |

[a]Sp2/0 cells transfected by electroporation with pING2114(pL6HL)
[b]ug/l measured by ELISA specific for human Kappa - human Bence-Jones protein standard.
[c]ug/l measured by ELISA specific for human gamma - human IgG standard.
ND - Not determined.
FBS: Fetal Bovine Serum (9) Studies Performed on the Chimeric L6 Antibody First, the samples were tested with a binding assay, in which cells of both an L6 antigen-positive and an L6 antigen-negative cell line were incubated with standard mouse monoclonal antibody L6, chimeric L6 antibody derived from the cell culture supernatants, and chimeric L6 antibody derived from ascites (as previously described) followed by a second reagent, fluorescein-isothiocyanate (FITC)-conjugated goat antibodies to human (or mouse, for the standard) immunoglobulin.

Since the binding assay showed strong reactivity of the chimeric L6 on the L6 antigen positive cell line and total lack of reactivity on the negative cell line, the next step was to test for the ability of the chimeric L6 to inhibit the binding of mouse L6 to antigen positive cells; such inhibition assays are used routinely to establish the identity of two antibodies' recognition of antigen. These data are discussed below ("Inhibition of binding"). As part of these studies, a rough estimate of antibody avidity was made.

Finally, two aspects of antibody function were studied, the ability to mediate ADCC in the presence of human peripheral blood leukocytes, and the ability to kill L6 positive tumor cells in the presence of human serum as a source of complement (see "Functional Assays" below).

Binding Assay

Cells from a human colon carcinoma line, 3347, which had been previously shown to express approximately 5×$10^5$ molecules of the L6 antigen at the cell surface, were used as targets. Cells from the T cell line HSB2 was used as a negative control, since they, according to previous testing, do not express detectable amounts of the L6 antigen. The target cells were first incubated for 30 min at 4° C. with either the chimeric L6 or with mouse L6 standard, which had been purified from mouse ascites. This was followed by incubation with a second, FITC-labelled, reagent, which for the chimeric antibody was goat-anti-human immunoglobulin, obtained from TAGO (Burlingame, Calif.), and used at a dilution of 1:50. For the and used at a dilution of 1:50. For the mouse standard, it was goat-anti-mouse immunoglobulin, also obtained from TAGO and used at a dilution of 1:50. Antibody binding to the cell surface was determined using a Coulter Model EPIC-C cell sorter.

As shown in Table 4 and Table 4A, both the chimeric and the mouse standard L6 bound significantly, and to approximately the same extent, to the L6 positive 3347 line. They did not bind above background to the L6 negative HSB2 line.

In view of the fact that the three different chimeric L6 samples presented in Table 4 behaved similarly in the binding assays, they were pooled for the inhibition studies presented below. The same inhibition studies were performed for chimeric L6 derived from ascites fluid presented in Table 4A.

Inhibition of Binding

As the next step was studied the extent to which graded doses of the chimeric L6 antibody, or the standard mouse L6, could inhibit the binding of an FITC-labelled mouse L6 to the surface of antigen positive 3347 colon carcinoma cells.

Both the chimeric and mouse standard L6 inhibited the binding of the directly labeled L6 antibody, with the binding curves being parallel. The chimeric antibody was slightly less effective than the standard, as indicated by the results which showed that 3.4 ug/ml of the pooled chimeric L6 MAb, as compared to 2.0 ug/ml of the standard mouse L6 MAb was needed for 50% inhibition of the binding, and that 5.5 ug/ml of the chimeric L6 (derived from ascites) as compared to 2.7 ug/ml of the standard mouse L6 MAb was needed for 50% inhibition of binding.

As part of these studies, a rough estimate was made of antibody avidity. The avidity of the standard mouse L6 had been previously determined to be approximately 4×$10^8$. The data indicated that there were no significant differences in avidity between the chimeric and the mouse L6.

Functional Assays

A comparison was made between the ability of the chimeric L6 and standard mouse L6 to lyse L6 antigen positive cells in the presence of human peripheral blood leukocytes as a source of effector cells (mediating Antibody Dependent Cellular Cytotoxicity, ADCC) or human serum as a source of complement (mediating Complement-Dependent Cytolysis, CDC).

As shown in Table 5 and Tables 5A–5D, the chimeric L6 was superior to the simultaneously tested sample of mouse L6 in causing ADCC, as measured by a 4 hr $^{51}$Cr release test.

Tables 6 and 6A–6B present the data from studies on complement-mediated target cell lysis. In this case, a high cytolytic activity was observed with both the mouse and the chimeric L6 antibodies.

Conclusions

The results presented above demonstrate a number of important, unexpected qualities of the chimeric L6 monoclonal antibody of the invention. Firstly, the chimeric L6 antibody binds to L6 antigen positive tumor cells to approximately the same extent as the mouse L6 standard and with approximately the same avidity. This is significant for the following reasons: the L6 antibody defines (a) a surface carbohydrate antigen, and (b) a protein antigen of about 20,000 daltons, each of which is characteristic of non-small cell lung carcinoma (NSCLC) and certain other human carcinomas. Significantly, the L6 antibody does not bind detectably to normal cells such as fibroblases, endothelial cells, or epithelial cells in the major organs. Thus the chimeric L6 monoclonal antibody defines an antigen that is specific for carcinoma cells and not normal cells.

In addition to the ability of the chimeric L6 monoclonal antibodies of the present invention to bind specifically to malignant cells and localize tumors, the chimeric L6 exerts profound biolgical effects upon binding to its target, which make the chimeric antibody a prime candidate for tumor immunotherapy. The results presented herein demonstrate that chimeric L6 is capable of binding to tumor cells and upon binding kills the tumor cells, either by ADCC or CDC. Such tumor killing activity was demonstrated using concentrations of chimeric L6 antibody as low as 0.01 ug/ml (10 ng/ml).

Although the prospect of attempting tumor therapy using monoclonal antibodies is attractive, with some partial tumor regressions being reported, to date such monoclonal antibody therapy has been met with limited success (Houghton, February 1985, *Proc. Natl. Acad. Sci.* 82:1242–1246). The therapeutic efficacy of mouse monoclonal antibodies (which are the ones that have been tried so far) appears to be too low for most practical purposes. The discovery of the profound biological activity of chimeric L6 coupled with its specificity for a carcinoma antigen makes the chimeric L6 antibody a choice therapeutic agent for the treatment of tumors in vivo. Moreover, because of the "human" properties which will make the chimeric L6 monoclonal antibodies more resistant to clearance in vivo, the chimeric L6 monoclonal antibodies will be advantageously used not only for therapy with unmodified chimeric antibodies, but also for development of various immunoconjugates with drugs, toxins, immunomodulators, isotopes, etc., as well as for diagnostic purposes such as in vivo imaging of tumors using appropriately labelled chimeric L6 antibodies. Such immunoconjugation techniques are known to those skilled in the art and can be used to modify the chimeric L6 antibody molecules of the present invention.

Two illustrative cell lines secreting chimeric L6 antibody were deposited prior to the filing date of this application at the ATCC, Rockville, Md. These are transfected hybridoma C255 (corresponds to 3E3 cells, supra), ATCC HB 9240 and transfected hybridoma C256 (D7 cells, supra), ATCC HB 9241.

The present invention is not to be limited in scope of the cell lines deposited since the deposited embodiment is intended as a single illustration of one aspect of the invention and all cell lines which are functionally equivalent are within the scope of the invention. Indeed, various modifications of the invention in addition to those shown in the art from the foregoing description and accompanying drawings are intended to fall within the scope of the appended claims.

TABLE 4

Binding Assays of Chimeric L6 Antibody and Mouse L6 Monoclonal Antibody on an L6 Antigen Positive and L6 Antigen Negative Cell Line.

| Antibody | Batch | GAM | GAH |
| --- | --- | --- | --- |
| | | Binding Ratio For* H3347 Cells (L6 +) | |
| Standard L6 | | 56.6 | 4.2 |
| Chimeric L6 | a | 1.3 | 110.3 |
| | b | 1.3 | 110.3 |
| | c | 1.3 | 110.3 |
| | | Binding Ratio For* HSB-2 Cells (L6 −) | |
| Standard L6 | | 1.1 | 1.1 |
| Chimeric L6 | a | 1.0 | 1.0 |
| | b | 1.0 | 1.1 |
| | c | 1.0 | 1.1 |

*All assays were conducted using an antibody conentration of 10 ug/ml. The binding ratio is the number of times brighter a test sample is than a control sample treated with GAM (FITC conjugated goat-anti-mouse) or GAH (FITC conjugated goat anti-human) alone. A ratio of 1 means that the test sample is just as bright as the control; a ratio of 2 means the test sample is twice as bright as the control, etc.

TABLE 4A

Binding Assays Of Chimeric L6 Antibody and Mouse Monoclonal Antibody on an L6 Antigen Positive and L6 Antigen Negative Cell Line.

| Antibody | Antibody Concentration (ug/ml) | GAM | GAH |
| --- | --- | --- | --- |
| | | Binding Ratio For* H3347 Cells (L6 +) | |
| Standard L6 | 30 | 38 | 4 |
| | 10 | 49 | 4 |
| | 3 | 40 | 3 |
| Chimeric L6 (Ascites) | 30 | 2 | 108 |
| | 10 | 2 | 108 |
| | 3 | 1 | 42 |
| Chimeric L6 (Cell Culture) | 30 | 1 | 105 |
| | 10 | 1 | 86 |
| | 3 | 1 | 44 |
| | | Binding Ratio For** HSB-2 Cells (L6 −) | |
| Standard L6 | 10 | 1 | 1 |
| Chimeric L6 (Ascites) | 10 | 1 | 1 |
| Chimeric L6 (Cell Culture) | 10 | 1 | 1 |

*The binding ratio is the number of times brighter a test sample is than a control sample treated with GAM (FITC conjugated goat anti-human) alone. A ratio of 1 means that the test sample is just as bright as the control; a ratio of 2 means the test sample is twice as bright as the control, etc.

TABLE 5

ADCC of Chimeric L6 (Mouse) L6 Antibodies On Colon Carcinoma Cell Line 3347.

| Antibody | Antibody Concentration (ug/ml) | PBL per Target Cell | % Cytolysis* |
| --- | --- | --- | --- |
| Chimeric L6 | 10 | 100 | 64 |
| | 5 | 100 | 70 |

TABLE 5-continued

ADCC of Chimeric L6 (Mouse) L6 Antibodies On Colon Carcinoma Cell Line 3347.

| Antibody | Antibody Concentration (ug/ml) | PBL per Target Cell | % Cytolysis* |
|---|---|---|---|
|  | 10 | 0 | 2 |
| Standard L6 | 10 | 100 | 24 |
|  | 5 | 100 | 17 |
|  | 10 | 0 | 2 |
| None | 0 | 100 | 1 |

*The target cells had been labelled with $^{51}Cr$ and were exposed for 4 hours to a combination of MAb and human peripheral blood leukocytes (PBL), and the release of $^{51}Cr$ was measured subsequently. The release of $^{51}Cr$ (after corrections of values for spontaneous release from untreated cells) is a measure of the percent cytolsis.

TABLE 5A

ADCC of Chimeric L6 and Standard (Mouse) L6 Antibodies On Colon Carcinoma Cell Line 3347.

| Antibody | Antibody Concentration (ug/ml) | PBL per Target Cell | % Cytolysis* |
|---|---|---|---|
| Chimeric L6 | 20 | 100 | 80 |
| (Ascites) | 10 | 100 | 74 |
|  | 5 | 100 | 71 |
|  | 2.5 | 100 | 71 |
|  | 20 | 0 | 0 |
| Chimeric L6 | 10 | 100 | 84 |
| (Cell | 5 | 100 | 74 |
| Culture) | 2.5 | 100 | 67 |
|  | 10 | 0 | 3 |
| Standard L6 | 20 | 100 | 32 |
|  | 10 | 100 | 26 |
|  | 20 | 0 | 0 |

*The target cells had been labelled with $^{51}Cr$ and were exposed for 4 hours to a combination of MAb and human peripheral blood leukocytes (PBL), and the release of $^{51}Cr$ was measured subsequently. The release of $^{51}Cr$ (after corrections of values for spontaneous release from untreated cells) is a measure of the percent cytolsis.

TABLE 5B

ADCC of Chimeric L6 and Standard (Mouse) L6 Antibodies On Colon Carcinoma Cell Line 3347.

| Antibody | Antibody Concentration (ug/ml) | PBL per Target Cell | % Cytolysis* |
|---|---|---|---|
| Chimeric L6 | 5 | 100 | 84 |
| (Ascites) | 2.5 | 100 | 78 |
|  | 1.25 | 100 | 85 |
|  | 0.63 | 100 | 81 |
|  | 0.31 | 100 | 80 |
|  | 0.16 | 100 | 71 |
|  | 0.08 | 100 | 65 |
|  | 5 | 0 | 0 |
| Standard L6 | 5 | 100 | 32 |
|  | 5 | 0 | 0 |
| None | 0 | 100 | 19 |

*The target cells had been labelled with $^{51}Cr$ and were exposed for 4 hours to a combination of MAb and human peripheral blood leukocytes (PBL), and the release of $^{51}Cr$ was measured subsequently. The release of $^{51}Cr$ (after corrections of values for spontaneous release from untreated cells) is a measure of the percent cytolsis.

TABLE 5C

ADCC of Chimeric L6 and Standard (Mouse) L6 Antibodies On Lung Carcinoma Cell Line H2669.

| Antibody | Antibody Concentration (ug/ml) | PBL per Target Cell | % Cytolysis* |
|---|---|---|---|
| Chimeric L6 | 10 | 100 | 35 |
| (Ascites) | 1 | 100 | 31 |
|  | 0.1 | 100 | 27 |
|  | 0.01 | 100 | 15 |
|  | 0.001 | 100 | 13 |
|  | 0.0001 | 0 | 15 |
| Standard L6 | 10 | 100 | 9 |
|  | 1 | 100 | 15 |
| None | 0 | 100 | 9 |
| Chimeric L6 | 10 | 10 | 19 |
| (Ascites) | 1 | 10 | 15 |
|  | 0.1 | 10 | 11 |
|  | 0.01 | 10 | 13 |
|  | 0.001 | 10 | 22 |
|  | 0.0001 | 10 | 11 |
| Standard L6 | 10 | 10 | 7 |
|  | 1 | 10 | 6 |
| None | 0 | 10 | 8 |
| Chimeric L6 | 10 | 0 | 4 |
| (Ascites) |  |  |  |
| Standard L6 | 10 | 0 | 9 |

*The target cells had been labelled with $^{51}Cr$ and were exposed for 4 hours to a combination of MAb and Human peripheral blood leukocytes (PBL), and the release of $^{51}Cr$ was measured subsequently. The release of $^{51}Cr$ (after corrections of values for spontaneous release from untreated cells) is a measure of the percent cytolsis.

TABLE 5D

ADCC of Chimeric L6 and Standard (Mouse) L6 Antibodies On Colon Carcinoma Cell Line H3347.

| Antibody | Antibody Concentration (ug/ml) | PBL per Target Cell | % Cytolysis* |
|---|---|---|---|
| Chimeric L6 | 10 | 100 | 62 |
| (Ascites) | 1 | 100 | 66 |
|  | 0.1 | 100 | 69 |
|  | 0.01 | 100 | 26 |
|  | 0.001 | 100 | 8 |
|  | 0.0001 | 0 | 3 |
|  | 10 | 0 | 0 |
| Standard L6 | 10 | 100 | 19 |
|  | 1 | 100 | 24 |
|  |  | 0 | 0 |
| None | 0 | 100 | 8 |

*The target cells had been labelled with $^{51}Cr$ and were exposed for 4 hours to a combination of MAb and Human peripheral blood leukocytes (PBL), and the release of $^{51}Cr$ (after corrections of value for spontaneous release from untreated cells) is a measure of the percent cytolysis.

TABLE 6

Complement-dependent cytotoxic effect of chimeric and standard (mouse) L6 on colon carcinoma cells from line 3347, as measured by a 4-hr $^{51}Cr$-release assay. Human serum from a healthy subject was used as the source of complement.

| Antibody | Human complement | % Cytolysis |
|---|---|---|
| L6 Standard 10 ug/ml | Yes | 90 |
| L6 chimeric 10 ug/ml | Yes | 89 |
| L6 Standard 10 ug/ml | No | 0 |
| L6 chimeric 10 ug/ml | No | 1 |

TABLE 6A

Complement Dependent Cytotoxic Effect of Chimeric L6 and Standard (Mouse) L6 Antibodies on Colon Carcinoma Cell Line 3347

| Antibody | Antibody Concentration (ug/ml) | PBL per Target Cell | % Cytolysis* |
|---|---|---|---|
| Chimeric L6 | 20 | + | 29 |
| (Ascites) | 10 | + | 23 |
|  | 5 | + | 18 |
|  | 2.5 | + | 8 |
|  | 20 | Inactivated | 0 |
|  | 10 | 0 | 0 |
| Chimeric L6 | 20 | + | 29 |
| (Cell Culture) | 5 | + | 26 |
|  | 2.5 | + | 18 |
|  | 20 | + | 4 |
|  | 10 | 0 | 4 |
| Standard L6 | 20 | + | 55 |
|  | 10 | + | 37 |
|  | 20 | Inactivated | 0 |
|  | 20 | 0 | 1 |
| None | 0 | + | 0 |

*Complement mediated cytolysis was measured by a 4 hour $^{51}$Cr-release assay. Human serum from a healthy subject was used as the source of complement.

TABLE 6B

Complement Dependent Cytotoxic Effect of Chimeric L6 and Standard (Mouse) L6 Antibodies on Colon Carcinoma Cell Line 3347

| Antibody | Antibody Concentration (ug/ml) | PBL per Target Cell | % Cytolysis* |
|---|---|---|---|
| Chimeric L6 | 10 | + | 209 |
| (Ascites) | 5 | + | 155 |
|  | 2.5 | + | 166 |
|  | 1.25 | + | 114 |
|  | 0.6 | + | 63 |
|  | 0.3 | + | 17 |
|  | 10 | 0 | 0 |
| Standard L6 | 10 | + | 96 |
|  | 5 | + | 83 |
|  | 2.5 | + | 48 |
|  | 1.25 | + | 18 |
|  | 0.6 | + | 7 |
|  | 0.3 | + | 4 |
|  | 10 | 0 | 2 |
| None | 0 | + | 0 |

*Complement mediated cytolysis was measured by a 4 hour $^{51}$Cr-release assay. Human serum from a healthy subject was used as the source of complement.

Example IV

A Human-Mouse Chimeric Antibody with Specificity for Human B-Cell Antigen

The 2H7 mouse monoclonal antibody (gamma $_{2b}$K) recognizes a human B-cell surface antigen, Bp35 (Clark, E. A., et al., *Proc. Nat. Acad. Sci. USA* 82:1766 (1985)). The Bp35 molecule plays a role in B-cell activation. mRNA was prepared from the 2H7 cell line. Two cDNA libraries were generated—one using the heavy chain UIG-H primer and the other, oligo(dT). One $V_H$ clone, pH2-11, was isolated upon screening with the same UIG-H oligonucleotide. To isolate the light chain clone, a mouse kappa-specific DNA fragment was used to screen the oligo(dT) library. Candidate clones were further screened with a mouse $J_K5$ sequences. One $V_K$ clone, pL2-12, was thus isolated. The light chain UIG-K was then used to engineer a restriction enzyme site in the J region.

The two cDNA clones were also modified at the 5' end to remove the artificial oligo d[C] sequence. In pH2-11 this was carried out by using the restriction enzyme NcoI which cuts one nucleotide residue 5' of the ATG initiator codon. In pL2-12 this was achieved by an oligonucleotide in vitro mutagenesis using a 22-mer container a SalI site.

The DNA sequences of these two clones were shown in FIGS. 21, 22. To construct the chimeric heavy chain plasmid, the $V_H$ module was joined to the human C gamma 1 module (pGMH6) at the $J_H$ BstEII site, and the chimeric light chain the $V_K$ module was joined to the human $C_K$ module (pGML60) at the $J_K$ HindIII site. The expression vector sequences were derived from pING2012-neo as well as pING2016-gpt. The constructed plasmids are pING2101 ($V_H$C gamma 1-neo), pING2106 ($V_K C_K$-neo), pING2107 ($V_K C_K$-gpt). pING2101 and pING2106 were also used to generate plasmids containing both genes. They are pHL2-11 and pHL2-26. In addition, pING2106 and pING2014 were combined to a two light chain plasmid, pLL2-25, to compensate for the poorer (compared to heavy chain) steady-state accumulation of light chain protein in transfected cells. (See FIG. 23.) FIG. 24 shows the changes made to the variable region sequences during the construction.

The plasmid, pHL2-11, was linearized by AatII; and the DNA was used to transfect Sp2/O cells by electroporation. Transformants were selected in G418-DMEM. One transformant, 1C9, produces 9.3 ng/ml chimeric kappa and 33–72 ng/ml chimeric gamma 1 protein as assayed by ELISA. Southern analysis of 1C9 DNA showed that there is one copy of the plasmid integrated in the Sp2/O genome.

Example V

Secretion of a Functional Chimeric Antibody from Yeast (1) Fusion of mature chimeric L6 light chain and heavy chain genes to the yeast invertase signal sequence and shortened phosphoglycerate kinase (PGK promoter).

Figure 26B:
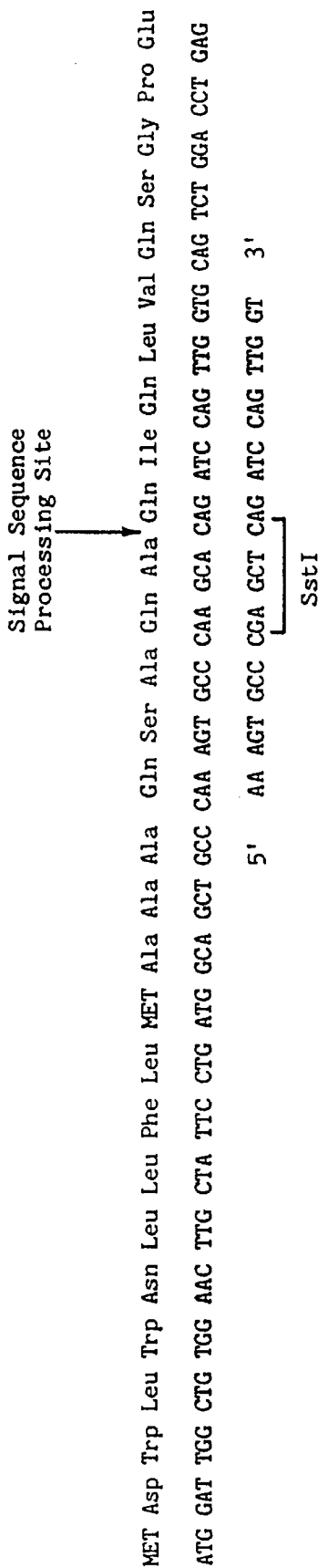
Figure 26C:
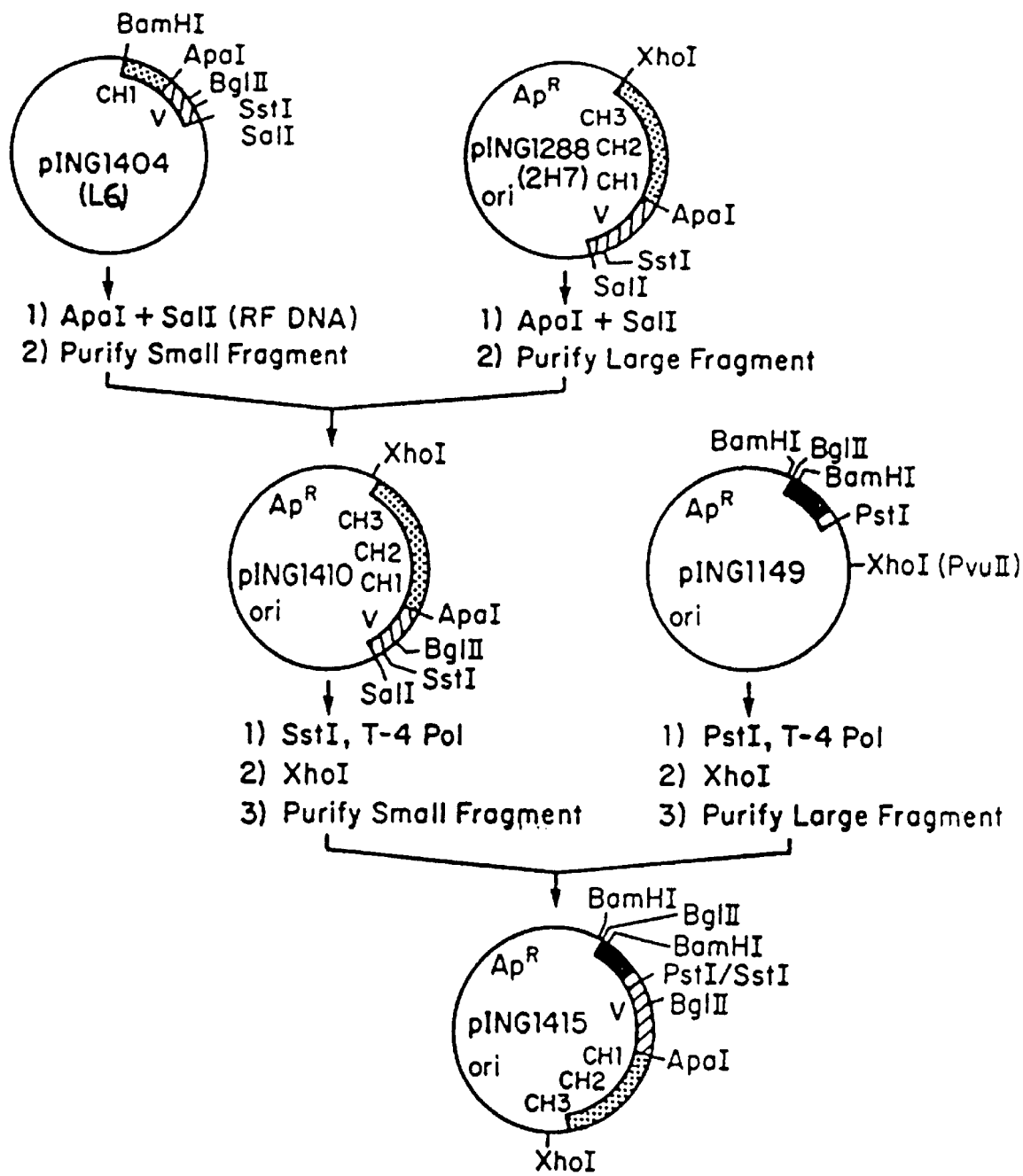

Yeast cells are capable of recognizing mammalian secretion signal sequences and of directing secretion of mammalian proteins (Hitzman et al., supra). There is, however, evidence which suggests that certain native yeast signal sequences are more effective than mammalian signal sequences at directing secretion of some mammalian proteins from yeast (Smith et al., *Science* 229:1219 (1985)). One example is the signal sequence for the yeast invertase gene. To improve the efficiency of light and heavy chain secretion, the mature light chain and heavy chain sequences were fused to the yeast invertase signal sequence and placed under transcriptional control of the shortened PGK promoter (U.S. patent application Ser. No. 797,477 abandoned) using the strategies outlined in FIGS. 25 and 26, respectively. An important element of these constructions is the use of in vitro mutagenesis to introduce a restriction site at the signal sequence processing site for both the invertase signal sequence (see U.S. patent application Ser. No. 797,477 abandoned) and the light and heavy chain genes. These restrictions sites are positioned such that a blunt-ended ligation of restriction enzyme-digested, T-4 DNA polymerase-treated DNA results in in-phase translational fusions of the 5' end of the mature immunoglobulin chains with the 3' end of the yeast invertase signal sequence. Such genes, when expressed in a yeast cell, may direct the synthesis, processing, and secretion of chimeric light and heavy chains with the same primary peptide sequence as chimeric light and heavy chains secreted from transfected mouse Sp2/O cells. The DNA sequences of the mutagenesis primers used for light and heavy chain genes as well as the corresponding unmutagenized sequences are shown in FIGS. 25B and 26B, respectively. Using this approach, the L6 chimeric light and heavy chains were fused to the yeast invertase signal sequence and shortened pGK promoter, resulting in plasmids pING1407-7 and pING1415 (FIGS. 25C and 26C).

(2) Removal of non-yeast 3' untranslated DNA.

Recent studies on expression of hepatitis B surface antigen in yeast demonstrated that removal of non-yeast 3' and 5' untranslated sequences can result in increased levels of heterologous gene expression in yeast (Knieskin et al., Gene 46:135 (1986)). The light chain gene sequence of chimeric L6 antibody in pING1407-7 (FIG. 25C) contains approximately 200 bp of 3' untranslated DNA followed by 70 bp of poly A and 20 bp of poly G sequences. An initial treatment of the chimeric L6 light chain DNA with the double-stranded exonuclease Bal31, removed the poly A and poly G sequences and all but 90 bp of 3' untranslated DNA, generating the plasmid pING2121b (FIGS. 27A and B). A restriction fragment from pING2121b containing only $C_k$ was cloned into a derivative of pBR322, generating pING1419 (FIG. 27A). A second Bal31 digestion was next used to remove all but 13 bp of non-yeast 3' untranslated DNA generating the plasmid, pING1431 (FIG. 27A). The chimeric L6 heavy chain gene in pING1415 (FIG. 26C) also contains extensive 3' untranslated sequence which includes 80 bp of poly A. All but 11 bp of the 3' untranslated DNA were removed using the strategy shown in FIG. 28, generating the plasmid pING1429.

Site-directed in vitro mutagenesis can introduce, at a low frequency, unwanted base pair changes in regions of the DNA outside of the area being mutagenized. To ensure that such mutations were not present in the chimeric L6 light and heavy chain sequences which had been cloned into M13 and subjected to site-directed mutagenesis, we constructed light and heavy chain genes fused to the invertase signal sequence and the shortened PGK promoter which consisted of coding sequences that were either confirmed by DNA sequence analysis or proven to be functional by virtue of their expression in transfected mouse Sp2/O cells to produce functional chimeric L6 antibody. The plasmids, pING1439 (light chain, FIG. 27B) and pING1436 (heavy chain, FIG. 28) were generated by these constructions.

(3) Construction of yeast expression plasmids containing chimeric L6 light and heavy chain genes from pING1439 and pING1436, respectively, fused to the PGK polyadenylation signal.

In order for yeast to produce an intact functional antibody molecule, a balanced synthesis of both light and heavy chain protein within the host cell is preferred. One approach is to place the light and heavy chain genes on separate expression vectors each containing a different selective marker. A yeast strain defective in the selective markers found on the plasmids can then be either simultaneously or sequentially transformed with these plasmids.

The chimeric L6 light and heavy chain genes from pING1439 (FIG. 27B) and pING1436 (FIG. 28) were cloned as BglII-XhoI and BamHI-XhoI fragments, respectively, in two different medium copy number (about 20 copies/cell) expression vectors (yeast-E. coli shuttle). One of these pING804CVS, contains the complete yeast 2-micron circle, the PGK transcription termination and polyadenylation signals, and the leu2 gene as the selective marker. The other vector, pING1150, contains the yeast origin of replication, oriY, a cis-acting sequence (REP3) from the yeast endogenous 2-micron plasmid, the PGK transcription termination and polyadenylation signals, and the ura3 gene as the selective marker. Both plasmids also contain the β-lactamase gene (bla) for ampicillin resistance and the bacterial origin of replication (oriB) from pBR322 for selection and amplification in bacteria. Four plasmids resulted from these constructions: pING1441—light chain, leu2 and pING1443—light chain, ura3 (FIG. 29); pING1440—heavy chain, leu2 and pING1442—heavy chain, ura3 (FIG. 30).

(4) Secretion of chimeric L6 antibody from transformed yeast cells.

Two separate transformation experiments were performed in an attempt to obtain both light and heavy chain synthesis in yeast cells. Four µg each of pING1440 and pING1443, and separately of pING1442 and pING1441 were cotransformed into Saccharomyces cerevisiae strains BB331C (MATa, ura3, leu2) by selecting for growth on SD agar (2% glucose, 0.67% yeast-nitrogen base, 2% agar). Ura$^+$ Leu$^+$ transformants appeared at 2–3 days of incubation at 30° C. Approximately 100 transformants were obtained for pING1440 plus pING1443; only 15 transformants were obtained for pING1442 plus pING1441. Ten colonies were inoculated from each plate into 5 ml SD broth supplemented with 50 mM sodium succinate, pH 5.5, and grown for 65 hours at 30° C. The cells were removed by centrifugation and the culture supernatants analyzed by ELISA for the levels of light chain and heavy chain and for the degree of association of the secreted light and heavy chains. The latter was assessed using a goat anti-human kappa antiserum to coat the microtiter wells and a peroxidase-labeled goat anti-human gamma antiserum to detect the level of heavy chain bound to the anti-kappa coat. The results of these assays (Table 7) revealed that all of the culture supernatants from the cells transformed with pING1440 (heavy chain, leu2) plus pING1443 (light chain, ura3) contained a disproportionately high level of light chain protein relative to the levels of heavy chain protein, and no evidence (at least as determined by ELISA) of assembled light and heavy chains. On the other hand, the supernatants from the cells transformed with pING1442 (heavy chain, ura3)+pING1441 (light chain, leu2) contained a more balanced production of light and heavy chain proteins, and eight of ten isolates appeared to contain some assembled light and heavy chains as determined by ELISA. Two of these isolates, No. 1 and No. 5, produced a significant proportion of assembled light and heavy chain.

TABLE 7

LEVELS OF SECRETED CHIMERIC L6 LIGHT AND HEAVY CHAIN BY YEAST TRANSFORMANTS[a]

| Plasmids[b] | Isolate No. | Kappa[c] | Gamma[d] | Kappa/Gamma[e] |
|---|---|---|---|---|
| pING1440 + | 1 | 284 | 39 | 0 |
| pING1443 | 2 | 324 | 33 | 0 |
| | 3 | 473 | 52 | 0 |
| | 4 | 387 | 40 | 0 |
| | 5 | 316 | 34 | 0 |
| | 6 | 188 | 28 | 0 |
| | 7 | 381 | 45 | 0 |
| | 8 | 455 | 45 | 0 |
| | 9 | 380 | 26 | 0 |
| | 10 | 579 | 32 | 0 |
| pING1441 + | 1 | 128 | 79 | 35 |
| pING1442 | 2 | 150 | 30 | 1 |

TABLE 7-continued

LEVELS OF SECRETED CHIMERIC L6 LIGHT AND HEAVY CHAIN BY YEAST TRANSFORMANTS[a]

| Plasmids[b] | Isolate No. | Kappa[c] | Gamma[d] | Kappa/Gamma[e] |
|---|---|---|---|---|
| | 3 | 124 | 29 | 0 |
| | 4 | 185 | 55 | 5 |
| | 5 | 114 | 52 | 35 |
| | 6 | 139 | 23 | 5 |
| | 7 | 149 | 34 | 5 |
| | 8 | 245 | 57 | 12 |
| | 9 | 202 | 26 | 11 |
| | 10 | 157 | 19 | 7 |

[a]*S. cerevisiae* strain BB331C (MATa, leu2, ura3) transformed to Ura+ Leu+ with plasmids carrying ura3 and leu2 with light or heavy chains.
[b]Plasmids: pING1440 = heavy chain + leu2; pING1443 = light chain + ura3; pING1442 = heavy chain + ura3; pING1441 = light chain + leu2.
[c]ng/ml measured by ELISA specific for human kappa with human Bence Jones protein as standard.
[d]ng/ml measured by ELISA specific for human gamma with human as IgG standard.
[e]ng/ml measured by ELISA using anti-human kappa as coating antibody and anti-human gamma as second antibody with human IgG standard.

Further analysis was performed to determine if this association was the result of the synthesis of an $H_2L_2$-size protein. The culture supernatants from isolates Nos. 1 and 5, as well as from isolate No. 8, which contained a much lower level of apparent light and heavy chain association, were concentrated by ultra-filtration on a Centricon 30 filter (Amicon Corp.). The concentrated supernatants were run on a 7% polyacrylamide gel under non-reducing conditions, blotted to nitrocellulose, and probed with goat anti-human kappa antiserum. The concentrated supernatants from isolates No. 1 and 5, but not from No. 8, contained a single immunoreactive band which co-migrated with the purified chimeric L6 antibody from transfected Sp2/O cells. These results suggested that isolates No. 1 and 5 were synthesizing and secreting assembled L6 chimeric antibody.

(5) Purification of chimeric L6 antibody from yeast culture supernatant.

In order to further characterize the $H_2L_2$-size protein secreted by the yeast and determine if this was assembled L6 chimeric antibody, a sufficient quantity of yeast-produced material was purified to allow the performance of various binding and functional assays. The pING1442+1441 transformant isolate No. 5 was grown for 58 hours at 30° C. in a 10-liter fermentor using a synthetic medium (Table 8). The cells were initially grown in 9 liters of the column A medium until the glucose level fell below 1 g/L at which time they were fed with a total volume of 2.5 L of medium from column B. Glucose levels were maintained at 0.5 g/L during the remaining course of the fermentation. The cells were removed by centrifugation and the culture supernatant was analyzed by ELISA for the presence of light and heavy chain proteins and for association of the heavy and light chains. The supernatant contained approximately 250 μg/L of light chain, 240 μg/L of heavy chain, and 130 μg/L of heavy chain associated with light chain. The culture supernatants were next concentrated by ultrafiltration over a D.C. 10 unit (Amicon Corp.), filtered through 0.45 micron filter and concentrated over a YM30 filter (Amicon Corp.) to 250 ml. The concentrated supernatant was adjusted to pH 7.4 with KOH, brought to 500 ml with PBS (10 mM sodium phosphate, pH 7.4, 150 mM sodium chloride) and loaded on a 1 ml protein A-Sepharose (Sigma) column, pre-equilibrated with PBS. The column was washed first with 20 ml PBS, followed by 10 ml 0.1 M sodium citrate, pH 3.5, then by 10 ml 0.1 M citric acid pH=2.2. The pH 3.5 and 2.2 eluates were each collected in a tube containing 1 ml 2 M Tris base (Sigma). The bulk of the light and heavy chain immunoreactive proteins were in the pH 3.5 eluate which was next concentrated over a Centricon 30 (Amicon Corp.) to a final volume of 106 ul. Analysis of this protein on non-reducing polyacrylamide gels using coomassie blue staining and immunoblotting with anti-human kappa antiserum (Sigma) to visualize the proteins revealed an $H_2L_2$-size, 150 kilodaltons, protein band. This protein was purified away from other proteins by HPLC using an $AB_x$ 5-micron column equilibrated with buffer A (10 mM $KPO_4$, pH 6.8). After loading the sample on the column, the column was washed with buffer A for 10 minutes (flow rate=1 ml/minute) and subjected to a linear gradient of 0% to 50% buffer B (250 mM $KPO_4$, pH 6.8) over 50 minutes at 1 ml/minute.

TABLE 8

MEDIUM USED FOR YEAST FERMENTATION TO PRODUCE SECRETED L6 CHIMERIC ANTIBODY[a]

| Ingredients | A[b] | B[c] |
|---|---|---|
| 1. Cerelose (Glucose) | 119 g/l | 538 g/l |
| 2. $(NH_4)_2SO_4$ | 13.9 g/l | 83.3 g/l |
| 3. Thiamine HCL | 0.011 g/l | 0.05 g/l |
| 4. Biotin | 0.00011 g/l | 0.005 g/l |
| 5. Pantothenic acid | 0.002 g/l | 0.009 g/l |
| 6. Inositol | 0.194 g/l | 0.875 g/l |
| 7. $H_3PO_4$ | 5.67 ml/l | 25.5 ml/l |
| 8. $KH_2PO_4$ | 5.78 g/l | 26.0 g/l |
| 9. $MgSO_4.7H_2O$ | 3.33 g/l | 15.2 g/l |
| 10. $CaCl_2.2H_2O$ | 0.33 g/l | 1.5 g/l |
| 11. $FeSO_4.7H_2O$ | 0.072 g/l | 0.34 g/l |
| 12. $ZnSO_4.7H_2O$ | 0.022 g/l | 0.104 g/l |
| 13. $MnCl_2.4H_2O$ | 0.0039 g/l | 0.018 g/l |
| 14. $CuSO_4.5H_2O$ | 0.0067 g/l | 0.031 g/l |
| 15. $Conc.H_2SO_4$ | 0.0056 ml/l | 0.026 ml/l |

[a]Fermentation was performed as described in text.
[b]Constituents of initial 9-liter batch.
[c]Constituents of 2.5-liter feed batch.

The bulk of the protein resolved into a single large broad peak between 20 and 50 minutes as determined by absorbance at 280 nm. A second smaller peak was observed at 52–56 minutes, which corresponded to the normal elution position for chimeric L6 antibody from transfected Sp2/O cells. ELISA analysis of the column fractions revealed a major heavy+light chain cross-reactive peak corresponding to the U.V. absorbance peak at 52–56 minutes. Analysis of the 52–56 minute fractions on non-reducing SDS polyacrylamide gels using coomassie blue staining and immunoblotting revealed an essentially pure protein which co-migrated with L6 chimeric antibody purified from transfected Sp2/O cells.

(6) Studies performed on the chimeric L6 antibody secreted by yeast.

The purified yeast-derived antibody was assessed for function in several ways. First, the purified antibody was tested for its ability to bind directly to an L6 antigen-positive cell line. Second, the antibody was tested for its ability to inhibit binding of mouse L6 antibody to antigen-positive cells. Finally, the purified antibody was tested for two aspects of antibody function—the ability to mediate ADCC in the presence of human peripheral blood leuokocytes and the ability to kill L6 positive tumor cells in the presence of human complement.

Direct Binding Assay

Cells from a human colon carcinoma line, 3347, which expresses approximately $5 \times 10^5$ molecules of the L6 antigen per cell on the cell surface, were used as targets. Cells from the T cell line, T51, were used as a negative control since they, according to previous testing, do not express detectable amounts of the L6 antigen. The target cells were first incubated for 30 min at 4° C. with either the Sp2/O cell- or yeast-derived chimeric L6 antibody or with mouse L6 antibody standard purified from mouse ascites. This was followed by incubation with FITC-labeled goat-anti-human immunoglobulin for the chimeric antibodies or with FITC-labeled goat-anti-mouse immunoglobulin for the mouse standard. Both labeled antibodies were obtained from TAGO (Burlingame, Calif.) and used at a dilution of 1:50. Antibody binding to the cell surface was determined using a Coulter Model EPIC-C cell sorter.

As shown in Table 9, both the mammalian and yeast-derived chimeric L6 antibodies bound significantly, and to approximately the same extent, to the L6 positive 3347 line. They did not bind above background to the L6 negative T51 line.

Inhibition of Binding

As the next step, the yeast chimeric L6 antibody and the SP2/O cell-derived chimeric L6 antibody were tested for their ability to inhibit the binding of an FITC-labeled mouse L6 antibody to the surface of antigen-positive 3347 colon carcinoma cells.

Both the yeast-derived and Sp2/O-derived chimeric L6 antibodies inhibited the binding of labeled mouse L6 antibody and the binding curves were parallel. Based on the results of these studies, a rough estimate was made of antibody avidity. The avidity of the Sp2/O cell-derived chimeric L6 had been previously determined to be approximately $4 \times 10^8$. The data indicated that there were no significant differences between the avidities of yeast-derived chimeric L6 and Sp2/O cell-derived chimeric L6 antibodies for the L6 antigen.

Functional Assays

A comparison was made between the ability of the yeast-derived chimeric L6, Sp2/O cell-derived chimeric L6 and standard mouse L6 antibodies to lyse L6 antigen-positive cells in the presence of human peripheral blood leukocytes as a source of effector cells mediating Antibody Dependent Cellular Cytotoxicity (ADCC). As shown in Table 10, the chimeric L6 from yeast was slightly better than Sp2/O-cell-derived chimeric L6 and as previously observed, both were superior to the standard mouse L6 in causing ADCC, as measured by a four-hour $^{51}$Cr release test.

A comparison was next made between the yeast-derived chimeric L6, Sp2/O cell-derived chimeric L6 and standard mouse L6 antibodies for their abilities to lyse L6 antigen-positive cells by complement-dependent cytoloysis (CDC) when human serum was used as the source of complement. The results of this comparison (Table 11) demonstrated that while both the Sp2/O-cell-derived chimeric L6 and standard mouse L6 antibodies exhibited high cytolytic activity, the yeast-derived L6 antibody failed to cause any cytolysis even at the highest antibody concentration. These results were unexpected and demonstrate that the yeast-derived antibody has new and unique properties.

(7) Conclusions

A process is disclosed by which yeast can be genetically engineered to secrete functional antibodies. The yeast-derived chimeric antibody in this example binds to the appropriate target antigen with approximately the same avidity as the chimeric antibody produced by lymphoid (Sp2/0) cells. The yeast-derived antibody also displays similar ADCC activity as does Sp2/0-derived antibody. Unlike the Sp2/0 cell-derived antibody, the yeast-derived antibody displayed no CDC activity, thus demonstrating the new and unique properties of the yeast-derived antibody. This process should be applicable for the production of a variety of monoclonal antibodies and chimeric antibodies carrying chosen antigen binding domains linked to a chosen constant domain isotype. Genetically engineered antibodies and derivatives thereof produced in yeast also will exhibit novel functional properties, for example, the ability to selectively mediate target killing by ADCC without any detectable CDC activity. The technology described herein may also be suitable for the production of various other heterologous multimeric secreted proteins by genetically engineered yeast.

TABLE 9

BINDING ASSAYS OF CHIMERIC L6 ANTIBODY PRODUCED BY YEAST OR MOUSE Sp2/O CELLS ON AN L6 ANTIGEN-POSITIVE AND AN L6 ANTIGEN-NEGATIVE CELL LINE

| Antibody[a] | Binding Ratio[b] for: | |
|---|---|---|
| | H3347 Cells (L6+) | T51 Cells (L6−) |
| Standard Mouse L6 | 95 | 1.0 |
| Sp2/O Chimeric L6 | 116 | 1.0 |
| Yeast Chimeric L6 | 116 | 1.0 |

[a]All antibodies were used at a concentration of 10 μg/ml.
[b]The binding ratio is the number of times brighter a test sample is than a control sample treated with FITC-conjugated second antibody. Goat anti-mouse antibody was used as the second antibody for standard mouse L6 monoclonal antibody. Goat anti-human antibody was used as the second antibody for the yeast and Sp2/O chimeric L6 antibody.

TABLE 10

ADCC OF CHIMERIC L6 ANTIBODY DERIVED FROM YEAST OR Sp2/O CELLS AND STANDARD (MOUSE) L6 ANTIBODY ON COLON CARCINOMA CELL LINE 3347

| Antibody | Antibody Concentration (μg/ml) | % Cytolysis* |
|---|---|---|
| Standard mouse L6 | 5.0 | 42 |
| | 1.0 | 48 |
| Sp2/O Chimeric L6 | 1.0 | 96 |
| | 0.1 | 71 |
| | 0.01 | 54 |
| | 0.001 | 37 |
| Yeast Chimeric L6 | 1.0 | 114 |
| | 0.1 | 108 |
| | 0.01 | 76 |
| | 0.001 | 60 |
| None | 0 | 23 |

*The target cells had been labeled with $^{51}$Cr and were exposed for four hours to a combination of MAb and human peripheral blood leukocytes at 100 per target cell, and the release of $^{51}$Cr was measured subsequently. The release of $^{51}$Cr (after corrections of values for spontaneous release from untreated cells) is a measure of the percent cytolysis.

TABLE 11

HUMAN COMPLEMENT-DEPENDENT CYTOTOXIC EFFECTS OF CHIMERIC L6 ANTIBODY PRODUCED BY YEAST OR MOUSE Sp2/O CELLS ON COLON CARCINOMA CELL LINE 3347

| Antibody | Antibody Concentration (μg/ml) | Complement[a] (+ or −) | Percent Cytolysis |
|---|---|---|---|
| Standard mouse L6 | 5 | + | 122 |
| | 1 | + | 53 |
| | 5 | − | 1 |
| Sp2/O Chimeric L6 | 5 | + | 73 |

TABLE 11-continued

HUMAN COMPLEMENT-DEPENDENT CYTOTOXIC EFFECTS OF CHIMERIC L6 ANTIBODY PRODUCED BY YEAST OR MOUSE Sp2/O CELLS ON COLON CARCINOMA CELL LINE 3347

| Antibody | Antibody Concentration (μg/ml) | Complement[a] (+ or −) | Percent Cytolysis |
|---|---|---|---|
|  | 1 | + | 22 |
|  | 0.1 | + | 5 |
|  | 5 | − | 2 |
| Yeast Chimeric L6 | 5 | + | 3 |
|  | 1 | + | 2 |
|  | 0.1 | + | 4 |
|  | 5 | − | 2 |

[a]Human serum from a healthy subject was used as the source of complement.
[b]Complement-mediated cytolysis was measured by a four-hour $^{51}$Cr-release assay.

Example VI

Secretion of Functional Chimeric Fab from Yeast

The Fab portion of IgG consists of a single light chain molecule coupled by a disulfide bridge to a single truncated heavy chain molecule consisting of the variable region and $C_H1$ (FIG. 31). This heavy chain fragment is known as Fd. Fabs are potentially useful for a variety of therapeutic and diagnostic procedures. In addition, they are amenable to production by microbial fermentation.

The usual method for production of Fab involves the digestion of intact IgG with papain (see FIG. 31) followed by purification of the Fab away from the Fc fragments generated in the digest. While this procedure is relatively straightforward and can result in high yields of Fab, it is somewhat time-consuming in that it first requires the production and purification of whole antibody followed by generation and, finally, purification of Fab. Furthermore, one-third of the whole antibody molecule—the Fc portion (FIG. 31)—is not utilized.

The recent advances in gene cloning and site-specific mutagenesis technology make possible a more direct and simple alternative approach for production of Fab molecules. In this approach, a stop codon is introduced in the heavy chain gene within the hinge region at approximately the codon for the amino acid at which papain digestion occurs. The Fab is then produced directly by simultaneous expression of both the light chain and Fd genes to produced their respective proteins which assemble and are secreted from the cell.

(1) Introduction of a stop codon in the hinge region of L6 chimeric heavy chain.

Figure 32B:
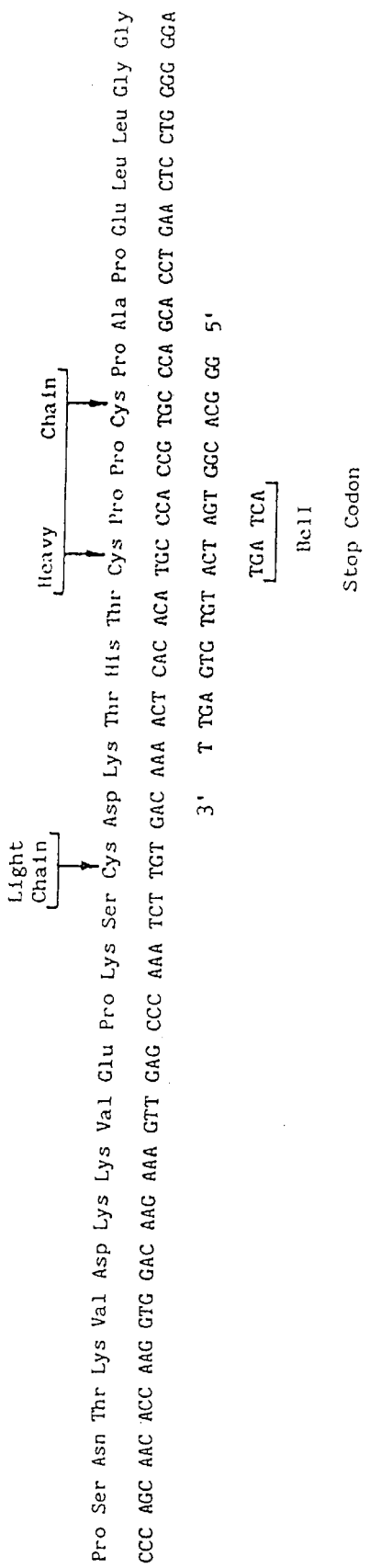

The strategy for introduction of a stop codon into the hinge region of L6 chimeric heavy chain is outlined in FIG. 32A. The location of the stop codon within the hinge region and the DNA sequence of the mutagenesis primer are shown in FIG. 32B. The stop codon placement corresponds to amino acid 226 in FIG. 31. This procedure generated the plasmid pING1402 containing an Fd gene which codes for a protein consisting of 228 amino acids and extends six amino acids beyond the cysteine to which the light chain is coupled. The mutagenesis also introduced a unique BclI site at the stop codon which can be readily utilized for subsequent manipulations of the 3' end of Fd. These include, but are not necessarily limited to, removal of heavy chain 3' untranslated DNA as well as the engineering of various types of modifications of Fd including the addition of coding sequences for specific amino acids and the production of fusion proteins.

(2) Fusion of the mature Fd gene to yeast invertase signal sequence and shortened PGK promoter.

The strategy for fusion of the Fd gene to the yeast invertase signal sequence is outlined in FIG. 33. This approach made use of the prior construction of the yeast invertase signal sequence—mature L6 heavy chain fusion (FIG. 26C) and utilized a unique ApaI site in the J region of the chimeric L6 heavy chain to replace the constant region in pING1415 consisting of $C_H1$, $C_H2$, and $C_H3$ with the constant region from pING1412 containing the stop codon in the hinge region. This procedure generated the plasmid, pING1418.

(3) Removal of non-yeast 3' untranslated DNA.

The introduction of a unique BclI site at the stop codon of the Fd chain provided a convenient method for removal of all non-yeast 3' untranslated DNA. This was accomplished using the strategy outlined in FIG. 34, and generated the plasmid, pING1428.

Since the stop codon was introduced into the hinge region by site-specific mutagenesis of a heavy chain fragment cloned into M13, the possibility existed that unwanted mutations could have been introduced during the mutagenesis step. To ensure that such mutations were not present, an Fd gene fused to the invertase signal sequence and shortened PGK promoter and consisting of known coding sequences was constructed using the strategy outlined in FIG. 34, generating the plasmid, pING1444.

(4) Construction of yeast expression plasmids containing the chimeric L6 Fd gene from pING1444 fused to the PGK polyadenylation signal.

In order for yeast to produce an intact, functional Fab molecule, a balanced synthesis of both light and Fd-chain proteins must occur simultaneously within the cell. As described in Example V, one approach is to place the light chain and Fd genes on separate shuttle vectors containing separate selective markers and to transform these vectors into a yeast strain defective for both selective markers.

The Fd gene from pING1444 (FIG. 34) was cloned as a BamHI-XhoI fragment into two medium copy number yeast—E. coli shuttle vectors containing sequences for replication in yeast and the PGK polyadenylation, transcription termination signal: pING804CVS for leu2 selection and pING1150 for ura3 selection (see FIGS. 29, 30). The two plasmids resulting from these constructions—pING1445 (ura3) and pING1446 (leu2) are shown in FIG. 35.

(5) Secretion of chimeric L6 Fab from transformed yeast cells.

Two separate transformation experiments were performed in an attempt to obtain both light and Fd-chain synthesis in yeast cells. Four μg each of pING1445 (FIG. 35) and pING1441 (FIG. 30) and separately of pING1446 (FIG. 35) and pING1442 (FIG. 30) were co-transformed into S. cerevisiae strain BB331c (MATa, ura3, leu2) by selecting for growth on SD agar (2% glucose, 0.67% yeast nitrogen base, 2% agar). Ura$^+$ Leu$^+$ transformants appeared at two to three days of incubation at 30° C.

Five colonies were inoculated from each plate into 6 ml SD broth supplemented with 50 mM sodium succinate, pH 5.5, and grown for 65 hours at 30° C. The cells were removed by centrifugation and analyzed by ELISA for the levels of light chain. The results of these assays revealed that the levels of light chain in the culture supernatants of the pING1446+pING1443 transformants were three to six times higher than the levels in the culture supernatants of the pING1445+pING1441 transformants. The culture supernatants for each group of transformants were next concentrated by ultrafiltration on a Centricon 30 filter (Amicon Corp.) and run on a 10% polyacrylamide gel under non-reducing conditions. The proteins were blotted to nitrocellulose paper and probed with goat anti-human kappa antiserum followed by peroxidase-labeled rabbit-anti-goat antiserum. The concentrated supernatant from the pING1446 and pING1443 transformants contained a significant anti-kappa cross-reactive smear over a large portion of the blot with only a faint cross-reactive band at the position expected for the Fab protein. By comparison, the concentrated supernatants from pING1445+pING1441 transformants contained relatively little smeared anti-human kappa cross-reactive protein on the blot. In addition, one of the five samples (No. 4) contained an especially intense, distinct anti-kappa cross-reactive band which migrated at the position expected for an Fab protein.

(6) Purification of chimeric L6 Fab from yeast culture supernatant.

To establish that the Fab-size anti-kappa cross-reactive protein secreted by the yeast is indeed L6 chimeric Fab protein required the purification of sufficient quantities for performance of binding assays. The pING1441+pING1445 transformant isolate No. 4 was, therefore, grown in one liter of SD broth supplemented with 50 mM sodium succinate, pH 5.5, for 95 hours at 30° C. The cells were removed by centrifugation and the culture supernatant was analyzed by ELISA for the level of light chain protein. The supernatant contained approximately 130 µg/L of light chain protein. The culture supernatant was next concentrated by ultrafiltration over an Amicon YM30 filter to 20 ml. The concentrated supernatant was washed with 130 ml 10 mM potassium phosphate, pH 7.5 (buffer A) and re-concentrated over the YM30 filter to 12.5 ml. The concentrated supernatant was next brought to 54 ml with buffer A and loaded onto a 1.5 ml S-Sepharose column equilibrated with buffer A. The column was washed with 20 ml buffer A and subjected to a linear gradient of 0 to 200 mM sodium chloride in buffer A (40 ml total volume). ELISA analysis of the column fractions revealed a large anti-kappa cross-reactive peak between fractions 8 and 21 corresponding to a salt concentration of approximately 60 mM. These fractions were pooled, concentrated on Amicon YM10 and Centricon-10 filters (Amicon Corp.) to 51 µl and analyzed on non-reducing and reducing polyacrylamide gels using coomassie blue staining and Western blotting with anti-human kappa and anti-human Fab antisera. These analyses revealed an essentially pure protein which migrated at approximately 46 kd on the non-reducing gel and resolved into two bands running at approximately 23 and 24.5 kd on the reducing gel which corresponds to the predicted (based on amino acid sequence) molecular weights for light chain and Fd proteins, respectively. The smaller of the two bands strongly reacted with anti-human kappa antiserum on the Western blot. Both of the protein bands reacted with anti-human Fab antiserum on the Western blot.

(7) Studies performed on the chimeric L6 Fab secreted by yeast.

The primary activity of an Fab molecule is its ability to bind to the target antigen. The yeast-derived chimeric Fab was, therefore, tested for its ability to bind directly to an L6 antigen-positive cell line and for its ability to inhibit binding of mouse L6 antibody to antigen-positive cells.

Direct Binding Assay.

Cells from the human colon carcinoma cell line 3347, which contains the L6 antigen at the cell surface, were used as targets. Cells from the antigen-negative cell line, T51, were used as a negative control. The target cells were first incubated for 30 minutes at 4° C. with either yeast-derived chimeric L6 Fab, Sp2/0 cell-derived chimeric L6 antibody, or with mouse L6 antibody. This was followed by incubation with FITC-labelled goat anti-human kappa immunoglobulin for the chimeric Fab, FITC-labelled goat anti-human IgG for chimeric antibody, or with FITC-labelled goat anti-mouse immunoglobulin for the mouse antibody. Both labelled antibodies were obtained from TAGO (Burlingame, Calif.) and used at a dilution of 1:50. Antibody binding to the cell surface was determined using a Coulter Model EPIC-C cell sorter.

As shown in Table 12, the yeast-derived chimeric L6 Fab bound to the L6 positive 3347 line. The yeast-derived chimeric L6 Fab did not bind above background to the L6 negative T51 line.

Inhibition of Binding.

As the next step, we studied the extent to which graded doses of the yeast-derived chimeric L6 Fab or Sp2/0-cell-derived chimeric L6 antibody could inhibit binding of an FITC-labelled mouse L6 antibody to the surface of antigen positive colon carcinoma 3347 cells.

The yeast-derived chimeric L6 Fab inhibited the binding of the directly labeled mouse L6 antibody. A higher concentration of the yeast L6 Fab, however, was required to achieve 50% inhibition of mouse L6 antibody binding to the target cells than was required for the same degree of binding inhibition by Sp2/0 cell-derived chimeric L6 antibody.

(8) Conclusions

A process is disclosed by which yeast can be genetically engineered to secrete functional Fab domains of immunoglobulins. The yeast-derived chimeric Fab in this example binds to the appropriate target antigen. Such Fab molecules provide convenient targeting agents for a variety of diagnostic and therapeutic uses. This process also demonstrates the feasibility of secretion of heterologous hetero-dimeric molecules from yeast.

TABLE 12

BINDING ASSAYS OF CHIMERIC L6 FAB PRODUCED BY YEAST ON AN L6 ANTIGEN-POSITIVE AND AN L6 ANTIGEN-NEGATIVE CELL LINE

| | Binding Ratio[b] for: | |
|---|---|---|
| Antibody[a] | 3347 Cells (L6+) | T51 Cells (L6−) |
| Sp2/0 Chimeric L6 | 103 | 1 |
| Yeast Chimeric L6 Fab | 32 | 1 |

[a]All antibodies were used at a concentration of 10 µg/ml.
[b]The binding ratio is the number of times brighter a test sample is than a control sample treated with FITC-conjugated second antibody. Goat anti-human antibody was used as the second antibody for the Sp2/0 chimeric L6 antibody and goat-anti-human kappa antibody was used as the second antibody for the yeast Fab.

Example VII

Secretion of Functional Chimeric Fab Molecules From Bacteria

Bacteria are suited for production of chimeric antibodies expressed from mammalian cDNA since entire coding sequences can be expressed from well characterized promoters. *Escherichia coli* is one of many useful bacterial species for production of foreign proteins (Holland, I. B., et al., *BioTechnology* 4:427 (1986)), since a wealth of genetic information is available for optimization of its gene expression. *E. coli* can be used for production of foreign proteins internally or for secretion of proteins out of the cytoplasm, where they most often accumulate in the periplasmic space (Gray et al., *Gene* 39:247 (1985); Oka et al., *Proc. Natl. Acad. Sci. USA* 82:7212 (1985)). Secretion from the *E. coli* cytoplasm has been observed for many proteins and requires a signal sequence. Proteins produced internally in bacteria are often not folded properly and precipitate into subcellular particles called inclusion bodies (Schoner et al., *BioTechnology* 3:151 (1985)). Protein secreted from bacteria, however, is often folded properly and assumes native secondary and tertiary structures (Hsiung et al., *BioTechnology* 4:991 (1986)). Although immunoglobulin peptides have been synthesized in genetically engineered *E. coli* (Cabilly et al., *Proc. Natl. Acad. Sci. USA* 81:3273 (1984); Liu et al., *Proc. Natl. Acad. Sci. USA* 81:5369 (1984); Boss et al., *Nucl. Acids Res.* 12:3791 (1984)), there are no reports of secretion of these peptides from *E. coli* as functional antibodies or antibody fragments.

An Fab molecule consists of two nonidentical protein chains linked by a single disulfide bridge. These two chains are the intact antibody light chain and the V, J, and $C_H1$ portions of the antibody heavy chain, Fd. The proper cDNA clones for the L6 chimeric light and Fd gene have already been identified. In this example, these cDNA clones were organized into a single bacterial operon (a dicistronic message) as gene fusions to the pectate lyase (pelB) gene leader sequence from *Erwinia carotovora* (Lei et al., *J. Bacteriol.*, in press (1987)) and expressed from either of two strong, regulated promoters. The result is a system for the simultaneous expression of two protein chains in *E. coli*, and the secretion of immunologically active, properly assembled Fab of L6 chimeric antibody into the culture growth media.

A. Construction of *E. coli* expression systems for L6 Chimeric Fab.

1. Assembly of the pelB leader sequence cassette.

*Erwinia carotovora* EC codes for several pectate lyases (polygalacturonic acid trans-eliminase) (Lei et al., *Gene* 35:63 (1985)). Three pectate lyase genes have been cloned, and the DNA sequence of these genes has been determined. When cloned into *E. coli* under the control of a strong promoter, the pelB gene is expressed and large quantities of pectate lyase accumulate in the periplasmic space. The pelB signal sequence functions efficiently in *E. coli* and was used as a secretion signal for antibody genes in this example. The nucleotide sequence surrounding the signal sequence of the pelB gene is shown in FIG. 36a.

The pelB signal sequence contains a HaeIII restriction site at amino acid 22, adjacent to the signal peptidase cleavage site: ala—ala. Plasmid pSS1004 (Lei et al., *J. Bacteriol.*, in press (1987)), containing the pelB gene in plasmid vector pUC8 (Vieirra and Messing, *Gene* 19:259 (1982)), was digested with HaeIII and EcoRI. This DNA was ligated with an eight base pair SstI linker to SspI and EcoRI cut pBR322. The resulting plasmid contained a 300 bp fragment which included the 22 amino acid leader sequence of pelB and about 230 bp of upstream *E. caratovora* DNA. This plasmid pING173, contains an insert that upon digestion with Sst1 and treatment with T4 DNA polymerase can be ligated directly to a DNA fragment flanked by the first amino acid of a mature coding sequence for any gene to generate a protein fusion containing a functional bacterial leader sequence in frame with the incoming gene. The Sst1 to EcoRI restriction fragment in pING173 was cloned into pUC18 (Yanich-Perron et al., *Gene* 33:103 (1985)) to generate pRR175, which contains the pelB leader and adjacent upstream non-coding sequence (including a ribosome binding site) downstream of the lac promoter. The construction of pRR175 is outlined in FIG. 36b.

2. Preparation of chimeric L6 light gene for bacterial expression.

The intact L6 chimeric light chain gene containing an AatII restriction site at the signal sequence processing site and a unique BglII site downstream of the gene was excised from the yeast expression plasmid pING1298 (FIG. 25a) as a 1200 bp DNA fragment. This fragment was inserted into plasmid pRR175. The resulting plasmid, pRR177–8, contained an in-frame fusion of the pelB leader and the L6 light chain downstream of the lac promoter residing in the parent plasmid. A number of derivatives of this plasmid were constructed to delete noncoding sequences from both the 5' and 3' ends of the pelB::light chain gene fusion in pRR177–8. Upstream noncoding sequences were deleted making use of an NdeI restriction site at −48 bp from the pelB leader sequence initiation codon (FIG. 36) generating pRR180–2. The 3' noncoding sequences were eliminated by substituting a fragment from the plasmid optimized for L6 light chain expression in yeast, pING1431 (see FIG. 27a), into pRR179 to generate pRR191. Another plasmid, pRR190, is similar to pRR191 but contains 90 bp of noncoding eukaryotic DNA at the 3' end of the light chain gene. These constructions are shown in FIG. 37.

3. Preparation of chimeric L6 Fd gene for bacterial expression.

The intact L6 chimeric Fd gene containing an SstI restriction site at the signal sequence processing site, a BclI site introduced by site directed mutagenesis (FIGS. 32a, b) and creating a termination codon at amino acid 226, and a unique BamHI restriction site downstream of the gene was excised from the plasmid pING1406 (FIG. 33A) as a 880 bp DNA fragment. This DNA fragment was inserted into plasmid pRR175 generating an in-frame fusion of the pelB leader sequence and the L6 Fd gene downstream of the lac promoter, pRR178-5. A number of derivatives were constructed to delete noncoding sequences from both the 5' and 3' ends of the sequence contained in pRR178-5. The 3' noncoding sequences were eliminated by substituting a restriction fragment from the plasmid optimized for L6 Fd expression in yeast, pING1428 (FIG. 34), which contains an XhoI linker immediately following the termination codon of the Fd gene, generating plasmid pRR186. Removal of *E. caratovora* DNA sequences upstream of the NdeI site at −48 from the leader sequence generated plasmid pRR196. The construction of these plasmids is shown in FIGS. 38(A and B).

4. Multicistronic expression system for light chain and Fd gene.

For production of bacterially derived Fab, both light chain and Fd need to be produced simultaneously within the cell. Using the plasmids constructed with each of these genes separately, a series of expression vectors were constructed that contain both genes aligned so that transcription from a single promoter will specify both genes. This was done in a way that minimized the noncoding DNA between the two genes to 60 bp. Each gene has a ribosome binding site needed for translation initiation and the identical DNA sequence from −48 to the pelB leader::antibody gene junction. Several cloning steps were required to align the two genes together. A portion of the light chain gene linked to the pelB leader in pRR180-2 was cloned downstream of the Fd gene in pRR186 to generate pFK100. The remainder of the light chain gene was subcloned into pFK100 from pRR177-8 to generate pFK101. Similarly, DNA fragments containing 3' deletions of eukaryotic sequences from pRR190 and pRR191 were cloned into pFK101 generating pFK103 and pFK102 respectively. DNA fragments from pRR192 and pFK101 were ligated to generate pFK104 which contains a deletion of sequences upstream of −48 bp from the Fd gene. Maps of the Fd and light chain gene cassettes in these plasmids are shown in FIG. 39.

5. Placement of the dicistronic message for light chain and Fd under the control of inducible promoters.

Plasmids pFK101, pFK102, pFK103, and pFK104 contain Fd and light chain genes cloned sequentially under the control of the lac promoter in vector pUC18 or pUC19. In *E. coli* strains such as JM103 F'laciQ (Messing et al., *Nucl. Acids. Res.* 9:309 (1981)), the amount of light chain that accumulates in the periplasm is not affected by the lac promoter inducing agent isoprpl B-D-thiogalactopyranoside (IPTG), see Table 13. In addition, bacterial growth is slower (compared to cells containing pUC18), and bacterial colonies exhibit an altered morphology being small, dry and rough, suggesting that constitutive foreign gene expression is deleterious to cell growth. Two strategies were used to place this gene cassette under more tightly regulated promoters.

First, a PstI to EcoRI fragment from pFK104 was ligated to pIT206 to place the Fd and light chain gene cassette under the direct control of the *Salmonella typhimurium* araB promoter, a well characterized, strong promoter in *E. coli*. A restriction map of pIT206 and construction of pIT104 is shown in FIG. 40(A). Use of the araB promoter and its regulatory protein araC for the expression of bacterial genes is described in U.S. patent application Ser. Nos. 695,309 filed Jan. 28, 1985, abandoned and 797,472, filed Nov. 13, 1985, abandoned. As is seen in Table 14, the resulting plasmid, pIT104, is now regulated for the synthesis of light chain by the addition of arabinose to the culture growth media. At least 10 fold induction is effected by arabinose addition. Although Fab secreted into the growth medium increases more than 10 fold, cell growth stops after induction with arabinose. This confirms that high level expression of the Fab genes is deleterious to cell growth. Bacterial colonies harboring pIT104 are phenotypically indistinguishable from *E. coli* harboring pIT206 when grown in the absence of arabinose.

Figure 40B:
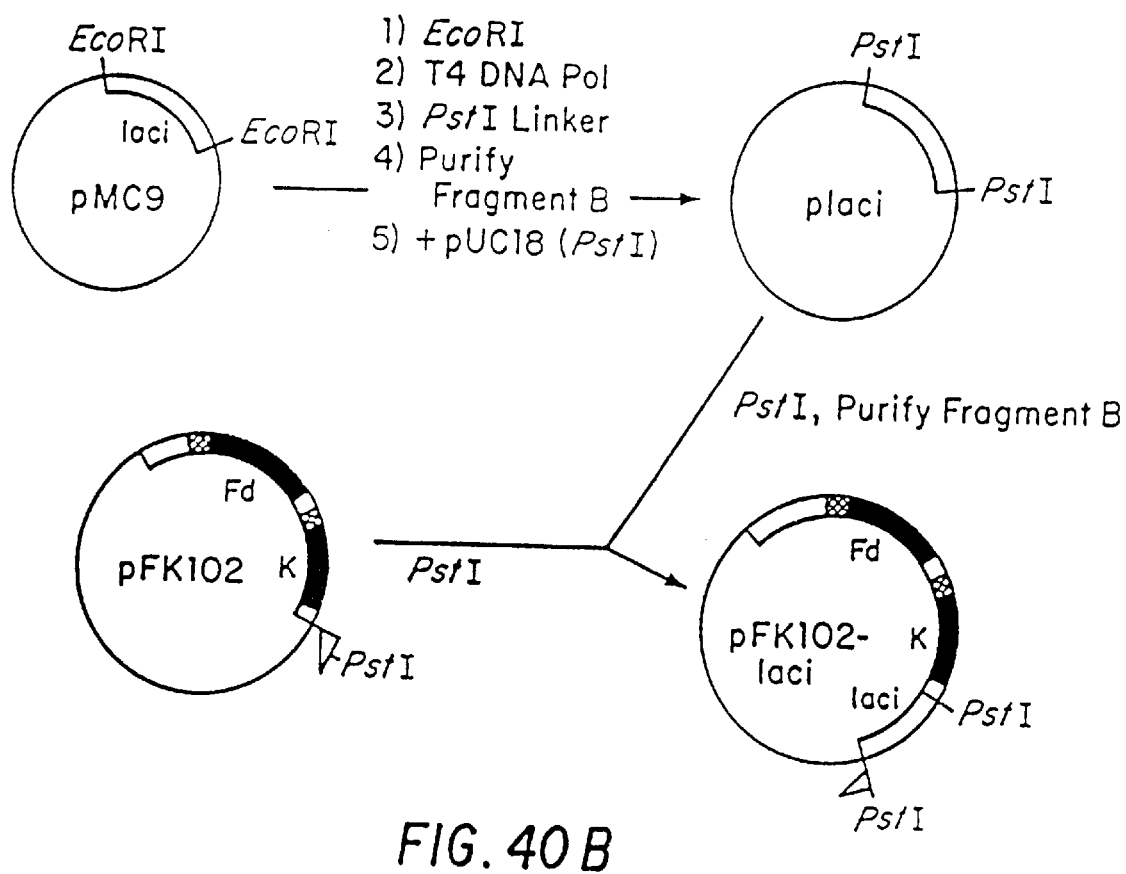

Second, a DNA fragment containing the laci gene, a repressor of the lac promoter, was cloned into the high copy expression vector pFK102. Expression of laci from a high copy number vector is useful to regulate expression of the lac promoter on a high copy number vector (Russel et al., *Plasmid*, in press (1987); Hsuing et al., *Biotechnology* 4:991 (1986)). A 1.7 kb EcoRI fragment containing the laci gene on pMC9 (Calos et al., *Proc. Natl. Acad. Sci. USA* 80:3015 (1983)) was excised, filled in with T4 polymerase to blunt ends, ligated with PstI linkers and cloned into the unique PstI site of pFK102 to generate pFK102laci. The map of pFK102laci is shown in FIG. 40B. The selection procedure used to identify the correct clone assured that the resulting plasmid, pFK102laci, contained a functionally repressed lac promoter. All white or light pink colonies on MacConkey-lactose plates contained plasmids with laci inserts while transformants containing pFK102 alone were red, indicating the functional repression of the lac promoter by the high copy number laci gene. Table 14 shows that expression of bacterial Fab from cells containing pFK102laci is similar to expression from pFK102. Unlike cells containing pFK102, which formed aberrant colonies and grew slowly in broth culture, cells containing pFK102laci resembled those containing pUC18.

B. Expression, SDS-PAGE, and Purification of Bacterially Produced Fab

1. Growth of *E. coli* harboring cloned antibody genes.

Plasmid DNA was transformed into either *E. coli* JM103 or MC1061 by standard *E. coli* transformation procedures. Bacterial cultures were grown in TYE (tryptone 1.5%, yeast extract 1.0%, and NaCl 0.5%) supplemented with the appropriate antibiotics (penicillin 250 ug/ml, tetracycline 15 ug/ml). Bacterial cultures were grown in volumes of 5 ml to 1 liter at 37° C. to an optical density OD600=0.8 (approximately 4×108 cell/ml) and aliquots were induced with IPTG (0.2 mM), lactose (1.0%), or arabinose (1.0%). Cultures were grown for an additional time period of 4 to 21 hr. Portions of each culture were analyzed for light chain production. Protein was released from the periplasmic space of *E. coli* cells by osmotic shock as described (Yanagida et al., *J. Bacteriol.* 166:937 (1986)). Alternatively, culture supernatants were assayed directly for the presence of antibody chains.

Quantitation of L6 light chain was by ELISA with goat anti-human Kappa light chain antibody (Cappel, Malvern, Pa.). Fd could be detected by ELISA with mouse monoclonal anti-human Fd antibody (Calbiochem, San Diego, Calif.). Table 13 shows representative data for expression of light chain reactive material in *E. coli* periplasmic extracts. Light chain is secreted from the bacterial cytoplasm into the periplasm. Antibody chains are also released from the bacteria into the culture supernatant. This is an unusual discovery and may be a unique property of the L6 Fab among eukaryotic proteins expressed in *E. coli*. Under certain conditions, however, bacterial proteins are known to be released from *E. coli* (Abrahmsen et al., *Nucl. Acids Res.* 14:7487 (1986); Pages et al., *J. Bacteriol.* 169:1386 (1986)). Table 14 compares the amount of light chain secreted into the periplasm with the amount secreted into the culture supernatant. Light chain reactive material is present in plasmid containing cultures harboring cloned light chain alone or light chain plus Fd. The best producers of Fab (pFK102, pFK104, and pFK102laci) typically secrete 300–1000 ng/ml of ELISA reactive light chain into the culture media. A separate construct was made in which the light chain gene is followed by the Fd gene (pFK107). This construct directs synthesis and secretion of Fab at similar levels to the constructs with the genes in the inverse order. Thus, the gene order is not critical for secretion of Fab.

2. SDS-PAGE of bacterially produced chimeric L6 light chain and Fd.

Bacterially produced antibody chains were analyzed by polyacrylamide gel electrophoresis under reducing and non-reducing conditions. Protein extracts of lysed whole bacterial cells, protein released from the periplasmic space by osmotic shock, and protein secreted into the culture supernatant were analyzed electrophoretically. Transfer of gell separated protein under full reducing conditions to nitrocellulose and immunological staining with goat anti-human light chain antibody by Western analysis revealed that a protein of the same molecular weight as authentic L6 chimeric light chain was present (about 23 Kd). Analysis of protein samples of SDS-PAGE under non-reducing conditions showed that extracts from cells harboring a plasmid with the light chain gene alone (pRR191 or pRR190)

contained a large proportion of the light chain reactive material associated into a higher molecular weight form. Much of this material ran at about 46 Kd in what is likely to be a light chain dimer. Light chain dimers have been observed from myeloma cells producing only light chain. There are also other immunoreactive protein bands that may represent non-specific disulfide formation between light chain and *E. coli* proteins. Protein samples (periplasmic extracts or culture supernatants) from *E. coli* cells harboring both the light chain and the Fd genes contain a light chain reactive band at about 48 Kd when separated under non-reducing gel conditions which runs at a slightly higher molecular weight than the bacterial light chain dimer. This material is bacterially produced L6 chimeric Fab. In *E. coli* harboring pFK102laci, pFK101, pFK102, pFK103, or pFK104 the 48 Kd band observed on an SDS gel run under non-reducing conditions is the most prominent immunoreactive specie. In addition, the background smear of immunoreactive proteins seen in extracts containing the light chain only is greatly reduced in extracts from cells containing both light chain and Fd.

3. Purification of bacterially produced chimeric L6 Fab.

Immunologically and functionally active (see below) bacterial Fab was purified from either culture supernatants or periplasmic protein extracts of *E. coli* harboring pFK102laci or pIT104. For purification of periplasmic material, the periplasmic fraction from 1 liter of cells induced for 4 hours was released into 50 ml of distilled water. This material was centrifuged for 20 minutes at 5000 g and filtered through a 0.45 μm filter. The periplasmic extract was then concentrated over a YM10 membrane (Amicon) to about 5 ml. This material was diluted 8 fold into starting buffer (10 mM K2HPO4, pH 7.5) and applied to a 1 ml S-Sepharose column at a flow rate of 1.0 ml/min. The column was washed with 25 ml of starting buffer and eluted with a 0 to 200 mM NaCl gradient in starting buffer (200 ml total volume). The immunoreactive gradient peak was pooled (elution was at about 100 mM) and concentrated on a Centricon 10. Purified Fab was stored in PBS+2.0% BSA.

For purification of secreted Fab from 1 liter of bacterial culture supernatant, the cells were removed by centrifugation after growth for 21 hours with inducing agents and the supernatant was filtered through a 0.45 μm filter. The media was concentrated over a YM10 membrane (Amicon) to about 16 ml, then diluted with 10 mM K2HPO4 to 105 ml. This material was applied to a 1.6 ml S-Sepharose column and eluted with a 0 to 200 mM NaCl gradient in 40 ml. Fab recovered from S-Sepharose chromatography was greater than 70% pure as determined by densitometry tracing of a nonreducing, coomassie stained, 10% acrylamide gel. The Fab purified from bacterial culture supernatants resolves into two major protein bands of about 23 Kd and 24.5 Kd on a 15% reducing gel. The molecular weight of Fd and light chain based on the DNA sequence are 24.5 Kd and 23 Kd which corresponds well to the observed protein sizes. The smaller of the two bands strongly reacted with goat anti-human Kappa light chain antiserum on a Western blot. Bacterial Fab purified from either the periplasmic space or bacterial culture supernatants are indistinguishable by all analytical criteria tested here.

4. Functional binding activity of bacterially produced chimeric L6 Fab to the L6 antigen.

Bacterially produced Fab purified by S-Sepharose chromatography was tested for binding to L6 antigen containing cells. As shown in Table 15, bacterial Fab binds specifically to the human colon carcinoma cell line 3347. Cells from the T cell line T51 were used as a negative control. Target cells were incubated for 30 minutes at 4° C. with bacterially produced L6 chimeric Fab, intact L6 chimeric antibody produced in Sp2/0 cells, or mouse L6 antibody purified from mouse ascites. This was followed by incubation with FITC-labelled goat anti-human light chain antibody for Fab detection, FITC-labelled goat anti-human immunoglobulin for chimeric antibody detection, or with FITC-labelled goat anti-murine immunoglobulin for mouse antibody detection. Antibody binding to the cell surface was determined using a Coulter Model EPIC-C cell sorter.

Bacterially produced Fab also exhibits characteristic binding inhibition of FITC-labelled mouse L6 antibody to the surface of antigen positive 3347 colon carcinoma cells. Bacterially produced Fab and Sp2/0 derived chimeric L6 have similar binding inhibition profiles, thereby suggesting that the avidity of bacterially produced Fab and Sp2/0 derived chimeric L6 are similar.

Conclusions

A novel process is disclosed whereby *E. coli* has been used as a host to produce functionally active Fab domains of immunoglobulins and to secrete these into the periplasmic space and also in the culture medium. This molecule exhibits binding properties expected of a properly assembled antibody recognition site. This technology can be used to express antibody genes with other binding specificities in *E. coli*.

1. Proteins encoded by modified antibody DNA clones can be secreted from bacteria using a signal sequence.

2. Two antibody genes can be expressed from a single bacterial promoter as a dicistronic message.

3. Two foreign proteins (in this example antibody light chain and Fd) can assemble properly, i.e., assume correct secondary, tertiary, and quaternary structure when secreted from bacteria.

4. At least two, and probably many bacterial promoters can be used for expression of antibody genes.

5. This example is a general method whereby genes encoded other antibody chains can be expressed together as a dicistronic message; these include either light chain and Fd genes or light chain and intact heavy chain genes.

6. The gene order with respect to the promoter is not important in the ability of *E. coli* to produce Fab. A construct of the Fd gene followed by the light chain works as well as the genes organized in the inverse order.

7. Fab can be secreted from *E. coli* into the culture supernatant where it is stable and can be purified. Most Fab chains that pass the cytoplasmic membrane are secreted into the culture supernatant.

Microorganism Deposits

*Saccharomyces cerevisiae* BB331C (41/42-5), G187 was deposited at the ATCC on Jul. 9, 1987 and given access number 20856. *Escherichia coli* JM 103 (pFK1021 aci), G186 was also deposited therein on the same date and given access number 67457. Both deposits were under the Budapest Treaty.

TABLE 13

QUANTITATION OF LIGHT CHAIN FROM E. COLI PERIPLASM

| plasmid | ng/ml of culture | | plasmid | ng/ml of culture | |
|---|---|---|---|---|---|
| | − | + | | − | + |
| pRR175 | 0 | 0 | pFK101 | 36 | 28 |
| pRR177-8 | 8.5 | 11 | pFK102 | 68 | 55 |
| pRR180 | 399 | 412 | pFK103 | 38 | 45 |
| pRR190 | 200 | 241 | pFK104 | 91 | 68 |
| pRR191 | 463 | 772 | | | |

E. coli JM103 or MC1061 (results similar) was transformed with each plasmid. Fresh transformants were cultured in TYE at 37° C. to an OD600 = 0.8. Cultures were divided and the inducer (IPTG) was added to 0.2 mM to one aliquot (− or + IPTG). Cells were grown at 37° C. for 4 hours. Periplasmic protein extracts were prepared, and aliquots were tested for light chain by ELISA with goat anti human Kappa antibody. Each value is the average of at least two separate experiments. Removal of non-coding sequences both 5' and 3' to the antibody gene effected in increase in light chain accumulation an the periplasm.

TABLE 14

ACCUMULATION OF LIGHT CHAIN IN THE SUPERNATANT AND PERIPLASM AFTER INDUCTION

| Plasmid | Inducer | Supernatant | | Periplasm | |
|---|---|---|---|---|---|
| | | 4 hr | 21 hr | 4 hr | 21 hr |
| pRR190 | − | 0 | nd | 200 | nd |
| pRR190 | + | 5 | 188 | 241 | nd |
| pFK102 | − | 12 | nd | 68 | nd |
| pFK102 | + | 57 | 828 | 55 | 40 |
| pFK104 | − | 13 | nd | 91 | nd |
| pFK104 | + | 150 | 290 | 68 | 35 |
| pFK102laci | − | 25 | 360 | 50 | 100 |
| pFK102laci | + | 72 | 606 | 37 | 40 |
| pIT104 | − | 13 | nd | 10 | nd |
| pIT104 | + | 150 | 216 | 19 | 35 |

Plasmid containing E. coli strains were grown, prepared, and assayed as described in Table 13. For pRR190, pFK102, pFK104, and pFK102laci cells were induced with 0.2 mM IPTG; pIT104 was induced with 1% arabinose. Each value is the average of at least two separate experiments. For analysis of E. coli culture supernatants, bacteria were removed by centrifugation and culture supernatants were passed through a 0.45 uM filter. Values are expressed in ng/ml of culture.
nd - not determined

TABLE 15

BINDING ASSAYS OF BACTERIAL Fab

| | Binding ratio* | |
|---|---|---|
| Antibody | 3347 cells L6+ | T51 cells L6− |
| Standard mouse L6 | 95 | 1 |
| Sp2/0 chimeric L6 | 116 | 1 |
| Bacterial L6 Fab | 54 | 1 |
| Standard L6 Fab | 16 | 1 |

*The binding ratio is the number of times brighter a test sample is than a control sample treated with FITC-conjugated second antibody.
Standard L6 Fab was prepared by enzymatic digestion of mouse L6 antibody.

Example VIII

Expression of Pectate Lyase B Plasmid Construction

Plasmid pSH2111 (Lei et al., Gene 35: 63–70, 1985) contains the pectate lyase genes from Erwinia carotovora. The pelB gene is positioned between two DraI restrictions sites; isolation of the gene is achieved by digestion of plasmid pSH2111 with DraI and identification of a 1.9 kilobase fragment on an agarose gel. The isolated fragment was then ligated into plasmid pUC8 which had been digested with SmaI. The resultant plasmid is pSS1004 (see FIG. 41).

The plasmid pSS1004 was then treated with NdeI $T_4$ DNA polymerase and Hind III, and the resultant fragment ligated into plasmid pIT2, which had been digested with NcoI, $T_4$ DNA polymerase and HindIII, to produce plasmid pSS1038 (FIG. 41). The plasmid pIT2 contains both the Salmonella typhimurium araBAD promoter and the araC gene (Johnson et al.—Gene 34: 137–145, 1985). The plasmid was then used to transform E. coli strain 706. The expression of the pelB gene on plasmid pSS1038 was thus expected to be under the control of the araBAD promoter and turned on by the presence of arabinose in the growth medium.

Excretion and Purification of PLB

E. coli cell 706 (F−, pro, thr, leu, arqH, his, lac, phoSt, rpsL, lky-207) carrying plasmid pSS1038 was used to characterize the production and excretion of PLb. The E. coli cells were grown in TYE (1.5% tryptone, 1% yeast extract and 0.5% NaCl), incubated at 37° C., at log phase of growth (around $O.D._{540}$=0.6), 1% of arabinose was added to the growth medium to turn on the araBAD promoter and start producing PLb. After four hours of induction $O.D._{540}$ was about 2.5), the culture broth was centrifuged and PLb was directly purified from this E. coli cell culture medium. The culture fluid was concentrated and desalted by Amicon (membrane YM2) and then the protein was purified by passing through a CM-52 column at pH 7.4 and then eluted with 0.2 M NaCl. The PL purified from these simple steps has greater than 95% purity, as judged by electrophoresis on SDS gels followed by staining with Coomassie blue.

Construction of the Secretion Vector

The pSS1004 plasmid was used as the source of the signal sequence for pelB. The sequence was isolated from pSS1004 digestion with restriction enzyme HaeIII, ligation with SstI DNA linker, and then digestion with EcoRI. The EcoRI-SstI DNA fragment, which contains the 5'-end non-coding region and the leader peptide was then ligated into a pBR322 plasmid digested with SspI and EcoRI. The plasmid so produced containing the signal peptide, is pING173. FIG. 36 describes both the DNA sequence for the signal peptide, and the procedure for preparing the pING173 plasmid. This plasmid is used to construct additional derivatives, as described below.

Production and Secretion of Thaumatin Background

Thaumatin is a protein sweetener originally isolated from the plant Thaumatococcus danielli. Thaumatin contains 207 amino acids and is 2,000–5,000 fold sweeter than sucrose. It has eight disulfide bonds and the tertiary structure of thaumatin is essential for its biological function.

Construction of a Plasmid Carrying a Pectate Lyase B Signal Sequence and the Synthesized Plant Thaumatin Gene The DNA sequence which codes for PLb signal peptide from plasmid pING173, described above was cloned in front of the thaumatin gene from plasmid pING174 to secrete thaumatin in an E. coli host system. The resulting plasmid, pING177-1, was used to express and secrete thaumatin in *E. coli*. It has the araBAD promoter and part of the araB gene fused to 50 bp of the 5'-non-coding region of the PLb leader peptide. To prepare this plasmid, the SstI and EcoRI fragment of plasmid pING173 was cloned into the plasmid pING174, which contains the thaumatin gene. pING174 was digested with BamHI and PstI, and the leader sequence from pING173 ligated into the restriction sites, to produce pING176. The latter plasmid was digested with NdeI and XhoI, and the resulting fragment, containing the pectate lyase leader sequence adjacent to the thaumatin gene, was cloned into the SalI, XhoI sites on the plasmid pING61. The resulting plasmid contained the gene coding for the PLb leader sequence and the thaumatin gene, under the control of the araBAD promoter and was referred to as pING177-1. The detailed construction scheme is shown in FIG. 42).

Production and Characterization of Thaumatin from *E. Coli* Recombinant Strain

The *E. coli* strain 706 harboring plasmid pING177-1 was grown in one liter of TYE broth. At O.D.=0.35, the cells were induced with 1% w/v arabinose for approximately 12 hours. The culture was then harvested and the periplasmic space protein was characterized by SDS-PAGE, Western analysis and the RIA assay for properly folded thaumatin. Both SDS-PAGE and Western analysis indicated that thaumatin could be synthesized by *E. coli* cells. RIA assay also indicated that the secreted thaumatin in the periplasmic space of the *E. coli* was properly folded (Table 16). The pre-thaumatin signal peptide was also used to secrete thaumatin in *E. coli*. Plasmid pING177-3, which contains the pre-thaumatin signal peptide sequence and the thaumatin structural gene, was used to produce thaumatin, the detailed construction scheme is shown in FIG. 43). The conditions for cell growth and induction are the same as those described previously. The results of the RIA assay indicated that the production of properly-folded thaumatin directed by the pre-thaumatin signal peptide is less efficient than directed by the PLb leader peptide (Table 16).

TABLE 16

Secretion of Thaumatin in *Escherichia coli* (*E. Coli* K-12; 706)

| Plasmid | Media | RIA cross reactive Thaumatin (ug)/gram wet wt. cells | |
|---------|-------|-------------------|---------------|
|         |       | Soluble Cell Extract | Total Secreted |
| 177-1   | 5.4   | 35.2              | 40.6          |
| 177-3   | 1.8   | 6.3               | 8.1           |

What is claimed is:

1. A process for preparing an immunoglobulin that is capable of binding antigen, said immunoglobulin comprising (a) a heavy chain or heavy chain fragment and (b) a light chain or light chain fragment, said process comprising expressing, in a bacetrial cell, of a first nucleic acid that encodes a bacterial signal sequence operably linked to either said heavy chain or to said heavy chain fragment, and a second nucleic acid that encodes a bacterial signal sequence operably linked to either said light chain or to said light chain fragment, such that the bacterial signal sequences bring about the transport of said heavy chain or said heavy chain fragment and said light chain or said light chain fragment through the cytoplasmic membrane of a bacterial cell, and, obtaining said immunoglobulin from the periplasmic space or culture medium, wherein said immunoglobulin is capable of binding antigen.

2. The process of claim 1, wherein (a) is said heavy chain.

3. The process of claim 1, wherein (a) is said heavy chain fragment.

4. The process of claim 3, wherein said heavy chain frament is Fd.

5. The process of claim 1, wherein (b) is said light chain.

6. The process of claim 1, wherein (b) is said light chain fragment.

7. The process of claim 1, wherein (a) is said heavy chain and (b) is said light chain.

8. The process of claim 1, wherein (a) is said heavy chain fragment and (b) is said light chain fragment.

9. The process of claim 1, wherein (a) is said heavy chain fragment and (b) is said light chain.

10. The process of claim 9, wherein said immunoglobulin is Fab.

11. The process of claim 1, wherein one or more chains selected from the group consisting of said heavy chain, said heavy chain fragment, said light chain and said light chain fragment, contains a variable region and a constant region that are from different antibodies.

12. The process of claim 11, wherein said light chain or said light chain fragment contains a variable region and a constant region that are from different antibodies.

13. The process of claim 11, wherein said heavy chain or said heavy chain fragment contains a variable region and a constant region that are from different antibodies.

14. The process of claim 11, wherein each chain in said immunoglobulin contains a variable region and a constant region that are from different antibodies.

15. the process of any one claims 11–14, wherein said variable region is from the same species as that of the constant region.

16. The process of claim 15, wherein said species is human.

17. The process of any one of claims 11–14, wherein said variable region is from a different species than that of the constant region.

18. The process of claim 17, wherein said variable region is from a non-human species.

19. The process of claim 18, wherein said constant region is a human constant region.

20. The process of claim 1 or 2–11, wherein said first nucleic acid and said second nucleic acid comprise a dicistronic transcription unit.

21. The process of any one of claims 1 or 2–11, wherein said first nucleic acid and said second nucleic acid are on the same or different plasmids.

22. The process of claim 21, wherein both said first nucleic acid and said second nucleic acid are on the same plasmid.

23. The process of claim 21, wherein said first nucleic acid is on a different plasmid than said second nucleic acid.

24. The process of any one of claims 1 or 2–11, wherein said immunoglobulin fragment is obtained from said periplasmic space of said bacterial cell.

25. The process of claim 24, wherein said bacterial cell is *E. coli*.

26. The process of any one of claims 1 or 2–11, wherein said immunoglobulin fragment is obtained from said culture medium.

27. The process of claim 26, wherein said bacterial cell is *E. coli*.

28. The process of any one of claims 1 or 2–11, wherein said bacterial signal sequence encoded by said first nucleic acid or said bacterial signal sequence encoded by said second nucleic acid, or both, is a pectate lyase signal sequence.

29. The process of claim 28, wherein said bacterial cell is *E. coli*.

30. The process of any one of claims 1 or 2–11, wherein said nucleic acid encoding said heavy chain or heavy chain fragment, and said light chain or light chain fragment is on a bacteriophage vector.

31. A process for preparing an immunoglobulin that is capable of binding antigen, said immunoglobulin comprising (a) a heavy chain variable region and (b) a light chain variable region, said process comprising operably linking a nucleic acid encoding a bacterial signal sequence to a nucleic acid encoding said heavy chain variable region or said light chain variable region or both of said variable regions such that the bacterial signal sequence or sequences bring about the transport of said variable regions through the cytoplasmic membrane of a bacterial cell, expressing said nucleic acid in said bacterial cell, and obtaining said immunoglobulin from the periplasmic space or culture medium, wherein said immunoglobulin is capable of binding antigen.

32. The process of claim 31, wherein said immunoglobulin comprises a full length heavy chain.

33. The process of claim 31, wherein said immunoglobulin comprises a heavy chain constant region.

34. The process of claim 31, wherein said immunoglobulin comprises Fd.

35. The process of claim 31, wherein said immunoglobulin comprises a full length light chain.

36. The process of claim 31, wherein said immunoglobulin comprises a light chain constant region.

37. The process of claim 31, wherein said immunoglobulin comprises a full length heavy chain and a full length light chain.

38. The process of claim 33, wherein said immunoglobulin comprises a heavy chain constant region and a light chain constant region.

39. The process of claim 31, wherein said immunoglobulin comprises a heavy chain constant region and a full length light chain.

40. The process of claim 39, wherein said immunoglobulin is Fab.

41. The process of claim 31, wherein said immunoglobulin comprises a heavy chain constant region that is from a different antibody than that of said heavy chain variable region or comprises a light chain constant region that is from a different antibody than that of said light chain variable region.

42. The process of claim 41, wherein said light chain constant region is from a different antibody than that of said light chain variable region.

43. The process of claim 41, wherein said heavy chain constant region is from a different antibody than that of said heavy chain variable region.

44. The process of claim 31, wherein said immunoglobulin comprises a heavy chain constant region that is from a different antibody than said heavy chain variable region and a light chain constant region that is from a different antibody than that of said light chain variable region.

45. The process of claim 41 or 44, wherein said light chain variable region is from the same species as that of said light chain constant region or said heavy chain variable region is from the same species as that of said heavy chain constant region.

46. The process of claim 45, wherein said species is human.

47. The process of claim 41 or 44, wherein said light chain variable region is from a different species than that of said light chain constant region or said heavy chain variable region is from a different species than that of said heavy chain region.

48. The process of claim 47, wherein said light chain variable region or said heavy chain variable region is from a non-human species.

49. The process of claim 48, wherein said light chain constant region or said heavy chain constant region is a human constant region.

50. The process of any one of claims 31–41, wherein said nucleic acid encoding said light chain variable region and said heavy chain variable region comprises a dicistronic transcription unit.

51. The process of any one of claims 31–41, wherein said nucleic acid encoding said light chain variable region and said heavy chain variable region are on the same or different plasmids.

52. The process of claim 51, wherein said nucleic acid encoding said light chain variable region and said heavy chain variable region are on the same plasmid.

53. The process of claim 51, wherein said nucleic acid encoding said light chain variable region and said heavy chain variable region are on different plasmids.

54. The process of any one claims 31–41, wherein said immunoglobulin is obtained from said periplasmic space of said bacterial cell.

55. The process of claim 54, wherein said bacterial cell is *E. coli*.

56. The process of any one claims 31–41, wherein said immunoglobulin is obtained from said culture medium.

57. The process of claim 56, wherein said bacterial cell is *E. coli*.

58. The process of any one of claims 31–41, wherein said bacterial signal sequence that is operably linked to said light chain variable region or said heavy chain variable region, or both, is a pectate lyase signal sequence.

59. The process of claim 58, wherein said bacterial cell is *E. coli*.

60. The process of any one of claims 31–41, wherein said nucleic acid encoding said variable regions is on a bacteriophage vector.

\* \* \* \* \*